United States Patent [19]

Hellstrom et al.

[11] Patent Number: 5,980,896
[45] Date of Patent: Nov. 9, 1999

[54] ANTIBODIES REACTIVE WITH HUMAN CARCINOMAS

[75] Inventors: Ingegerd Hellstrom; Karl Erik Hellstrom; Kim Folger Bruce, all of Seattle; George J. Schreiber, Redmond; Clay Siegall, Edmonds, all of Wash.; Stephen McAndrew, Newtown, Pa.

[73] Assignee: Bristol-Myers Squibb Company, Princeton, N.J.

[21] Appl. No.: 08/077,253

[22] Filed: Jun. 14, 1993

Related U.S. Application Data

[63] Continuation-in-part of application No. 08/057,444, May 5, 1993, Pat. No. 5,491,088, and application No. 07/892,501, Jun. 1, 1992, abandoned, which is a continuation-in-part of application No. 07/544,246, Jun. 26, 1990, abandoned, which is a continuation-in-part of application No. 07/374,947, Jun. 30, 1989, abandoned, said application No. 08/057,444, May 5, 1993, Pat. No. 5,491,088, is a continuation of application No. 07/544,246.

[51] Int. Cl.$^6$ .................... A61K 38/395; C07K 16/30; C07K 19/00; C12N 5/12
[52] U.S. Cl. ...................... 424/183.1; 424/181.1; 424/178.1; 424/138.1; 424/134.1; 424/141.1; 424/135.1; 424/136.1; 424/155.1; 530/391.7; 530/387.3; 530/387.5; 530/387.7
[58] Field of Search .............. 530/391.7, 387.3, 530/387.7, 387.5; 435/240.27, 172.2, 70.21, 326; 424/183.1, 178.1, 181.1, 138.1, 134.1, 141.1, 135.1, 136.1, 155.1

[56] References Cited

U.S. PATENT DOCUMENTS

| | | |
|---|---|---|
| 4,474,893 | 10/1984 | Reading . |
| 4,507,391 | 3/1985 | Pukel et al. . |
| 4,579,827 | 4/1986 | Sakamoto et al. . |
| 4,612,282 | 9/1986 | Schlom et al. . |
| 4,676,980 | 6/1987 | Segal . |
| 4,708,930 | 11/1987 | Kortright et al. . |
| 4,713,351 | 12/1987 | Knauf . |
| 4,713,352 | 12/1987 | Bander et al. . |
| 4,737,579 | 4/1988 | Helstrom et al. . |
| 4,753,894 | 6/1988 | Frankel et al. . |

FOREIGN PATENT DOCUMENTS

| | | |
|---|---|---|
| 8809344 | 12/1988 | WIPO . |
| WO8905309 | 6/1989 | WIPO . |
| 9100295 | 1/1991 | WIPO . |
| 9207466 | 5/1992 | WIPO . |

OTHER PUBLICATIONS

Schreiber, et al., "An Unmodified Anticarcinoma Antibody, BR96, Localizes to and Inhibits the Outgrowth of Human Tumors in Nude Mice", *Cancer Reserch*, 52:3262–3266 (1992) (Exhibit 131).
Siegell, et al., "In Vitro and In Vivo Characteriation of BR96 sFv–PE40", *Journal of Immunology*, 152:2377–2384 (1994) (Exhibit 132).
Friedman, et al., "BR96 sFv–PE40, a Potent Single–Chain Immunotoxin That Selectively Kills Carcinoma Cells", *Cancer Research*, 53:334–339 (1993) (Exhibit 133).
Willner, et al., 6–Maleimidocaproyl) hydrazone of Doxorubicin–A New Derivative for the Preparation of Immunoconjugates of Doxorubicin, *Bioconjugate Chem.*, 4:521–527 (1993) (Exhibit 134).
Yarnold, et al., "Chimerization of Antitumor Antibodies via Homologous Recombination Conversion Vectors", *Cancer Research*, 54:506–512 (1994) (Exhibit 135).
Friedman, et al., Antitumor Activity of the Single–Chain Immunotoxin BR96 sFv–PE40 Against Established Breast and Lung Tumor Xenografts:, *Journal of Immunology*, 150:3054–3061 (1993) (Exhibit 136).
Zhao, et al., "Determination of Immunoreactivity of Doxorubicin Antibody Immunoconjugates by a Ley Competitive RIA", *Bioconjugate Chem.*, 3:549–553 (1992) (Exhibit 137).
Abraham, et al., "The Influence of Periodate Oxidation on Monoclonal Antibody Avidity and Immunoreactivity", *Journal of Immunological Methods* 144:77–86 (1991) (Exhibit 138).
Chang, et al., "Crystallization and Preliminary X–ray Analysis of the Monoclonal Anti–tumor Antibody BR96 and its Complex with the Lewis Y Determinant", *J. Mol. Biol.* (1994) 235:372–376 (Exhibit 139).
Friedman et al. J. Immunol. 150:3054–61 1993.
Siegall et al. Bioconjugate Chem. 3:302–7 1992.
Pastan et al; Annu Rev Biochem 61:331–341 1992.
Schreiber et al., Cancer Res 52:3262–6 1992 (Jun. 15).
Stoerz et al., PNAS USA 83:1453–7, 1986.

(List continued on next page.)

*Primary Examiner*—Lila Feisee
*Assistant Examiner*—Geetha P. Bansal
*Attorney, Agent, or Firm*—Merchant, Gould, Smith, Edell, Welter & Schmidt

[57] ABSTRACT

The present invention relates to novel antibodies, antibody fragments and antibody conjugates and single-chain immunotoxins reactive with human carcinoma cells. More particularly, the antibodies, conjugates and single-chain immunotoxins of the invention include: a murine monoclonal antibody, BR96; a human/murine chimeric antibody, ChiBR96; a F(ab')$_2$ fragment of BR96; ChiBR96-PE, ChiBR96-LysPE40, ChiBR96 F(ab')$_2$-LysPE40 and ChiBR96 Fab'-LysPE40 conjugates and recombinant BR96 sFv-PE40 immunotoxin. These molecules are reactive with a cell membrane antigen on the surface of human carcinomas. The BR96 antibody and its functional equivalents, displays a high degree of selectivity for carcinoma cells and possess the ability to mediate antibody-dependent cellular cytotoxicity and complement-dependent cytotoxicity activity. In addition, the antibodies of the invention internalize within the carcinoma cells to which they bind and are therefore particularly useful for therapeutic applications, for example, as the antibody component of antibody-drug or antibody-toxin conjugates. The antibodies also have a unique feature in that they are cytotoxic when used in the unmodified form, at specified concentrations.

35 Claims, 74 Drawing Sheets

OTHER PUBLICATIONS

Hellstrom et al. Cancer Res 50:2183–90, 1990 (Apr. 1).
Harris et al. Tibtech 11:42–44, 1993.
Osband et al,. Immunol. Today 11:193–5, 1990.
Trail et al. Science 261:212–215, Jul. 9, 1993.
Hird et al. in "Genes and Cancer", Carney et al., Ed., John Wiley & Sons Ltd., 1990 pp. 83–9.
Schlom, in "Molecular Foundations of Oncology", Broder, Ed., Williams & Wilklins, 1991, 95–134.
Kimmel et al., J. Neurosurg. 66:161–171, 1987.
Hellstrom et al., "Antitumor Effects of L6, An IgG2a Antibody that Reacts with Most Human Carcinomas", *Proc. Natl. Acad. Sci. USA* 83:7059–7063 (1986).
Drebin et al., "Monoclonal Antibodies Specific for the Neu Oncogene Product Directly Mediate Anti–Tumor Effects In Vivo", *Oncogene* 2:387–394 (1998).
Papsidero, "Recent Progress in the Immunological Monitoring of Carcinomas Using Monoclonal Antibodies", *Sem. in Surg. Onc.* 1:171–181 (1985).
Schlom and Weeks, "Potential Clinical Utility of Monoclonal Antibodies in the Management of Human Carcinomas", *Important Adv. Oncol.* pp. 170–192 (1985).
Allum et al., "Monoclonal Antibodies in the Diagnosis and Treatment of Malignant Conditions", *Surg. Ann.* 18:41–64 (1986).
Houghton and Scheinberg, "Monoclonal Antibodies: Potential Applications to the Treatment of Cancer", *Sem. in. Oncol.* 13(2):165–179 (1986).
Fink and Clarke, "Monoclonal Antibodies as Diagnostic Reagents for the Identification and Characterization of Human Tumor Antigens", *Prog. Clin. Pathol.* 9:121–133 (1984).
Johnston, "Applications of Monoclonal Antibodies in Clinical Cytology as Exemplified by Studies with Monoclonal Antibody B72.3", *Acta. Cytol.* 1(5):537–556 (1987).
Young et al., "Production of Monoclonal Antibodies Specific for Two Distinct Steric Portions of the Glycolipid Anglio–N–Tiosylceramide (Asialo $GM_2$)", *J. Exp. Med.* 150:1008–1019 (1979).
Kniep et al., "Gangliotriaoslyceramide (Asialo $GM_2$) A Glycosphingolipid Marker for Cell Lines Derived from Patients with Hodgkin's Disease", *J. Immunol.* 131:1591–1594 (1983).
Rosen et al., "Analysis of Human Small Cell Lung Cancer Differentiation Antigens Using A Panel of Rat Monoclonal Antibodies", *Cancer Res.* 44:s052–2061 (1984).
Varki et al., "Antigens Associated with a Human Lung Adenocarcinoma Defined by Monoclonal Antibodies", *Cancer Res.* 44:681–685 (1984).
Embleton and Garnett, "Antibody Targeting of Anti–Cancer Agents", in "Monoclonal Antibodies for Cancer Detection and Therapy" pp. 317–344, Academic Press (1985).
Domingo and Trowbridge, "Transferrin Receptor as a Target for Antibody–Drug Conjugates", *Methods Enzymol.* 112:238–247 (1985).
Kohler and Milstein, "Continous Cultures of Fused Cells Secreting Antibody of Predefined Specificity", *Nature* (London) 256:495–497 (1975).
Oi et al., "Immunoglobulin Gene Expression in Transformed Lymphoid Cells", *Proc. Natl. Acad. Sci. USA* 80:825 (1983).
Potter et al., "Enhancer–Dependent Expression of Human K Immunoglobulin Genes Introduced Into Mouse Pre–B Lymphocytes by Electroporation", *Proc. Natl. Acad. Sci. USA* 81:7161–7165 (1984).
Morrison et al., "Chimeric Human ANtibody Molecules: Mouse Antigen–Binding Domains with Human Constant Region Domains", *Proc. Natl. Acad. Sci. USA* 81:6851–6855 (1984).
Sahagan et al., "A Genetically Engineered Murine/Human Antibody Retains Specificity for Human Tumor–Associated Antigen", *J. Immunol.* 137:1066–1074 (1986).
Sun et al., "Chimeric Antibody with Human Constant Regions and Mouse Variable Regions Directed Aganist Carcinoma–Associated Antigen 17–1A", *Proc. Natl. Acad. Sci. USA* 84:214 (1987).
Boulianne et al., "Production of Functional Chimaeric Mouse/Human Antibody", *Nature* 312:643 (1984).
Sharon et al., "Expression of a $V_H C_K$ Chimaeric Protein in Mouse Myeloma Cells", *Nature* 309:364–367 (1984).
Tan et al., "A Human–Mouse Chimeric Immunoglobulin Gene with a Human Variable Region is Expressed in Mouse Myeloma Cells", *J. Immunol.* 135:3564–3567 (1985).
Folger et al., "Analysis of Homologous Recombination in Cultured Mammalian Cells", *Symp. Quant. Biol.* 49:123–138 (1984).
Folger et al., "Patterns of Integration of DNA Microinjected into Cultured Mammalian Cells: Evidence for Homologous Recombination Between Injected Plasmic DNA Molecules", *Mol. Cell Biol.* 2:1372–1387 (1982).
Kucherlapati, "Homolgous Recombination between Plasmids in Mammalian Cells Can Be Enhanced by Treatment of Input DNA", *Proc. Natl. Acad. Sci. USA* 81:3153–3157 (1984).
Lin et al., "Recombination in Mouse L Cells Between DNA Introduced into Cells and Homologous Chromosomal Sequences", *Proc. Natl. Acad. Sci. USA* 82:1391–1395 (1985).
de Saint Vincent et al., "Homologous Recombination in Mammalian Cells Mediates Formation of a Functional Gene from Two Overlapping Gene Fragments", *Proc. Natl. Acad. Sci. USA* 80:2002–2006 (1983).
Shaul et al., "Homologous Recombination Between a Defective Virus and a Chromosomal Sequence in Mammalian Cells", *Proc. Natl. Acad. Sci. USA* 82:3781–3784 (1985).
Thomas et al., "High Frequency Targeting of Genes to Specific Sites in the Mammalian Genome", *Cell* 44:419–428 (1986).
Smithies et al., "Insertion of DNA Sequences into the Human Chromosomal B–Globin Locus by Homologous Recombination", *Nature* 317:230–234 (1985).
Smith et al., "Homologous Recombination Between Defective Neo Genes in Mouse 3T6 Cells", *Symp. Quant. Bio.* 49:171–181 (1984).
Song et al., "Accurate Modification of a Chromosomal Plasmid by Homologous Recombination in Human Cells", *Proc. Natl. Acad. Sci. USA* 84:6820–6824 (1987).
Rubnitz and Subramani, "Extrachromosomal and Chromosomal Gene Conversion in Mammalian Cells", *Mol. Cell Biol.* 6:1608–1614 (1986).
Liskay, "Evidence for Intrachromosomal Gene Conversion in Cultured Mouse Cells", *Cell* 35:157–165 (1983).
Fell et al., "Homologous Recombination in Hybridoma Cells: Heavy Chain Chimeric Antibody Produced by Gene Targeting", *Proc. Natl. Acad. Sci. USA* 86:8507–8511 (1989).
Hellstrom et al., "Immunological Approaches to Tumor Therapy: Monoclonal Antibodies, Tumor Vaccines, and Anti–Idiotypes" in Covalently Modified Antigens and Antibodies in Diagnosis and Therpay, Quash/Rodwell, (Eds). Marcel Dekker, Inc. (Publ., 1988).

Hellstrom et al., "Strong Antitumor Activities of IgG3 Antibodies to a Human Melanoma–Associated Ganglioside", *Proc. Natl. Acad. Sci. USA* 82:1499–1502 (1985).

Nudelman et al., "Characterization of a Human Melanoma–Associated Ganglioside Antigen Defined by a Monoclonal Antibody, 4.2", *J. Biol. Chem.* 257(21):12752–12756 (1982).

Hakomori, "Tumor–Associated Carbohydrate Antigens", *Ann. Rev. Immunol.* 2:103–126 (1984).

Abe et al., The Monoclonal Antibody Directed to Difucosylated Type 2 Chain (Fucα 1→2Galβ 1→4 [Fucα 1→3] GlcNAc; Y Determinant:, *J. Biol. Chem.* 258:11793–11797 (1983).

Lloyd et al., "Mouse Monoclonal Antibody F–3 Recognizes the Difucosyl Type–2 Blood Group Structure", *Immunogenetics* 17:537–541 (1983).

Brown et al., "A Monoclonal Antibody Against Human Colonic Adenoma Recognizes Difucosylated Type–2–Blood–Group Structure", *Biosci. Reports*, 3:163–170 (1983).

Hellstrom et al., "Monoclonal Mouse Antibodies Raised Against Human Lung Carcinoma", *Cancer Res.* 46:3917–3923 (1986).

Abe et al., "Differential Expression of Difucosyl Type 2 Chain (Le$^Y$) Defined by Monoclonal Antibody AH6 in Different Locations of Colonic Epithelia, Various Histological Types of Colonic Polyps and Adenocarcinomas", *Cancer Res.* 46:2639–2644 (1986).

Brown et al., "Structural Characterization of Human Melanoma–Associated Antigen p97 with Monoclonal Antibodies", *J. Immunol.* 127(2):539–546 (1981).

Brown et al., "Protein Antigens of Normal and Malignant Human Cells Identified by Immunoprecipitation with Monoclonal Antibodies", *J. Biol. Chem.* 255:4980–4983 (1980).

Yeh et al., "Cell Surface Antigens of Human Melanoma Identified by Monoclonal Antibody", *Proc. Natl. Acad. Sci. USA* 76(6):2927–2931 (1979).

Yeh et al., "A Cell–Surface Antigen which is Present in the Ganglioside Fraction and Shared by Human Melanomas", *Int. J. Cancer* 29:269–275 (1982).

Zola et al., "Techniques for the Production and Characterization of Monoclonal Hybridoma Antibodies", in Monoclonal Hybridoma Antibodies: Techniques and Applications, Hurell (Ed.), pp. 51–52, CRC Press (1982).

Rousseaux et al., "Optimal Conditions for the Preparation of Proteolytic Fragments from Monoclonal IgG of Different Rat IgG Subclasses" in *Methods Enzymol.* 121:663–669 Academic Press (1986).

Bagshawe, "Tumour Markers—Where Do We Go From Here?", *Br. J. Cancer* 48:167–173 (1983).

Thammana et al., "Immunoglobulin Heavy Chain Class Switch from IgM to IgG in a Hybridoma", *Eur. J. Immunol.* 13:614–619 (1983).

Spira et al., "The Identification of Monoclonal Class Switch Variants by Sibselection and an Elisa Assay", *J. Immunol. Meth.* 74:307–315 (1984).

Neuberger et al., "Recombinant Antibodies Possessing Novel Effector Functions", *Nature* 312:604–608 (1984).

Oi et al., "Chimeric Antibodies", *Biotechniques* 4(3):214–221 (1986).

Nepom et al., "Anti–Idiotypic Antibodies and the Induction of Specific Tumor Immunity", in *Cancer and Metastasis Reviews* 6:489–502 (1987).

Ciocca et al., "Immunohistochemical Techniques Using Monoclonal Antibodies", *Meth. Enzymol.* 121:562–579 (1986).

Kimball (Ed.), Introduction to Immunology (2nd Ed.), pp. 113–117 (Macmillan Publ. Co.) (1986).

Uotilla et al., "Two–Site Sandwich Enzyme Immunoassay with Monoclonal Antibodies to Human Alpha–Fetoprotein", *J. Immunol. Methods* 42:11–15 (1981).

Sikora et al., (Eds.), *Monoclonal Antibodies* pp. 32–52 (Blackwell Scientific Publ., 1984).

Wensel and Meares, "'Bifunctional' Chelating Agents for Binding Metal Ions to Proteins", Radioimmunoimaging and Radioimmunotherapy. pp. 185–195, Elsevier, New York (1983).

Colcher et al., "Use of Monoclonal Antibodies as Radiopharmaceuticals for the Localization of Human Carcinoma Xenografts in Athymic Mice", *Meth. Enzymol.* 121:802–816 (1986).

Bradwell et al., "Developments in Antibody Imaging", in Monoclonal Antibodies for Cancer Detection and Therapy, Baldwin et al., (Eds.) pp. 65–85, Academic Press (1985).

Arnon et al., "Monoclonal Antibodies for Immunotargeting of Drugs in Cancer Therapy" in Monoclonal Antibodies and Cancer Therapy, Reisfeld et al., (Eds.) pp. 243–256 (Alan R. Liss, Inc. 1985).

Hellstrom et al., "Antibodies for Drug Delivery"in Controlled Drug Delivery (2nd Ed.), Robinson et al., (Eds.) pp. 623–653, (Marcel Dekker Inc., 1987).

Thorpe, "Antibody Carriers of Cytotoxic Agents in Cancer Therapy: A Review", In Monoclonal Antibodies '84: Biological and Clinical Applications, Pinchera et al. (Eds.), pp. 475–506 (1985).

Thorpe et al., "The Preparation and Cytotoxic Properties of Antibody–Toxin Conjugates", *Immunol. Rev.* 62:119–158 (1982).

Order, "Analysis, Results and Future Prospective of the Therapeutic Use of Radiolabeled Antibody in Cancer Therapy", in Monoclonal Antibodies for Cancer Detection and Therapy, Baldwin (Eds.) pp. 203–216, Academic Press (1985).

Senter et al., "Anti–Tumor Effects of Antibody–Alkaline Phosphatase Conjugates in Combination with Etoposide Phosphate", *Proc. Natl. Acad. Sci. USA* 85:4842–4846 (1988).

Senter, "Enhancement of the in vitro and in vivo Antitumor Activities of Phosphorylated Mitomycin C and Etoposide Derivatives by Monoclonal Antibody–Alkaline Phosphatase Conjugates", *Cancer Res.*, 49:5789–5792 (1989).

Ramsey et al, "Bone Marrow Purging Using Monoclonal Antibodies", *J. Clinical Immunol.* 8(2):81–88 (1988).

Kohler and Milstein, "Derivation of Specific Antibody–Producing Tissue Culture and Tumor Lines by Cell Fusion", *Eur. J. Immunol.* 6:511–519 (1976).

Douillard and Hoffman, "Enzyme–Linked Immunosorbent Assay for Screening Monoclonal Antibody Production Using Enzyme–Labeled Second Antibody", *Meth. Enzymol.*, 92:168–174 (1983).

Sternberger, "The Unlabeled Antibody Peroxidase–Antiperoxidase (PAP) Method", *Immunochemistry*, pp. 104–169 (John Wiley & Sons, New York, 1979).

Garrigues et al., "Detection of a Human Melanoma–Associated Antigen, p97, in Histological Sections of Primary Human Melanomas", *Int. J. Cancer*, 29:511–515 (1982).

Hellstrom et al., "Monoclonal Antibodies to Two Determinants of Melanoma–Antigen p97 Act Synergistically in Complement–Dependent Cytotoxicity", *J. Immunol.* 127:157–160 (1981).

Brown et al., "Quantitative Analysis of Melanoma–Associated Antigen p97 in Normal and Neoplastic Tissues", *Proc. Natl. Acad. Sci. USA*, 78:539–543 (1981).

Blakey et al., "Effect of Chemical Deglycosylation of Ricin A Chain on the in vivo Fate and Cytotoxic Activity of an Immunotoxin Composed of Ricin A Chain and Anti–Thy 1.1 Antibody", *Cancer Res.*, 47:947–952 (1987).

Lambert et al., "Purified Immunotoxins that are Reactive with Human Lymphoid Cells", *J. of Biolog. Chem.*, 260:12035–12041 (1985).

Knowles and Thorpe, "Purification of Immunotoxins Containing Ricin A–Chain and Abrin A–Chain Using Blue Sepharose CL–6B", *Analytic. Biochem.*, 160:440–443 (1987).

Krishan, "Rapid Flow Cytofluorometric Analysis of Mammalian Cell Cycle by Propidium Iodine Staining", *J. Cell Biol.* 66:188–193 (1975).

Yeh, "Propidium Iodide as a Nuclear Marker in Immunofluorescence. II. Use with Cellular Identification and Viability Studies", *J. Immunol. Methods*, 43:269–275 (1981).

Linsley et al., "Identification and Characterization of Cellular Receptors for the Growth Regulator, Oncostatin M", *J. Biol. Chem.*, 264:4282–4289 (1989).

Goding in *Monoclonal Antibodies: Principles and Practices*, pp. 118–125, Academic Press Inc. London (1983).

Hellstrom et al., "Highly Tumor–Reactive, Internalizing, Mouse Monoclonal Antibodies to $Le^y$–related Cell Surface Antigens", *Cancer Res.* 50:2183–2190 (1990).

KanNagi et al., "New Globoseries Glycosphingolipids in Human Teratocarcinoma Reactive with the Monoclonal Antibody Directed to a Developmentally Regulated Antigen, Stage–Specific Embryonic Antigen 3", *J. Biol. Chem.*, 258(14):8934–8942 (1983).

Kim et al., "Expression of $Le^y$ and Extended $Le^y$ Blood Group–Related Antigens in Human Malignant, Premalignant and Normalignant Colonic Tissues", *Cancer Res.* 46:5985–5992 (1986).

Morrison, "Transfectomas Provide Novel Chimeric Antibodies", *Science* 229:1202–1207 (1985).

Drebin et al., "Monoclonal Antibodies Reactive with Distinct Domains of the neu Oncogene–Encoded p185 Molecules Exert Synergistic and Anti–Tumor Effects in vivo", *Oncogene* 2:275–277 (1988).

Pastan and FitzGerald, "Recombinant Toxins for Cancer Treatment", *Science*, 254:1173–1177 (1991).

FitzGerald and Pastan, "Redirecting Pseudomonas Exotoxin", *Seminars in Cell Biology*, 2:31–17 (1991).

Vivetta et al., (1987) *Science* 238:1098–1104.

Iglewski et al., "NAD–Dependent Inhibition of Protein Synthesis by Pseudomonas Aeruginosa Toxin", *Proc. Natl. Acad. Sci. USA*, 72:2284–2288 (1975).

Allured et al, "Structure of Exotoxin A of Pseudomonas Neruginosa at 3.0–Angstrom Resolution", *Proc. Natl. Acad. Sci. USA*, 83:1320–1324 (1986).

Hwang et al., "Functional Domains of Pseudomonas Exotoxin Identified by Deletion Analysis of the Gene Expressed in *E. Coli*", *Cell*, 48:129–136 (1987).

Siegall et al., "Functional Analysis of Domains II, Ib, and III of Pseudomonas Exotoxin", *J. Biol. Chem.*, 264:14256–14261 (1989).

Kondo et al., "Activity of Immunotoxins Constructed with Modified Pseudomonas Exotoxin A Lacking the Cell Recognition Domain", *J. Biol. Chem.*, 263:9470–9475 (1988).

Batra et al., "Antitumor Activity in Mice of an Immunotoxin Made with Anti–Transferrin Receptor and A Recombinant Form of Pseudomonas Exotoxin", *Proc. Natl. Acad. Sci. USA*, 86:8545–8549 (1989).

Pai et al., "Anti–Tumor Activities of Immunotoxins Made of Monoclonal Antibody B3 and Various Forms of Pseudomonas Exotoxin", *Proc. Natl. Acad. Sci. USA*, 88:3358–3362 (1991).

Covell et al., "Pharmacokinetics of Monoclonal Immunoglobulin $G_1$, $F(ab')_2$, and Fab' in Mice", *Cancer Research*, 46:3969–3978 (1986).

Chaudhary et al., "A Recombinant Immunotoxin Consisting of Two Antibody Variable Domains Fused to Pseudomonas Exotoxin", *Nature*, 339:394 (1989).

Siegall et al., "Cytotoxic Activity of an Interleukin 6–Pseudomonas Exotoxin Fusion Protein on Human Myeloma Cells", *Proc. Natl. Acad. Sci. USA*, 85:9738–9742 (1988).

Kahn et al., "Monoclonal Antiidiotypic Antibodies Related to the p97 Human Melanoma Antigen", *Cancer Res.*, 49:3157–3162 (1989).

Kabat et al., in Sequences of Proteins of Immunological Interest, Fourth Edition, U.S. Dept. of Health and Human Services, Washington, DC (1987).

Crowl et al., "Versatile Expression Vectors for High–Level Synthesis of Cloned Gene Products in *Escherichia Coli*", *Gene*, 38:31–38 (1985).

Studier et al., "Use of Bacteriophage T7 RNA Polymerase to Direct Selective High–Level Expression of Cloned Genes", *J. Mol.Biol.*, 189:113–130 (1986).

Senter, "Activation of Prodrugs by Antibody–Enzyme Conjugates: A New Approach to Cancer Therapy" *FASEB J.*, 4:188–193 (1990).

Cerotinni and Brunner, "Cell–Mediated Cytotoxicity, Allograft Rejection, and Tumor Immunity", *Adv. Immunol.*, 18:67–132 (1974).

Hellstrom et al., "Lymphocyte–Dependent Antibodies to Antigen 3.1. A Cell–Surface Antigen Expressed by a Subgroup of Human Melanomas", *Int. J. Cancer*, 27:281–285 (1981).

Hellstrom et al., "Antibody–Dependent Cellular Cytotoxicity to Human Melanoma Antigens", *Monoclonal Antibodies and Cancer Therapy*, UCLA Symposia on Molecular and Cellular Biology, Reisfeld (ed.), pp. 149–164 vol. 27, (Liss, New York, 1985).

Lamoyi, "Preparation of $F(ab')_2$ Fragments from Mouse IgG of Various Subclasses", *Meth. Enzymol.*, 121:652–663 (1986).

Hellstrom et al., "Epitope Mapping and Use of Anti–Idiotypic Antibodies to the L6 Monoclonal Anticarcinoma Antibody", *Cancer Res.*, 50:2449–2454 (1990).

Coffino et al., "Cloning of Mouse Myeloma Cells and Detection of Rare Variants", *J. Cell Physiol.*, 79:(3)429–440 (1972).

Brennan et al., "Preparation of Bispecific Antibodies by Chemical Recombination of Monoclonal Immunoglobulin $G_1$ Fragments", *Science*, 229(05):81–83 (1985).

Bara et al., "Ectopic Expression of the Y ($Le^y$) Antigen Defined by Monoclonal Antibody 12–4LE in Distal Colonic Adenocarcinomas", *Int. J. Cancer*, 41:683–689 (1988).

Brady et al., "Therapeutic and Diagnostic Uses of Modified Monoclonal Antibodies", *I. J. Radiation Oncology Biol. Phys.*, 13(10):1535–1544 (1987).

Drebin et al., "Down–Modulation of an Oncogene Protein Product and Reversion of the Transformed Phenotype by Monoclonal Antibodies", *Cell* 41:695–706 (1985).

Drebin et al., "Inhibition of Tumor Growth by a Monoclonal Antibody Reactive with an Oncogene–Encoded Tumor Antigen", *Proc. Natl. Acad. Sci. USA*, 83:9129–9133 (1986).

```
       10          20          30          40
ATG GAG GTG CAG CTG GTG GAG TCT GGG GGA GGC TTA GTG CAG CCT GGG
Met Glu Val Gln Leu Val Glu Ser Gly Gly Gly Leu Val Gln Pro Gly 50          60          70          80          90
TCC CTG AAA GTC TCC TGT GTA ACC TCT GGA TTC ACT TTC AGT GAC TAT
Ser Leu Lys Val Ser Cys Val Thr Ser Gly Phe Thr Phe Ser Asp Tyr 100         110         120         130         140
TAC ATG TGG GTT CGC CAG ACT CCA GAG AAG AGG CTG GAG TGG GTC GCA
Tyr Met Trp Val Arg Gln Thr Pro Glu Lys Arg Leu Glu Trp Val Ala 150         160         170         180         190
TAC ATT AGT CAA GGT GAT ATA ACC GAC TAT CCA GAC ACT GTA AAG GGT
Tyr Ile Ser Gln Gly Asp Ile Thr Asp Tyr Pro Asp Thr Val Lys Gly 200         210         220         230         240
CGA TTC ACC ATC TCC AGA GAC AAT AAG AAC ACC CTG TAC CTG CAA ATG
Arg Phe Thr Ile Ser Arg Asp Asn Lys Asn Thr Leu Tyr Leu Gln Met 250         260         270         280
AGC CGT CTG AAG TCT GAG GAC ACA GCC ATG TAT TGT GCA AGA GGC CTG
Ser Arg Leu Lys Ser Glu Asp Thr Ala Met Tyr Cys Ala Arg Gly Leu 290         300         310         320         330
GAC GAC GGG GCC TGG TTT GCT TAC TGG GGC CAA GGG ACC ACG ACC GTC
Asp Asp Gly Ala Trp Phe Ala Tyr Trp Gly Gln Gly Thr Thr Thr Val 340         350         360         370         380
TCC TCA GGA TCC GGA GGT GGA GGT TCT GGT GGA GGT GGA TCT GGA GGT
Ser Ser Gly Ser Gly Gly Gly Gly Ser Gly Gly Gly Gly Ser Gly Gly
```

FIG. 35A

```
       390             400             410             420             430
GGA TCT AAG CTT GAT GTT TTG ATG ACC CAA ATT CCA GTC TCC CTG CCT
Gly Ser Lys Leu Asp Val Leu Met Thr Gln Ile Pro Val Ser Leu Pro 440             450             460             470             480
GTC AGT CTT GGA CAA GCG TCC ATC TCT TGC AGA TCT AGT CAG ATC ATT
Val Ser Leu Gly Gln Ala Ser Ile Ser Cys Arg Ser Ser Gln Ile Ile 490             500             510             520
GTA CAT AAT AAT GGC AAC ACC TTA GAA TGG TAC CTG CAG AAA CCA GGC
Val His Asn Asn Gly Asn Thr Leu Glu Trp Tyr Leu Gln Lys Pro Gly 530             540             550             560             570
CAG TCT CCA CAG CTC CTG ATC TAC AAA GTT AAC CGA TTT TCT GGG GTC
Gln Ser Pro Gln Leu Leu Ile Tyr Lys Val Asn Arg Phe Ser Gly Val 580             590             600             610             620
CCA GAC AGG TTC AGC GGC AGT GGA TCA GGG ACA GAT TTC CTC AAG ATC
Pro Asp Arg Phe Ser Gly Ser Gly Ser Gly Thr Asp Phe Leu Lys Ile 630             640             650             660             670
AGC AGA GTG GAG GCT GAG GAT CTG GGA GTT TAT TAC TGC TTT CAA GTT
Ser Arg Val Glu Ala Glu Asp Leu Gly Val Tyr Tyr Cys Phe Gln Val 680             690             700             710             720
CAT GTT CCA TTC ACG TTC GGC TCG GGG ACC AAG CTG GAG ATC AAA CGC
His Val Pro Phe Thr Phe Gly Ser Gly Thr Lys Leu Glu Ile Lys Arg
```

FIG. 35B

|  | Human IgG | Chimeric BR96 |
|---|---|---|
| KB | 2.7 | 36.3 |
| A2780 | 1.6 | 104.8 |
| RCA | 7.6 | 146.1 |
| L2987 | 3.9 | 176.7 |
| MCF7 | 2.5 | 180.3 |

FIG. 41

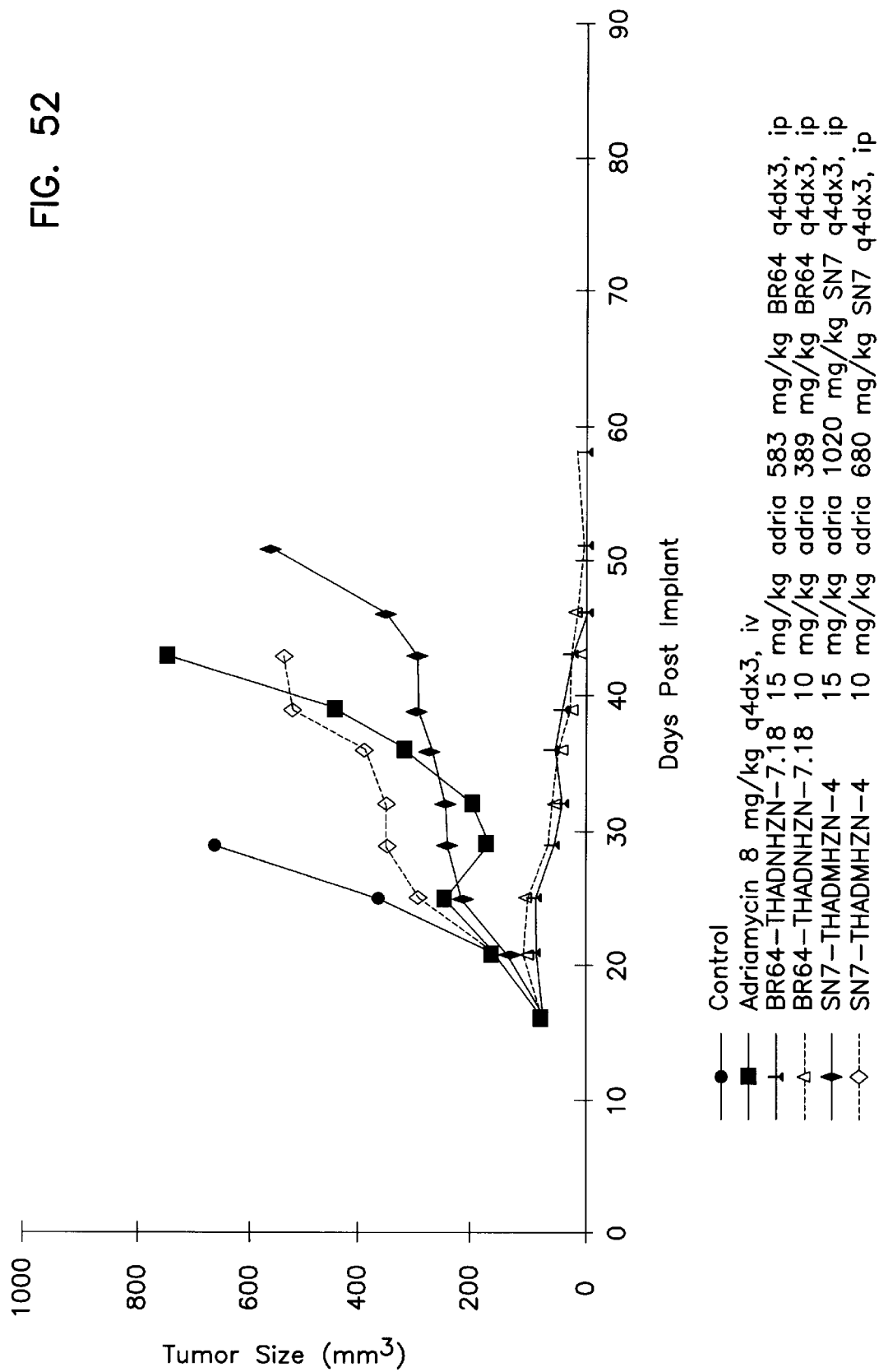

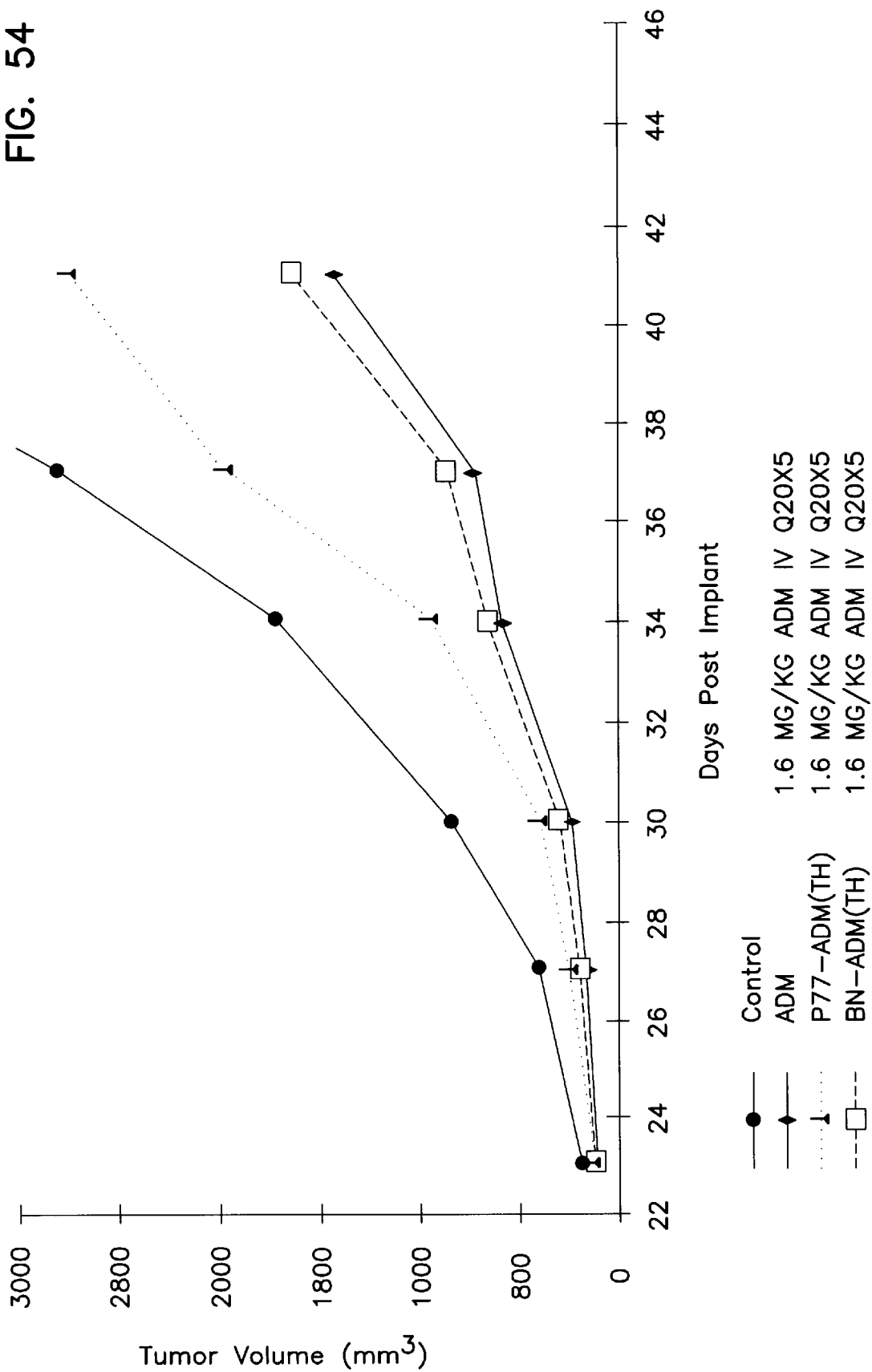

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Plasmid pBR96

(xi) SEQUENCE DESCRIPTION: SEQ ID NO:1:

GCTAGACATA TGGAGGTGCA GCTGGTGGAG TCT            33

(2) INFORMATION FOR SEQ ID NO:2:

(i) SEQUENCE CHARACTERISTICS:
      (A) LENGTH: 33 base pairs
      (B) TYPE: nucleic acid
      (C) STRANDEDNESS: single (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Plasmid pBR96

(xi) SEQUENCE DESCRIPTION: SEQ ID NO:2:

```
GCTGTGGAGA CTGGCCTGGT TTCTGCAGGT ACC                                33
```

(2) INFORMATION FOR SEQ ID NO:3:

(i) SEQUENCE CHARACTERISTICS:
       (A) LENGTH: 720 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Mus musculus (ix) FEATURE:
       (A) NAME/KEY: CDS
       (B) LOCATION: 1..720

(xi) SEQUENCE DESCRIPTION: SEQ ID NO:3:

```
ATG GAG GTG CAG CTG GTG GAG TCT GGG GGA GGC TTA GTG CAG CCT GGG      48
Met Glu Val Gln Leu Val Glu Ser Gly Gly Gly Leu Val Gln Pro Gly
 1               5                  10                  15

TCC CTG AAA GTC TCC TGT GTA ACC TCT GGA TTC ACT TTC AGT GAC TAT      96
Ser Leu Lys Val Ser Cys Val Thr Ser Gly Phe Thr Phe Ser Asp Tyr
             20                  25                  30

TAC ATG TGG GTT CGC CAG ACT CCA GAG AAG AGG CTG GAG TGG GTC GCA     144
Tyr Met Trp Val Arg Gln Thr Pro Glu Lys Arg Leu Glu Trp Val Ala
         35                  40                  45

TAC ATT AGT CAA GGT GAT ATA ACC GAC TAT CCA GAC ACT GTA AAG GGT     192
Tyr Ile Ser Gln Gly Asp Ile Thr Asp Tyr Pro Asp Thr Val Lys Gly
     50                  55                  60

CGA TTC ACC ATC TCC AGA GAC AAT AAG AAC ACC CTG TAC CTG CAA ATG     240
Arg Phe Thr Ile Ser Arg Asp Asn Lys Asn Thr Leu Tyr Leu Gln Met
 65                  70                  75                  80

AGC CGT CTG AAG TCT GAG GAC ACA GCC ATG TAT TGT GCA AGA GGC CTG     288
Ser Arg Leu Lys Ser Glu Asp Thr Ala Met Tyr Cys Ala Arg Gly Leu
                 85                  90                  95

GAC GAC GGG GCC TGG TTT GCT TAC TGG GGC CAA GGG ACC ACG ACC GTC     336
Asp Asp Gly Ala Trp Phe Ala Tyr Trp Gly Gln Gly Thr Thr Thr Val
            100                 105                 110

TCC TCA GGA TCC GGA GGT GGA GGT TCT GGT GGA GGT GGA TCT GGA GGT     384
Ser Ser Gly Ser Gly Gly Gly Gly Ser Gly Gly Gly Gly Ser Gly Gly
        115                 120                 125

GGA TCT AAG CTT GAT GTT TTG ATG ACC CAA ATT CCA GTC TCC CTG CCT     432
Gly Ser Lys Leu Asp Val Leu Met Thr Gln Ile Pro Val Ser Leu Pro
    130                 135                 140

GTC AGT CTT GGA CAA GCG TCC ATC TCT TGC AGA TCT AGT CAG ATC ATT     480
Val Ser Leu Gly Gln Ala Ser Ile Ser Cys Arg Ser Ser Gln Ile Ile
145                 150                 155                 160

GTA CAT AAT AAT GGC AAC ACC TTA GAA TGG TAC CTG CAG AAA CCA GGC     528
```

```
Val His Asn Asn Gly Asn Thr Leu Glu Trp Tyr Leu Gln Lys Pro Gly
                165                 170                 175

CAG TCT CCA CAG CTC CTG ATC TAC AAA GTT AAC CGA TTT TCT GGG GTC          576
Gln Ser Pro Gln Leu Leu Ile Tyr Lys Val Asn Arg Phe Ser Gly Val
            180                 185                 190

CCA GAC AGG TTC AGC GGC AGT GGA TCA GGG ACA GAT TTC CTC AAG ATC          624
Pro Asp Arg Phe Ser Gly Ser Gly Ser Gly Thr Asp Phe Leu Lys Ile
        195                 200                 205

AGC AGA GTG GAG GCT GAG GAT CTG GGA GTT TAT TAC TGC TTT CAA GTT          672
Ser Arg Val Glu Ala Glu Asp Leu Gly Val Tyr Tyr Cys Phe Gln Val
    210                 215                 220

CAT GTT CCA TTC ACG TTC GGC TCG GGG ACC AAG CTG GAG ATC AAA CGC          720
His Val Pro Phe Thr Phe Gly Ser Gly Thr Lys Leu Glu Ile Lys Arg
225                 230                 235                 240
```

(2) INFORMATION FOR SEQ ID NO:4:

(i) SEQUENCE CHARACTERISTICS:
        (A) LENGTH: 240 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu Val Gln Leu Val Glu Ser Gly Gly Gly Leu Val Gln Pro Gly
1               5                   10                  15

Ser Leu Lys Val Ser Cys Val Thr Ser Gly Phe Thr Phe Ser Asp Tyr
            20                  25                  30

Tyr Met Trp Val Arg Gln Thr Pro Glu Lys Arg Leu Glu Trp Val Ala
        35                  40                  45

Tyr Ile Ser Gln Gly Asp Ile Thr Asp Tyr Pro Asp Thr Val Lys Gly
    50                  55                  60

Arg Phe Thr Ile Ser Arg Asp Asn Lys Asn Thr Leu Tyr Leu Gln Met
65                  70                  75                  80

Ser Arg Leu Lys Ser Glu Asp Thr Ala Met Tyr Cys Ala Arg Gly Leu
            85                  90                  95

Asp Asp Gly Ala Trp Phe Ala Tyr Trp Gly Gln Gly Thr Thr Thr Val
        100                 105                 110

Ser Ser Gly Ser Gly Gly Gly Ser Gly Gly Gly Ser Gly Gly
    115                 120                 125

Gly Ser Lys Leu Asp Val Leu Met Thr Gln Ile Pro Val Ser Leu Pro
130                 135                 140

Val Ser Leu Gly Gln Ala Ser Ile Ser Cys Arg Ser Ser Gln Ile Ile
145                 150                 155                 160

Val His Asn Asn Gly Asn Thr Leu Glu Trp Tyr Leu Gln Lys Pro Gly
                165                 170                 175

Gln Ser Pro Gln Leu Leu Ile Tyr Lys Val Asn Arg Phe Ser Gly Val
            180                 185                 190

Pro Asp Arg Phe Ser Gly Ser Gly Ser Gly Thr Asp Phe Leu Lys Ile
        195                 200                 205

Ser Arg Val Glu Ala Glu Asp Leu Gly Val Tyr Tyr Cys Phe Gln Val
    210                 215                 220

His Val Pro Phe Thr Phe Gly Ser Gly Thr Lys Leu Glu Ile Lys Arg
225                 230                 235                 240
```

ANTIBODIES REACTIVE WITH HUMAN CARCINOMAS

CROSS-REFERENCE TO RELATED APPLICATIONS

This application is a continuation-in-part of U.S. Ser. No. 07/892,501, filed Jun. 1, 1992, now abandoned, which is a continuation-in-part of U.S. Ser. No. 07/544,246, filed Jun. 26, 1990, now abandoned, which is a continuation-in-part of Ser. No. 07/374,947, filed Jun. 30, 1989, now abandoned. In addition, this application is a continuation-in-part of U.S. Ser. No. 08/057,444, filed May 5, 1993, now U.S. Pat. No. 5,491,088, which is a continuation of U.S. Ser. No. 07/544,246, filed Jun. 26, 1990, now abandoned, which is a continuation-in-part of U.S. Ser. No. 07/374,947, filed Jun. 30, 1989, now abandoned. The entire disclosures of these applications are hereby incorporated by reference.

TECHNICAL FIELD OF THE INVENTION

The present invention relates to novel antibodies reactive with carcinoma cells. More particularly, the invention relates to a murine monoclonal antibody and a chimeric monoclonal antibody, including immunoconjugates and recombinant immunotoxins made therefrom, that react with cell membrane antigens associated with a large variety of carcinomas including carcinomas of the colon, breast, ovary and lung. The murine monoclonal antibody is highly specific for carcinomas, showing no to very low reactivity with normal animal tissues or other types of tumors such as lymphomas or sarcomas.

BACKGROUND OF THE INVENTION

1. Monoclonal Antibodies Directed Against Cell Membrane Antigens.

Monoclonal antibodies (MAbs) to human tumor-associated differentiation antigens offer promises for the "targeting" of various antitumor agents such as radioisotopes, chemotherapeutic drugs, and toxins. [Order, in "Monoclonal Antibodies for Cancer Detection and Therapy", Baldwin and Byers, (eds.),London, Academic Press (1985)].

In addition, some monoclonal antibodies have the advantage of killing tumor cells via antibody-dependent cellular cytotoxicity (ADCC) or complement-dependent cytotoxicity (CDC) in the presence of human effector cells or serum [Hellstrom et al., *Proc. Natl. Acad. Sci. USA* 83:7059–7063 (1986)], and there are a few monoclonal antibodies that have a direct antitumor activity which does not depend on any host component [Drebin et al., *Oncogene* 2:387–394 (1988)].

Many monoclonal antibodies reactive with carcinoma-associated antigens are known [see, e.g., Papsidero, "Recent Progress In The Immunological Monitoring Of Carcinomas Using Monoclonal Antibodies", *Semin. Surg. Oncol.,* 1 (4):171–81 (1985); Schlom et al., "Potential Clinical Utility Of Monoclonal Antibodies In The Management Of Human Carcinomas", *Important Adv. Oncol.,* 170–92 (1985); Allum et al., "Monoclonal Antibodies In The Diagnosis And Treatment of Malignant Conditions", *Surg. Ann.,* 18:41–64 (1986); and Houghton et al., "Monoclonal Antibodies: Potential Applications To The Treatment Of Cancer", *Semin. Oncol.,* 13(2):165–79 (1986)].

These known monoclonal antibodies can bind to a variety of different carcinoma-associated antigens including glycoproteins, glycolipids and mucins [see, e.g., Fink et al., "Monoclonal Antibodies As Diagnostic Reagents for The Identification And Characterization Of Human Tumor Antigens", *Prog. Clin. Pathol.,* 9:121–33 (1984)].

For example, monoclonal antibodies that bind to glycoprotein antigens on specific types of carcinomas include those described in U.S. Pat. No. 4,737,579 (monoclonal antibodies to non-small cell lung carcinomas), U.S. Pat. No. 4,753,894 (monoclonal antibodies to human breast cancer), U.S. Pat. No. 4,579,827 (monoclonal antibodies to human gastrointestinal cancer), and U.S. Pat. No. 4,713,352 (monoclonal antibodies to human renal carcinoma).

Monoclonal antibody B72.3, which is one of the antibodies studied the most, recognizes a tumor-associated mucin antigen of greater than 1,000 kd molecular weight that is selectively expressed on a number of different carcinomas. Thus, B72.3 has been shown to react with 84% of breast carcinomas, 94% of colon carcinomas, 100% of ovarian carcinomas and 96% of non-small cell lung carcinomas [see Johnston, "Applications of Monoclonal Antibodies In Clinical Cytology As Exemplified By Studies With Monoclonal Antibody B72.3",*Acta Cytol.,* 1(5): 537–56 (1987) and U.S. Pat. No. 4,612,282, issued to Schlom et al.]. Another patented monoclonal antibody, KC-4, [see U.S. Pat. No. 4,708, 930], recognizes an approximately 400–500 kd protein antigen expressed on a number of carcinomas, such as colon, prostate, lung and breast carcinoma. It appears that neither the B72.3 nor KC-4 antibodies internalize within the carcinoma cells with which they react.

Monoclonal antibodies reactive with glycolipid antigens associated with tumor cells have been disclosed. For example, Young et al., "Production Of Monoclonal Antibodies Specific For Two Distinct Steric Portions Of The Glycolipid Ganglio-N-Triosylceramide (Asialo $GM_2$)", *J. Exp. Med.,* 150: 1008–1019 (1979) disclose the production of two monoclonal antibodies specific for asialo $GM_2$, a cell surface glycosphingolipid antigen that was established as a marker for BALB/c V3T3 cells transformed by Kirsten murine sarcoma virus. See, also, Kniep et al., "Gangliotriasylceramide (Asialo $GM_2$) A Glycosphingolipid Marker For Cell Lines Derived From Patients With Hodgkin's Disease", *J. Immunol.,* 131(3): 1591–94 (1983) and U.S. Pat. No. 4,507,391 (monoclonal antibody to human melanoma).

Other monoclonal antibodies reactive with glycolipid antigens on carcinoma cells include those described by Rosen et al., "Analysis Of Human Small Cell Lung Cancer Differentiation Antigens Using A Panel Of Rat Monoclonal Antibodies", *Cancer Research,* 44:2052–61 (1984) (monoclonal antibodies to human small cell lung cancer), Varki et al., "Antigens Associated with a Human Lung Adenocarcinoma Defined by Monoclonal Antibodies", *Cancer Research* 44:681–87 (1984); (monoclonal antibodies to human adenocarcinomas of the lung, stomach and colon and melanoma), and U.S. Pat. No. 4,579,827 (monoclonal antibodies to human colon adenocarcinoma). See, also, Hellstrom et al., "Antitumor Effects Of L6, An IgG2a Antibody That Reacts With Most Human Carcinomas", *Proc. Natl. Acad. Sci. USA,* 83:7059–63 (1986) which describes the L6 monoclonal antibody that recognizes a carbohydrate antigen expressed on the surface of human non-small cell lung carcinomas, breast carcinomas and colon carcinomas.

Antibodies to tumor-associated antigens which are not able to internalize within the tumor cells to which they bind are generally not useful to prepare conjugates with antitumor drugs or toxins, since these would not be able to reach their site of action within the cell. Other approaches would then be needed so as to use such antibodies therapeutically.

Additional monoclonal antibodies exhibiting a high specific reactivity to the majority of cells from a wide range of carcinomas are greatly needed. This is so because of the antigenic heterogeneity of many carcinomas which often necessitates, in diagnosis or therapy, the use of a number of different monoclonal antibodies to the same tumor mass. There is a further need, especially for therapy, for so called "internalizing" antibodies, i.e., antibodies that are easily taken up by the tumor cells to which they bind. Antibodies of this type find use in therapeutic methods for selective cell killing utilizing antibody-drug or antibody-toxin conjugates ("immunotoxins") wherein a therapeutic antitumor agent is chemically or biologically linked to an antibody or growth factor for delivery to the tumor, where the antibody binds to the tumor-associated antigen or receptor with which it is reactive and "delivers" the antitumor agent inside the tumor cells [see, e.g., Embleton et al., "Antibody Targeting Of Anti-Cancer Agents", in *Monoclonal Antibodies For Cancer Detection and Therapy,* pp. 317–44 (Academic Press, 1985)].

2. Immunotoxins.

Immunotoxins have been investigated as a new approach for treating metastatic tumors in man [Pastan and FitzGerald, *Science* 254:1173–1177 (1991); FitzGerald and Pastan, *Seminars in Cell Biology* 2:31–37 (1991) and Vitetta et al., *Science* 644:650 (1987)]. Pseudomonas exotoxin A ("PE") is a cytotoxic agent produced by *Pseudomonas aeruginosa* that kills cells by ADP-ribosylating elongation factor 2, thereby inhibiting protein synthesis [Iglewski et al., *Proc. Natl. Acad. Sci. USA* 72:2284–2285 (1975)].

PE is a polypeptide comprising three domains [Allured et al., *Proc. Natl. Acad. Sci. USA* 83:1320–1324 (1986)].

Domain I encodes the cell-binding ability; domain II encodes the proteolytic sensitivity site and the membrane translocation ability; and domain III encodes the ADP-ribosylation activity of the toxin [Hwang et al., *Cell* 48:129–136 (1987), Siegall et al., *J. Biol. Chem.* 264:14256–14261 (1989)]. By removing domain I from PE, a truncated 40 kDa toxin is formed ("PE40") [Kondo et al., *J. Biol. Chem.* 263:9470–9475 (1988)].

PE40 is weakly toxic to cells because it lacks the cell binding domain for the PE receptor [Id.] For conjugation of this molecule to an antibody, the amino terminus of PE40 is modified to include a lysine residue to form "LysPE40" [Batra et al., supra]. Immunotoxins using PE, have shown promise in preclinical models using human tumor xenografts in nude mice [Batra et al., *Proc. Natl. Acad. Sci. USA* 86:8545–8549 (1989); and Pai et al., *Proc. Natl. Acad. Sci. USA* 88:3358–3362 (1991)].

Several internalizing antibodies reacting with lymphocyte antigens are known. In contrast, such antibodies are rare when dealing with solid tumors. One of the few examples of an internalizing antibody reacting with carcinomas is an antibody disclosed in Domingo et al., "Transferrin Receptor As A Target For Antibody-Drug Conjugates," *Methods Enzymol.* 112:238–47 (1985). This antibody is reactive with the human transferrin-receptor glycoprotein expressed on tumor cells. However, because the transferrin-receptor is also expressed on many normal tissues, and often at high levels, the use of an anti-transferrin-receptor antibody in an antibody-drug or antibody-toxin conjugate may have significant toxic effects on normal cells. The utility of this antibody for selective killing or inhibition of tumor cells is therefore questionable. Another internalizing antibody is BR64 (disclosed in co-pending patent applications U.S. Ser. No. 289,635, filed Dec. 22, 1988, and Ser. No. 443,696 filed Nov. 29, 1989, and incorporated by reference herein), which binds to a large spectrum of human carcinomas.

3. Chimeric Antibodies.

The cell fusion technique for the production of monoclonal antibodies [Kohler and Milstein, *Nature* (London) 256:495 (1975)] has permitted the development of a number of murine monoclonal antibodies reactive with antigens, including previously unknown antigens.

However, murine monoclonal antibodies may be recognized as foreign substances by the human immune system and neutralized such that their potential in human therapy is not realized. Therefore, recent efforts have focused on the production of so-called "chimeric" antibodies by the introduction of DNA into mammalian cells to obtain expression of immunoglobulin genes [Oi et al., *Proc. Natl. Acad. Sci. USA* 80:825 (1983); Potter et al., *Proc. Natl. Acad. Sci. USA* 81:7161; Morrison et al., *Proc. Natl. Acad. Sci. USA* 81:6581 (1984); Sahagan et al., *J. Immunol.* 137:1066 (1986); Sun et al., *Proc. Natl. Acad. Sci.* 84:214 (1987)].

Chimeric antibodies are immunoglobulin molecules comprising a human and non-human portion. More specifically, the antigen combining region (variable region) of a chimeric antibody is derived from a non-human source (e.g. murine) and the constant region of the chimeric antibody which confers biological effector function to the immunoglobulin is derived from a human source. The chimeric antibody should have the antigen binding specificity of the non-human antibody molecule and the effector function conferred by the human antibody molecule.

In general, the procedures used to produce chimeric antibodies involve the following steps:

a) identifying and cloning the correct gene segment encoding the antigen binding portion of the antibody molecule; this gene segment (known as the VDJ, variable, diversity and joining regions for heavy chains or VJ, variable, joining regions for light chains or simply as the V or variable region) may be in either the cDNA or genomic form;

b) cloning the gene segments encoding the constant region or desired part thereof;

c) ligating the variable region with the constant region so that the complete chimeric antibody is encoded in a form that can be transcribed and translated;

d) ligating this construct into a vector containing a selectable marker and gene control regions such as promoters, enhancers and poly(A) addition signals;

e) amplifying this construct in bacteria;

f) introducing this DNA into eukaryotic cells (transfection) most often mammalian lymphocytes;

g) selecting for cells expressing the selectable marker;

h) screening for cells expressing the desired chimeric antibody; and i) testing the antibody for appropriate binding specificity and effector functions.

Antibodies of several distinct antigen binding specificities have been manipulated by these protocols to produce chimeric proteins [e.g. anti-TNP: Boulianne et al., *Nature* 312:643 (1984); and anti-tumor antigens: Sahagan et al., *J. Immunol.* 137:1066 (1986)]. Likewise, several different effector functions have been achieved by linking new sequences to those encoding the antigen binding region. Some of these include enzymes [Neuberger et al., *Nature* 312:604 (1984)], immunoglobulin constant regions from another species and constant regions of another immunoglobulin chain [Sharon et al., *Nature* 309:364 (1984); Tan et al., *J. Immunol.* 135:3565–3567 (1985)].

4. Modifying Genes in Situ Encoding Monoclonal Antibodies.

The discovery of homologous recombination in mammalian cells permits the targeting of new sequences to specific chromosomal loci. Homologous recombination occurs when cultured mammalian cells integrate exogenous DNA into chromosomal DNA at the chromosome location which contains sequences homologous to the plasmid sequences [Folger et al., *Mol. Cell. Biol.* 2:1372–1387 (1982); Folger et al., *Symp. Quant. Biol.* 49:123–138 (1984); Kucherlapati et al., *Proc. Natl. Acad. Sci. USA* 81:3153–3157 (1984); Lin et al., *Proc. Natl. Acad. Sci. USA* 82:1391–1395 (1985); de Saint Vincent et al., *Proc. Natl. Acad. Sci. USA* 80:2002–2006 (1983); Shaul et al., *Proc. Natl. Acad. Sci. USA* 82:3781–3784 (1985)].

The potential for homologous recombination within cells permits the modification of endogenous genes in situ. Conditions have been found where the chromosomal sequence can be modified by introducing into the cell a plasmid DNA which contains a segment of DNA homologous to the target locus and a segment of new sequences with the desired modification [Thomas et al., *Cell* 44:419–428 (1986); Smithies et al., *Nature* 317:230–234 (1985); Smith et al., *Symp. Quant. Biol.* 49:171–181 (1984)]. Homologous recombination between mammalian cell chromosomal DNA and the exogenous plasmid DNA can result in the integration of the plasmid or in the replacement of some of the chromosomal sequences with homologous plasmid sequences. This can result in placing a desired new sequence at the endogenous target locus.

The process of homologous recombination has been evaluated using genes which offer dominant selection such as NEO and HPRT for a few cell types [Song et al., *Proc. Natl. Acad. Sci. USA* 84:6820–6824 (1987); Rubinitz and Subramani, *Mol. Cell Biol.* 6:1608–1614 (1986); and Liskay, *Cell* 35:157–164 (1983)]. Recently, procedures for modifying antibody molecules and for producing chimeric antibody molecules using homologous recombination to target gene modification have been described [Fell et al., *Proc. Natl. Acad. Sci. USA* 86:8507–8511 (1989); and co-pending U.S. patent application Ser. No. 243,873 filed Sep. 14, 1988, and Ser. No. 468,035 filed Jan. 22, 1990, assigned to the same assignee as the present application, all of which are incorporated by reference herein].

5. Monoclonal Antibodies in Therapy.

The most direct way to apply antitumor monoclonal antibodies clinically is to administer them in unmodified form, using monoclonal antibodies which display antitumor activity in vitro and in animal (such as humans, dogs, cows, pigs, horses, cats, rats, and mice) models. Most monoclonal antibodies to tumor antigens do not appear to have any antitumor activity by themselves, but certain monoclonal antibodies are known which mediate complement-dependent cytotoxicity (complement-dependent cytotoxicity), i.e. kill human tumor cells in the presence of human serum as a source of complement [see, e.g. Hellstrom et al., *Proc. Natl. Acad. Sci. USA* 82:1499–1502 (1985)], or antibody-dependent cellular cytotoxicity (antibody-dependent cellular cytotoxicity) together with effector cells such as human NK cells or macrophages.

To detect antibody-dependent cellular cytotoxicity and complement-dependent cytotoxicity activity monoclonal antibodies are tested for lysing cultured $^{51}$Cr-labeled tumor target cells over a 4-hour incubation period.

Target cells are labeled with $^{51}$Cr and then exposed for 4 hours to a combination of effector cells (in the form of human lymphocytes purified by the use of a lymphocyte-separation medium) and antibody, which is added in concentrations varying between 0.1 µg/ml and 10 µg/ml. The release of $^{51}$Cr from the target cells is measured as evidence of tumor-cell lysis (cytotoxicity). Controls include the incubation of target cells alone or with either lymphocytes or monoclonal antibody separately.

The total amount of $^{51}$Cr that can be released is measured and antibody-dependent cellular cytotoxicity is calculated as the percent killing of target cells observed with monoclonal antibody plus effector cells as compared to target cells being incubated alone. The procedure for complement-dependent cytotoxicity is identical to the one used to detect antibody-dependent cellular cytotoxicity except that human serum, as a source of complement, (diluted 1:3 to 1:6) is added in place of the effector cells.

Monoclonal antibodies with antibody-dependent cellular cytotoxicity and complement-dependent cytotoxicity activity are considered for therapeutic use because they often have anti-tumor activities in vivo. Antibodies lacking antibody-dependent cellular cytotoxicity and complement-dependent cytotoxicity activity in vitro, on the other hand, are commonly ineffective in vivo unless used as carriers of antitumor agents.

The ability of a monoclonal antibody to activate the host's complement may prove to be therapeutically beneficial not only because tumor cells may be killed, but also because the blood supply to tumors may increase, thus facilitating the uptake of drugs [see Hellstrom et al., "Immunological Approaches to Tumor Therapy: Monoclonal Antibodies, Tumor Vaccines, and Anti-Idiotypes, in Covalently Modified Antigens and Antibodies in Diagnosis and Therapy", Quash & Rodwell, eds., Marcel Dekker, pp. 15–18 (1989)].

Among mouse monoclonal antibodies, the IgG2a and IgG3 isotypes are most commonly associated with antibody-dependent cellular cytotoxicity and complement-dependent cytotoxicity. Antibodies having both antibody-dependent cellular cytotoxicity and complement-dependent cytotoxicity activity have high selectivity for killing only the tumor cells to which they bind and would be unlikely to lead to toxic effects if non-specifically trapped in lung, liver or other organs. This may give such antibodies an advantage over radiolabeled antibodies or certain types of immunoconjugates.

Therapeutic modalities directed to treating tumors are commonly available. For example, chemotherapy is an effective treatment for selected human tumors. However, with chemotherapy only modest progress has been made for treating the majority of carcinomas, including carcinomas of breast, lung, and colon.

The introduction of monoclonal antibody (MAb) technology in the 1970s raised hopes that tumor-specific MAbs could be used to target anti-tumor agents and provide more effective therapy (K. E. Hellstrom, and I. Hellstrom, in: *Biologic Therapy of Cancer: Principles and Practice,* V. T. DeVita, S. Hellman, and S. A. Rosenberg, Eds. (J. P. Lippincott Company, Philadelphia, Pa., 1991) pp. 35–52).

6. Immunoconjugates in Therapy.

Various immunoconjugates in which antibodies were used to target chemotherapeutic drugs (P. N. Kularni, A. H. Blair, T. I. Ghose, *Cancer Res.* 41, 2700 (1981); R. Arnon, R. and M. Sela, *Immunol. Rev.* 62, 5 (1982); H. M. Yang and R. A. Resifeld, *Proc. Natl. Acad. Sci. U.S.A.,* 85, 1189 (1988); R. O. Dilman, D. E. Johnson, D. L. Shawler, J. A. Koziol, *Cancer Res.* 48, 6097 (1988); L. B. Shih, R. M. Sharkey, F. J. Primus, D. M. Goldenberg, *Int. J. Cancer* 41, 832 (1988); P. A. Trail, et al., *Cancer Res.* 52, 5693 (1992)), or plant and bacterial toxins (I. Pastan, M. C. Willingham, D. J.

Fitzgerald, Cell 47, 641 (1986); D. C. Blakey, E. J. Wawrzynczak, P. M. Wallace, P. E. Thorpe, in *Monoclonal Antibody Therapy Prog. Allergy*, H. Waldmann, Ed. (Karger, Basel, 1988), pp. 50–90) have been evaluated in preclinical models and found to be active in vitro and in vivo.

However, activity of these MAbs was usually assessed against newly implanted rather than established tumors and was typically superior to matching, but not optimal, doses of the unconjugated drug.

Although conjugates have been described with anti-tumor activity against established tumors that were superior to that of an optimal dose of unconjugated drug, the therapeutic index was low and superior activity was achieved only at or near the maximum tolerated dose (MTD) of the conjugate (P. A. Trail, et al., *Cancer Res.* 52, 5693 (1992)).

The results of clinical studies of drug and toxin conjugates (i.e., immunoconjugates) have also been disappointing, particularly for solid tumors (E. S. Vitetta, R. J. Fulton, R. D. May, M. Till, J. W. Uhr, *Science* 238, 1098 (1987); H. G. Eichler, *Biotherapy* 3, 11 (1991); E. Wawrzynczak, *Br. J. Cancer* 64, 624 (1991); G. A. Pietersz and I. F. C. McKenzie, *Immunol. Rev.* 129, 57 (1992)).

Very few antibodies are able to kill tumor cells by themselves, that is, in the absence of effector cells or complement as in antibody-dependent cellular cytotoxicity or complement-dependent cytotoxicity. BR96 is such an antibody, because it can kill cells by itself at an antibody concentration of approximately 10 $\mu$g/ml or higher. Such antibodies are of particular interest since they can interfere with some key event in the survival of neoplastic cells.

Presently, chemotherapeutic agents, by themselves, do not distinguish between malignant and normal cells. They are absorbed by both cell types. Tumors that are detected early on such as acute lymphocytic leukemia and lymphomas are highly susceptible to drugs.

Tumors that are hidden until growth has reached a plateau, such as cancer of the lung and colon, have little sensitivity to drugs. Normal cells with high growth fraction are inevitably attacked by today's anti-cancer drugs, explaining the prevalence of severe side effects in the gastrointestinal tract and of hair loss. This holds true whether the cytotoxicity of the drug is due to alkylation, intercalation, or disruption of biosynthesis/antimetabolites.

The molecules of the invention, e.g., the immunotoxins, are homogeneous molecules that retain the specificity of the cell binding portion with the cytotoxic potential of the toxin.

It is thus apparent that antibodies, antibody conjugates and immunotoxins that display a high degree of selectivity to a wide range of carcinomas, have anti-tumor activity, and are capable of being readily internalized by tumor cells, may be of great benefit in tumor therapy.

SUMMARY OF THE INVENTION

The present invention provides internalizing antibodies, antibody conjugates and recombinant, single-chain immunotoxins that are highly selective for a range of human carcinomas. More specifically, the novel antibodies of the invention, designated as BR96 antibodies, are a murine monoclonal antibody and a chimeric antibody that bind to a cell membrane antigen found on human carcinoma cells.

The novel conjugates and single-chain immunotoxins contain an exotoxin such as PE and bind to the antigen on tumor cells. The antibodies, conjugates and single-chain immunotoxins are highly reactive with carcinoma cells, such as those derived from breast, lung, colon and ovarian carcinomas, showing no or limited reactivity with normal human cells or other types of tumors such as lymphomas or sarcomas. In addition, the antibodies of the invention internalize within the carcinoma cells to which they bind and they are capable of killing tumor cells by themselves, i.e., not in conjugated form, and without effector cells or complement.

Thus the BR96 antibodies are of particular use in therapeutic applications, for example to react with tumor cells, and in conjugates and single-chain immunotoxins as target-selective carriers of various agents which have antitumor effects including chemotherapeutic drugs, toxins, immunological response modifiers, enzymes and radioisotopes. The antibodies can thus be used as a component of various immunoconjugates including antibody-drug and antibody-toxin conjugates, including ricin and PE-antibodies and ricin and PE-antibody fragment immunotoxins, where internalization of the conjugate is favored, and after radiolabeling to deliver radioisotope to tumors. The BR96 antibodies can also be therapeutically beneficial even in the unmodified form. Furthermore, the antibodies are useful for in vitro or in vivo diagnostic methods designed to detect carcinomas.

BRIEF DESCRIPTION OF THE FIGURES

FIG. 35 (SEQ ID NO: 3) is the DNA and amino acid sequence for BR96 sFv encoded by plasmid pBR96 Fv, as described in Example 14, infra.

IgG with BR96 sFv-PE40 (closed circle), BR96 IgG (open square) and L6 IgG (open circle), as described in Example 14, infra.

Figure 40:
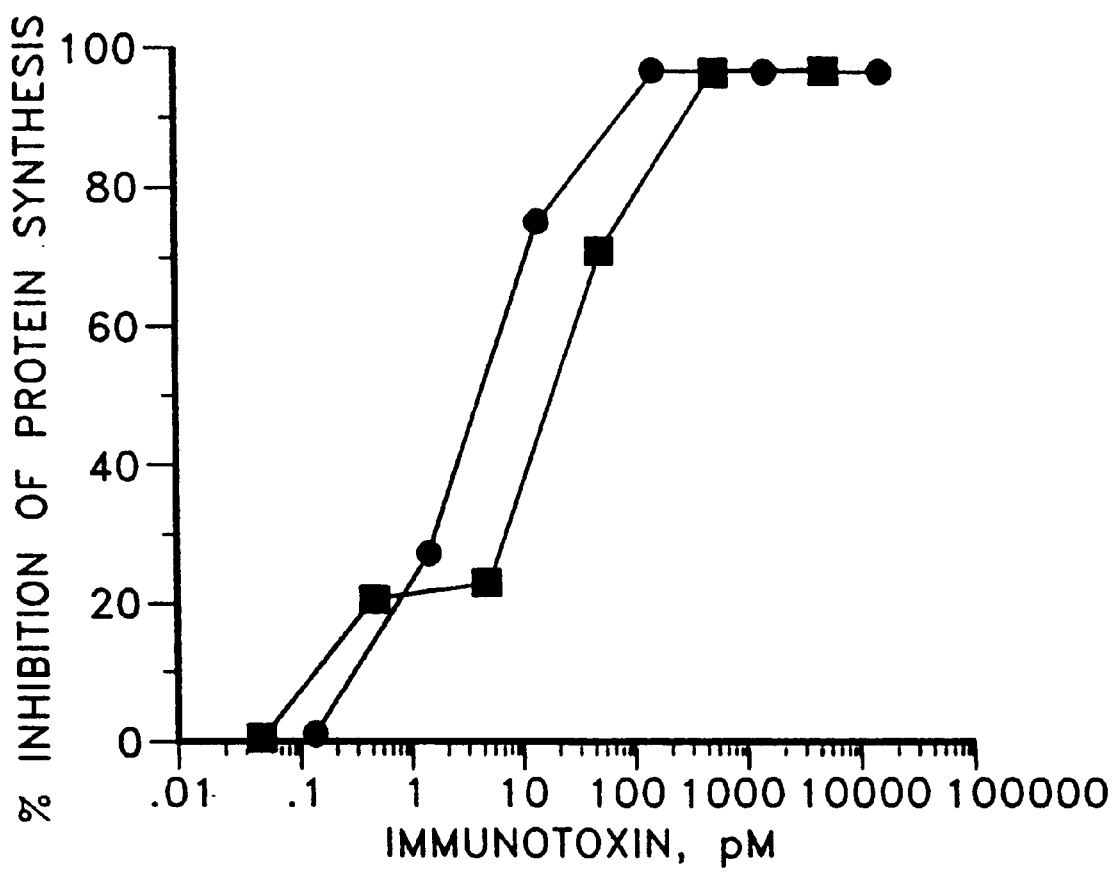

FIG. 40 is a graph showing the results of cytotoxicity analysis of BR96 sFv-PE40 inhibition of protein synthesis in MCF-7 cells as described in Example 14, infra (BR96 sFv-PE40 (closed circle) and ChiBR96-LysPE40 (closed square)).

FIG. 41 are histograms of FACS analysis of five human carcinoma lines as described in Example 14, infra (data is displayed in each histogram as the mean channel number for BR96 IgG or a human IgG control antibody. Fluorescence intensity for each cell line is determined by subtracting the human IgG mean channel number from the BR96 mean channel number).

Figure 42:
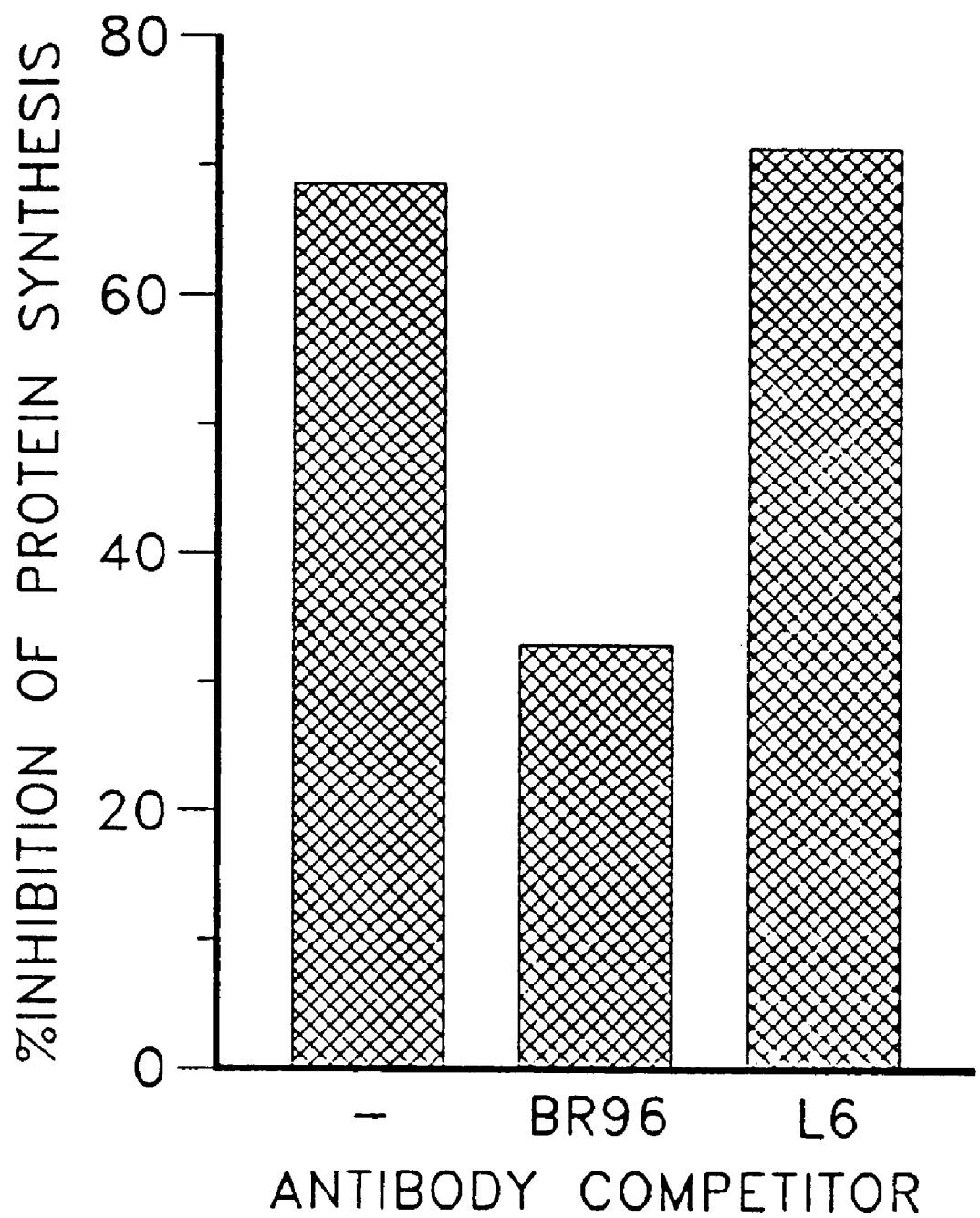

FIG. 42 is a bar graph showing the results of competitive cytotoxic analysis of BR96 sFv-PE40 inhibition of protein synthesis in L2987 cells by BR96 sFv-PE40 (50 ng/ml) alone or in the presence of either BR96 IgG or L6 IgG (100 μg/ml) as described in Example 14, infra.

Figure 43:
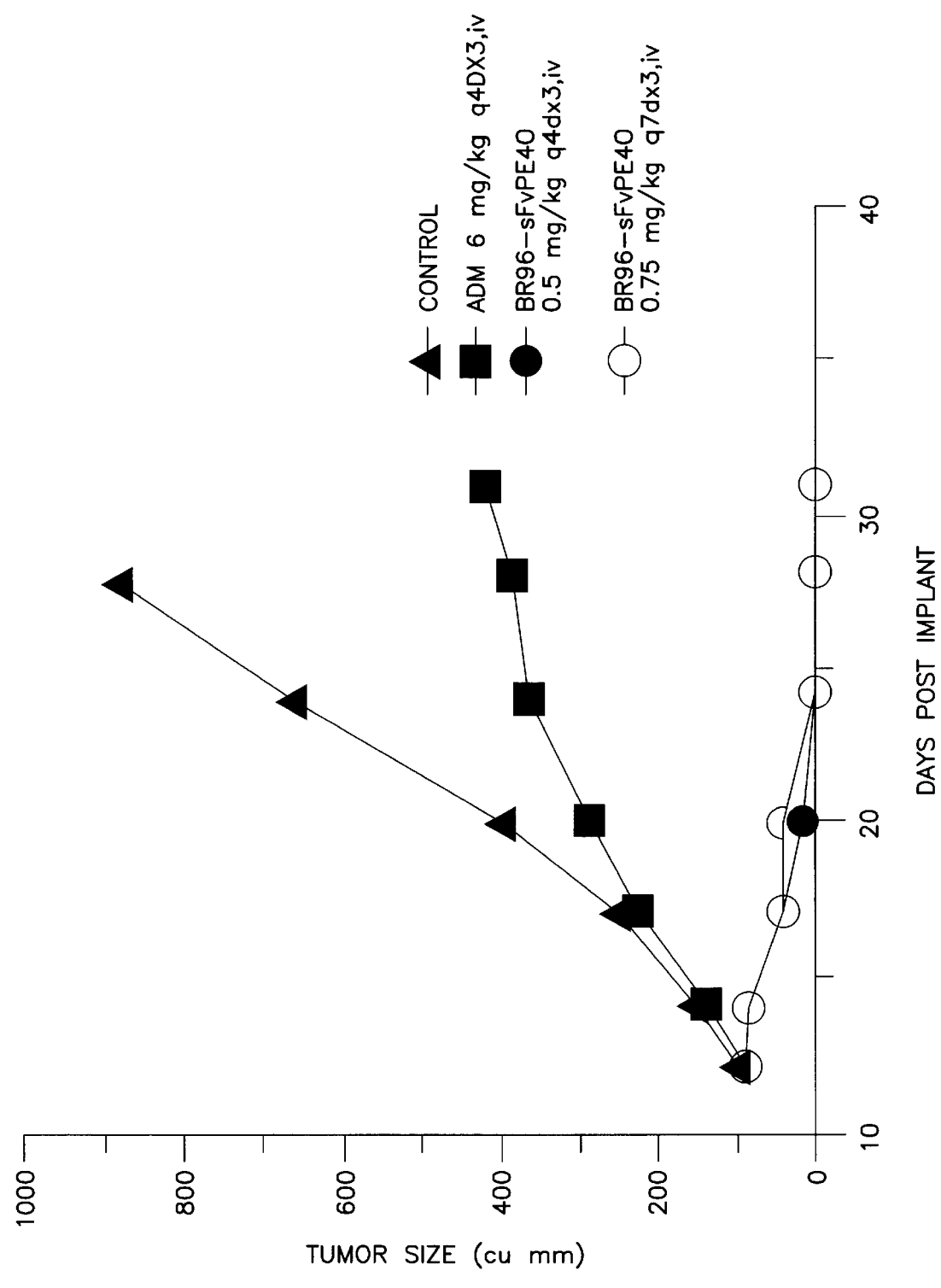

FIG. 43 is a graph showing anti-tumor effects of BR96-sFvPE40 in vivo against MCF-7 human breast tumor xenografts, as described in Example 15, infra (ADM 6 mg/kg (closed square), BR96-sFvPE40 0.50 mg/kg (closed circle), BR96-sFvPE40 0.75 mg/kg (open circle), control (closed triangle)).

Figure 44:
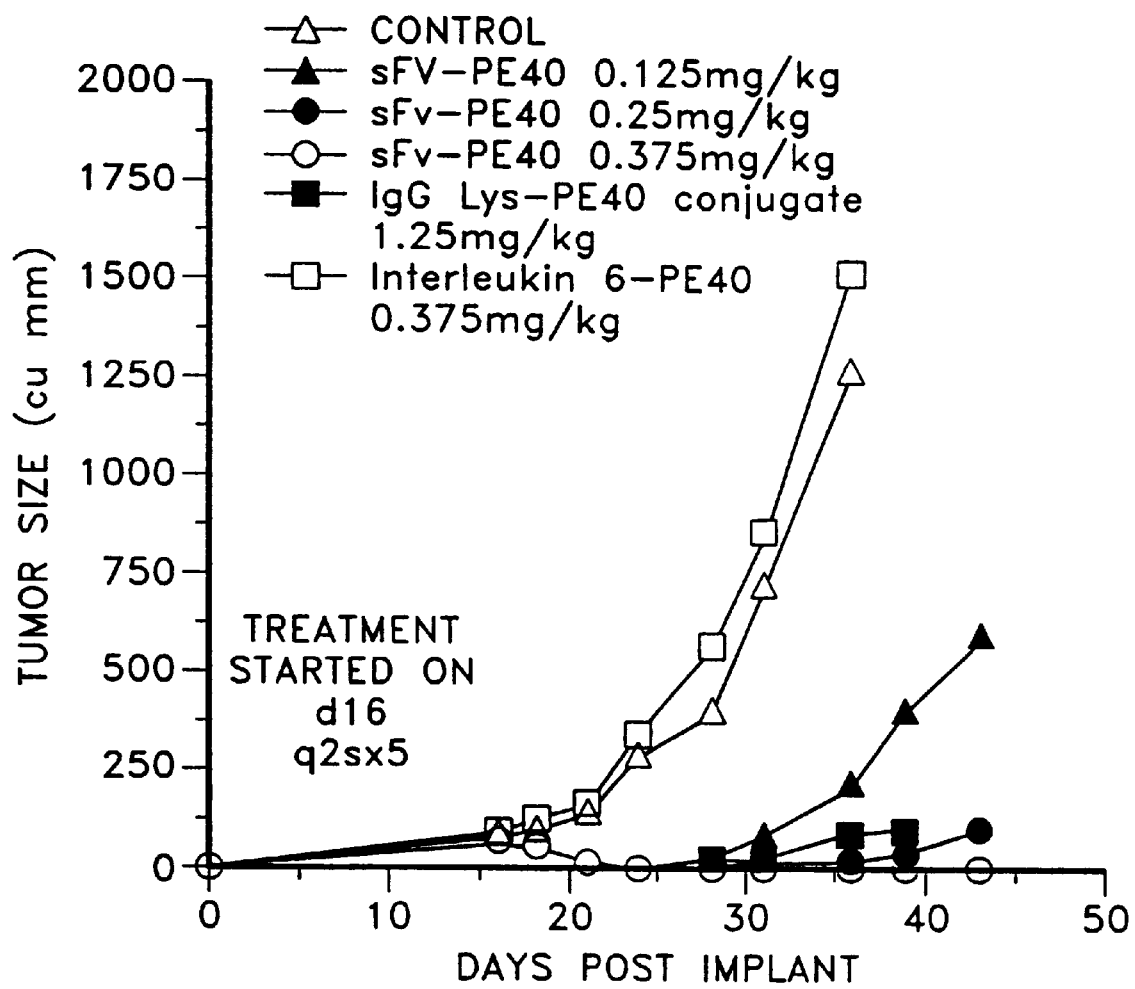

FIG. 44 is a graph showing anti-tumor activity of BR96-immunotoxins against L2987 human lung tumor xenografts as described in Example 15, infra (sFv-PE40 0.125 mg/kg (closed triangle), sFv-PE40 0.25 mg/kg (closed circle), sFv-PE40 0.375 mg/kg (open circle), IgG Lys-PE40 conjugate 1.25 mg/kg (closed square), Interleukin 6-PE40 0.375 mg/kg (open square), control (closed triangle)).

Figure 45:
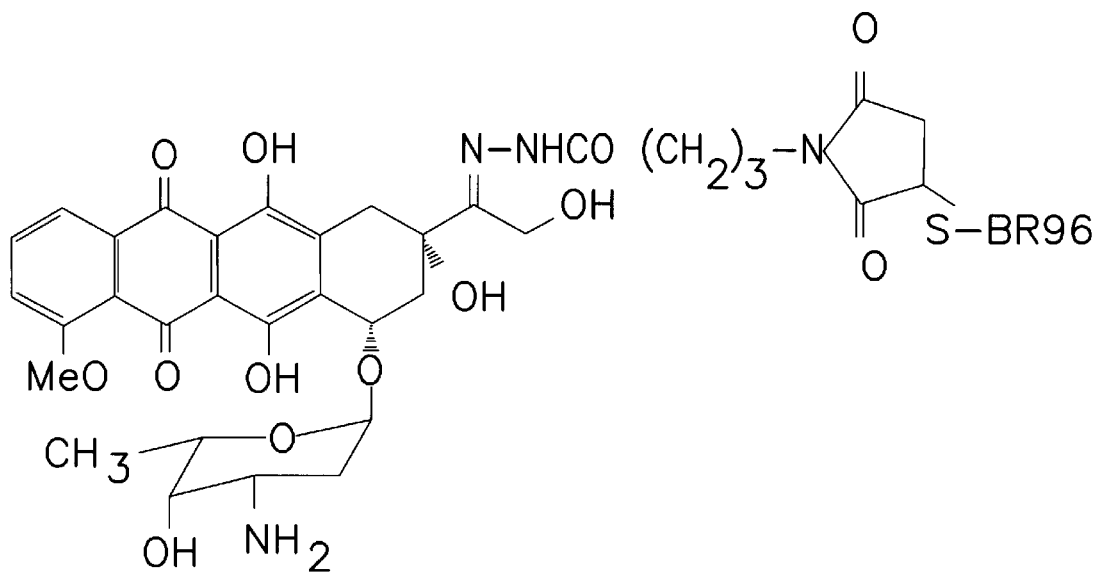

FIG. 45 is a drawing of the structure of BR96-DOX.

FIGS. 46A–D are line graphs showing the antigen-specific antitumor activity of BR96-DOX.

(A) Control animals (closed square); animals treated with BR96-DOX (5 mg/kg DOX) (closed circle), IgG-DOX (5 mg/kg DOX) (closed triangle); or optimized DOX (8 mg/kg) (open square).

(B) Control animals (closed square); animals treated with BR96-DOX (10 mg/kg) (closed circle), IgG-DOX (10 mg/kg) (closed triangle), or optimized DOX (8 mg/kg) (open square).

(C) Control animals (closed square); animals treated with BR96-DOX (5 mg/kg) (closed circle), IgG-DOX (5 mg/kg) (closed triangle), or DOX (6 mg/kg) (open square).

(D) Control animals (closed square) animals treated with BR96-DOX (8 mg/kg) (closed circle), or DOX (8 mg/kg) (open triangle).

Figure 47:
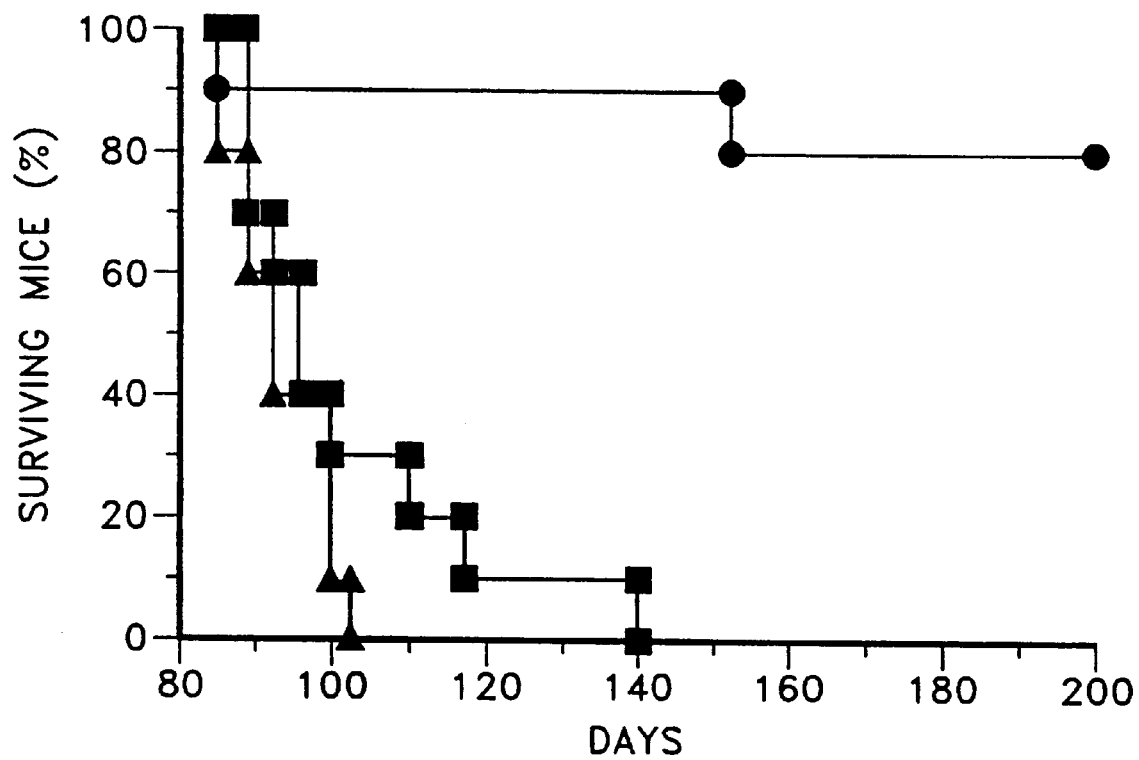

FIG. 47 is a line graph showing that BR96-DOX cures athymic mice of large disseminated tumors. Untreated controls (closed triangle), BR96-DOX treated (8 mg/kg) (closed circle) or DOX treated (8 mg/kg) (closed square) 82, 86 and 90 days after inoculation of tumor cells.

Figure 48:
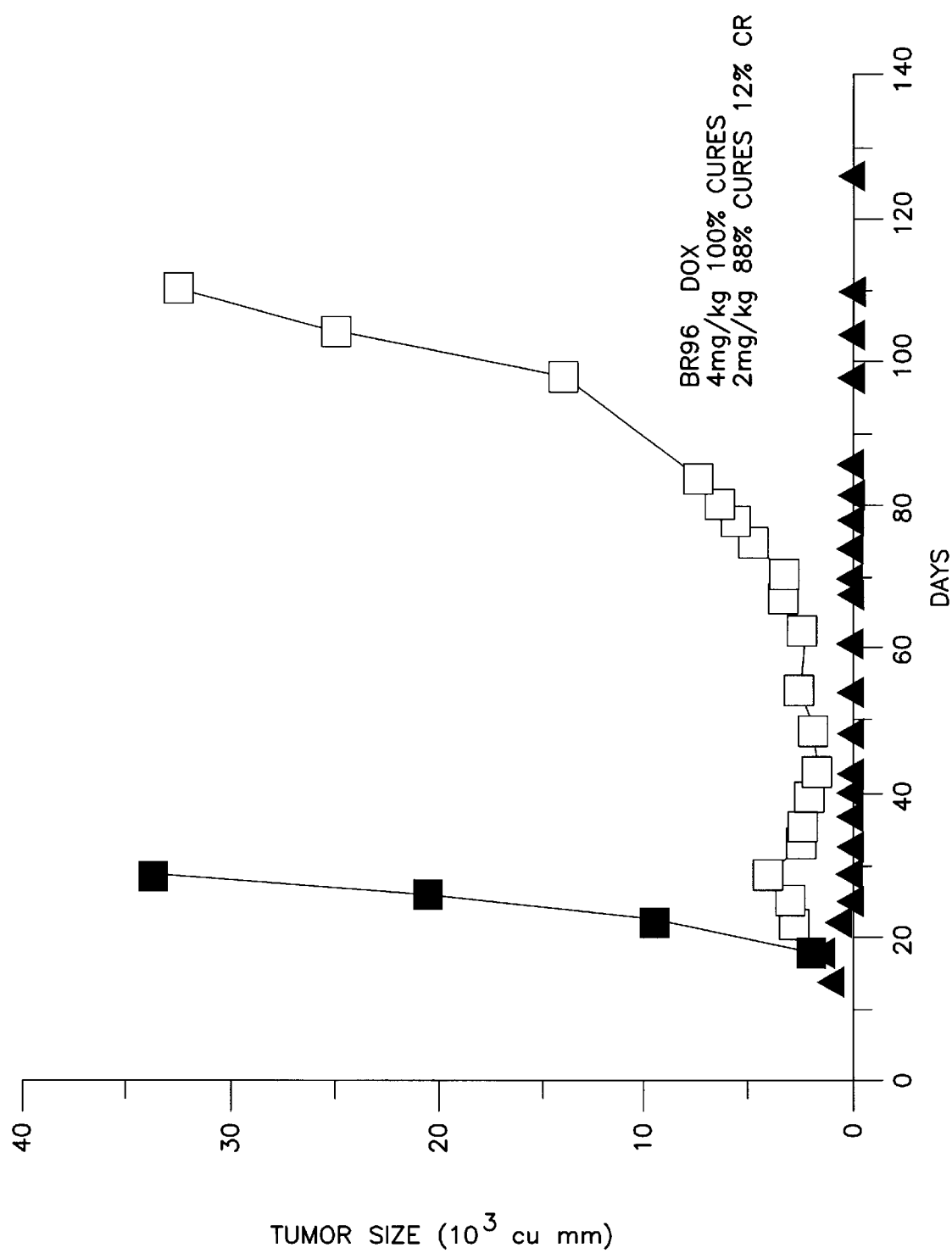

FIG. 48 is a line graph showing that BR96-DOX cures human lung tumors implanted in athymic rats. Control animals (closed square), animals treated with BR96-DOX (4 mg/kg) (open circle), BR96-DOX (2 mg/kg) (closed triangle), or DOX (4 mg/kg) (open square).

Figure 49A:
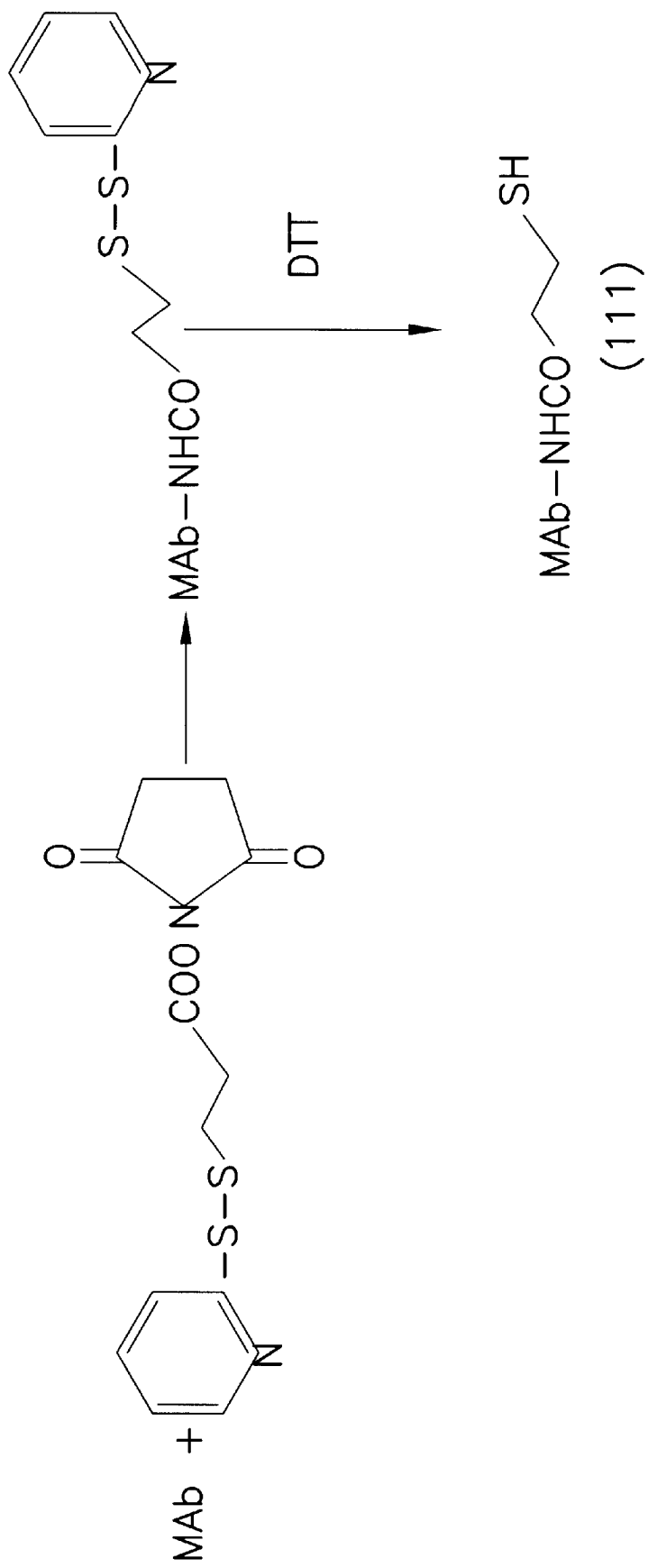

FIG. 49(a) provides a synthetic scheme for preparing a thiolated antibody using SPDP as the thiolation agent.

Figure 49B:
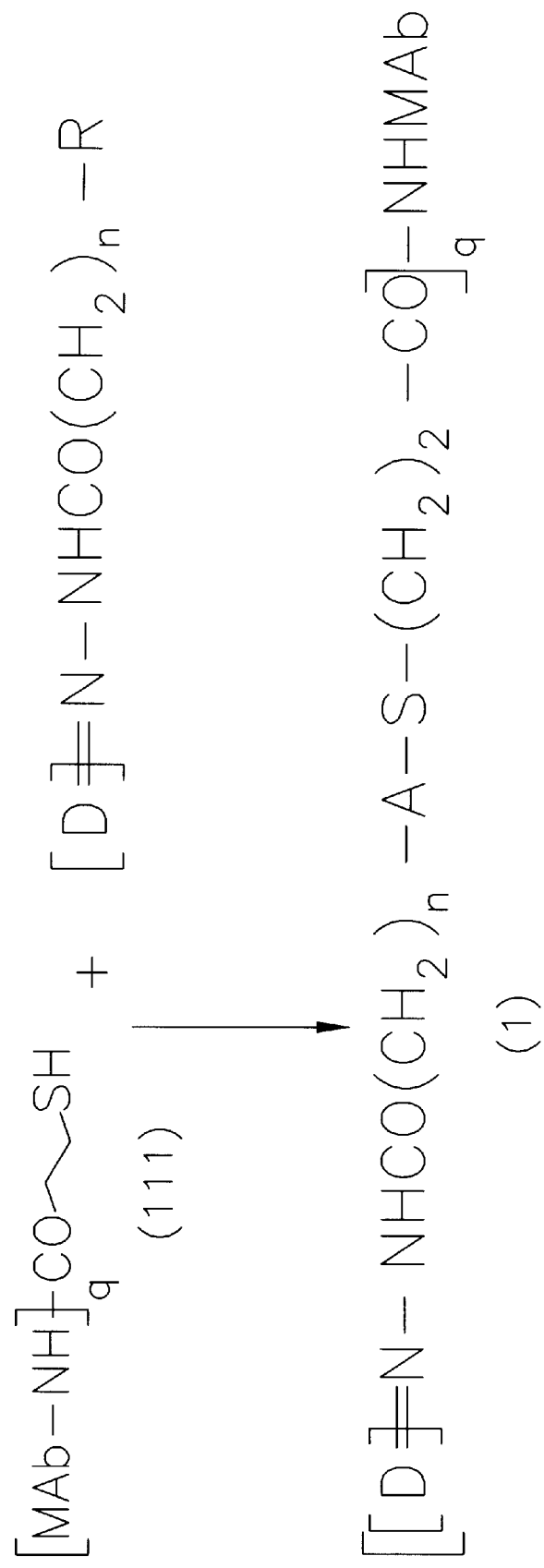

FIG. 49(b) provides a synthetic scheme for preparing an immunoconjugate of the invention in which the ligand is a SPDP-thiolated antibody.

Figure 49C:
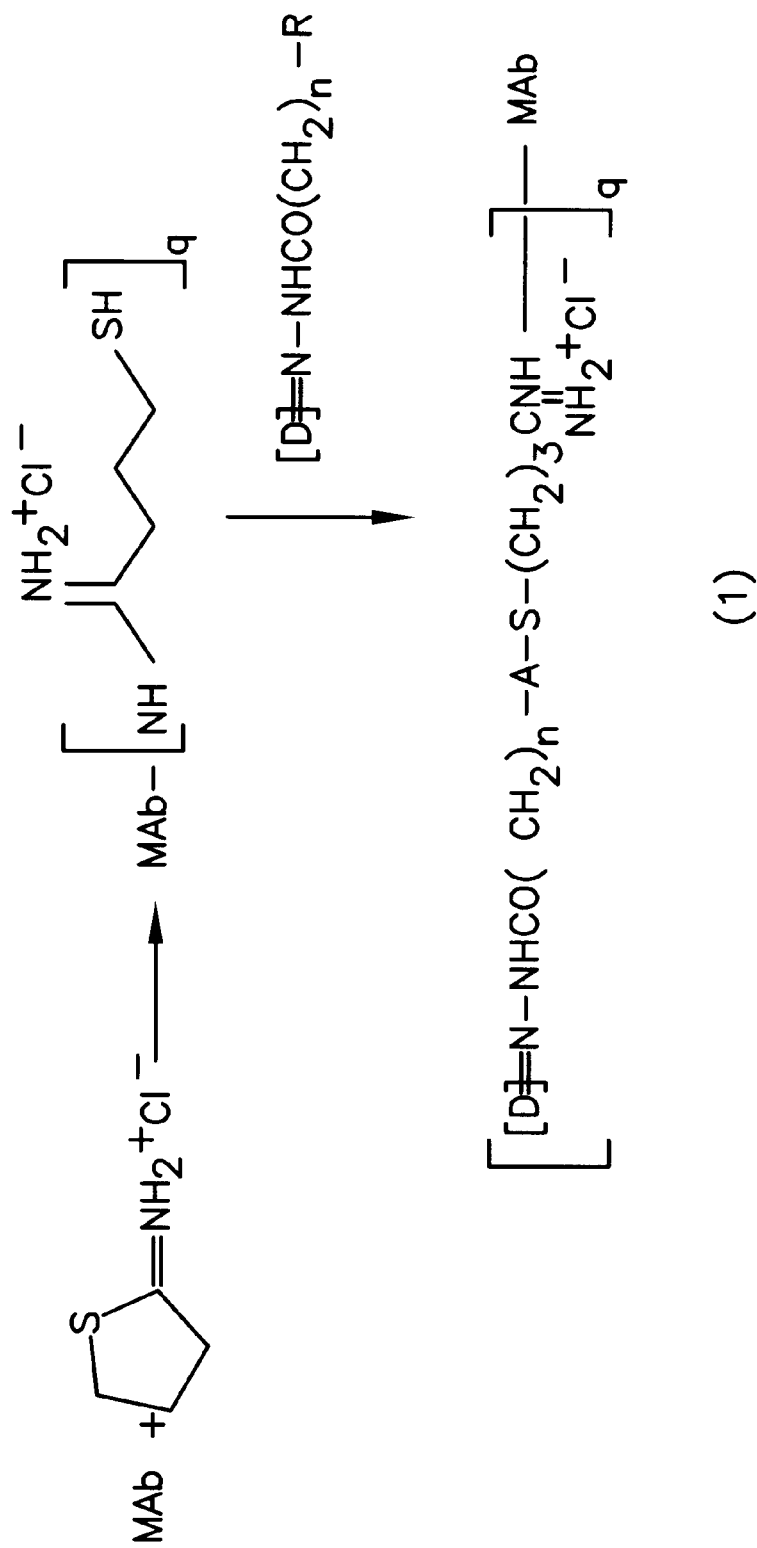

FIG. 49(c) provides a synthetic scheme for preparing an immunoconjugate of the invention in which the ligand is an iminothiolane-thiolated antibody.

Figure 50:
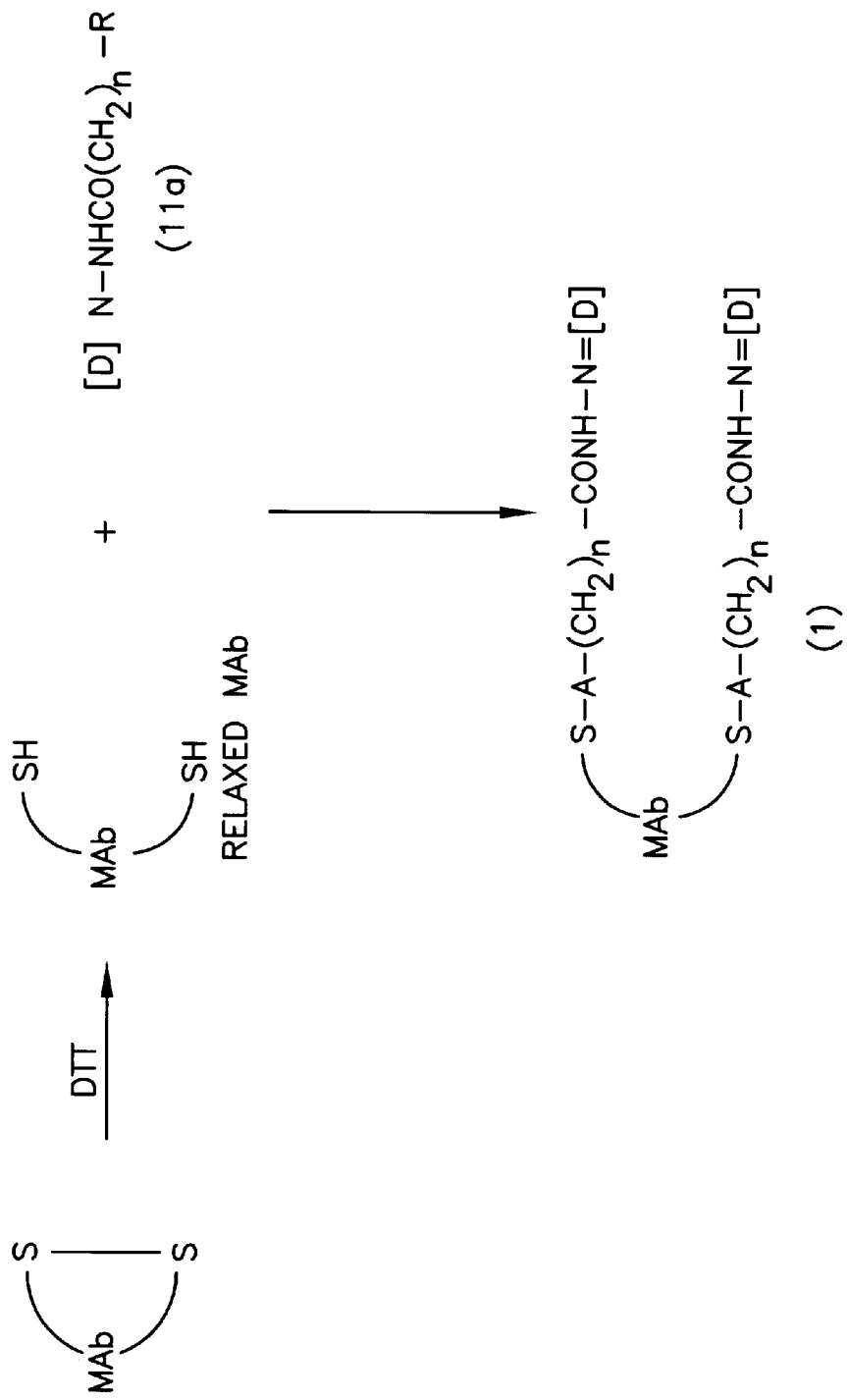

FIG. 50 shows a process for reducing with DTT an antibody to prepare a "relaxed" antibody and synthesis of an immunoconjugate of the invention.

Figure 51:
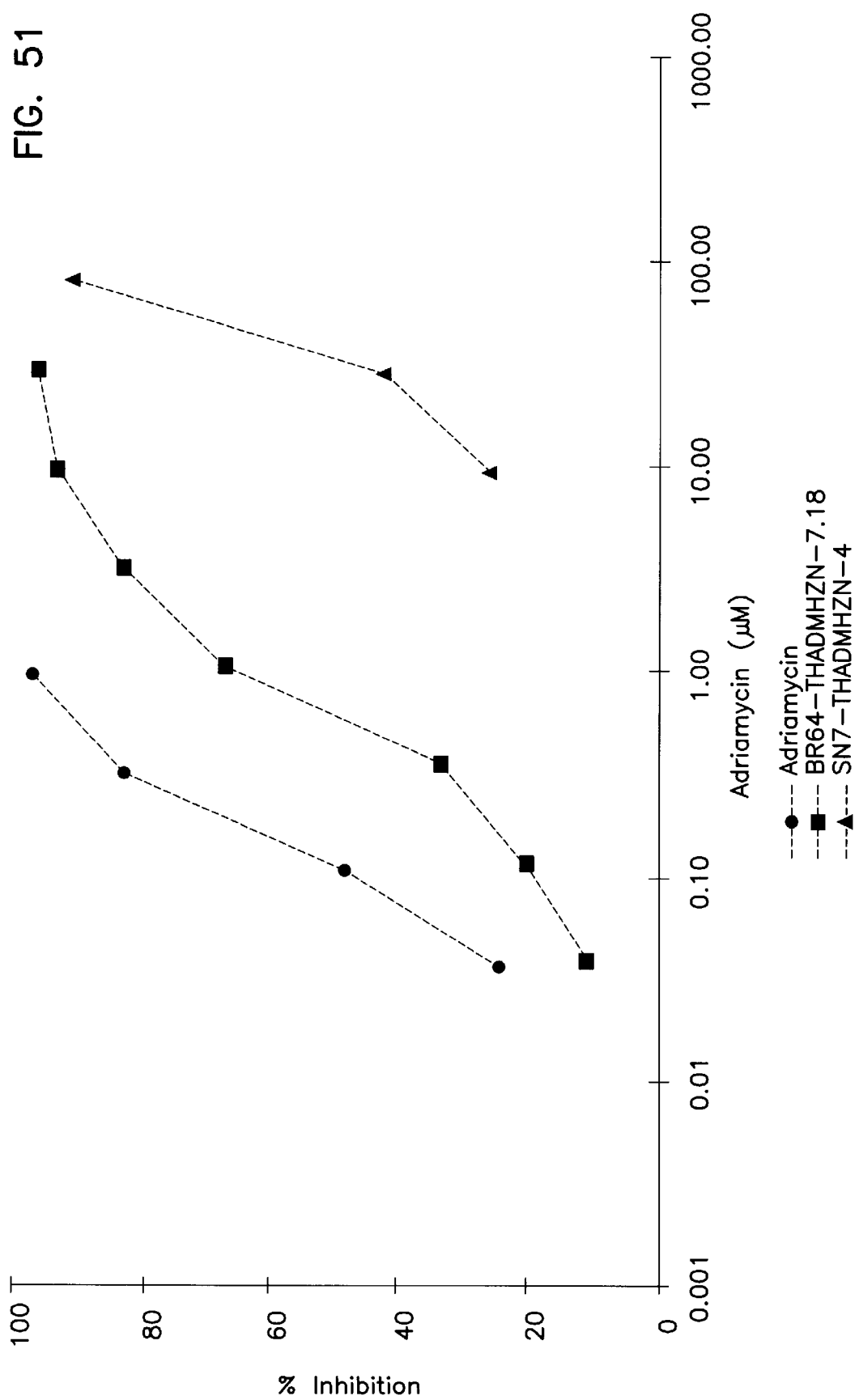

FIG. 51 provides in vitro cytotoxic activity data for BR64-Adriamycin conjugates of the invention against L2987 tumors.

FIG. 52 provides in vivo cytotoxic activity data for BR64-Adriamycin conjugates of the invention against L2987 tumors.

Figure 53A:
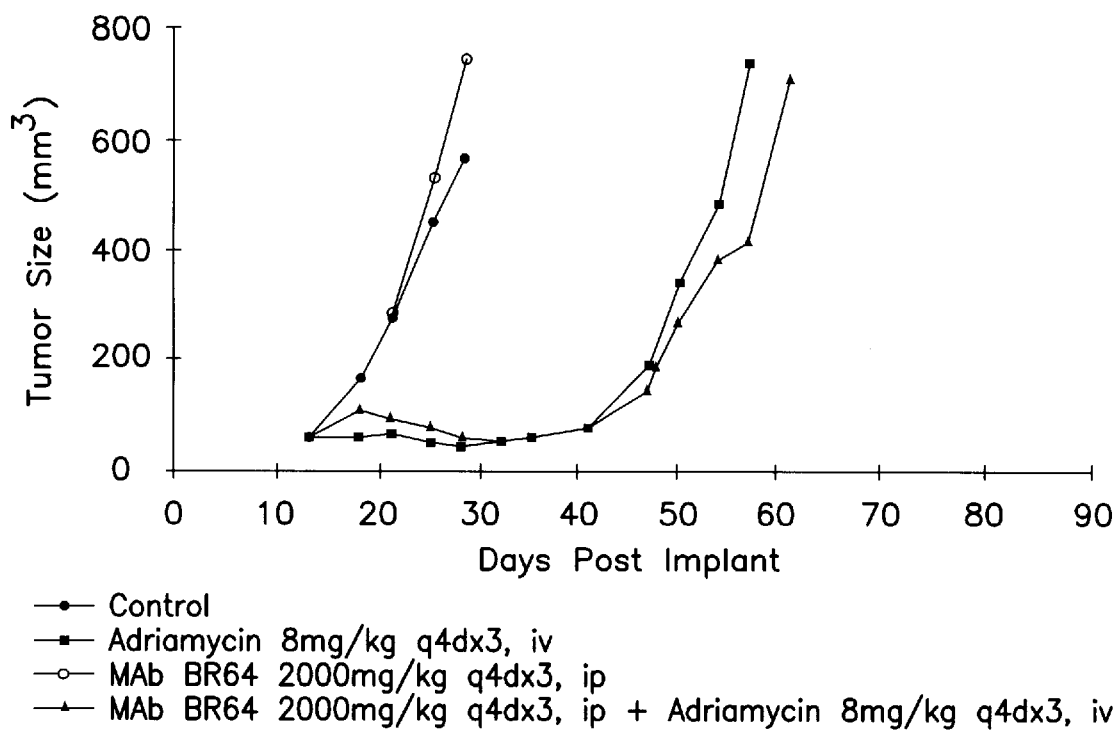
Figure 53B:
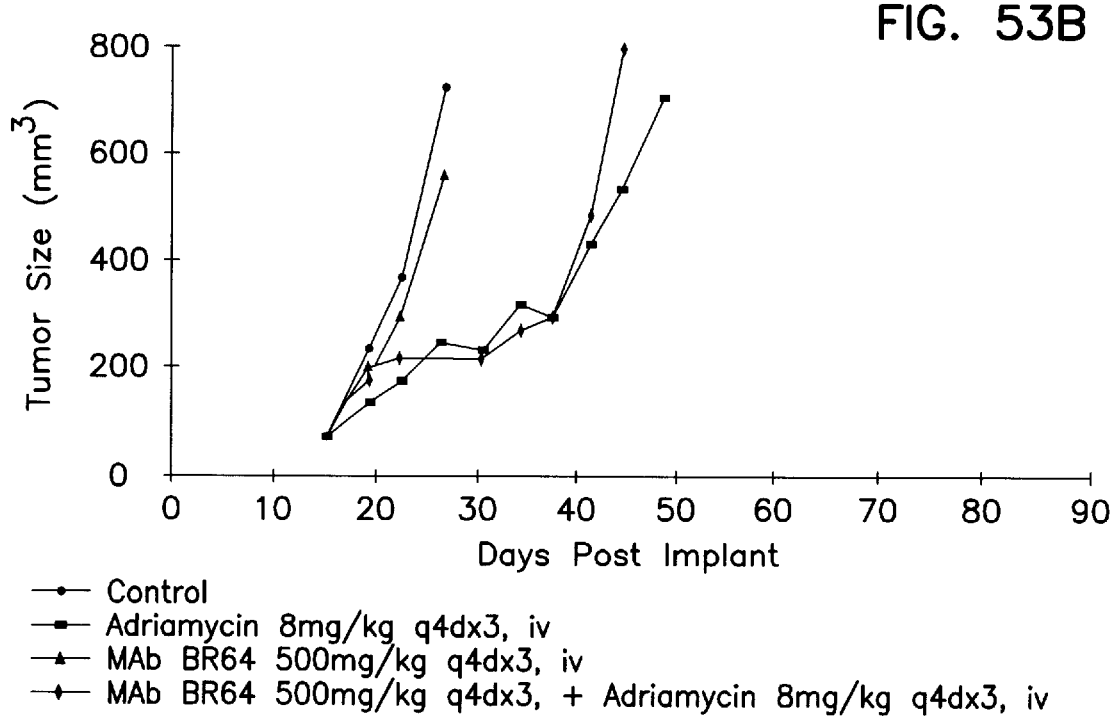
Figure 53C:
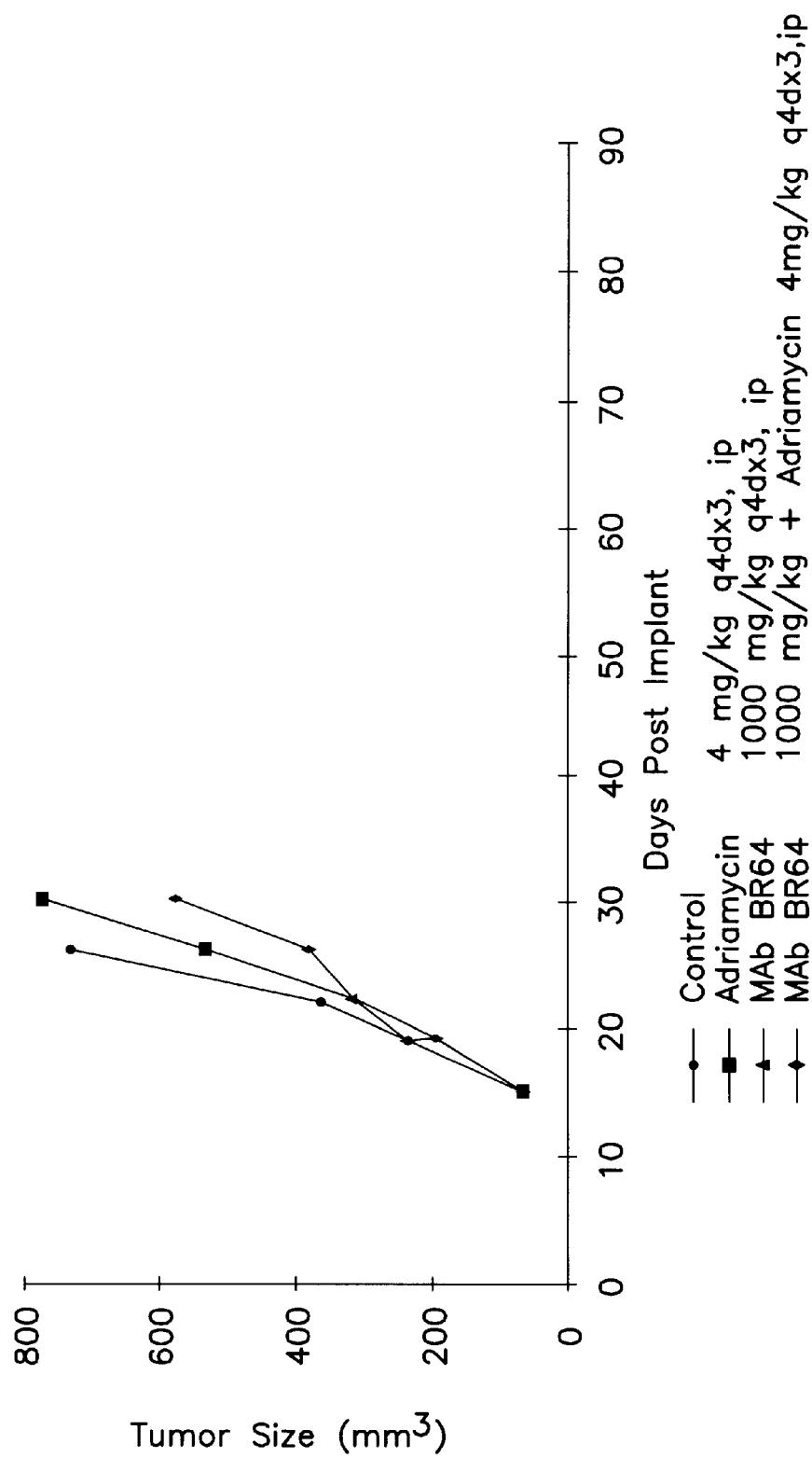

FIGS. 53A/B/C provides comparative in vivo cytotoxic data for combination therapy using BR64, Adriamycin and non-binding conjugate (SN7-Adriamycin).

FIG. 54 provides in vivo cytotoxic activity data for Bombesin-Adriamycin conjugates of the invention against H345 tumors.

Figure 55:
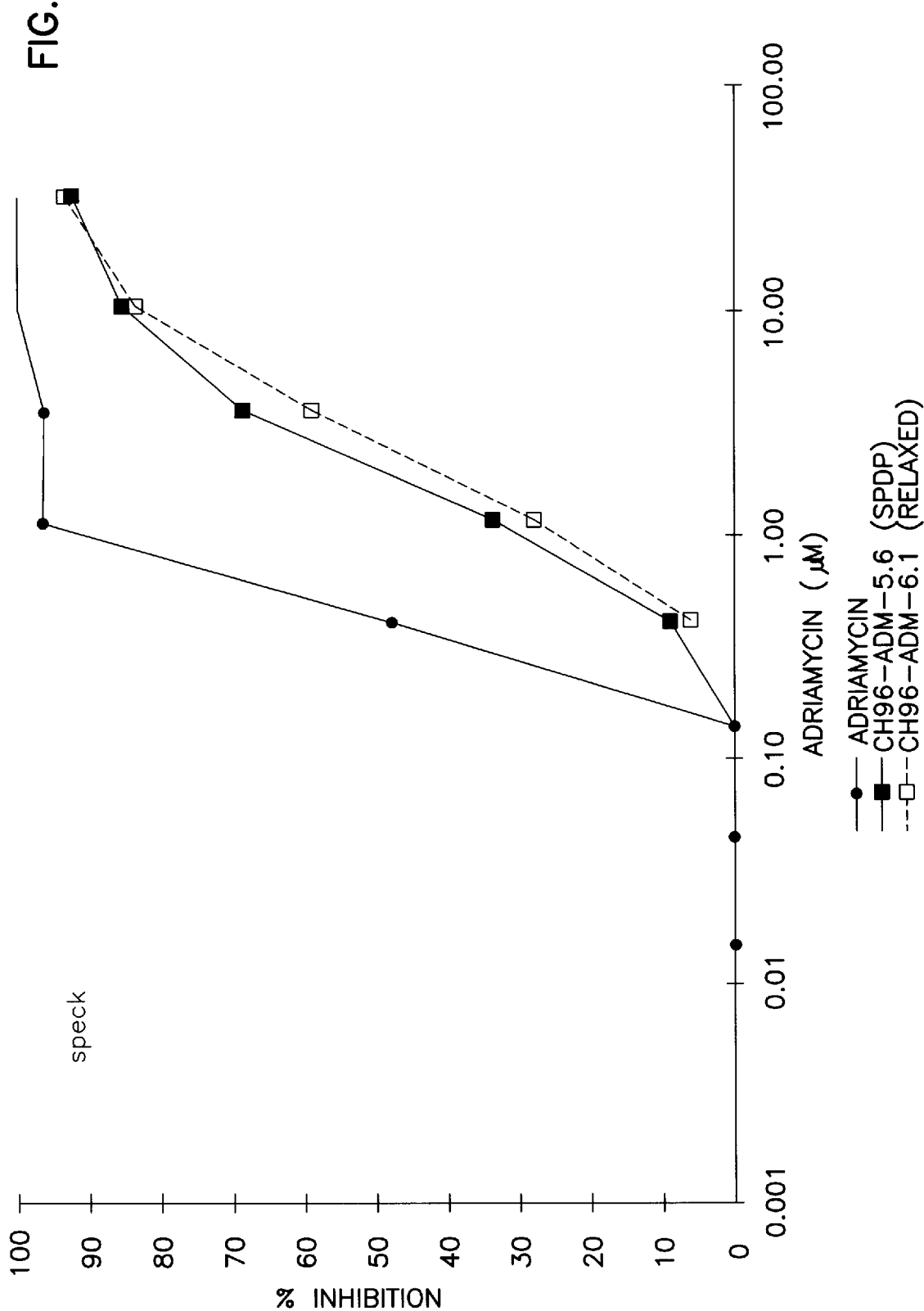

FIG. 55 provides in vitro cytotoxic activity data for Adriamycin conjugates of relaxed chimeric BR96 and SPDP-thiolated chimeric BR96.

Figure 56:
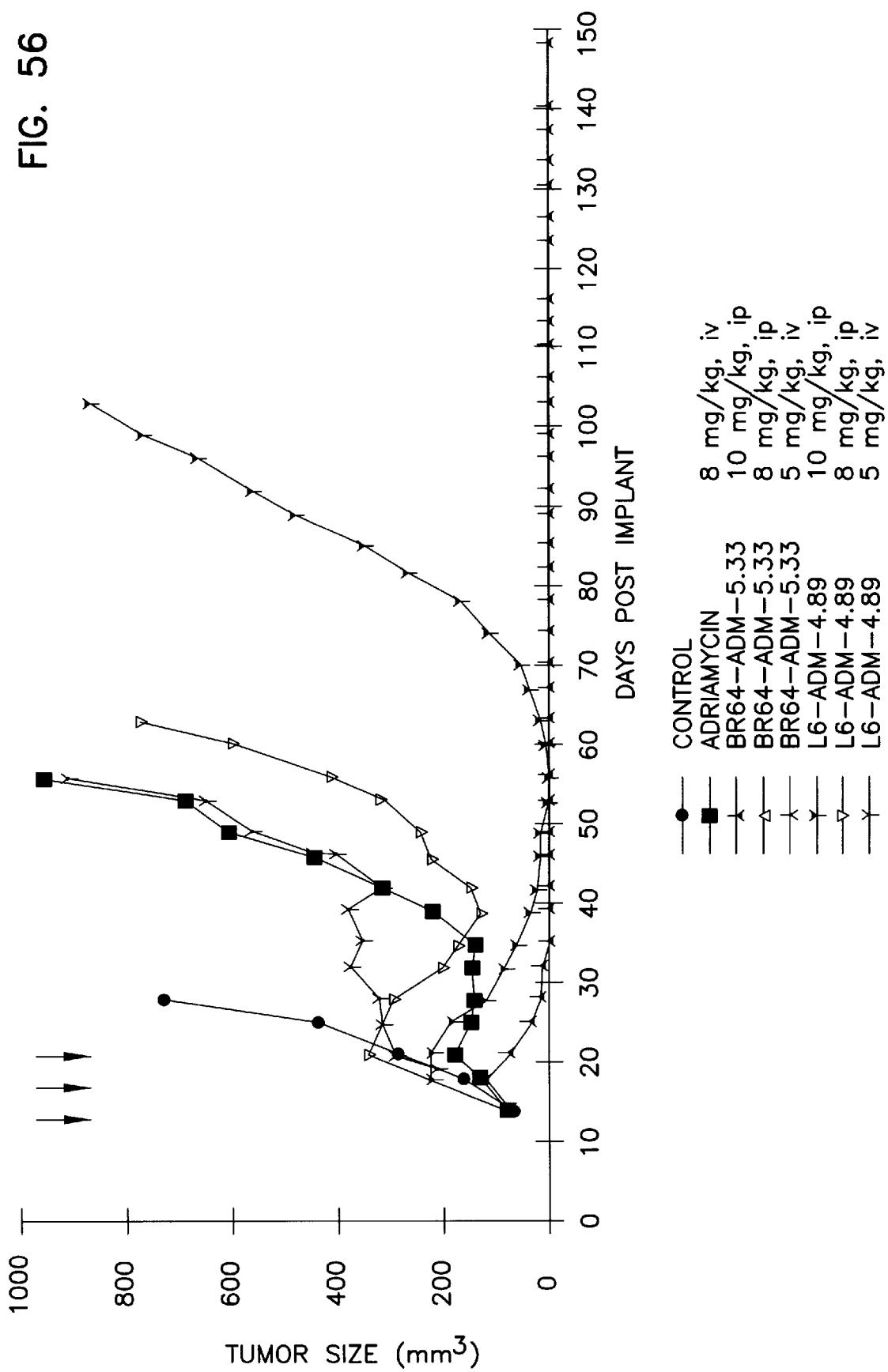

FIG. 56 provides in vivo cytotoxic activity data for Adriamycin conjugates of relaxed BR64 and relaxed chimeric L6 against L2987 tumors.

Figure 57:
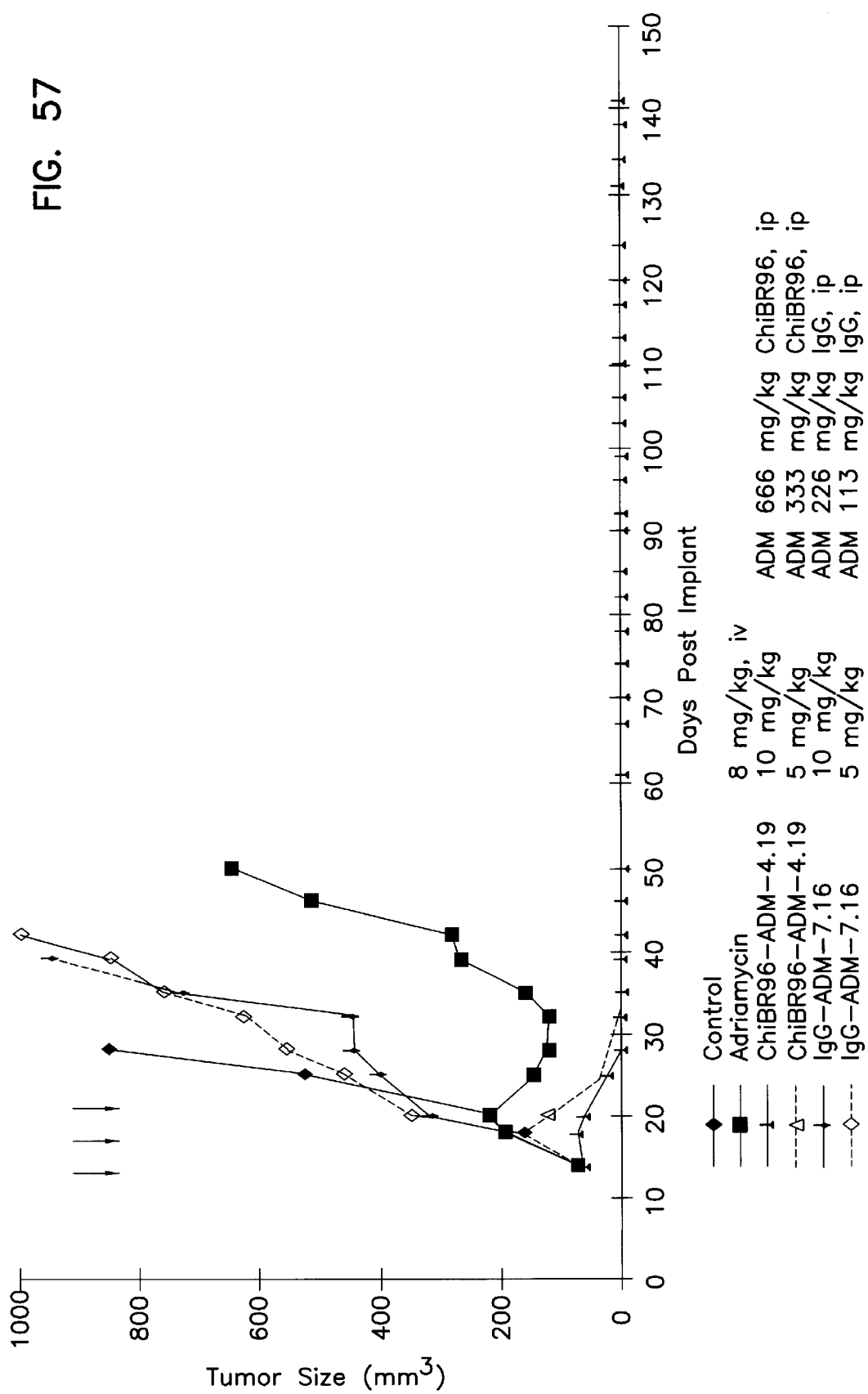
Figure 58:
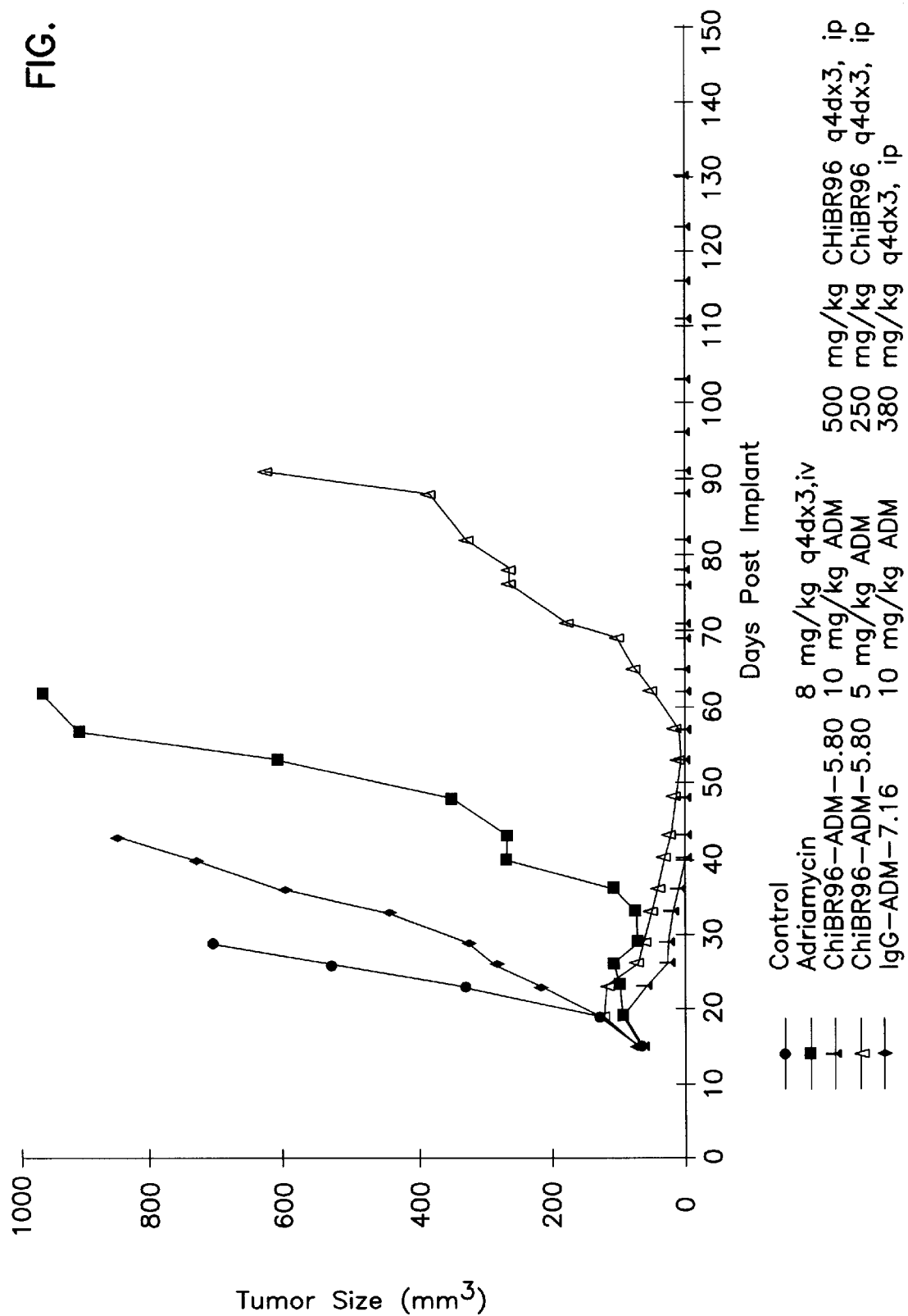
Figure 59:
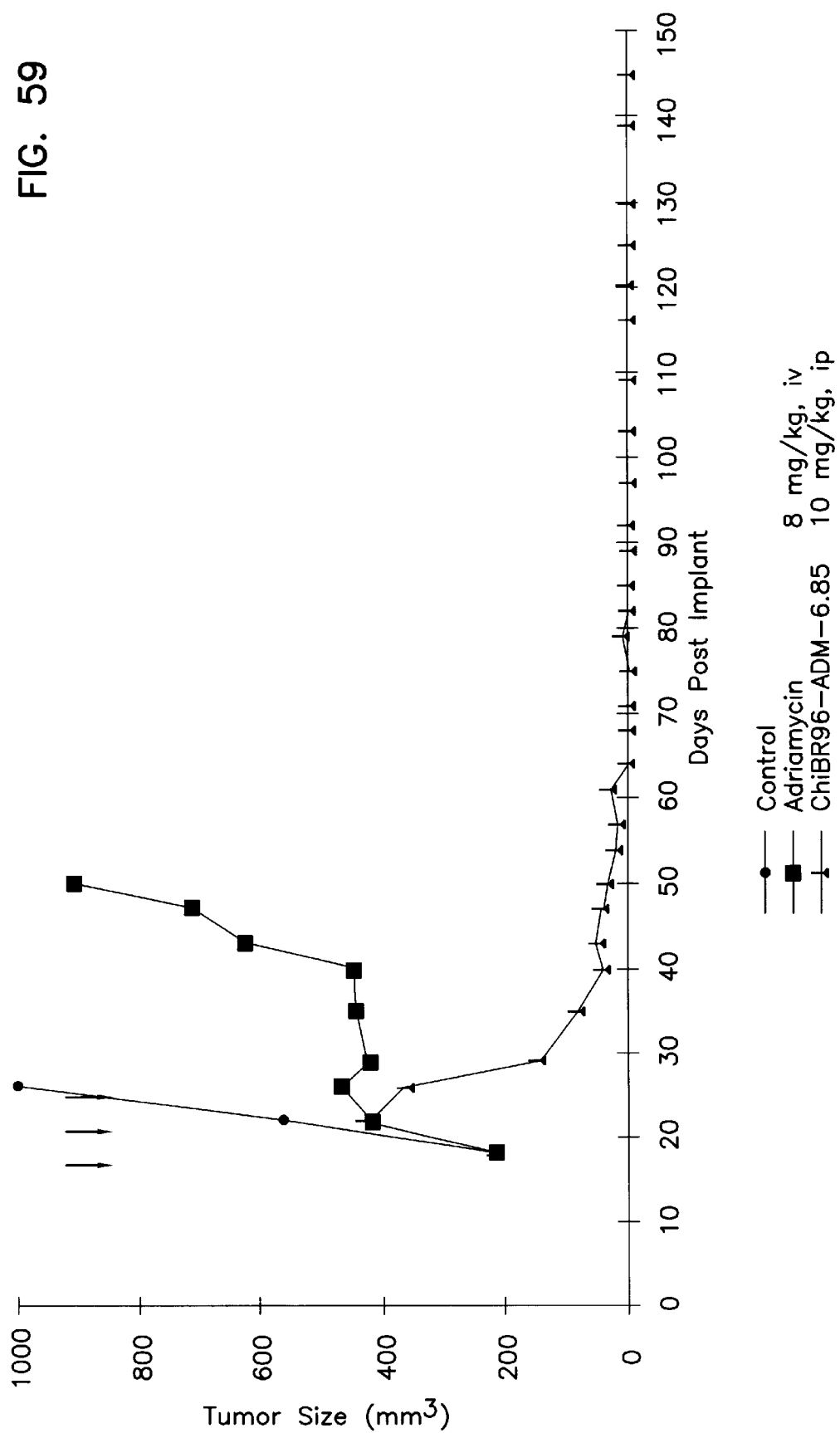

FIGS. 57 to 59 provide in vivo cytotoxic activity data against L2987 tumors for Adriamycin conjugates of relaxed chimeric BR96 compared to free Adriamycin and non-binding conjugates.

Figure 60:
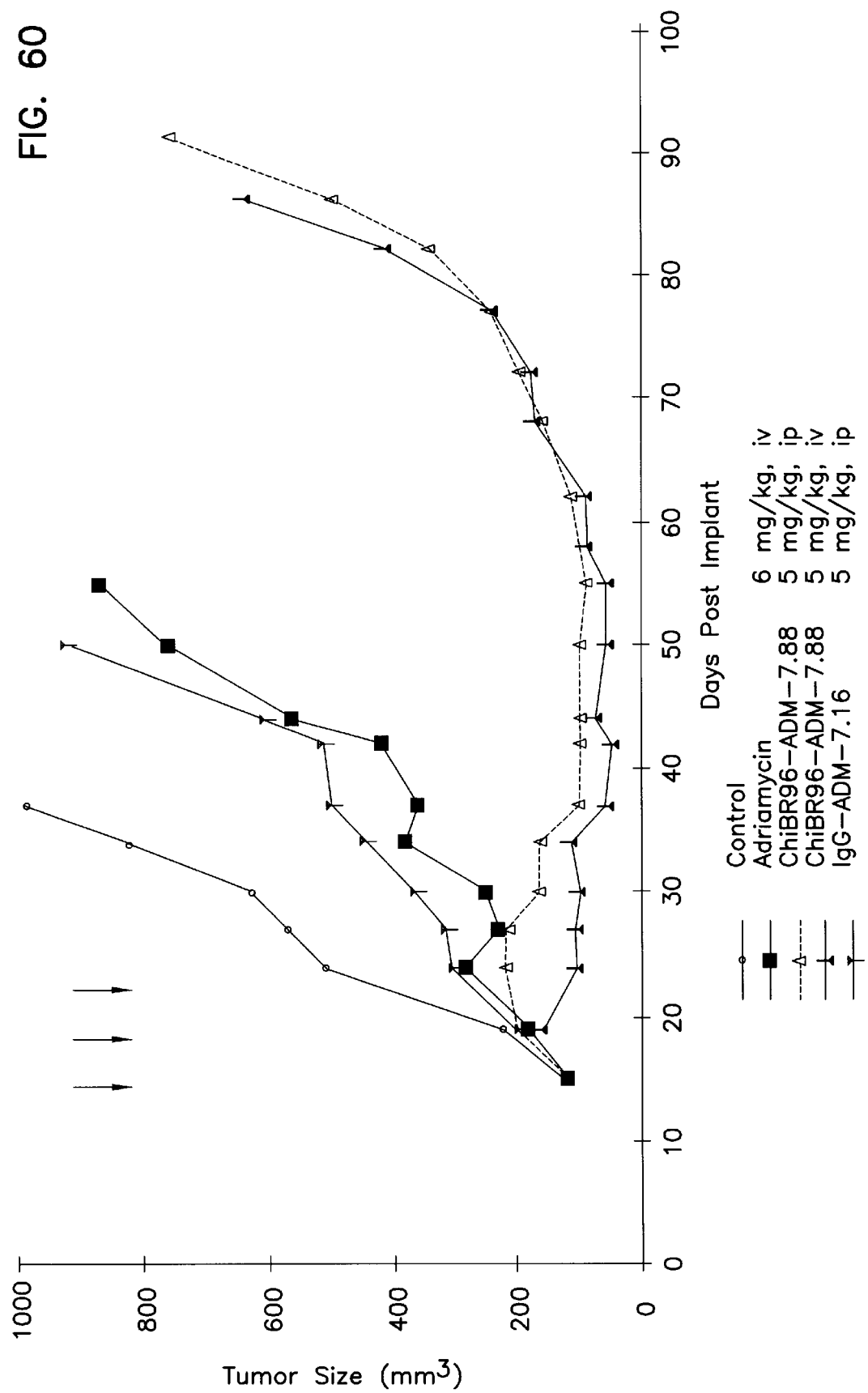

FIG. 60 provides in vivo cytotoxic activity data for Adriamycin conjugates of relaxed chimeric BR96 against RCA Human Breast Tumors.

Figure 61:
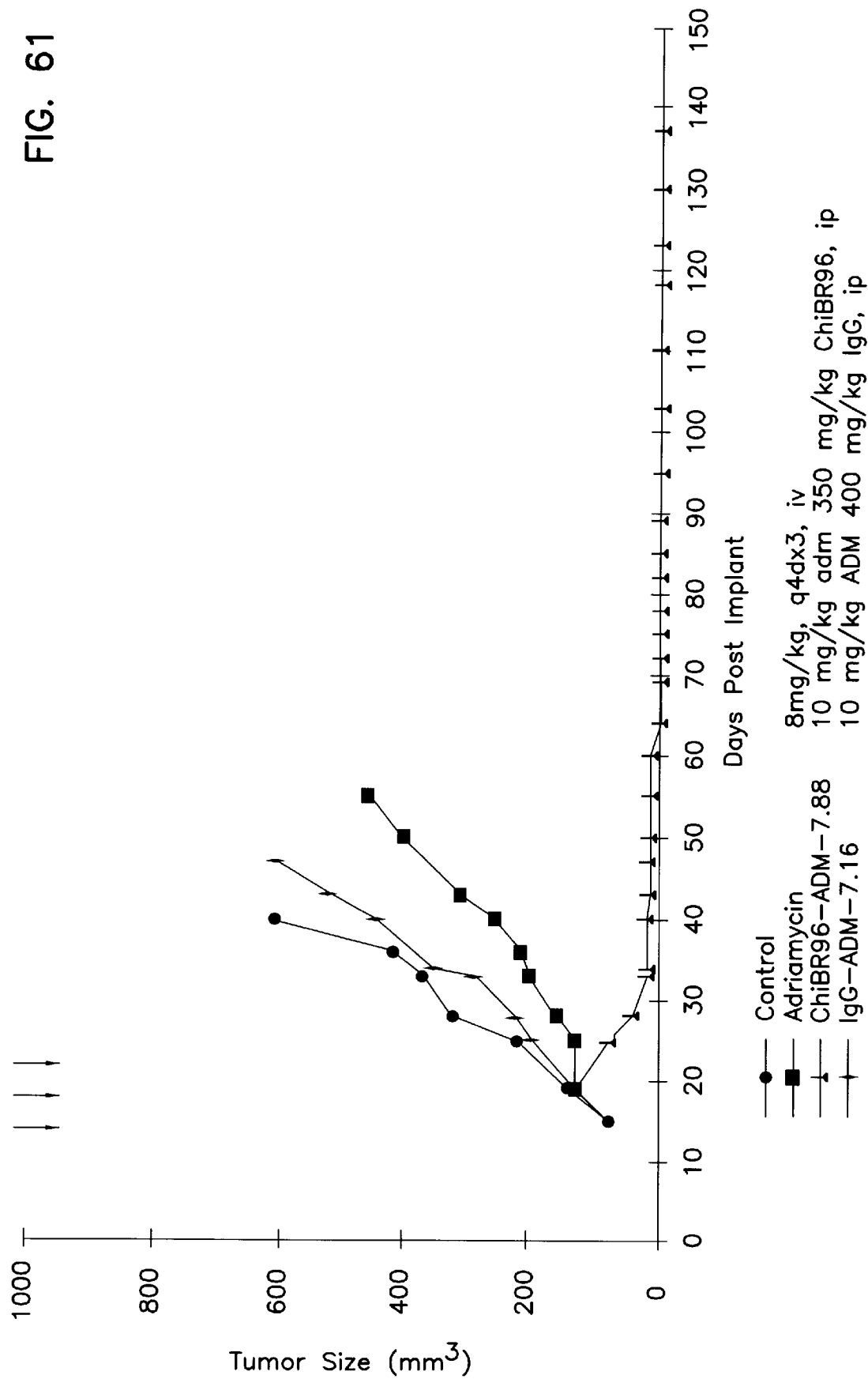

FIG. 61 provides in vivo cytotoxic activity data for Adriamycin conjugates of relaxed chimeric BR96 against RCA Human Colon Tumors.

Figure 62:
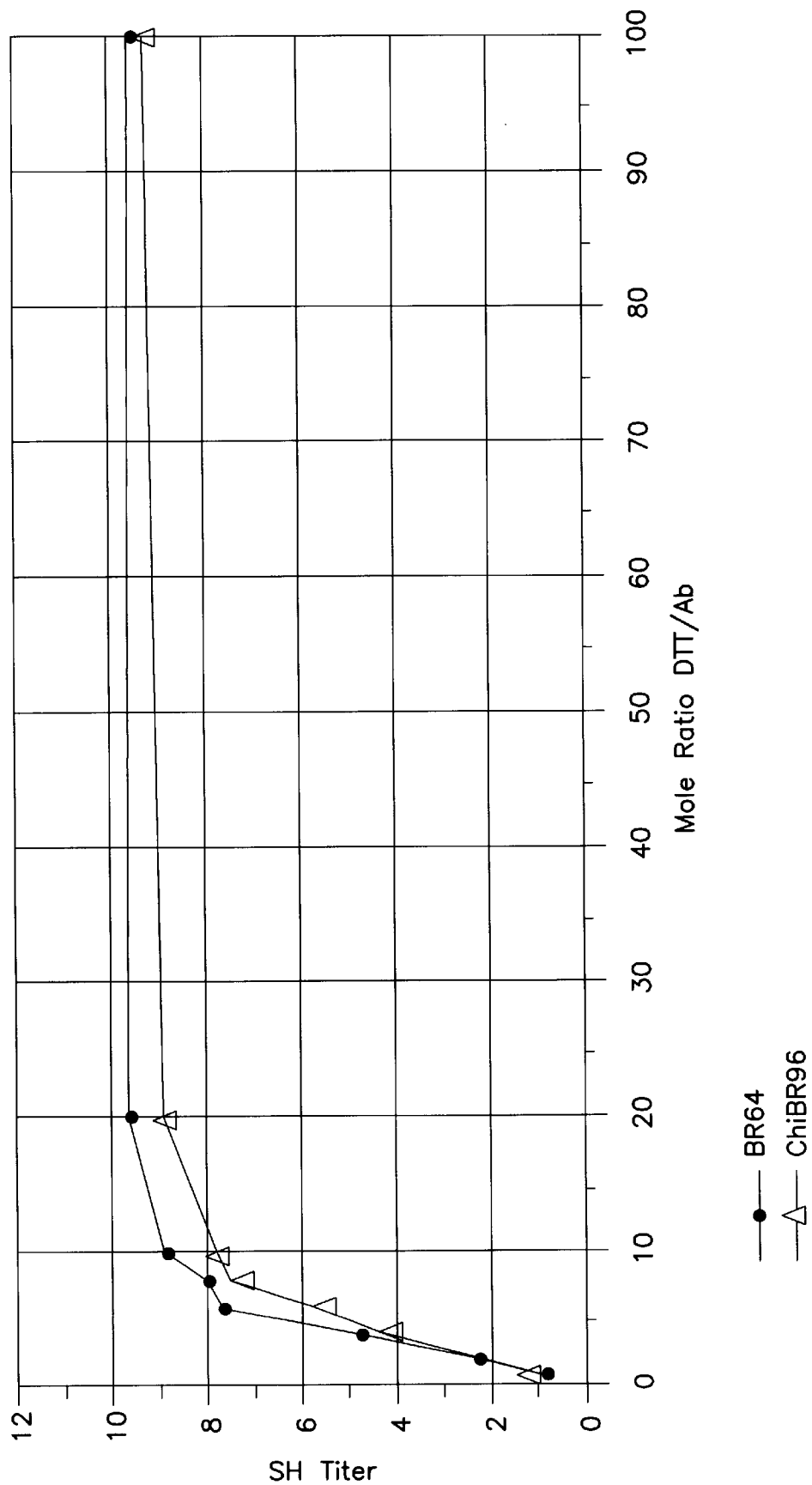

FIG. 62 provides a graph of the effect on —SH titer as a function of mole ratio of DTT to antibody in the preparation, under an inert atmosphere, of a relaxed antibody.

DETAILED DESCRIPTION OF THE INVENTION

DEFINITIONS

As used in this application, the following words or phrases have the meanings specified.

As used herein, "functional equivalent" means being capable of (1) binding the antigen binding site to which BR96 is directed (i.e. competitively inhibit the antigen binding site), (2) binding carcinoma cells, (3) being internalized within the carcinoma cells to which they bind, and/or (4) mediating ADCC and CDC effector functions.

As used herein, "joined" means to couple directly or indirectly one molecule with another by whatever means, e.g., by covalent bonding, by non-covalent bonding, by ionic bonding, or by non-ionic bonding. Covalent bonding includes bonding by various linkers such as thioether linkers or thioester linkers. Direct coupling involves one molecule attached to the molecule of interest. Indirect coupling involves one molecule attached to another molecule not of interest which in turn is attached directly or indirectly to the molecule of interest.

As used herein, "recombinant molecule" means a molecule produced by genetic engineering methods.

As used herein, "fragment" is defined as at least a portion of the variable region of the immunoglobulin molecule which binds to its target, i.e. the antigen binding region. Some of the constant region of the immunoglobulin may be included.

As used herein, an "immunoconjugate" means any molecule or ligand such as an antibody or growth factor chemically or biologically linked to a cytotoxin, a radioactive agent, an anti-tumor drug or a therapeutic agent. The antibody or growth factor may be linked to the cytotoxin, radioactive agent, anti-tumor drug or therapeutic agent at any location along the molecule so long as it is able to bind its target. Examples of immunoconjugates include immunotoxins and antibody conjugates.

As used herein, "selectively killing" means killing those cells to which the antibody binds.

As used herein, examples of "carcinomas" include bladder, breast, colon, liver, lung, ovarian, and pancreatic carcinomas.

As used herein, "immunotoxin" means an antibody or growth factor chemically or biologically linked to a cytotoxin or cytotoxic agent.

As used herein, an "effective amount" is an amount of the antibody, immunoconjugate, recombinant molecule which kills cells or inhibits the proliferation thereof.

As used herein, "competitively inhibits" means being capable of binding to the same target as another molecule. With regard to an antibody, competitively inhibits mean that the antibody is capable of recognizing and binding the same antigen binding region to which another antibody is directed.

As used herein, "antigen-binding region" means that part of the antibody, recombinant molecule, the fusion protein, or the immunoconjugate of the invention which recognizes the target or portions thereof.

As used herein, "therapeutic agent" means any agent useful for therapy including anti-tumor drugs, cytotoxins, cytotoxin agents, and radioactive agents.

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, mytotane (O,P'-(DDD)), interferons and radioactive agents.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

As used herein, "a radioactive agent" includes any radioisotope which is effective in destroying a tumor. Examples include, but are not limited to, cobalt-60 and X-rays. Additionally, naturally occurring radioactive elements such as uranium, radium, and thorium which typically represent mixtures of radioisotopes, are suitable examples of a radioactive agent.

As used herein, "administering" means oral administration, administration as a suppository, topical contact, intravenous, intraperitoneal, intramuscular or subcutaneous administration, or the implantation of a slow-release device such as a miniosmotic pump, to the subject.

As used herein, "directly" means the use of antibodies coupled to a label. The specimen is incubated with the labeled antibody, unbound antibody is removed by washing, and the specimen may be examined.

As used herein, "indirectly" means incubating the specimen with an unconjugated antibody, washing and incubating with a fluorochrome-conjugated antibody. The second or "sandwich" antibody thus reveals the presence of the first.

As used herein "reacting" means to recognize and bind the target. The binding may be non-specific. Specific binding is preferred.

As used herein, "curing" means to provide substantially complete tumor regression so that the tumor is not palpable for a period of time, i.e., $\geq 10$ tumor volume doubling delays (TVDD=the time in days that it takes for control tumors to double in size).

As used herein, "tumor associated antigens" means any cell surface antigen which is generally associated with tumor cells, i.e., occurring to a greater extent as compared with normal cells. Such antigens may be tumor specific. Alternatively, such antigens may be found on the cell surface of both tumorigenic and non-tumorigenic cells. These antigens need not be tumor specific. However, they are generally more frequently associated with tumor cells than they are associated with normal cells.

As used herein, "tumor targeted antibody" means any antibody which recognizes cell surface antigens on tumor (i.e., cancer) cells. Although such antibodies need not be tumor specific, they are tumor selective, i.e. bind tumor cells more so than it does normal cells.

As used herein, "internalizing tumor targeted antibody" includes any tumor targeted antibody which is easily taken up by the tumor cells to which they bind.

As used herein, "internalizing tumor targeted antibody which recognizes the $Le^y$ determinant" includes internalizing tumor targeted antibody which specifically recognizes at least a portion of the $Le^y$ determinant.

As used herein, "inhibit proliferation" means to interfere with cell growth by whatever means.

As used herein, "mammalian tumor cells" include cells from animals such as human, ovine, porcine, murine, bovine animals.

As used herein, "pharmaceutically acceptable carrier" includes any material which when combined with the antibody retains the antibody's immunogenicity and non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules.

Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

In order that the invention herein described may be more fully understood, the following description is set forth.

1. Novel Antibodies of the Invention.

The present invention relates to novel antibodies that are highly specific for carcinoma cells. More particularly, the antibodies react with a range of carcinomas such as breast, lung, ovary and colon carcinomas, while showing none or limited reactivity with normal human tissues or other types of tumors such as sarcomas or lymphomas.

One type of novel antibodies of the invention is designated BR96. The BR96 antibodies can be used to isolate and characterize the antigen to which they bind. Thus, the BR96 antibodies can be used as a probe to identify and characterize the epitope recognized and to further define the cell membrane antigen with which they react [see, e.g., Nudelman et al., "Characterization of Human Melanoma-Associated Ganglioside Antigen Defined By A Monoclonal Antibody, 4.2", *J. Biol. Chem.,* 257 (1)12752–56 (1982) and Hakomori, "Tumor Associated Carbohydrate Antigens", *Ann. Rev. Immunol.,* 2:103–26 (1984)].

BR96 recognizes as at least part of its binding site a portion of an epitope of a Le$^y$ carbohydrate determinant which is a portion of an antigen abundantly expressed on carcinomas of the colon, breast, ovary, and lung and, to a lesser extent, on epithelial cells from the gastrointestinal tract. Further, BR96 in the absence of effector cells or complement can inhibit tumor cell DNA synthesis.

Results of preliminary epitope screens conducted on monoclonal antibody BR96 have indicated that the epitope which is a portion of the antigen on the carcinoma cells to which BR96 antibody binds is a fucosylated variant of Lewis Y (Le$^y$). Le$^y$ has been described by Abe et al., *J. Biol. Chem.* 258:8934 (1983); Lloyd et al., *Immunogenetics* 17:537 (1983); Brown et al., *Biosci. Rep.* 3:163 (1983); and Hellstrom et al., *Cancer Res.* 46:3917 (1986). Certain fucosylated variants of Lewis Y have been described by Abe et al., *Cancer Res.* 46:2639–2644 (1986).

The monoclonal antibody of the invention can be produced using well-established hybridoma techniques first introduced by Kohler and Milstein [see, Kohler and Milstein, "Continuous Cultures Of Fused Cells Secreting Antibody Of Pre-Defined Specificity", *Nature,* 256:495–97 (1975). See, also, Brown et al., "Structural Characterization Of Human Melanoma-Associated Antigen p97 with Monoclonal Antibodies", *J. Immunol.,* 127 (2):539–46 (1981)]; Brown et al., "Protein Antigens Of Normal And Malignant Human Cells Identified By Immunoprecipitation With Monoclonal Antibodies", *J. Biol. Chem.,* 255:4980–83 (1980); Yeh et al., "Cell Surface Antigens Of Human Melanoma Identified By Monoclonal Antibody", *Proc. Natl. Acad. Sci. USA,* 76(6):297–31 (1979); and Yeh et al., "A Cell-Surface Antigen Which is Present In the Ganglioside Fraction And Shared By Human Melanomas", *Int. J. Cancer,* 29:269–75 (1982)].

These techniques involve the injection of an immunogen (e.g., cells or cellular extracts carrying the antigen or purified antigen) into an animal (e.g., a mouse) so as to elicit a desired immune response (i.e., antibodies) in that animal. After a sufficient time, antibody-producing lymphocytes are obtained from the animal either from the spleen, lymph nodes or peripheral blood. Preferably, the lymphocytes are obtained from the spleen. The splenic lymphocytes are then fused with a myeloma cell line, usually in the presence of a fusing agent such as polyethylene glycol (PEG). Any of a number of myeloma cell lines may be used as a fusion partner according to standard techniques; for example, the P3-NS1/1Ag4-1, P3-x63-Ag8.653 or Sp2/O Ag14 myeloma lines. These myeloma lines are available from the American Type Culture Collection ("ATCC") in Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting conditions to obtain isolated clones. The supernatants of the hybridomas are screened for the presence of antibody of that desired specificity, e.g., by immunoassay techniques using the antigen that had been used for immunization. Positive clones can then be subcloned under limiting dilution conditions and the monoclonal antibody produced can be isolated. Hybridomas produced according to these methods can be propagated in vitro or in vivo (in ascites fluid) using techniques known in the art [see, generally, Fink et al., supra at page 123, FIGS. 6–11].

Commonly used methods for purifying monoclonal antibodies include ammonium sulfate precipitation, ion exchange chromatography, and affinity chromatography [see, e.g., Zola et al., "Techniques For The Production And Characterization Of Monoclonal Hybridoma Antibodies", in *Monoclonal Hybridoma Antibodies: Techniques And Applications,* Hurell (ed.), pp. 51–52 (CRC Press 1982)].

According to a preferred embodiment, a monoclonal antibody of this invention, designated BR96, was produced via the hybridoma techniques described hereinbelow using a breast cancer cell line 3396 as the immunogen. The BR96 hybridoma, prepared as described hereinbelow and producing the BR96 antibody, was deposited on Feb. 22, 1989 with the American Type Culture Collection (ATCC), 12301 Parklawn Drive, Rockville, Md. 20852 and has there been identified as follows:

BR96 ATCC Accession No.: HB 10036

The BR96 antibody is of the IgG3 subclass. The antibody displays a high specificity for carcinoma cells of different organ types, for example, tumors of the breast, lung, colon and ovary as well as cultured cell lines established from various breast, lung and colon carcinomas. Furthermore, the BR96 antibody shows no binding to other types of tumor cells such as the T-cell lymphoma cells lines, CEM and MOLT-4, the B cell lymphoma cell line P3HR-1 or melanoma cell lines. The BR96 antibody is able to be internalized in antigen-positive tumor cells, is toxic to antigen-positive tumor cells, mediates antibody-dependent cellular cytotoxicity and complement-dependent cytotoxicity activity, and surprisingly, is cytotoxic alone, i.e. in unmodified form. The BR96 antibodies appear to recognize a novel epitope of the Le$^y$ determinant.

The present invention provides an immunoconjugate comprising a molecule having the antigen-binding region of the BR96 monoclonal antibody joined to doxorubicin. It would be clear that doxorubicin may be joined at any location along the molecule so long as it retains its ability to bind its target. Doxorubicin may be joined by any means including chemical and biological means.

Clearly analogs and homologs of doxorubicin are encompassed by the invention. For example, an improved analog of doxorubicin is Fe-chelate.

2. Fragments of the Monoclonal Antibodies of the Invention.

According to another embodiment, F(ab')$_2$ fragments of the BR96 monoclonal antibody were produced by pepsin digestion of purified BR96 [Lamoyi, "Preparation of F(ab')$_2$ Fragments from Mouse IgG of Various Subclasses", *Methods of Enzymol.* 121:652–663 (1986)], as described hereinbelow. The binding of the F(ab')$_2$ fragments to tumor (3396) and MCF7 cells was shown to be comparable to the binding of the whole BR96 monoclonal antibody.

3. Chimeric Antibodies of the Invention.

In another preferred embodiment, a chimeric (murine/human) antibody of the invention was produced using a two-step homologous recombination procedure as described by Fell et al., in *Proc. Natl. Acad. Sci. USA* 86:8507–8511 (1989) and in co-pending patent application U.S. Ser. No. 243,873, filed Sep. 14, 1988, and Ser. No. 468,035, filed Jun. 22, 1990, assigned to the same assignee as the present application; the disclosures of all of these documents are incorporated in their entirety by reference herein. This two-step protocol involves use of a target vector encoding human IgGγ1 heavy chain to transfect a mouse hybridoma cell line expressing murine BR96 monoclonal antibody (hybridoma ATCC No. HB 10036) to produce a hybridoma expressing a BR96 chimeric antibody containing human IgGγ1 heavy chain. This hybridoma is then transfected with a target vector containing DNA encoding human kappa (K) light chain to produce a murine hybridoma expressing a BR96 chimeric antibody containing human IgGγ1 heavy chain and human K light chain. The target vectors used to transfect the hybridomas are the phγ1HC-D vector digested with Xba1 enzyme (Bristol-Myers Squibb Co., Seattle, Wash., NRRL No. B 18599) and the HindIII digested pSV$_2$gpt/C$_K$ vector (Bristol-Myers Squibb Co., Seattle, Wash., NRRL No. B 18507).

The chimeric BR96 hybridoma, identified herein as ChiBR96, prepared as described hereinbelow and producing the chimeric human/murine BR96 antibody, was deposited on May 23, 1990, with the ATCC, 12301 Parklawn Drive, Rockville, Md. 20852 and has there been identified as follows:

ChiBR96 ATCC Accession No.: HB 10460

Once the hybridoma that expresses the chimeric antibody is identified, the hybridoma is cultured and a desired chimeric molecules are isolated from the cell culture supernatant using techniques well known in the art for isolating monoclonal antibodies.

The term "BR96 antibody" as used herein includes whole, intact polyclonal and monoclonal antibody materials such as the murine BR96 monoclonal antibody produced by hybridoma ATCC No. HB 10036, and chimeric antibody molecules such as chimeric BR96 antibody produced by hybridoma ATCC No. 10460. The BR96 antibody described above includes any fragments thereof containing the active antigen-binding region of the antibody such as Fab, F(ab')$_2$ and Fv fragments, using techniques well established in the art [see, e.g., Rousseaux et al., "Optimal Conditions For The Preparation of Proteolytic Fragments From Monoclonal IgG of Different Rat IgG Subclasses", in *Methods Enzymol.,* 121:663–69 (Academic Press 1986)]. The BR96 antibody of the invention also includes fusion proteins.

In addition, the BR96 antibody of this invention does not display any immunohistologically detectable binding to normal human tissues from major organs, such as kidney, spleen, liver, skin, lung, breast, colon, brain, thyroid, heart, lymph nodes or ovary. Nor does the antibody react with peripheral blood leukocytes. BR96 antibody displays limited binding to some cells in the tonsils and testes, and binds to acinar cells in the pancreas, and to epithelial cells in the stomach and esophagus. Thus, the BR96 antibody is superior to most known antitumor antibodies in the high degree of specificity for tumor cells as compared to normal cells [see, e.g., Hellstrom et al., "Immunological Approaches To Tumor Therapy: Monoclonal Antibodies, Tumor Vaccines, And Anti-Idiotypes", in *Covalently Modified Antigens And Antibodies In Diagnosis And Therapy,* Quash/Rodwell (eds.), pp. 1–39 (Marcel Dekker, Inc., 1989) and Bagshawe, "Tumour Markers—Where Do We Go From Here", *Br. J. Cancer,* 48:167–75 (1983)].

Also included within the scope of the invention are anti-idiotypic antibodies to the BR96 antibody of the invention. These anti-idiotypic antibodies can be produced using the BR96 antibody and/or the fragments thereof as immunogen and are useful for diagnostic purposes in detecting humoral response to tumors and in therapeutic applications, e.g., in a vaccine, to induce an anti-tumor response in patients [see, e.g., Nepom et al., "Anti-Idiotypic Antibodies And The Induction Of Specific Tumor Immunity", in *Cancer And Metastasis Reviews,* 6:487–501 (1987)].

In addition, the present invention encompasses antibodies that are capable of binding to the same antigenic determinant as the BR96 antibodies and competing with the antibodies for binding at that site. These include antibodies having the same antigenic specificity as the BR96 antibodies but differing in species origin, isotype, binding affinity or biological functions (e.g., cytotoxicity). For example, class, isotype and other variants of the antibodies of the invention having the antigen-binding region of the BR96 antibody can be constructed using recombinant class-switching and fusion techniques known in the art [see, e.g., Thammana et al., "Immunoglobulin Heavy Chain Class Switch From IgM to IgG In A Hybridoma", *Eur. J. Immunol.,* 13:614 (1983); Spira et al., "The Identification Of Monoclonal Class Switch Variants By Subselection And ELISA Assay", *J. Immunol. Meth.,* 74:307–15 (1984); Neuberger et al., "Recombinant Antibodies Possessing Novel Effector Functions", *Nature,* 312: 604–608 (1984); and Oi et al., "Chimeric Antibodies", *Biotechniques,* 4 (3):214–21 (1986)]. Thus, other chimeric antibodies or other recombinant antibodies (e.g., fusion proteins wherein the antibody is combined with a second protein such as a lymphokine or a tumor inhibitory growth factor) having the same binding specificity as the BR96 antibodies fall within the scope of this invention.

Genetic engineering techniques known in the art are used as described herein to prepare recombinant immunotoxins produced by fusing antigen binding regions of antibody BR96 to a therapeutic or cytotoxic agent at the DNA level and producing the cytotoxic molecule as a chimeric protein.

Examples of therapeutic agents include, but are not limited to, antimetabolites, alkylating agents, anthracyclines, antibiotics, and anti-mitotic agents.

Antimetabolites include methotrexate, 6-mercaptopurine, 6-thioguanine, cytarabine, 5-fluorouracil decarbazine.

Alkylating agents include mechlorethamine, thiotepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin.

Anthracyclines include daunorubicin (formerly daunomycin) and doxorubicin (also referred to herein as adriamycin). Additional examples include mitozantrone and bisantrene.

Antibiotics include dactinomycin (formerly actinomycin), bleomycin, mithramycin, and anthramycin (AMC).

Antimyotic agents include vincristine and vinblastine (which are commonly referred to as vinca alkaloids).

Other cytotoxic agents include procarbazine, hydroxyurea, asparaginase, corticosteroids, mytotane (O,P'-(DDD)), interferons.

Further examples of cytotoxic agents include, but are not limited to, ricin, doxorubicin, taxol, cytochalasin B, gramicidin D, ethidium bromide, etoposide, tenoposide, colchicin, dihydroxy anthracin dione, 1-dehydrotestosterone, and glucocorticoid.

Clearly analogs and homologs of such therapeutic and cytotoxic agents are encompassed by the present invention. For example, the chemotherapuetic agent aminopterin has a correlative improved analog namely methotrexate.

Further, the improved analog of doxorubicin is an Fe-chelate. Also, the improved analog for 1-methylnitrosourea is lomustine. Further, the improved analog of vinblastine is vincristine. Also, the improved analog of mechlorethamine is cyclophosphamide.

4. Immunotoxins of the Invention.

Recombinant immunotoxins, particularly single-chain immunotoxins, have an advantage over drug/antibody conjugates in that they are more readily produced than these conjugates, and generate a population of homogenous molecules, i.e. single peptides composed of the same amino acid residues.

The techniques for cloning and expressing DNA sequences encoding the amino acid sequences corresponding to the single-chain immunotoxin BR96 sFv-PE40, e.g synthesis of oligonucleotides, PCR, transforming cells, constructing vectors, expression systems, and the like are well-established in the art, and most practitioners are familiar with the standard resource materials for specific conditions and procedures [see, e.g. Sambrook et al., eds., Molecular Cloning, A Laboratory Manual, 2nd Edition, Cold Spring Harbor Laboratory Press (1989)].

Details of the construction of the single-chain recombinant immunotoxin of the invention, BR96 sFv-PE40 are provided in Example 13, infra. Briefly, polymerase chain reaction (PCR) [Mullis et al., U.S. Pat. Nos. 4,683,195 and 4,683,202; Mullis and Faloona, *Methods Enzymol.* 154:335–350 (1987)] is used to amplify a 550 bp BR96 sFv sequence (FIG. 35) encoded by plasmid pBR96 Fv using the selected primers.

After PCR amplification and enzymatic digestion the 550 bp fragment is ligated using standard procedures into a 4220 bp fragment from vector pMS8 [Covell et al., *Cancer Res.* 46:3969–3978 (1986)] encoding the gene for PE40 to form intermediate vector pBW 7.01.

A fragment from pBR96 Fv is then subcloned into pBW 7.01 to form plasmid pBW 7.0 encoding the BR96 sFv-PE40 gene fusion. Correct ligations for vector construction are confirmed by DNA sequence analysis using known procedures [Sanger et al., *Proc. Natl. Acad. Sci. USA* 74:5463 (1977) and Messing et al. *Nucleic Acids Res.* 9:309 (1981)]. Colonies are then screened by restriction enzyme digestion for the appropriate plasmids.

The following include preferred embodiments of the immunoconjugates of the invention. Other embodiments which are known in the art are encompassed by the invention. Specific embodiments are set forth in the Examples which follow.

The invention is not limited to these specific immunoconjugates, but also includes other immunoconjugates incorporating antibodies and/or antibody fragments according to the present invention.

The conjugates comprise at least one drug molecule connected by a linker of the invention to a targeting ligand molecule that is reactive with the desired target cell population. The ligand molecule can be an immunoreactive protein such as an antibody, or fragment thereof, a non-immunoreactive protein or peptide ligand such as bombesin or, a binding ligand recognizing a cell associated receptor such as a lectin or steroid molecule.

As previously noted, a conjugate of the invention is represented by general Formula (I):

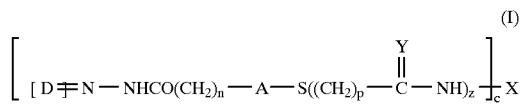

in which
D is a drug molecule;
n is 1 to 10;
p is 1 to 6;
Y is O or NH$_2^+$Cl$^-$;
z is 0 or 1;

q is about 1 to about 10;
X is a ligand; and,
A is Michael Addition Adduct

For a better understanding of the invention, the drugs and ligands will be discussed individually. The intermediate used for the preparation of the conjugates and the synthesis of the conjugates then will be explained.

THE DRUG

One skilled in the art understands that the present invention requires the drug and ligand to be linked by means of an acylhydrazone linkage, through a Michael Addition Adduct and thioether-containing linker. Neither the specific drug nor the specific ligand is to be construed as a limitation on the present invention. The linkers of the present invention may be used with any drug having any desired therapeutic, biological activity-modifying or prophylactic purpose, limited only in that the drug used in preparing the conjugate be able to form an hydrazone bond. Preferably, to prepare the hydrazone, the drug should have a reactively available carbonyl group, such as, for example, a reactive aldehyde or ketone moiety (represented herein as "[D-(C=O)]") which is capable of forming a hydrazone (i.e. a —C=N—NH— linkage). The drug hydrazone linkage is represented herein as "[D≈N—NH—". In addition, the reaction of that reactively available group with the linker preferably must not destroy the ultimate therapeutic activity of the conjugate, whether that activity is the result of the drug being released at the desired site of action or whether the intact conjugate, itself, is responsible for such activity.

One skilled in the art understands that for those drugs which lack a reactively available carbonyl group, a derivative containing such a carbonyl group may be prepared using procedures known in the art. As can be appreciated, the conjugate prepared from such derivatized drug must retain therapeutic activity when present at the active site, whether this is due to the intact conjugate, or otherwise. Alternatively, the derivatized drug or, for example, a prodrug, must be released in such a form that a therapeutically active form of the drug is present at the active site.

The present linker invention may be used in connection with drugs of substantially all therapeutic classes including, for example, antibacterials, antivirals, antifungals, anticancer drugs, antimycoplasmals, and the like. The drug conjugates so constructed are effective for the usual purposes for which the corresponding drugs are effective, and have superior efficacy because of the ability, inherent in the ligand, to transport the drug to the desired cell where it is of particular benefit.

Further, because the conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factory ("GM-CSF"), granulocyte colony stimulating factory ("G-CSF"), or other growth factors.

The preferred drugs for use in the present invention are cytotoxic drugs, particularly those which are used for cancer therapy. Such drugs include, in general, alkylating agents, anti-proliferative agents, tubulin binding agents and the like. Preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, carminomycin, daunorubicin, aminopterin, methotrexate, methopterin, dichloromethotrexate, mitomycin C, porfiromycin, 5-fluorouracil, 6-mercaptopurine, cytosine arabinoside, podophyllotoxin, or podophyllotoxin derivatives such as etoposide or etoposide phosphate, melphalan, vinblastine, vincristine, leurosidine, vindesine, leurosine and the like. As noted previously, one skilled in the art may make chemical modifications to the desired compound in order to make reactions of that compound more convenient for purposes of preparing conjugates of the invention.

A highly preferred group of cytotoxic agents for use as drugs in the present invention include drugs of the following formulae:

THE METHOTREXATE GROUP OF FORMULA (2):

$R^9$ is hydroxy or a moiety which completes a salt of the carboxylic acid;

THE MITOMYCIN GROUP OF FORMULA (3):

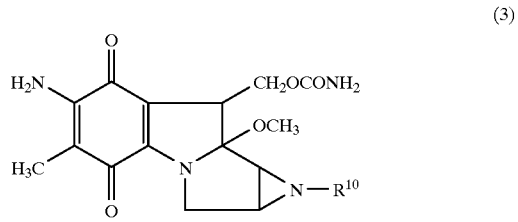

(3)

in which $R^{10}$ is hydrogen or methyl;

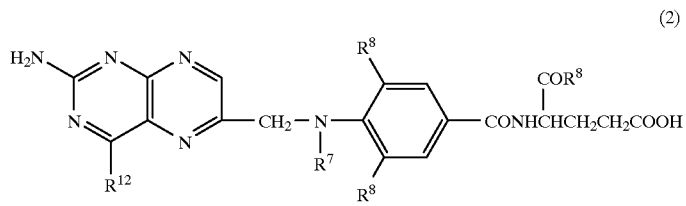

(2)

in which $R^{12}$ is amino or hydroxy;

$R^7$ is hydrogen or methyl;

$R^8$ is hydrogen, fluoro, chloro, bromo or iodo;

THE BLEOMYCIN GROUP OF FORMULA (4):

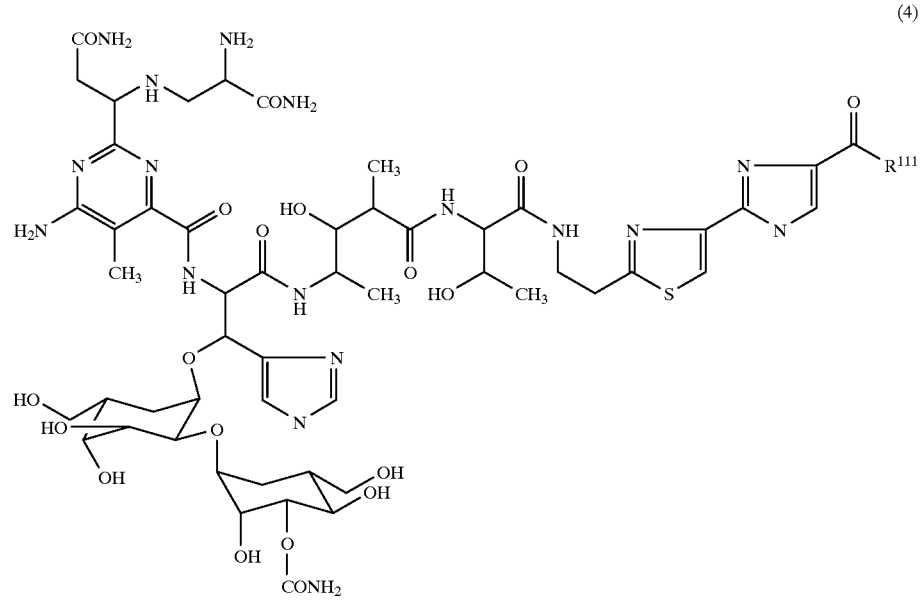

(4)

in which $R^{11}$ is hydroxy, amino, $C_1$–$C_3$ alkylamino, di($C_1$–$C_3$ alkyl)amino, $C_4$–$C_6$ polymethylene amino,

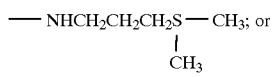

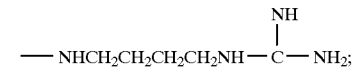

MELPHALAN OF FORMULA (5):

(5)

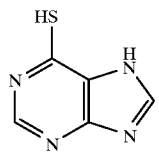

6-MERCAPTOPURINE OF FORMULA (6):

(6)

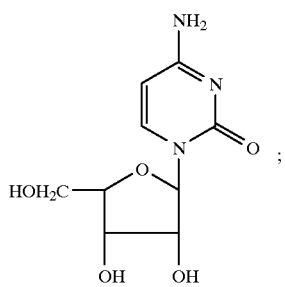

A CYTOSINE ARABINOSIDE OF FORMULA (7):

(7)

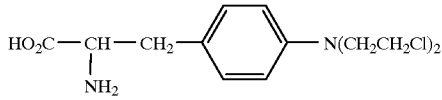

THE PODOPHYLLOTOXINS OF FORMULA (8):

(8)

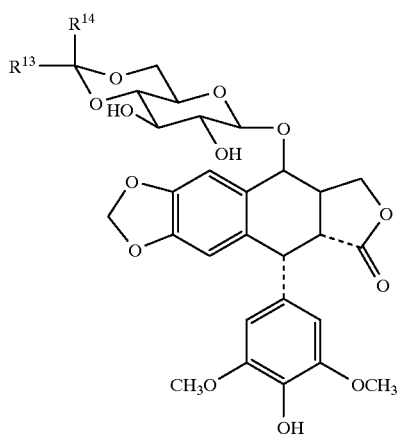

in which
$R^{13}$ is hydrogen or methyl;
$R^{14}$ is methyl or thienyl;
or a phosphate salt thereof;

THE VINCA ALKALOID GROUP OF DRUGS OF FORMULA (9):

(9)

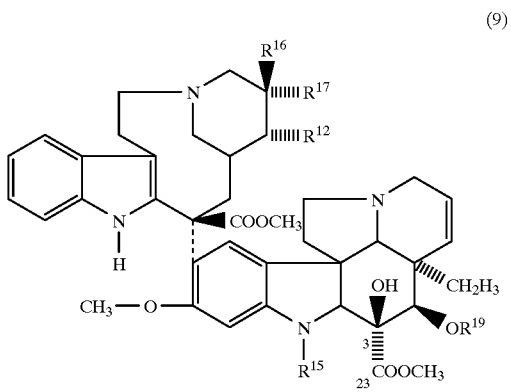

in which $R^{15}$ is H, $CH_3$ or CHO; when $R^{17}$ and $R^{18}$ are taken singly, $R^{18}$ is H, and one of $R^{16}$ and $R^{17}$ is ethyl and the other is H or OH; when $R^{17}$ and $R^{18}$ are taken together with the carbons to which they are attached, they form an oxirane ring in which case $R^{16}$ is ethyl; $R^{19}$ is hydrogen, ($C_1$–$C_3$ alkyl)-CO, or chlorosubstituted ($C_1$–$C_3$ alkyl)-CO;

DIFLUORONUCLEOSIDES OF FORMULA (10):

(10)

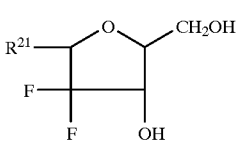

in which $R^{21}$ is a base of one of the formulae:

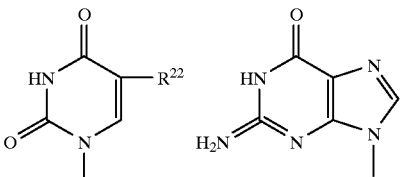

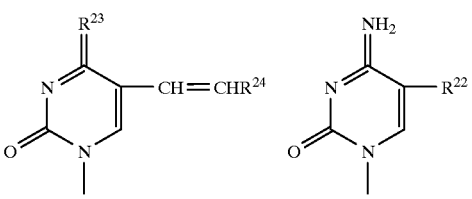

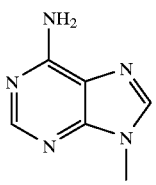

in which
$R^{22}$ is hydrogen, methyl, bromo, fluoro, chloro or iodo;
$R^{23}$ is —OH or —$NH_2$;

$R^{24}$ is hydrogen, bromo, chloro or iodo;

THE ANTHRACYCLINES ANTIBIOTICS OF FORMULA (11):

of anthracycline drugs and their generic or trivial names and which are especially preferred for use in the present invention.

TABLE 14

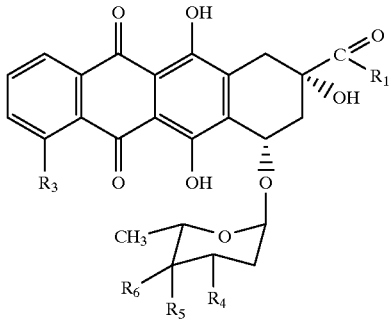

Formula (1)

| Compound | $R_1$ | $R_3$ | $R_4$ | $R_5$ | $R_6$ |
|---|---|---|---|---|---|
| Daunorubicin[a] | $CH_3$ | $OCH_3$ | $NH_2$ | OH | H |
| Adriamycin[b] | $CH_2OH$ | $OCH_3$ | $NH_2$ | OH | H |
| Detorubicin | $CH_2OCOCH(OC_2H_5)_2$ | $OCH_3$ | $NH_2$ | OH | H |
| Carminomycin | $CH_3$ | OH | $NH_2$ | OH | H |
| Idarubicin | $CH_3$ | H | $NH_2$ | OH | H |
| Epirubicin | $CH_2OH$ | $OCH_3$ | $NH_2$ | H | OH |
| Esorubicin | $CH_2OH$ | $OCH_3$ | $NH_2$ | H | H |
| THP | $CH_2OH$ | $OCH_3$ | $NH_2$ | OTHP | H |
| AD-32 | $CH_2OCO(CH_2)_3CH_3$ | $OCH_3$ | $NHCOCF_3$ | OH | H |

[a]"Daunomycin" is an alternate name for daunorubicin
[b]"Doxorubicin" is an alternate name for adriamycin

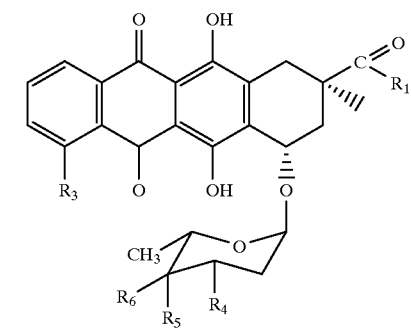

(11)

wherein $R_1$ is —$CH_3$, —$CH_2OH$, —$CH_2OCO(CH_2)_3CH_3$ or —$CH_2OCOCH(OC_2H_5)_2$ $R_3$ is —$OCH_3$, —OH or —H $R_4$ is —$NH_2$, —$NHCOCF_3$, 4-morpholinyl, 3-cyano-4-morpholinyl, 1-piperidinyl, 4-methoxy-1-piperidinyl, benzylamine, dibenzylamine, cyanomethylamine, or 1-cyano-2-methoxyethyl amine $R_5$ is —OH, —OTHP, or —H; and, $R_6$ is —OH or —H provided that $R_6$ is not —OH when $R_5$ is —OH or —OTHP.

The most highly preferred drugs are the anthracycline antibiotic agents of Formula (11), described previouly. One skilled in the art understands that this structural formula includes compounds which are drugs, or are derivatives of drugs, which have acquired in the art different generic or trivial names. Table 14, which follows, represents a number Of the compounds shown in Table 14, the most highly preferred drug is adriamycin. Adriamycin (also referred to herein as "ADM") is that anthracycline of formula (11) in which $R_1$ is —$CH_2OH$, $R_3$ is —$OCH_3$, $R_4$ is —$NH_2$, $R_5$ —OH, and $R_6$ is —H.

THE LIGANDS

One skilled in the art understands that "ligand" includes within its scope any molecule that specifically binds or reactively associates or complexes with a receptor or other receptive moiety associated with a given target cell population. This cell reactive molecule, to which the drug reagent is linked via the linker in the conjugate, can be any molecule that binds to, complexes with or reacts with the cell population sought to be therapeutically or otherwise biologically modified and, which possesses a free reactive sulfhydryl (—SH) group or can be modified to contain a such a sulfhydryl group. The cell reactive molecule acts to deliver the therapeutically active drug moiety to the particular target cell population with which the ligand reacts. Such molecules include, but are not limited to, large molecular weight proteins (generally greater than 10,000 daltons) such as, for example, antibodies, smaller molecular weight proteins (generally, less than 10,000 daltons), polypeptide or peptide ligands, and non-peptidyl ligands.

The non-immunoreactive protein, polypeptide, or peptide ligands which can be used to form the conjugates of this invention may include, but are not limited to, transferrin, epidermal growth factors ("EGF"), bombesin, gastrin, gastrin-releasing peptide, platelet-derived growth factor, IL-2, IL-6, tumor growth factors ("TGF"), such as TGF-α and TGF-β, vaccinia growth factor ("VGF"), insulin and insulin-like growth factors I and II. Non-peptidyl ligands may include, for example, steroids, carbohydrates and lectins.

The immunoreactive ligands comprise an antigen-recognizing immunoglobulin (also referred to as "antibody"), or antigen-recognizing fragment thereof. Particularly preferred immunoglobulins are those immunoglobulins which can recognize a tumor-associated antigen. As used, "immunoglobulin" may refer to any recognized class or subclass of immunoglobulins such as IgG, IgA, IgM, IgD, or IgE. Preferred are those immunoglobulins which fall within the IgG class of immunoglobulins. The immunoglobulin can be derived from any species. Preferably, however, the immunoglobulin is of human, murine, or rabbit origin. Further, the immunoglobulin may be polyclonal or monoclonal, preferably monoclonal.

As noted, one skilled in the art will appreciate that the invention also encompasses the use of antigen recognizing immunoglobulin fragments. Such immunoglobulin fragments may include. For example, the Fab', F(ab')$_2$, F$_v$, or Fab fragments, or other antigen recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing such immunoglobulin fragments are well-known to those skilled in the art. See generally, Parham, *J. Immunology*, 131, 2895 (1983); Lamoyi et al., *J. Immunological Methods*, 56, 235 (1983); Parham, id., 53, 133 (1982); and Matthew et al., id., 50, 239 (1982).

The immunoglobulin can be a "chimeric antibody" as that term is recognized in the art. Also, the immunoglobulin may be a "bifunctional" or "hybrid" antibody, that is, an antibody which may have one arm having a specificity for one antigenic site, such as a tumor associated antigen while the other arm recognizes a different target, for example, a hapten which is, or to which is bound, an agent lethal to the antigen-bearing tumor cell. Alternatively, the bifunctional antibody may be one in which each arm has specificity for a different epitope of a tumor associated antigen of the cell to be therapeutically or biologically modified. In any case, the hybrid antibodies have a dual specificity, preferably with one or more binding sites specific for the hapten of choice or one or more binding sites specific for a target antigen, for example, an antigen associated with a tumor, an infectious organism, or other disease state.

Biological bifunctional antibodies are described, for example, in European Patent Publication, EPA 0 105 360, to which those skilled in the art are referred. Such hybrid or bifunctional antibodies may be derived, as noted, either biologically, by cell fusion techniques, or chemically, especially with cross-linking agents or disulfide bridge-forming reagents, and may be comprised of whole antibodies and/or fragments thereof. Methods for obtaining such hybrid antibodies are disclosed, for example, in PCT application W083/03679, published Oct. 27, 1983, and published European Application EPA 0 217 577, published Apr. 8, 1987, both of which are incorporated herein by reference. Particularly preferred bifunctional antibodies are those biologically prepared from a "polydoma" or "quadroma" or which are synthetically prepared with cross-linking agents such as bis-(maleimido)-methyl ether ("BMME"), or with other cross-linking agents familiar to those skilled in the art.

In addition the immunoglobin may be a single chain antibody ("SCA"). These may consist of single chain Fv fragments ("scFv") in which the variable light ("$V_L$") and variable heavy ("$V_H$") domains are linked by a peptide bridge or by disulfide bonds. Also, the immunoglobulin may consist of single $V_H$ domains (dAbs) which possess antigen-binding activity. See, e.g., G. Winter and C. Milstein, *Nature*, 349, 295 (1991); R. Glockshuber et al., *Biochemistry* 29, 1362 (1990); and E. S. Ward et al., *Nature* 341, 544 (1989).

Especially preferred for use in the present invention are chimeric monoclonal antibodies, preferably those chimeric antibodies having specificity toward a tumor associated antigen. As used herein, the term "chimeric antibody" refers to a monoclonal antibody comprising a variable region, i.e. binding region, from one source or species and at least a portion of a constant region derived from a different source or species, usually prepared by recombinant DNA techniques. Chimeric antibodies comprising a murine variable region and a human constant region are especially preferred in certain applications of the invention, particularly human therapy, because such antibodies are readily prepared and may be less immunogenic than purely murine monoclonal antibodies. Such murine/human chimeric antibodies are the product of expressed immunoglobulin genes comprising DNA segments encoding murine immunoglobulin variable regions and DNA segments encoding human immunoglobulin constant regions. Other forms of chimeric antibodies encompassed by the invention are those in which the class or subclass has been modified or changed from that of the original antibody. Such "chimeric" antibodies are also referred to as "class-switched antibodies". Methods for producing chimeric antibodies involve conventional recombinant DNA and gene transfection techniques now well known in the art. See, e.g., Morrison, S. L. et al., *Proc. Nat'l Acad. Sci.*, 81, 6851 (1984).

Encompassed by the term "chimeric antibody" is the concept of "humanized antibody", that is those antibodies in which the framework or "complementarity determining regions" ("CDR") have been modified to comprise the CDR of an immunoglobulin of different specificity as compared to that of the parent immunoglobulin. In a preferred embodiment, a murine CDR is grafted into the framework region of a human antibody to prepare the "humanized antibody". See, e.g., L. Riechmann et al., *Nature* 332, 323 (1988); M. S. Neuberger et al., *Nature* 314, 268 (1985). Particularly preferred CDR's correspond to those representing sequences recognizing the antigens noted above for the chimeric and bifunctional antibodies. The reader is referred to the teaching of EPA 0 239 400 (published Sep. 30, 1987), incorporated herein by reference, for its teaching of CDR modified antibodies.

One skilled in the art will recognize that a bifunctional-chimeric antibody can be prepared which would have the benefits of lower immunogenicity of the chimeric or humanized antibody, as well as the flexibility, especially for therapeutic treatment, of the bifunctional antibodies described above. Such bifunctional-chimeric antibodies can be synthesized, for instance, by chemical synthesis using cross-linking agents and/or recombinant methods of the type described above. In any event, the present invention should not be construed as limited in scope by any particular method of production of an antibody whether bifunctional, chimeric, bifunctional-chimeric, humanized, or an antigen-recognizing fragment or derivative thereof.

In addition, the invention encompasses within its scope immunoglobulins (as defined above) or immunoglobulin fragments to which are fused active proteins, for example, an enzyme of the type disclosed in Neuberger, et al., PCT application, WO86/01533, published Mar. 13, 1986. The disclosure of such products is incorporated herein by reference.

As noted, "bifunctional", "fused", "chimeric" (including humanized), and "bifunctional-chimeric" (including humanized) antibody constructions also include, within their individual contexts constructions comprising antigen recognizing fragments. As one skilled in the art will recognize, such fragments could be prepared by traditional enzymatic cleavage of intact bifunctional, chimeric, humanized, or chimeric-bifunctional antibodies. If, however, intact antibodies are not susceptible to such cleavage, because of the nature of the construction involved, the noted constructions can be prepared with immunoglobulin fragments used as the starting materials; or, if recombinant techniques are used, the DNA sequences, themselves, can be tailored to encode the desired "fragment" which, when expressed, can be combined in vivo or in vitro, by chemical or biological means, to prepare the final desired intact immunoglobulin "fragment". It is in this context, therefore, that the term "fragment" is used.

Furthermore, as noted above, the immunoglobulin (antibody), or fragment thereof, used in the present invention may be polyclonal or monoclonal in nature. Monoclonal antibodies are the preferred immunoglobulins, however. The preparation of such polyclonal or monoclonal antibodies now is well known to those skilled in the art who, of course, are fully capable of producing useful immunoglobulins which can be used in the invention. See, e.g., G. Kohler and C. Milstein, *Nature* 256, 495 (1975). In addition, hybridomas and/or monoclonal antibodies which are produced by such hybridomas and which are useful in the practice of the present invention are publicly available from sources such as the American Type Culture Collection ("ATCC") 12301 Parklawn Drive, Rockville, Md. 20852 or, commercially, for example, from Boehringer-Mannheim Biochemicals, P. O. Box 50816, Indianapolis, Ind. 46250.

Particularly preferred monoclonal antibodies for use in the present invention are those which recognize tumor associated antigens. Such monoclonal antibodies, are not to be so limited, however, and may include, for example, the following:

| Antigen Site Recongnized | Monoclonal Antibodies | Reference |
|---|---|---|
| Lung Tumors | KS1/4 | N. M. Varki, et al., Cancer Res. 44:681, 1984 |
| | 534, F8:604A9 | F. Cuttitta, et al., in: G. L. Wright (ed) Monoclonal AntibodiesandCancer Marcel Dekker, Inc., NY., p. 161, 1984. |
| Squamous Lung | G1, LuCa2, LuCa3, LuCa4 | Kyoizumi et al., CancerRes., 45:3274 1985. |
| Small Cell Lung Cancer | TFS-2 | Okabe et al., CancerRes. 45:1930, 1985. |
| Colon Cancer | 11.285.14 14.95.55 NS-3a-22, NS-10 NS-19-9, NS-33a NS-52a, 17-1A | G. Rowland, et al., Cancer Immunol. Immunother., 19:2, 1985 Z. Steplewski, et al., CancerRes., 41:2723, 1981. |
| Carcinoembryonic | MoAb 35 or ZCE025 | Acolla, R.S. et al., Proc.Natl. Acad.Sci.,(USA), 77:563, 1980. |
| Melanoma | 9.2.27 | T. F. Bumol and R. A. Reisfeld, Proc. Natl. Acad. Sci., (USA), 79: 1245, 1982 |
| p97 | 96.5 | K. E. Hellstrom, et al., MonoclonalAntibodiesand Cancer, loc. cit. p. 31. |
| Antigen T65 | T101 | Boehringer-Mannheim, P.O. Box 50816, Indianapolis, IN 46250 |
| Ferritin | Antiferrin | Boehringer-Mannheim, P.O. Box 50816, Indianapolis, IN 46250 |
| | R24 | W. G. Dippold, et al., Proc. |

-continued

| Antigen Site Recongnized | Monoclonal Antibodies | Reference |
|---|---|---|
| | | Natl.Acad.Sci.(USA), 77:6114, 1980 |
| Neuroblastoma | P1 153/3 | R. H. Kennet and F. Gilbert, Science, 203:1120, 1979. |
| | MIN 1 | J. T. Kemshead in Monoclonal AntibodiesandCancer, loc. cit. p. 49. |
| | UJ13A | Goldman et al., Pediatrics, 105:252, 1984. |
| Gliome | 5F7, GE2, CG12 | N. de Tribolet, et al., in MonoclonalAntibodiesand Cancer, loc. cit. p. 81 |
| Ganglioside | L6 | I. Hellstrom et al. Proc.NatlAcad.Sci.(U.S.A) 83:7059 (1986); U.S. Pat. Nos. 4,906,562, issued March 6, 1990 and 4,935,495, issued June 19, 1990. |
| | Chimeric L6 | U.S. Ser. No. 07/923,244, filed Oct. 27, 1986, equivalent to PCT Patent Publication, WO 88/03145, published May 5, 1988. |
| Lewis Y | BR64 | U. S. Ser. Nos. 07/289,635, filed December 22, 1988, and U. S. Ser. No. 07/443,696, filed Nov. 29, 1989, equivalent to European Patent Publication, EP A 0375 562, published June 27, 1990. |
| fucosylated Lewis Y | BR96, Chimeric BR96 | U.S. Ser. Nos. 07/374,947, filed June 30, 1989, and U. S. Ser. No. 07/544,246, filed June 26, 1990, equivalent to PCT Patent Publication, WO 91/00295, published January 10, 1991. |
| Breast Cancer | B6.2, B72.3 | D. Colcher, et al., in MonoclonalAntibodiesand Cancer, loc. cit. p. 121. |
| Osteogenic Sarcoma | 791T/48, 791T/36 | M. J. Embleton, ibid, p. 181 |
| Leukemia | CALL 2 | C. T. Teng, et al., Lancet, 1:01, 1982 |
| | anti-idiotype | R. A. Miller, et al., N.Eng. J.Med., 306:517, 1982 |
| Ovarian Cancer | OC 125 | R. C. Bast, et al., J.Clin. Invest., 68:1331, 1981. |
| Prostate Cancer | D83.21, P6.2, Turp-27 | J. J. Starling, et al., in MonoclonalAntibodiesand Cancer, loc. cit., P. 253 |
| Renal Cancer | A6H, DBD | P. H. Lange, et al., Surgery, 98:143, 1985. |

In the most preferred embodiment, the ligand containing conjugate is derived from chimeric antibody BR96, "ChiBR96", disclosed in U.S. Ser. No. 07/544,246, filed Jun. 26, 1990, and which is equivalent to PCT Published Application, WO 91/00295, published Jan. 10, 1991. ChiBR96 is an internalizing murine/human chimeric antibody and is reactive, as noted, with the fucosylated Lewis Y antigen expressed by human carcinoma cells such as those derived from breast, lung, colon, and ovarian carcinomas. The hybridoma expressing chimeric BR96 and identified as ChiBR96 was deposited on May 23, 1990, under the terms of the Budapest Treaty, with the American Type Culture Collection ("ATCC"), 12301 Parklawn Drive, Rockville, Md. 20852. Samples of this hybridoma are available under the accession number ATCC HB 10460. ChiBR96 is derived, in part, from its source parent, BR96. The hybridoma expressing BR96 was deposited, on Feb. 21, 1989, at the ATCC, under the terms of the Budapest Treaty, and is available under the accession number HB 10036. The desired hybridoma is cultured and the resulting antibodies are isolated from the cell culture supernatant using standard techniques now well known in the art. See, e.g., "Monoclonal Hybridoma Antibodies: Techniques and Applications", Hurell (ed.) (CRC Press, 1982).

In another highly preferred embodiment the immunoconjugate is derived from the BR64 murine monoclonal antibody disclosed in U.S. Ser. No. 07/289,635, filed Dec. 22, 1988, and, U.S. Ser. No. 07/443,696, filed Nov. 29, 1989, equivalent to European Published Application, EP A 0 375 562, published Jun. 27, 1990. As noted above, this antibody also is internalizing and is reactive with the Lewis Y antigen expressed by carcinoma cells derived from the human colon, breast, ovary and lung. The hybridoma expressing antibody BR64 and is identified as BR64 was deposited on Nov. 3, 1988, under the terms of the Budapest Treaty, with the ATCC and is available under the accession number HB 9895. The hybridoma is cultured and the desired antibody is isolated using standard techniques well known in the art, such as those referenced above.

In a third highly preferred embodiment, an immunoconjugate of the invention is derived from the L6 murine monoclonal antibody disclosed in U.S. Pat. No. 4,906,562, issued Mar. 6, 1990, and U.S. Pat. No. 4,935,495, issued Jun. 19, 1990. L6 is a non-internalizing antibody active against a ganglioside antigen expressed by human carcinoma cells derived from human non-small cell lung, breast, colon or ovarian carcinomas. The hybridoma expressing L6 and identified as L6 was deposited under the terms of the Budapest Treaty on Dec. 6, 1984 at the ATCC and is available under the accession number HB 8677. The hybridoma is cultured and the desired antibody is isolated using the standard techniques referenced above. A chimeric form of the L6 antibody, if desired, is described in U.S. Ser. No. 07/923,244, equivalent to PCT Published Application, WO 88/03145, published May 5, 1988.

Thus, as used "immunoglobulin" or "antibody" encompasses within its meaning all of the immunoglobulin/antibody forms or constructions noted above.

THE INTERMEDIATES AND THE CONJUGATES

The invention provides as intermediates a Michael Addition Receptor- and acylhydrazone-containing drug derivative of Formula (IIa):

$$[D\mathrel{\substack{=\\=}}N-NHCO(CH_2)_n-R] \quad \text{(IIa)}$$

in which D is a drug moiety, n is an integer from 1 to 10 and R is a Michael Addition Receptor, all of which are as defined above.

An especially preferred intermediate encompassed by Formula (IIa) and which is useful for preparation of a conjugate of the invention is one defined by Formula (IIb):

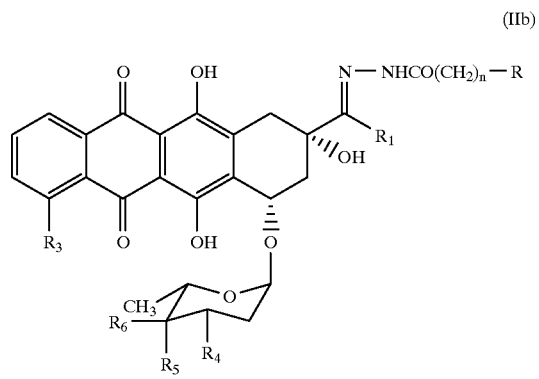
(IIb)

in which
$R_1$ is —$CH_3$, —$CH_2OH$, —$CH_2OCO(CH_2)_3CH_3$ or —$CH_2OCOCH(OC_2H_5)_2$;
$R_3$ is —$OCH_3$, —OH or hydrogen;
$R_4$ is —$NH_2$, —$NHCOCF_3$, 4-morpholinyl, 3-cyano-4-morpholinyl, 1-piperidinyl, 4-methoxy-1-piperidinyl, benzylamine, dibenzylamine, cyanomethyl amine or 1-cyano-2-methoxyethyl amine,
$R_5$ is —OH, —OTHP or hydrogen;
$R_6$ is —OH or hydrogen, provided that $R_6$ is not —OH when $R_5$ is —OH or —OTHP;
n is an integer from 1 to 10; and,
R is a Michael Addition receptor moiety.

The most preferred intermediate for use in the present invention is defined by Formula (IIc):

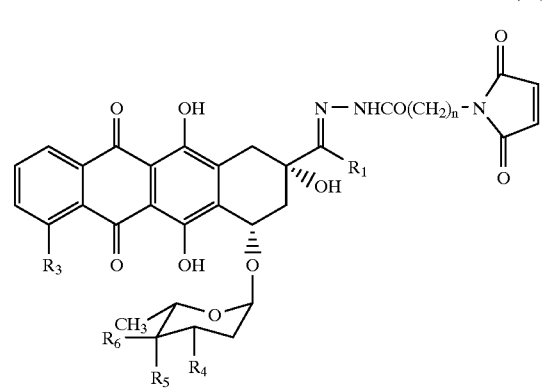
(IIc)

in which $R_1$, $R_3$, $R_4$, $R_5$ and $R_6$ are as defined above for Formula (IIb).

Also used as an intermediate in the invention is a targeting ligand which contains a freely reactive sulfhydryl group. The sulfhydryl group can be contained within the native targeting ligand or can be derived directly from the ligand or from a derivatized form of the ligand. In the preferred method for preparing the conjugates of the invention, a sulfhydryl group on the ligand or modified ligand reacts directly with the Michael Addition Receptor of intermediate of Formula (IIa) to form the final conjugate. Using this process, generally between about one and about ten drug molecules may be linked to each ligand. Thus, in Formula (I), q may be from about 1 to about 10.

When the conjugate is formed, the Michael Addition Receptor portion becomes a "Michael Addition Adduct", as used herein. Thus, for example, as one skilled in the art will appreciate, if the Michael Addition Receptor moiety in the Formulae (IIa) or (IIb) compound is a maleimido moiety, the corresponding "Michael Addition Adduct" portion of the final conjugate of Formula (I) will be a succinimido moiety. Thus, a "Michael Addition Adduct" refers to a moiety which would be obtained had a Michael Addition Receptor, as defined in more detail below, undergone a Michael Addition reaction.

One skilled in the art understands that in the synthesis of compounds of the invention, one may need to protect or block various reactive functionalities on the starting compounds and intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to *Protective Groups in Organic Chemistry*, McOmie, ed., Plenum Press, N.Y., N.Y. (1973); and, *Protective Groups in Organic Synthesis*, Greene, ed., John Wiley & Sons, New York, N.Y. (1981); for the teaching of protective groups which may be useful in the preparation of compounds of the present invention.

By way of example only, useful amino-protecting groups may include, for example, $C_1$-$C_{10}$ alkanoyl groups such as formyl, acetyl, dichloroacetyl, propionyl, hexanoyl, 3,3-diethylhexanoyl, γ-chlorobutyryl, and the like; $C_1$-$C_{10}$ alkoxycarbonyl and $C_5$-$C_{15}$ aryloxycarbonyl groups such as tert-butoxycarbonyl, benzyloxycarbonyl, allyloxycarbonyl, 4-nitrobenzyloxycarbonyl and cinnaemoyloxycarbonyl; halo-($C_1$-$C_{10}$)-alkoxycarbonyl such as 2,2,2-trichloroethoxycarbonyl; and $C_1$-$C_{15}$ arylalkyl and alkenyl groups such as benzyl, phenethyl, allyl, trityl, and the like. Other commonly used amino-protecting groups are those in the form of enamines prepared with β-keto-esters such as methyl or ethyl acetoacetate.

Useful carboxy-protecting groups may include, for example, $C_1$-$C_{10}$ alkyl groups such as methyl, tert-butyl, decyl; halo-$C_1$-$C_{10}$ alkyl such as 2,2,2-trichloroethyl, and 2-iodoethyl; $C_5$-$C_{15}$ arylalkyl such as benzyl, 4-methoxybenzyl, 4-nitrobenzyl, triphenylmethyl, diphenylmethyl, $C_1$-$C_{10}$ alkanoyloxymethyl such as acetoxymethyl, propionoxymethyl and the like; and groups such as phenacyl, 4-halophenacyl, allyl, dimethylallyl, tri-($C_1$-$C_3$ alkyl)silyl, such as trimethylsilyl, β-p-toluenesulfonylethyl, β-p-nitrophenyl-thioethyl, 2,4,5-trimethylbenzyl, β-methylthioethyl, phthalimidomethyl, 2,4-dinitrophenylsulphenyl, 2-nitrobenzhydryl and related groups.

Similarly, useful hydroxy protecting groups may include, for example, the formyl group, the chloroacetyl group, the benzyl group, the benzhydryl group, the trityl group, the 4-nitrobenzyl group, the trimethylsilyl group, the phenacyl group, the tert-butyl group, the methoxymethyl group, the tetrahydropyranyl group, and the like.

In general, the intermediate Michael Addition Receptor containing hydrazone drug derivative of Formulae (IIa), (IIb), or (IIc) may be prepared, depending on the Michael Addition Receptor moiety used, by reaction of the drug (or derivatized drug) with a hydrazide containing a Michael Addition Receptor in the general manner described in Method A:

METHOD A

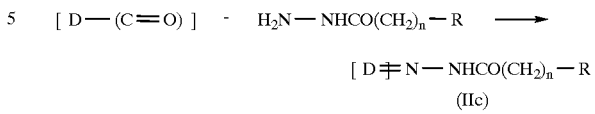

As noted below, Method A is the preferred method when the Michael Addition Receptor is a maleimido moiety.

Alternatively, the Formula (IIa) compound may be prepared by reaction of the drug with a hydrazide to form an intermediate hydrazone drug derivative followed by reaction of this compound with a Michael Addition Receptor containing moiety according to the general process described in Method B:

METHOD B

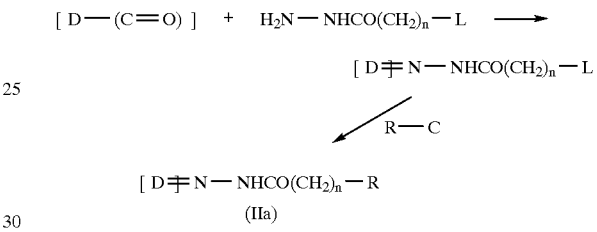

In Method A and Method B, D, n and R have the meanings previously noted. In Method B, L represents a leaving group, such as for example, halogen mesylate or tosylate, capable of undergoing nucleophilic displacement while C represents a group which renders the Michael Addition Receptor, R, a good nucleophilic reagent. Particularly useful groups represented by C may include, for example, alkali metal ions such as $Na^+$, $K^+$ or $Li^+$.

A "Michael Addition Receptor", as one skilled in the art will understand, is a moiety capable of reacting with a nucleophilic reagent so as to undergo a nucleophilic addition reaction characteristic of a Michael Addition reaction. As noted, after the nucleophilic addition occurs, the Michael Addition Receptor moiety is referred to as a "Michael Addition Adduct."

Michael Addition Receptors generally used in the Method A process may include, for example, α,β-ethylenic acids or α,β-thioacids such as those containing a —C=C—COOH, —C=C—C(O)SH, —C=C—C(S)SH, or a —C=C—C(S) OH moiety, α,β-ethylenic esters or thioesters where the alkyl moiety is other than methyl or ethyl, for example, those which contain a —C=C—COOR, —C=C—C(S)OR, —C=C—C(S)SR, or —C=C—C(O)—SR moiety, wherein R is an ester forming group other than methyl or ethyl; α,β-ethylenic amides, imides, thioamides and thiomides (whether cyclic or acylic), for example, those which contain a moiety such as —C=C—$CONR_2$, —C=CONHCO—, —C=C—$CSNR_2$, —C=C—CSNHCO—, or —C=C—CSNHCS—, whether cyclic or acyclic and in which —$CONR_2$ or —$CSNR_2$ represents a primary, secondary, or tertiary amide or thioamide moiety; α,β-acetylenic acids or thioacids, for example, those containing a moiety such as —C≡C—COOH, —C≡C—C(S)OH, —C≡C—C(S)SH, or —C≡C—C(O)—SH; α,β-acetylenic esters, for example those which contain a moiety such as —C≡C—COOR, —C≡C—C(S)OR, —C≡C—C(S)SR, or —C≡C—C(O)—SR in which R is an ester forming group other than methyl or ethyl; α,β-ethylenic nitriles, for example those containing a moiety such as —C=C—C≡N; Michael Addition reactive cyclopropane derivatives, for example, 1-cyano-1-ethoxycarbonyl cyclopropane

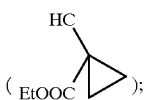

a vinyl dimethyl-sulphonium bromide, for example, one containing a —C=C—S(Me)$_2$Br moiety; an α,β-ethylenic sulfone, for example, one containing a

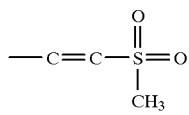

moiety, α,β-ethylenic nitro compounds, for example, one containing a —C=C—NO$_2$ moiety; α,β-ethylenic phosphonium compounds, for example one containing a

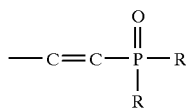

group; a compound containing a grouping such as C=C—C=N, as would be found, for example, in an aromatic heterocycle such as a 2- or 4-vinyl pyridine; or a compound containing an α,β-unsaturated thionium ion moiety, such as

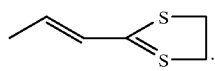

Michael Addition Receptors used in Method B may include α,β-ethylenic aldehydes, for example those compounds containing a —C=C—CHO moiety; α,β-ethylenic ketones, for example those compounds containing a

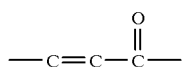

moiety; α,β-ethylenic esters or thio-esters such as compounds containing a —C=C—COOR, —C=C—C(S)OR, —C=C—C(S)SR, or —C=C—C(O)—SR moiety in which R is an ester-forming moiety which is methyl or ethyl, e.g.

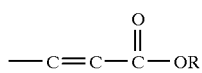

α,β-acetylenic aldehydes or ketones, for example compounds containing a —C≡C—CHO or —C≡C—CO— moiety; α,β-acetylenic esters or thio- esters that have methyl or ethyl as their alkyl moiety, for example a compound containing a —C≡C—COOR, —C≡C—C(S)OR, —C≡C—C(O)SR or —C≡C—CSSR group in which R is an ester forming moiety which is methyl or ethyl.

One skilled in the art may be familiar with other Michael Addition Receptors which may be used in the present invention. For a general discussion of the Michael Addition Reaction, the reader is referred to E. D. Bergman, D. Ginsberg, and R. Pappo, *Org. React.* 10, 179–555 (1959); and, D. A. Oare and C. H. Heathcock, *Topics in Stereochemistry*, Vol. 20, eds., E. L. Eliel and S. H. Wilen, John Wiley and Sons, Inc. (1991), and reference cited therein.

The precise reaction conditions used to prepare the intermediates of Formulae (IIa), (IIb), or (IIc) will depend upon the nature of the drug and the Michael Addition Receptor used in the reaction. The most preferred intermediate of the invention is that represented by Formula (IIc), above, in which the drug moiety is an anthracycline drug and the Michael Addition Receptor in a maleimido group. As noted earlier, or this reaction, Method A, described above, is used. Upon reaction with the ligand (thiolated, modified or otherwise), the maleimido Michael Addition Receptor of the intermediate becomes a succinimido group (the "Michael Addition Adduct") in the final conjugate.

The sulfhydryl containing ligands exist naturally (i.e. the ligand has not been modified) or may be produced, for example, (a) by thiolation of the ligand by reaction with a thiolating reagent such as SMCC or N-succinimid-yl-3-(2-pyridyldithio) propionate ("SPDP") followed by reduction of the product; (b) thiolation of the native ligand by reaction with iminothiolane ("IMT"); (c) addition of a sulfhydryl containing amino acid residue, for example, a cysteine residue, to the ligand should the ligand, for example, a protein peptide or polypeptide, fail to have a reactive and available sulfhydryl moiety; or, (d) reduction of a disulfide bond in a native molecule using a reducing agent useful for such purposes, for example, dithiothreitol ("DTT"). Method (d) is the most preferred method for production of sulfhydryl groups in antibody molecules used in the conjugates of the invention.

If a thiolating reagent such as SPDP or iminothiolane is used to prepare a conjugate of the invention, one skilled in the art will appreciate that a short "spacer" residue will be inserted between the Michael Addition Receptor moiety and the ligand in the conjugate of Formula (I). In such a case, z will be 1 in the Formula (I) compound. In the situation in which a free sulfhydryl group on the ligand is used directly, for example by use of a DTT reduced ligand (particularly a "relaxed" antibody prepared using for example, DTT), or in which a reactive residue, for example, cysteine is inserted into the ligand portion of the molecule, z in Formula (I) will be 0 and a direct thioether bond will exist between the binding ligand and the Michael Addition portion of the molecule.

To form the conjugate, the thiolated ligand, or ligand having a freely reactive sulfhydryl group, is reacted with the Michael Addition Receptor containing hydrazone of Formula (IIa). In general, the reaction conditions must be chosen with regard to the stability of the ligand, the drug and the desired number of drug moieties to be linked to the ligand. For example, one skilled in the art will appreciate that the average number of drug molecules linked to the ligand can be varied by (1) modifying the amount of the intermediate drug-hydrazone of Formula (IIa) relative to the number of reactive sulfhydryl groups on the ligand moiety of the conjugate; or, (2)(a) modifying the number of reactive sulfhydryl groups on the ligand by, for example, only partially reducing the ligand (in the case of a protein, peptide or polypeptide), (b) by inserting a limited number of, for example, cysteine residues to a protein, peptide or polypeptide, or (c) by limiting the degree of thiolation using less than maximal amounts of thiolation agents, for example, SPDP or iminothiolane. Although the —SH titer can be varied, the preferred level of free sulfhydryl groups, particularly for a relaxed antibody, is the maximum obtainable using the particular reagents in question. The degree of variation in the —SH titer is easily controlled in the relaxed antibody process. For example, FIG. 62 shows the effect on —SH titer for antibodies BR64 and chimeric BR96 depending on the mole ratio of DTT to ligand, at 37° C., for a 1.5 hour reaction. One skilled in the art will appreciate that different classes or subclasses of immunoglobulins can have different number of disulfide bridges susceptible to reduction by reagents such as DTT. Thus, a further consideration in determining the desired level of conjugation of an antibody or antibody fragment is the number of disulfide groups available for reduction to free —SH groups. In general, however, the preferred conjugate of Formula (I) will have, on the average from a given reaction, from about 1 to about 10 drug molecules per ligand molecule. An especially preferred average drug to ligand molar ratio ("MR") is about 4 to about 8.

After the reaction of the conjugate is complete, the conjugate may be isolated and purified using commonly known dialysis, chromatographic and/or filtration methods. A final solution containing the conjugate customarily may be lyophilized to provide the conjugate in a dry, stable form which can be safely stored and shipped. The lyophilized product eventually can be reconstituted with sterile water or another suitable diluent for administration. Alternatively, the ultimate product may be frozen, for example under liquid nitrogen, and thawed and brought to ambient temperature prior to administration.

In a first preferred embodiment the anthracyclic hydrazone of Formula (IIa) is made by reacting the anthracycline with a maleimido-($C_1$-$C_{10}$)-alkyl hydrazide, or a salt thereof. This reaction is outlined in Method A, described earlier. The reaction generally is carried out in two steps. First the maleimido-($C_1$-$C_{10}$)-alkyl hydrazide, or its salt, is prepared. After purification by, for example, chromatography and/or crystallization, either the free base of the hydrazide or the salt are reacted with the desired anthracycline or anthracyline salt. After concentration of the reaction solution, the maleimido-containing hydrazone reaction product of Formula (IIa) is collected, and if desired, purified by standard purification techniques.

The Formula (IIa) hydrazone then is reacted with a sulfhydryl-containing antibody as described earlier. If the antibody is thiolated using, for example, N-succinimidyl-3-(2-pyridyldithio)propionate ("SPDP"), the thiolation reaction generally is performed in two steps: (1) Reaction of a free amino group on the antibody with SPDP; and, (2) DTT reduction of the SPDP disulfide to yield a free —SH group. In a preferred procedure, in Step (1) of the thiolation reaction, the SPDP/antibody molar ratio ranges between about 7.5:1 to about 60:1, depending upon the number of sulfhydryl groups desired, with a preferred range of about 7.5:1 to about 30:1, especially for BR64, and preferably about 20:1 for BR96. The reaction is carried out between about 0° C. and about 50° C., with a most preferred temperature of about 30° C. The reaction may be carried out at a pH range of between about 6 and about 8 with the most preferred pH being about 7.4. The reduction in Step (2), using preferably DTT, is performed using a DTT/SPDP molar ratio of between about 2.5:1 to about 10:1. The most preferred DTT/SPDP molar ratio is about 5:1 and the number of moles of SPDP is that which is added in Step (1) of the reaction. The reaction generally is carried out at about 0° C. to about 40° C., preferably 0° C. and is usually complete after about 20 minutes. After dialysis and concentration of the solution of thiolated ligand (an antibody in the most preferred embodiment), the molar concentration of sulhydryl groups on the ligand is determined and the thiolated ligand is reacted with the desired molar ratio of the hydrazone derivative of Formula (IIa) relative to the molar amount of reactive sulhydryl groups on the ligand. Preferably, the ratio is at least about 1:1. This reaction generally is performed at a temperature of about 0° C. to about 25° C., preferably about 4° C. The resulting conjugate then may be purified by standard methods. This reaction scheme is outlined in FIGS. 49a and 49b.

In a second preferred embodiment, the hydrazone of Formula (IIa) is made as described above. The hydrazone then is reacted, as outlined in FIG. 49c, with an antibody which previously has been thiolated with iminothiolane ("IMT"). Thiolation of the ligand (preferably an antibody) with IMT generally is a one step reaction. The IMT/antibody ratio may range from between about 30:1 to about 80:1, preferably about 50:1. The reaction is performed for about 30 minutes to about 2 hours, preferably about 30 minutes, at a pH of about 7 to about 9.5, preferably at a pH of about 9, at a temperature of about 20° C. to about 40° C., preferably about 30° C. The reaction product then is reacted with the hydrazone of Formula (IIa) at a temperature of about 0° C. to about 25° C., preferably at about 4° C. and at a pH of about 7 to about 9.5, preferably about 7.4. The conjugate then is purified using methods standard in the art, for example, dialysis, filtration, or chromatography.

In a third especially preferred embodiment the intermediate hydrazone of Formula (IIa) is made as described above. The hydrazone then is reacted with a ligand, most preferably, an antibody, in which at least one disulfide group has been reduced to form at least one sulfhydryl group. An especially preferred ligand is a "relaxed antibody", as described below. The preferred reducing agent for preparing a free sulfhydryl group is DTT although one skilled in the art will understand that other reducing agents may be suitable for this purpose.

A "relaxed" antibody, is one in which one or more, or preferably, three or more, disulfide bridges have been reduced. Most preferably, a relaxed antibody is one in which at least four disulfide bridges have been reduced. In a preferred process for preparing a relaxed (i.e. reduced) antibody, the reduction, especially with DTT, and the purification of the reaction product, is carried out in the absence of oxygen, under an inert atmosphere, for example, under nitrogen or argon. This process, as described in detail below, allows one to carefully control the degree of reduction. Thus, this process allows one skilled in the art to reproduce at any time the desired level of reduction of a ligand and, therefore, the number of free —SH groups available for preparing a conjugate of the invention.

In an alternative procedure, the reaction is carried out under ambient conditions, however, a sufficiently large amount of the reducing agent, preferably DTT, is used to overcome any reoxidation of the reduced disulfide bonds which may occur. In either case, purification of the product, is carried out as soon as possible after the reaction is complete and most preferably under an inert atmosphere such as an argon or nitrogen blanket. The preferred method for preparing the free sulfhydryl containing ligand, however, is the process in which atmospheric oxygen is excluded from the reaction. An antibody produced by either method is referred to as a "relaxed" antibody. The product, however prepared, should be used for subsequent reaction as quickly as possible or stored under conditions which avoid exposure to oxygen, preferably under an inert atmosphere.

In the process in which oxygen is excluded from the reaction (i.e. the reaction is performed under an inert atmosphere), the ligand is incubated, for a period of about 30 minutes to about 4 hours, preferably about 3 hours, with a molar excess of DTT. The DTT/ligand ratios may range between about 1:1 to about 20:1, preferably about 1:1 to about 10:1, most preferably about 7:1 to about 10:1, depending upon the number of sulfhydryl groups desired. For a reduction performed in the presence of oxygen, the mole ratio of DTT to ligand ranges from about 50:1 to about 400:1, preferably from about 200:1 to about 300:1. This latter reaction is carried out for about 1 to about 4 hours, preferably 1.5 hours, at a temperature of between about 20° C. and about 50° C., with a preferred temperature being about 37° C. The reaction is carried out at a pH of between about 6 and about 8, preferably between about 7 to 7.5. The product then is purified using standard purification techniques such as dialysis, filtration and/or chromatography. A preferred purification method is diafiltration. To prevent reoxidation of —SH groups, during purification and storage, the product preferably is maintained under an inert atmosphere to exclude exposure to oxygen.

One skilled in the art will appreciate that different ligands, particularly an antibody, may possess different degrees of susceptibility to reduction and/or reoxidation. Consequently, the conditions for reduction described above may need to be modified in order to obtain a given reduced ligand such as that described above. Furthermore, alternate means for preparing a reduced antibody useful in the conjugation process will be evident to one skilled in the art. Thus, however prepared, a reduced ligand used in the preparation of a conjugate of Formula (I) is meant to be encompassed by the present invention.

To prepare a conjugate of Formula (I), as noted earlier, the reduced antibody reaction product is reacted with the hydrazone intermediate of Formula (IIc). The reaction preferably is performed under an inert atmosphere at a temperature of about 0° C. to about 10° C., preferably at about 4° C. and at a pH of about 6 to about 8, preferably about 7.4. The immunoconjugate is purified using standard techniques such as dialysis, filtration, or chromatography.

In another embodiment of the invention, an anthracycline of Formula (II) is joined to a ligand to which is added a moiety carrying a free sulfhydryl group. In one such embodiment, the ligand is a non-antibody ligand, for example, bombesin. The sulfhydryl may be, for example, part of a cysteine residue added to the native bombesin molecule. The anthracycline is joined through a hydrazone moiety to a Michael Addition Receptor containing moiety which then reacts with the modified bombesin to form a conjugate of Formula (I). The product then is purified with standard techniques such as dialysis, centrifugation, or chromatography.

PREPARATION 1

2,5-Dihydro-2,5-Dioxo-1H-Pyrrolo-1-Hexanoic Acid Hydrazide and its Trifluoroacetic Acid Salt ("Maleimidocaproyl Hydrazide")

Maleimidocaproic acid (2.11 g, 10 mmol) [See, e.g., D. Rich et al., *J. Med. Chem.*, 18, 1004 (1975); and, O. Keller, et al., *Helv. Chim. Acta,* 58 531 (1975)] was dissolved in dry tetrahydrofuran (200 mL). The solution was stirred under nitrogen, cooled to 4° C. and treated with N-methylmorpholine (1.01 g, 10 mmol) followed by dropwise addition of a solution of isobutyl chloroformate (1.36 g, 10 mmol) in THF (10 mL). After 5 min a solution of t-butyl carbazate (1.32 g, 10 mmol) in THF (10 mL) was added dropwise. The reaction mixture was kept at 4° C. for a half hour and at room temperature for 1 hour. The solvent was evaporated and the residue partitioned between ethyl acetate and water. The organic layer was washed with dilute HCl solution, water and dilute bicarbonate solution, dried over anhydrous sodium sulfate and the solvent evaporated. The material was purified by flash chromatography using a gradient solvent system of methylene chloride:methanol (100:1-2). The protected hydrazide was obtained in 70% yield (2.24 g).

This material (545 mg, 2.4 mmol) was dissolved and stirred in trifluoroacetic acid at 0°–4° C. for 8 min. The acid was removed under high vacuum at room temperature. The residue was triturated with ether to yield a crystalline trifluoroacetic acid salt of maleimidocaproyl hydrazide (384 mg, 70%). An analytical sample was prepared by crystallization from methanol-ether, to prepare the product, mp 102°–105° C. The NMR and MS were consistent with structure. Anal: Calc'd. for $C_{10}H_{15}N_3O_3 \cdot 0.8CF_3COOH$: C, 44.02; H, 4.99; N, 13.28. Found (duplicate analyses): C, 44.16, 44.13; H, 4.97, 5.00; N, 12.74, 12.75.

The salt (220 mg) was converted to the free base by chromatography over silica using a methylene chloride:methanol:concentrated $NH_4OH$ (100:5:0.5) solvent system. The material obtained (124 mg, 80%) was crystallized from methylene chloride-ether to prepare a final product, mp 92°–93° C. NMR and MS were consistent with the structure. Anal: Calc'd, for $C_{10}H_{15}N_3O_3$: C, 53.33; H, 6.67; N, 18.67. Found: C, 53.12; H, 6.67; N, 18.44.

PREPARATION 2

Maleimidocaproylhydrazone of Adriamycin

A mixture of adriamycin hydrochloride (44 mg, 0.075 mmol), maleimidocaproyl hydrazide (23 mg, 0.102 mmol), prepared according to the procedure outlined in Preparation 1, and 2–3 drops of trifluoroacetic acid in absolute methanol (25 mL) was stirred for 15 hours under nitrogen and protected from light. At the end of this period no free adriamycin was detected by HPLC (mobile phase 0.01 molar ammonium acetate:acetonitrile, (70:30)). The solution was concentrated at room temperature under vacuum to 10 mL and diluted with acetonitrile. The clear solution was concentration to a small volume, the solid was collected by centrifugation, and the product was dried under high vacuum to yield the title compound. The NMR was consistent with structure. High Resolution MS, calc'd. for $C_{31}H_{42}N_4O_{13}$: 751.2827; Found 751.2804.

The hydrazone also was formed by using adriamycin and the trifluoroacetic acid salt of the hydrazide. Thus, the salt (40 mg, 0.12 mmol), prepared according to the process outlined in Procedure 1, and adriamycin hydrochloride (50 mg, 0.086 mmol) and stirred in methanol (30 mL) for 15 hrs. The solution was concentrated to 2 mL and diluted with acetonitrile. The red solid was collected by centrifugation and dried under vacuum. The product (28 mg, 43%) was identical in NMR and TLC to the one described above. High Resolution MS calc'd. for $C_{31}H_{42}N_4O_{13}$: 751.2827; found 751.2819.

5. Expression and Purification of Coding Sequences for BR96 sFv-PE40

The DNA sequences encoding the single-chain immunotoxin may be expressed in a variety of systems as set forth below. The DNA may be excised from pBW 7.0 by suitable restriction enzymes and ligated into suitable prokaryotic or eukaryotic expression vectors for such expression.

To propagate the cloned DNA, the expression plasmid pBW 7.0, encoding the single-chain immunotoxin, is first transformed into suitable host cells, such as the bacterial cell line *E. coli* strain BL21 (lambdaDE3) [provided by Dr.

Studier, Brookhaven National Laboratories, New York, described by Chaudhary et al., *Proc. Natl. Acad. Sci. USA* 84:4538–4542 (1987)] using standard procedures appropriate to such cells. The treatment employing calcium chloride, as described by Cohen, *Proc. Natl. Acad. Sci. USA* (1972) 69:2110 (1972) or the $CaCl_2$ method described in Sambrook et al. (eds.), *Molecular Cloning: A Laboratory Manual*, 2nd Edition, Cold Spring Harbor Press, (1989), may be used for prokaryotes or other cells which contain substantial cell wall barriers.

Depending on the host cell used, transformation or transfection is performed using standard techniques appropriate to such cells. For example, transfection into mammalian cells is accomplished using DEAE-dextran mediated transfection, $CaPO_4$ co-precipitation, lipofection, electroporation, or protoplast fusion, and other methods known in the art including: lysozyme fusion or erythrocyte fusion, scraping, direct uptake, osmotic or sucrose shock, direct microinjection, indirect microinjection such as via erythrocyte-mediated techniques, and/or by subjecting host cells to electric currents. The above list of transfection techniques is not considered to be exhaustive, as other procedures for introducing genetic information into cells will no doubt be developed.

Expression in prokaryotic cells is preferred. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems [Chang et al., *Nature* 198: 1056 (1977)], the tryptophan (trp) promoter system [Goeddel et al., *Nucleic Acids Res.* 8:4057 (1980)] and the lambda derived $P_L$ promoter and N-gene ribosome binding site [Shimatake et al., *Nature* 292:128 (1981)].

Expression of the single-chain immunotoxin is detected by Coomassie stained SDS-PAGE and immunoblotting using both anti-idiotypic antibodies that bind to BR96, and anti-PE antibodies to bind to the PE40-portion of the fusion protein.

6. Recovery of Products

The recombinant immunotoxin may be produced along with a signal sequence in cells capable of processing this sequence for secretion. When secreted into the medium, the immunotoxin is recovered using standard protein purification techniques such as anion-exchange and gel-filtration chromatography. Purification may also be performed using antibodies reactive with the anti-immunoglobulin portion of the immunotoxin. However, while the procedures are more laborious, it is within the means known in the art to purify the molecule from sonicates or lysates of cells in which it is produced intracellularly in fused or mature form.

In the preferred embodiment described herein, BR96 sFV-PE40 was purified using anion-exchange and gel-filtration chromatographies with fast protein liquid chromatography (FPLC) as described by Siegall et al., *Proc. Natl. Acad. Sci. USA* 85:9738–9742 (1988).

7. Uses

The BR96 antibody of the invention is useful for diagnostic applications, both in vitro and in vivo, for the detection of human carcinomas that possess the antigen for which the antibodies are specific. In vitro diagnostic methods include immunohistological detection of tumor cells (e.g., on human tissue, cells or excised tumor specimens) or serologic detection of tumor-associated antigens (e.g., in blood samples or other biological fluids).

Immunohistochemical techniques involve staining a biological specimen such as a tissue specimen with the BR96 antibody of the invention and then detecting the presence on the specimen of the antibody complexed to its antigen. The formation of such antibody-antigen complexes with the specimen indicates the presence of carcinoma cells in the tissue. Detection of the antibody on the specimen can be accomplished using techniques known in the art such as immunoenzymatic techniques, e.g., the immunoperoxidase staining technique or the avidin-biotin (ABC) technique, or immunofluorescence techniques [see, e.g., Ciocca et al., "Immunohistochemical Techniques Using Monoclonal Antibodies", *Meth. Enzymol.*, 121:562–79 (1986); Hellstrom et al., "Monoclonal Mouse Antibodies Raised Against Human Lung Carcinoma", *Cancer Research,* 46:3917–23 (1986); and Kimball (ed.), *Introduction To Immunology* (2nd Ed.), pp. 113–117 (Macmillan Pub. Co. 1986)]. For example, immunoperoxidase staining was used as described in Example 2, infra, to demonstrate the reactivity of the BR96 antibody with lung, breast, colon, and ovary carcinomas and the low reactivity of the antibody with normal human tissue specimens.

8. Diagnostic Techniques.

Serologic diagnostic techniques involve the detection and quantitation of tumor-associated antigens that have been secreted or "shed" into the serum or other biological fluids of patients thought to be suffering from carcinoma. Such antigens can be detected in the body fluids using techniques known in the art such as radioimmunoassays (RIA) or enzyme-linked immunosorbent assays (ELISA) wherein an antibody reactive with the "shed" antigen is used to detect the presence of the antigen in a fluid sample [see, e.g., Uotila et al., "Two-Site Sandwich ELISA With Monoclonal Antibodies To Human AFP", *J. Immunol. Methods,* 42:11 (1981) and Allum et al., supra at pp. 48–51]. These assays, using the BR96 antibodies disclosed herein, can therefore be used for the detection in biological fluids of the antigen with which the BR96 antibodies react and thus the detection of human carcinoma in patients. Thus, it is apparent from the foregoing that the BR96 antibodies of the invention can be used in most assays involving antigen-antibody reactions. These assays include, but are not limited to, standard RIA techniques, both liquid and solid phase, as well as ELISA assays, immunofluorescence techniques, and other immunocytochemical assays [see, e.g., Sikora et al. (eds.), *Monoclonal Antibodies,* pp. 32–52 (Blackwell Scientific Publications 1984)].

The invention also encompasses diagnostic kits for carrying out the assays described above. In one embodiment, the diagnostic kit comprises the BR96 monoclonal antibody, fragments thereof, fusion proteins or chimeric antibody of the invention, and a conjugate comprising a specific binding partner for the BR96 antibody and a label capable of producing a detectable signal. The reagents can also include ancillary agents such as buffering agents and protein stabilizing agents (e.g., polysaccharides). The diagnostic kit can further comprise, where necessary, other components of the signal-producing system including agents for reducing background interference, control reagents or an apparatus or container for conducting the test. In another embodiment, the diagnostic kit comprises a conjugate of the BR96 antibodies of the invention and a label capable of producing a detectable signal. Ancillary agents as mentioned above can also be present.

The BR96 antibody of the invention is also useful for in vivo diagnostic applications for the detection of human carcinomas. One such approach involves the detection of tumors in vivo by tumor imaging techniques. According to this approach, the BR96 antibody is labeled with an appropriate imaging reagent that produces a detectable signal. Examples of imaging reagents that can be used include, but are not limited to, radiolabels such as $^{131}$I, $^{111}$In, $^{123}$I, $^{99m}$Tc, $^{32}$P, $^{125}$I, $^3$H, and $^{14}$C, fluorescent labels such as fluorescein and rhodamine, and chemiluminescers such as luciferin. The antibody can be labeled with such reagents using techniques known in the art. For example, see Wensel and Meares, *Radioimmunoimaging And Radioimmunotherapy*, Elsevier, N.Y. (1983) for techniques relating to the radiolabeling of antibodies [see also, Colcher et al., "Use Of Monoclonal Antibodies As Radiopharmaceuticals For The Localization Of Human Carcinoma Xenografts In Athymic Mice", *Meth. Enzymol.*, 121:802–16 (1986)].

In the case of radiolabeled antibody, the antibody is administered to the patient, localizes to the tumor bearing the antigen with which the antibody reacts, and is detected or "imaged" in vivo using known techniques such as radionuclear scanning using, e.g., a gamma camera or emission tomography [see, e.g., Bradwell et al., "Developments In Antibody Imaging", in *Monoclonal Antibodies For Cancer Detection And Therapy*, Baldwin et al. (eds.), pp. 65–85 (Academic Press 1985)]. The antibody is administered to the patient in a pharmaceutically acceptable carrier such as water, saline, Ringer's solution, Hank's solution or nonaqueous carriers such as fixed oils. The carrier may also contain substances that enhance isotonicity and chemical stability of the antibody such as buffers or preservatives. The antibody formulation is administered, for example, intravenously, at a dosage sufficient to provide enough gamma emission to allow visualization of the tumor target site. Sufficient time should be allowed between administration of the antibody and detection to allow for localization to the tumor target. For a general discussion of tumor imaging, see Allum et al., supra at pp. 51–55.

9. Therapeutic Applications of the Antibodies of the Invention and Fragments Thereof.

The properties of the BR96 antibody: a) very high specificity for tumor cells; b) internalization; c) toxicity to antigen-positive tumor cells alone, i.e. in unmodified form, when used at appropriate concentrations; and d) complement-dependent cytotoxicity and antibody-dependent cellular cytotoxicity activity, suggest a number of in vivo therapeutic applications. First, the BR96 antibody can be used alone to target and kill tumor cells in vivo.

The antibody can also be used in conjunction with an appropriate therapeutic agent to treat human carcinoma. For example, the antibody can be used in combination with standard or conventional treatment methods such as chemotherapy, radiation therapy or can be conjugated or linked to a therapeutic drug, or toxin, as well as to a lymphokine or a tumor-inhibitory growth factor, for delivery of the therapeutic agent to the site of the carcinoma.

Techniques for conjugating such therapeutic agents to antibodies are well known [see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243–56 (Alan R. Liss, Inc. 1985); Hellstrom et al., "Antibodies For Drug Delivery", in *Controlled Drug Delivery* (2nd Ed.), Robinson et al. (eds.), pp. 623–53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475–506 (1985); and Thorpe et al., "The Preparation And Cytotoxic Properties Of Antibody-Toxin Conjugates", *Immunol. Rev.*, 62:119–58 (1982)].

The BR96 antibody of the invention is particularly suited for use in a therapeutic conjugate because it is readily internalized within the carcinoma cells to which it binds and thus can deliver the therapeutic agent to intracellular sites of action.

Alternatively, the BR96 antibody can be coupled to high-energy radiation, e.g., a radioisotope such as $^{131}$I;, which, when localized at the tumor site, results in a killing of several cell diameters [see, e.g., Order, "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), pp. 303–16 (Academic Press 1985)]. According to yet another embodiment, the BR96 antibody can be conjugated to a second antibody to form an antibody heteroconjugate for the treatment of tumor cells as described by Segal in U.S. Pat. No. 4,676,980.

Still other therapeutic applications for the BR96 antibody of the invention include conjugation or linkage, e.g., by recombinant DNA techniques, to an enzyme capable of converting a prodrug into a cytotoxic drug and the use of that antibody-enzyme conjugate in combination with the prodrug to convert the prodrug to a cytotoxic agent at the tumor site [see, e.g., Senter et al., "Anti-Tumor Effects Of Antibody-alkaline Phosphatase", *Proc. Natl. Acad. Sci. USA*, 85:4842–46 (1988); "Enhancement of the in vitro and in vivo Antitumor Activities of Phosphorylated Mitomycin C and Etoposide Derivatives by Monoclonal Antibody-Alkaline Phosphatase Conjugates", *Cancer Research* 49:5789–5792 (1989); and Senter, "Activation of Prodrugs by Antibody-Enzyme Conjugates: A New Approach to Cancer Therapy," *FASEB J.* 4:188–193 (1990)].

Still another therapeutic use for the BR96 antibody involves use, either in the presence of complement or as part of an antibody-drug or antibody-toxin conjugate, to remove tumor cells from the bone marrow of cancer patients. According to this approach, autologous bone marrow may be purged ex vivo by treatment with the antibody and the marrow infused back into the patient [see, e.g., Ramsay et al., "Bone Marrow Purging Using Monoclonal Antibodies", *J. Clin. Immunol.*, 8(2):81–88 (1988)].

Furthermore, chimeric BR96, recombinant immunotoxins and other recombinant constructs of the invention containing the specificity of the antigen-binding region of the BR96 monoclonal antibody, as described earlier, may be used therapeutically. For example, the single-chain immunotoxin of the invention, BR96 sFv-PE40 may be used to treat human carcinoma in vivo.

Similarly, a fusion protein comprising at least the antigen-binding region of the BR96 antibody joined to at least a functionally active portion of a second protein having anti-tumor activity, e.g., a lymphokine or oncostatin can be used to treat human carcinoma in vivo. Furthermore, recombinant techniques known in the art can be used to construct bispecific antibodies wherein one of the binding specificities of the antibody is that of BR96 [see, e.g. U.S. Pat. No. 4,474,893], while the other binding specificity of the antibody is that of a molecule other than BR96.

Finally, anti-idiotypic antibodies of the BR96 antibody may be used therapeutically in active tumor immunization and tumor therapy [see, e.g., Hellstrom et al., "Immunological Approaches To Tumor Therapy: Monoclonal Antibodies, Tumor Vaccines, And Anti-Idiotypes", in *Covalently Modified Antigens And Antibodies In Diagnosis And Therapy*, supra at pp. 35–41].

The present invention provides a method for selectively killing tumor cells expressing the antigen that specifically binds to the BR96 monoclonal antibody or functional equivalent. This method comprises reacting the immunoconjugate (e.g. the immunotoxin) of the invention with said tumor cells. These tumor cells may be from a human carcinoma.

Additionally, this invention provides a method of treating carcinomas (for example human carcinomas) in vivo. This method comprises administering to a subject a pharmaceutically effective amount of a composition containing at least one of the immunoconjugates (e.g. the immunotoxin) of the invention.

In accordance with the practice of this invention, the subject may be a human, equine, porcine, bovine, murine, canine, feline, and avian subjects. Other warm blooded animals are also included in this invention.

The present invention also provides a method for curing a subject suffering from a cancer. The subject may be a human, dog, cat, mouse, rat, rabbit, horse, goat, sheep, cow, chicken. The cancer may be identified as a retinoblastoma, papillary cystadenocarcinoma of the ovary, Wilm's tumor, or small cell lung carcinoma and is generally characterized as a group of cells having tumor associated antigens on the cell surface. This method comprises administering to the subject a cancer killing amount of a tumor targeted antibody joined to a cytotoxic agent. Generally, the joining of the tumor targeted antibody with the cytotoxic agent is made under conditions which permit the antibody so joined to bind its target on the cell surface. By binding its target, the tumor targeted antibody acts directly or indirectly to cause or contribute to the killing of the cells so bound thereby curing the subject.

In accordance with the practice of the invention, the tumor targeted antibody is an internalizing tumor targeted antibody. Examples include BR96, fragments of BR96, and functional equivalents thereof. Functional equivalents of BR96 include any molecule which binds the antigen binding site to which BR96 is directed and is characterized by (1) binding carcinoma cells, (2) internalizing within the carcinoma cells to which they bind, and (3) mediating ADCC and CDC effector functions.

Further, in accordance with the practice of the invention, the tumor targeted antibody may be an internalizing tumor targeted antibody which recognizes and binds to the $Le^y$ determinant. Although, antibodies directed against the $Le^y$ determinant are known, such antibodies were not known to internalize within the carcinoma cells to which they bind and/or mediate ADCC and CDC effector functions.

Further, $Le^y$ is a fairly common determinant which is overexpressed in many cancer and some normal cells. Because its presence is widely found and thus common in both some tumor and non-tumorigenic cells others have questioned whether such antibodies which recognize $Le^y$ may be therapeutically useful.

The claimed invention also provides a method of inhibiting the proliferation of mammalian tumor cells. This method comprises contacting the mammalian tumor cells with a proliferation inhibiting amount (i.e. effective amount) of a tumor targeted antibody joined to a cytotoxic or therapeutic agent or anti-tumor drug so as to inhibit proliferation of the mammalian tumor cells.

In one example, the tumor targeted antibody is the monoclonal antibody BR96 produced by hybridoma ATCC HB10036. Other examples include functional equivalents of BR96 such as ChiBR96; fragments of BR96; bispecific antibodies with a binding specificity for two different antigens, one of the antigens being that with which the monoclonal antibody BR96 produced by hybridoma ATCC HB10036 binds; and a human/murine recombinant antibody, the antigen-binding region of which competitively inhibits the immunospecific binding of monoclonal antibody BR96 produced by hybridoma HB 10036 to its target antigen Also provided is a method of inhibiting the proliferation of mammalian tumor cells which comprises contacting the mammalian tumor cells with a sufficient concentration of the immunoconjugate of the invention so as to inhibit proliferation of the mammalian tumor cells.

Examples of such immunoconjugates include, but are not limited to, BR96-PE, PE-BR96 fragment, BR96-RA, BR96 (Fab)-lysPE40, BR96 F(ab')$_2$-lysPE40, ChiBR96-LysPE40, IL-6-PE40, BR96-DOX.

The subject invention further provides methods for inhibiting the growth of human tumor cells, treating a tumor in a subject, and treating a proliferative type disease in a subject. These methods comprise administering to the subject an effective amount of the composition of the invention.

It is apparent therefore that the present invention encompasses pharmaceutical compositions, combinations and methods for treating human carcinomas. For example, the invention includes pharmaceutical compositions for use in the treatment of human carcinomas comprising a pharmaceutically effective amount of a BR96 antibody and a pharmaceutically acceptable carrier.

The compositions may contain the BR96 antibody or antibody fragments, either unmodified, conjugated to a therapeutic agent (e.g., drug, toxin, enzyme or second antibody) or in a recombinant form (e.g., chimeric BR96, fragments of chimeric BR96, bispecific BR96 or single-chain immunotoxin BR96). The compositions may additionally include other antibodies or conjugates for treating carcinomas (e.g., an antibody cocktail).

The antibody, antibody conjugates and immunotoxin compositions of the invention can be administered using conventional modes of administration including, but not limited to, intravenous, intraperitoneal, oral, intralymphatic or administration directly into the tumor. Intravenous administration is preferred.

The compositions of the invention may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The compositions of the invention also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the compositions of this invention depends upon the severity and course of the disease, the patient's health and response to treatment and the judgment of the treating physician. Accordingly, the dosages of the compositions should be titrated to the individual patient. Nevertheless, an effective dose of the compositions of this invention may be in the range of from about 1 to about 2000 mg/m$^2$.

The molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration and dosage regimen for the molecules of the present invention depends upon the location of the tumor being treated, the severity and course of the cancer, the subject's health and response to treatment and the judgment of the treating physician. Accordingly, the dosages of the molecules should be titrated to the individual subject.

The interrelationship of dosages for animals of various sizes and species and humans based on mg/m² of surface area is described by Freireich, E. J., et al. Cancer Chemother., Rep. 50 (4): 219–244 (1966). Adjustments in the dosage regimen may be made to optimize the tumor cell growth inhibiting and killing response, e.g., doses may be divided and administered on a daily basis or the dose reduced pro- portionally depending upon the situation (e.g., several divided doses may be administered daily or proportionally reduced depending on the specific therapeutic situation.

It would be clear that the dose of the composition of the invention required to achieve cures may be further reduced with schedule optimization.

In accordance with the practice of the invention, the pharmaceutical carrier may be a lipid carrier. The lipid carrier may be a phospholipid. Further, the lipid carrier may be a fatty acid. Also, the lipid carrier may be a detergent. As used herein, a detergent is any substance that alters the surface tension of a liquid, generally lowering it.

In one example of the invention, the detergent may be a nonionic detergent. Examples of nonionic detergents include, but are not limited to, polysorbate 80 (also known as Tween 80 or (polyoxyethylenesorbitan monooleate), Brij, and Triton (for example Triton WR-1339 and Triton A-20).

Alternatively, the detergent may be an ionic detergent. An example of an ionic detergent includes, but is not limited to, alkyltrimethylammonium bromide.

Additionally, in accordance with the invention, the lipid carrier may be a liposome. As used in this application, a "liposome" is any membrane bound vesicle which contains any molecules of the invention or combinations thereof.

In order that the invention described herein may be more fully understood, the following examples are set forth. It should be understood that these examples are for illustrative purposes only and are not to be construed as limiting the scope of this invention in any manner.

ADVANTAGES OF THE INVENTION: Initial studies with various previously known immunoconjugates have been disappointing particularly with solid tumors. In our effort to improve antibody based therapy of carcinomas, we have developed and examined novel immunoconjugates and the anti-cancer drug doxorubicin (DOX).

BR96 is important for several reasons. It can trigger irreversible changes in membrane structure which leads to tumor cell death, most likely through the loss of osmotic control (J. Garrigues, U. Garrigues, I. Hellstrom, K.E. Hellstrom, Am. J. Pathol. 142, 607 (1993)). Further, it is an internalizing MAb that cycles in a nondegraded form between the intracellular compartment and the medium for extended periods of time. The latter characteristic makes BR96 an attractive candidate for targeting to tumors various agents for selective concentration in antigen positive cells.

The antigen for BR96 is abundantly expressed (>200,000 molecules/cell) on human carcinoma lines. BR96 binds, according to immunohistology, the majority of human carcinomas of the breast, lung and colon. Although BR96, like essentially all MAbs to human tumors, is not truly tumor-specific, it offers advantages over most other antibodies which recognize the Le$^y$ determinant (K. Lloyd, G. Larson, N. Stromberg, J. Thurin, K. A. Karlsson, Immunogenetics 17, 537 (1983); P. M. Pour, V. E. Tempero, C. Cordon-Cardo, P. Avner, Cancer Res. 48, 5422 (1988); J. Sakamoto et al., ibid. 49, 745 (1989); T. F. Orntoft, H. Wolf, H. Clausen, E. Dabelsteen, S. I. Hakomori, Int. J. Cancer, 43, 774 (1989)).

BR96 is more tumor selective and the normal tissues to which it binds primarily comprise differentiated cells of the esophagus, stomach, and intestine as well as acinar cells of the pancreas (Hellstrom I., Garrigues, H. J. Garrigues, U., Hellstrom, K. E. Cancer Res. 50, 2183 (1990)).

BR96 is rapidly internalized into lysosomes and endosomes after binding to cells expressing the antigen (J. Garrigues et al. 1993).

The antibodies mediate antibody-dependent cellular cytotoxicity "antibody-dependent cellular cytotoxicity", "complement-mediated cytotoxicity", and "complement-dependent cytotoxicity".

The antibodies can kill antigen-positive tumor cells in the unconjugated form if present at a sufficient concentration. The antibody conjugates and recombinant immunotoxins are useful as reagents for killing tumor cells. The antibodies are also useful in diagnostic methods, such as the detection of carcinomas by in vitro or in vivo technology.

EXAMPLE 1

Preparation Of The BR96 Monoclonal Antibody

The BR96 monoclonal antibody of the invention was produced using hybridoma fusion techniques as described previously by M. Yeh et al., Proc. Natl. Acad. Sci. USA, (1979), supra and Yeh et al., Int. J. Cancer (1982), supra. Briefly, a three month-old BALB/c mouse was immunized using as the immunogen explanted cultured cells from a human breast adenocarcinoma, designated 3396 or H3396 (from adenocarcinoma of the breast from a patient which had been established in culture at Bristol-Myers Squibb Co., Seattle, Wash.). Methods for establishing and maintaining cell lines from carcinomas isolated from patients are fully described in Yeh et al., Proc. Natl. Acad. Sci. USA 76:2927–2931 (1979) The mouse received injections on five occasions: on the first four occasions, the mouse received one intraperitoneal injection and 1 subcutaneous injection split between 4 sites on the mouse. On the fifth occasion, the mouse was given only one intraperitoneal injection. The total number of cells injected on each occasion was approximately 10$^7$ cells. Three days after the last immunization, the spleen was removed and spleen cells were suspended in RPMI culture medium. The spleen cells were then fused with P3-x63-Ag8.653 mouse myeloma cells in the presence of polyethylene glycol (PEG) and the cell suspension grown in microtiter wells in selective HAT medium as described by Yeh et al., supra [see, also, Kohler and Milstein, Nature, 256:495–97 (1975) and Eur. J. Immunol., 6:511–19 (1976)]. The mixture was seeded to form low density cultures originating from single fused cells or clones.

The supernatants from these hybridoma cultures were then screened for direct binding activity on the breast cancer cell line, 3396, and a fibroblast cell line obtained from a skin biopsy using an ELISA assay similar to that described by Douillard et al., "Enzyme-Linked Immunosorbent Assay For Screening Monoclonal Antibody Production Using Enzyme-Labeled Second Antibody", Meth. Enzymol., 92:168–74 (1983).

According to this assay, the antigen (with which the antibody being screened for is reactive) is immobilized on microtiter plates and then incubated with hybridoma supernatants. If a supernatant contains the desired antibody, the antibody will bind to the immobilized antigen and is detected by addition of an anti-immunoglobulin antibody-enzyme conjugate and a substrate for the enzyme which leads to a measurable change in optical density. In the present studies, breast cancer cells or control fibroblast cells were dispensed into a 96-well tissue culture plate (Costar Cambridge, Mass.) and incubated overnight in a humid 37° C. incubator (5% $CO_2$). The cells were then fixed with 100 µl of freshly prepared 1.0% glutaraldehyde to a final well concentration of 0.5% and incubated for 15 min at room temperature, followed by washing three times with 1 X phosphate buffered saline (PBS). The cells were next blocked for 30 min with 5% bovine serum albumin (BSA) in PBS and washed again three times with PBS. The supernatants from the hybridoma cultures were then added at 100 µl/well, the wells incubated for 1 h at room temperature, and the cells washed three times with PBS. Next, goat anti-mouse horseradish peroxidase (Zymed, Calif.) diluted in 0.1% BSA and PBS was added to a concentration of 100 µl/well. The reaction mixture was incubated for either 1 h at room temperature or 30 min at 37° C. and the cells were then washed three times with PBS. o-Phenylenediamine (OPD) was then added at 100 µl/well and the plates incubated in the dark at room temperature for 5–45 min. Antibody binding to the cells was detected by a color change in the wells that occurred within 10–20 min. The reaction was stopped by adding 100 µl/well $H_2SO_4$ and the absorbance read in a Dynatech (Alexandria, Va.) Microelisa autoreader at 490 nm.

It should be noted that this assay can be performed using intact cells or purified soluble antigen or cellular extracts as the immobilized antigen. When soluble antigen or cell extracts were used as antigen, the antigen was initially plated at 50 µl/well in PBS and the plates were incubated overnight at room temperature before beginning the assay. When using intact cells as antigen, they may be used fresh or after fixation. In either case, the cells were initially plated at $10^4$ cells in 100 µl/well in culture medium and incubated overnight in a 37° C. incubator (5% $CO_2$).

Hybridomas which produced antibodies binding to the breast cancer cell line and not to the human fibroblast cells were thus selected, and tested in a FACS cell sorter on peripheral blood leukocytes (PBLs), as described in Example 2, infra. Hybridomas that were negative on PBLs were cloned, expanded in vitro, and further tested for antibody specificity. Those hybridomas producing antibody reactive with human breast cancer were recloned, expanded, and injected into pristane-primed 3-month old BALB/c mice, where they grew as ascites tumors.

Following this procedure, hybridoma cell line BR96 was obtained, cloned and injected into mice to develop as an ascites tumor. As disclosed above, the BR96 hybridoma has been deposited with the ATCC. Monoclonal BR96 antibody was purified from ascites by affinity chromatography on immobilized recombinant protein A (Repligen, Cambridge, Mass.). Clarified ascites was diluted with an equal volume of binding buffer (1 M potassium phosphate, pH 8) and applied to a protein A column previously equilibrated with binding buffer. The column was extensively washed with binding buffer and then the antibody was eluted with 50 mM phosphoric acid, pH 3. The purified antibody fraction was neutralized with 1 M Tris, pH 9 and then dialyzed against phosphate buffered saline. Purified BR96 was finally sterile filtered and stored refrigerated or frozen.

EXAMPLE 2
Characterization Of The BR96 Monoclonal Antibody
Isotype Determination To determine the class of immunoglobulin produced by the BR96 hybridoma, the following techniques were utilized:

(a) Ouchterlony Immunodiffusion

An aliquot of supernatant of the hybridoma cells was placed into the center well of the a 25 agar plate. Monospecific rabbit anti-mouse Ig isotype antibodies (Southern Biotechnology, Birmingham, Ala.) were placed in the outer wells and the plate was incubated for 24–28 h at room temperature. Precipitation lines were then read.

(b) ELISA Isotyping

Dynatech Immulon 96-well plates were coated with goat anti-mouse Ig antibodies at 1 µg/ml concentration, 50 µl/well in PBS and left covered overnight at 4° C. The plates were washed with PBS/Tween 20, 0.05% and blocked with medium at 100 µl/well for 1 h at room temperature. After washing the plates, supernatants from the BR96 hybridoma were added and incubated at room temperature for 1 h. After washing with PBS containing 2% bovine serum albumin (BSA), plates were incubated at 37° C. for 30 min with monospecific rabbit anti-mouse Ig isotype antibodies coupled to peroxidase (Zymed, South San Francisco, Calif.). After further washing, the plates were incubated with 1 mg/ml OPD and 0.03% $H_2O_2$ in 0.1 M citrate buffer, pH 4.5. Optical density at 630 nm was determined on a Dynatec ELISA plate reader.

Based on these procedures, it was determined that the BR96 monoclonal antibody is of the IgG3 isotype.
Characteristics Of The BR96 Monoclonal Antibody The BR96 antibody shows a high degree of reactivity with a wide range of carcinomas and displays only limited reactivity with normal cells. This was shown by experiments involving immunohistological studies on frozen tissue sections as well as binding studies using intact cultured cells.
Immunohistology The peroxidase-antiperoxidase (PAP) technique of L. A. Sternberger as described in *Immunochemistry*, pp. 104–69 (John Wiley & Sons, New York, 1979) and as modified by J. Garrigues et al., "Detection Of A Human Melanoma-Associated Antigen, p97, In Histological Sections Of Primary Human Melanomas", *Int. J. Cancer*, 29:511–15 (1982), was used for the immunohistological studies. The target tissues for these tests were obtained at surgery and frozen within 4 h of removal using isopentane precooled in liquid nitrogen. Tissues were then stored in liquid nitrogen or at −70° C. until used. Frozen sections were prepared, air dried, treated with acetone and dried again [see Garrigues et al., supra]. Sections to be used for histologic evaluation were stained with hematoxylin. To decrease non-specific backgrounds sections were preincubated with normal human serum diluted 1/5 in PBS [see Garrigues et al., supra]. Mouse antibodies, rabbit anti-mouse IgG, and mouse PAP were diluted in a solution of 10% normal human serum and 3% rabbit serum. Rabbit anti-mouse IgG (Sternberger-Meyer Immunochemicals, Inc., Jarettsville, Md.), was used at a dilution of 1/50. Mouse PAP complexes (Sternberger-Meyer Immunochemicals, Inc.) containing 2 mg/ml of specifically purified PAP was used at a dilution of 1/80.

The staining procedure consisted of treating serial sections with either specific antibody, i.e., BR96, or a control antibody for 2.5 h, incubating the sections for 30 min at room temperature with rabbit anti-mouse IgG diluted 1/50 and then exposing the sections to mouse PAP complexes diluted 1/80 for 30 min at room temperature. After each treatment with antibody, the slides were washed twice in PBS.

The immunohistochemical reaction was developed by adding freshly prepared 0.5% 3,3'-diaminobenzidine tetrahydrochloride (Sigma Chemical Co., St. Louis, Mo.) and 0.01% $H_2O_2$ in 0.05 M Tris buffer, pH 7.6, for 8 min [see Hellstrom et al., *J. Immunol.*, 127:157–60 (1981)]. Further exposure to a 1% OsO$_4$ solution in distilled water for 20 min intensified the stain. The sections were rinsed with water, dehydrated in alcohol, cleared in xylene, and mounted on slides. Parallel sections were stained with hematoxylin.

The slides were each evaluated under code and coded samples were checked by an independent investigator.

Typical slides were photographed by using differential interference contrast optics (Zeiss-Nomarski). The degree of antibody staining was evaluated as 0 (no reactivity), + (a few weakly positive cells), ++ (at least one third of the cells positive), +++ (most cells positive), ++++ (approximately all cells strongly positive). Because differences between + and 0 staining were less clear cut than between + and ++ staining, a staining graded as ++ or greater was considered "positive". Both neoplastic and stroma cells were observed in tumor samples. The staining recorded is that of the tumor cells because the stroma cells were not stained at all or were stained much more weakly than the tumor cells.

Table 1 below demonstrates the immunohistological staining of various tumor and normal tissue specimens using the BR96 monoclonal antibody. As the table clearly demonstrates, the BR96 antibody reacts with a wide range of human carcinoma specimens, does not react with sarcoma and displays only infrequent reactivity with melanoma.

Furthermore, it shows only limited reactivity with any of the large number of normal human tissues tested. The only reactivity detected with normal cells was binding to a small subpopulation of cells in the tonsils and in the testis, and to acinar cells in the pancreas, and to certain epithelial cells of the stomach and esophagus.

TABLE 1

Immunoperoxidase Staining of Human Tumors and Normal Tissue Specimens with BR96 Monoclonal Antibody

| TISSUE TYPE | NUMBER POSITIVE/ NUMBER TESTED | |
|---|---|---|
| Tumors | | |
| Lung carcinoma (non-small cell) | 14/17 | |
| Breast carcinoma | 17/19 | |
| Colon carcinoma | 15/18 | |
| Ovary carcinoma | 4/4 | |
| Endometrial carcinoma | 2/2 | |
| Melanoma | 2/5 | |
| Sarcoma | 0/5 | |
| Stomach carcinoma | 2/2 | |
| Pancreatic carcinoma | 2/2 | |
| Esophagus carcinoma | 2/2 | |
| Cervical carcinoma | 2/2 | |
| Normal Tissue | | |
| Lung | 0/7 | |
| Spleen | 0/5 | |
| Breast | 0/2 | |
| Colon | 0/7 | |
| Kidney | 0/7 | |
| Liver | 0/5 | |
| Brain | 0/2 | |
| Heart | 0/3 | |
| Skin | 0/2 | |
| Thyroid | 0/2 | |
| Adrenal | 0/1 | |
| Ovary | 0/2 | |
| Lymph nodes | 0/2 | |
| Lymphocyte pellet | 0/4 | |
| Pancreas | 2/2 | (only acinar cells were positive) |
| Uterus | 0/7 | |
| Retina | 0/1 | |
| Testis | 2/2 | (only small sub-population of cells were positive) |
| Tonsil | 2/2 | (only small sub-population of cells were positive) |
| Stomach | 2/2 | (epithelial cells positive) |
| Esophagus | 2/2 | (epithelial cells positive) |

The binding of the BR96 antibody to various cultured cell lines was also evaluated. Antibody binding to the cell surface of intact cultured cells was identified either by a direct binding assay with $^{125}$I-labeled antibody as described in Brown et al., "Quantitative Analysis Of Melanoma-Associated Antigen p97 In Normal And Neoplastic Tissues", *Proc. Natl. Acad. Sci. USA*, 78:539–43 (1981), or by direct immunofluorescence using a Coulter Epics C fluorescence activated cell sorter (FACS) II [Hellstrom et al., *Cancer Res.* 46:3917–3923 (1986)].

For binding analyses using a FACS cell sorter, 2×10$^5$ to 1×10$^6$ cultured cells were aliquoted in 15% fetal bovine serum (FBS) in IMDM media (Gibco, N.Y.) to a total volume of 500 μl/tube. The cells were centrifuged for 1.5 min on a Serofuge and the supernatant removed. 100 μl of the BR96 monoclonal antibody at 10 μl/ml was added to each tube, the contents of which was then mixed and incubated on ice for 30 min. The reaction mixture was washed three times with 500 μl of 15% FBS/IMDM by centrifugation for 1.5 min on the Serofuge (tubes were blotted after the third wash). Then, 50 μl of optimized FITC-conjugated goat anti-mouse IgG antibody (Tago, Burlingame, Calif.) diluted 1:25 in 15% FBS/IMDM was added to each tube and the reaction mixture was mixed and incubated for 30 min. The wash step was then repeated and after blotting of the tubes, each pellet was resuspended in 200–500 μl of PBS. Each sample was run on a Coulter Epics C FACS and the mean fluorescence intensity (MFI) was determined. From the MFI, the linear fluorescent equivalent (LFE) was determined. The LFE of each test sample divided by the LFE of a negative control gave a ratio between the brightness of cells stained by specific versus control antibody. The binding data is shown in Table 2 below.

TABLE 2

FACS Analysis of the Binding of BR96 to Various Types of Suspended Cells

| Cell line | | Ratio (10 μg/ml) |
|---|---|---|
| Breast carcinoma | 3396 | 54 |
| Breast carcinoma | MCF-7 | 38 |
| Breast carcinoma | 3630 | 22 |
| Breast carcinoma | 3680 | 22 |
| Lung carcinoma | 2987 | 15 |
| Lung carcinoma | 2707 | 30 |
| Lung carcinoma | 2964 | 2 |
| Lung carcinoma | 3655-3 | 18 |
| Colon carcinoma | RCA | 34 |
| Colon carcinoma | 3619 | 22 |
| Colon carcinoma | 3347 | 5 |

TABLE 2-continued

FACS Analysis of the Binding of BR96 to Various Types of Suspended Cells

| Cell line | | Ratio (10 μg/ml) |
|---|---|---|
| Colon carcinoma | HCT116 | 1 |
| Colon carcinoma | CB5 | 27 |
| Colon carcinoma | C | 30 |
| Colon carcinoma | 2600 | 16 |
| Ovary carcinioma | 2633-3 | 11 |
| Melanoma | 2669 | 1 |
| Melanoma | 3606 | 1 |
| Melanoma | 3620 | 1 |
| T cell lymphoma line | CEM | 1 |
| T cell lymphoma line | MOLT-4 | 1 |
| B cell lymphoma line | P3HR1 | 1 |
| Peripheral blood leukocytes | | 1 |

As Table 2 demonstrates, the BR96 monoclonal antibody reacted with most breast, lung and colon carcinoma cell lines but did not react with melanoma lines or with T or B lymphoma lines nor with normal peripheral blood leukocytes. Scatchard analysis using radiolabeled antibody indicated that the approximate association constant ($K_a$) of BR96 was calculated to be $3.6 \times 10^6$ antigen sites/cell for the 3396 line which binds BR96.

These data demonstrate that monoclonal antibody BR96 recognize cell surface antigens abundantly expressed (up to $10^6$ molecules/cell) on the majority of human carcinomas.

EXAMPLE 3
Internalization Of The BR96 Monoclonal Antibody Within Carcinoma Cells Studies were conducted to measure internalization of the BR96 monoclonal antibody within antigen-positive carcinoma cells. According to one procedure, BR96 was conjugated to the ricin A chain toxin to form an immunotoxin, BR96-RA, whose internalization by carcinoma cells was then determined. Uptake of the conjugate by the carcinoma cells was assessed by determining to what extent the tumor cells were killed by ricin A chain.

Conjugation of the antibody to the toxin was carried out as follows: Deglycosylated ricin-A chain (Inland Labs, Austin, Tex.) [see, also, Blakey et al., *Cancer Res.*, 47:947–952 (1987)] was treated with dithiothreitol (5 mM) prior to gel filtration on G-25 Sephadex using PBS, pH 7.2 as eluant. This was added in a 2:1 molar ratio to the antibody in PBS, the antibody having been previously modified with N-succinimidyl-3-(2-pyridyldithio) propionate (SPDP) (Pierce, Rockford, Ill.) according to the procedure of Lambert et al., *J. Biol. Chem.* 260:12035–12041 (1985). Reaction was allowed to proceed for 12–24 h at room temperature, and the solution was then diluted with 1 volume of $H_2O$. Removal of unconjugated antibody was achieved using Blue Sepharose CL-6B (Pharmacia, Uppsala, Sweden) [see Knowles et al., *Anal. Biochem.*, 160:440–443 (1987)].

The conjugate and excess ricin-A chain were eluted with high salt (10×PBS) and subjected to further purification on Sephacryl-300 (Pharmacia) using PBS as eluant. The resulting conjugate was free of unbound monoclonal antibody or ricin A-chain and consisted mostly of 1:1 adducts.

The internalization of BR96-RA by various carcinoma cell lines was then measured using a thymidine uptake inhibition assay. According to this assay, the inhibition of $^3$H-thymidine incorporation into the DNA of the carcinoma cells (i.e., the inhibition of cell proliferation) is a measure of the cytotoxic effect of BR96-RA on the cells and thus a measure of the internalization of the immunotoxin within the cell.

For the assay, carcinoma cells were plated into a 96-well microtiter plate at $1 \times 10^4$ cells/well in 100 μl of IMDM medium with 15% fetal calf serum (FCS). The plates were incubated for 12–18 h at 37° C. to let the cells adhere. Then the media was removed. Plates were kept on ice. The BR96-RA immunotoxin (100 μl) was then added in log 10 serial dilutions, starting at 10 μg/ml final concentration down to 0.01 μg/ml. The reaction mixture was incubated for 4 h on ice. The plates were washed and 200 μl/ml media was added and further incubated at 37° C. for 18 h. At this point, 50 μl of $^3$H-thymidine was added at 1 μCi/well and the plates incubated for 6 h at 37° C. In a 5% $CO_2$ incubator. The assay plates were then frozen at −70° C. for at least 1 h and thawed in a gel dryer for 15 min. The cells were harvested onto glass fiber filters (Filter Strips, No. 240-1, Cambridge Technology) in plastic scintillation vials using a PHD cell harvester. 3 ml of scintillation counting liquid was added to the vials and the vials were counted on a Beckman LS3891 beta scintillation counter at 1 minute per sample.

Graphs of the percent inhibition of thymidine incorporation vs. immunotoxin concentration for each cell line tested were plotted and are shown in FIGS. 1–5. In each assay, a control was run. The results of the assay are expressed as a percentage of the $^3$[H] thymidine incorporated by untreated control cells.

Figure 1:
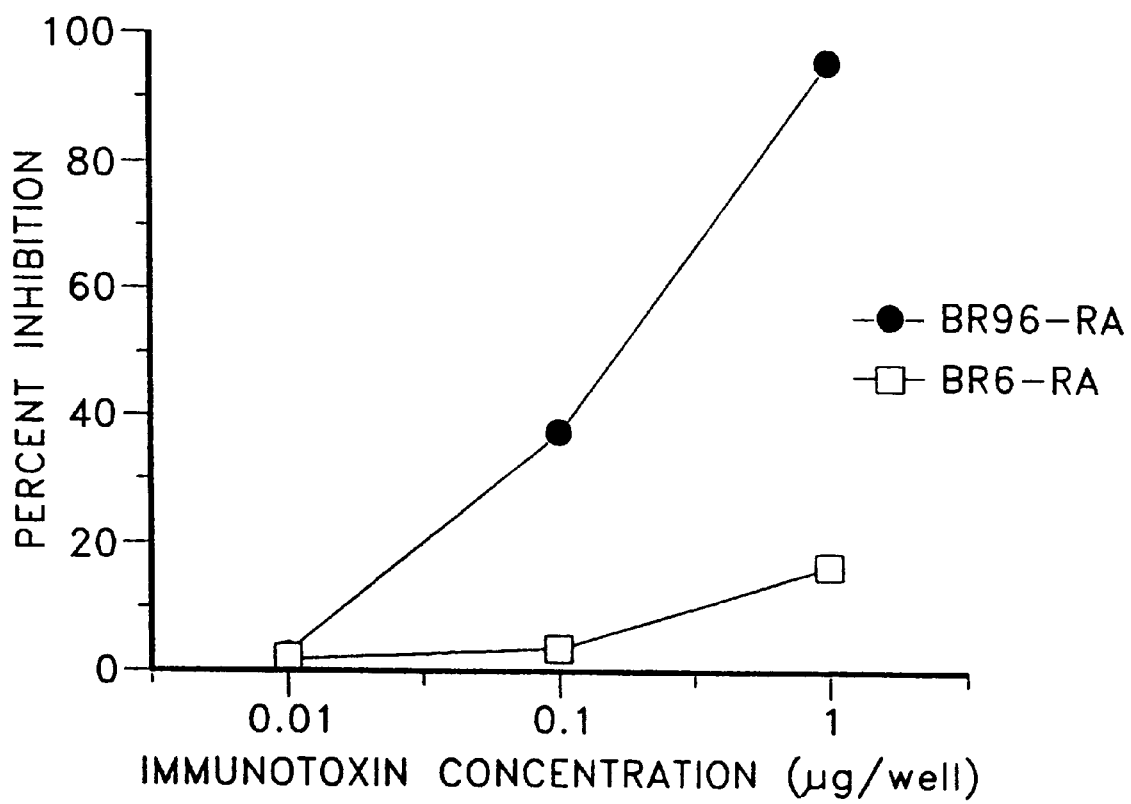
FIG. 1 depicts the percent inhibition of thymidine incorporation into the DNA of 3396 breast carcinoma cells treated with a BR96-RA immunotoxin at varying concentrations as described in Example 3, infra. BR6-RA is an internalizing antibody which is used as a negative control because it does not bind to the 3396 cells.
Figure 2:
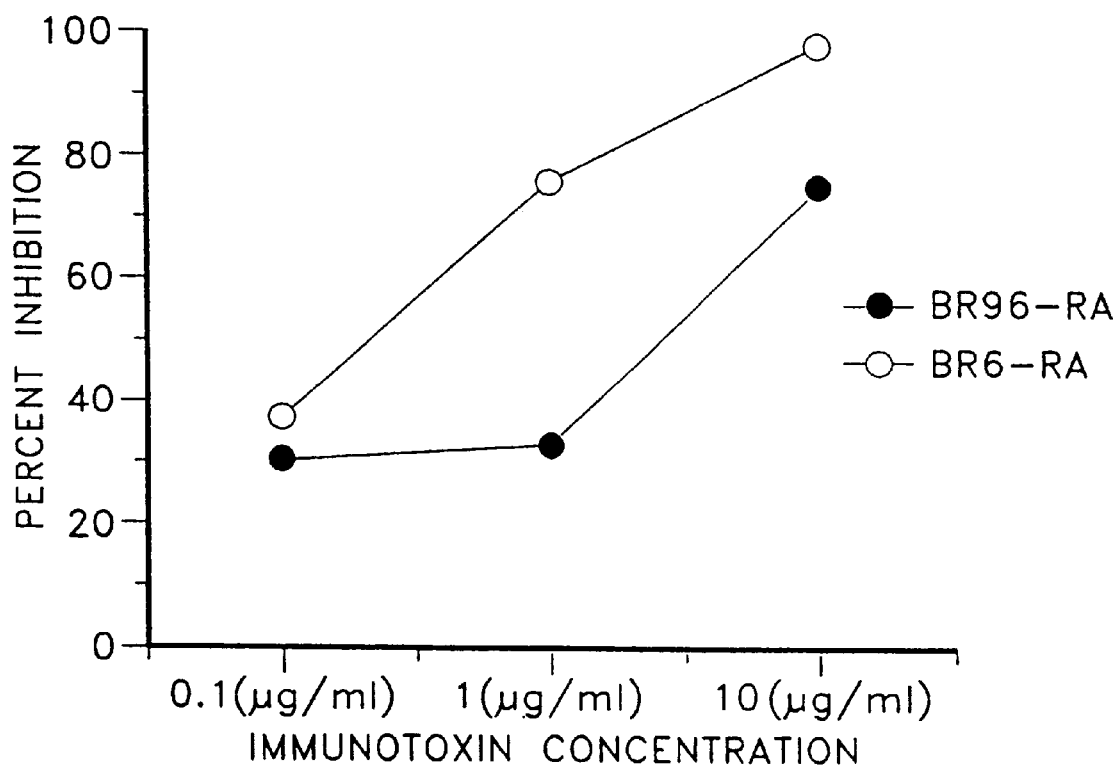
FIG. 2 depicts the percent inhibition of thymidine incorporation into the DNA of 2707 lung carcinoma cells treated with a BR96-PA immunotoxin at varying concentrations as described in Example 3, infra. BR6-RA is an internalizing antibody which also binds to the 2707 cells.
Figure 3:
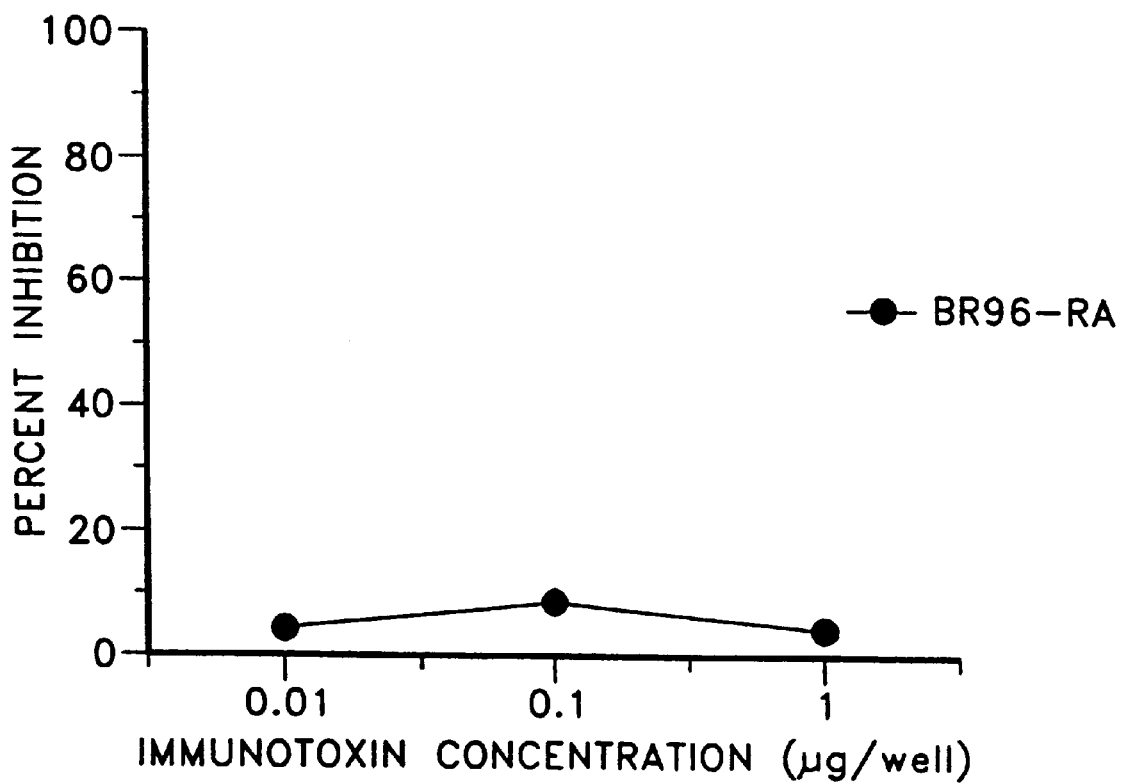
FIG. 3 depicts the percent inhibition of thymidine incorporation into the DNA of HCT116 colon carcinoma cells treated with a BR96-RA immunotoxin at varying concentrations as described in Example 3, infra. BR96 does not bind to HCT 116 cells.
Figure 4:
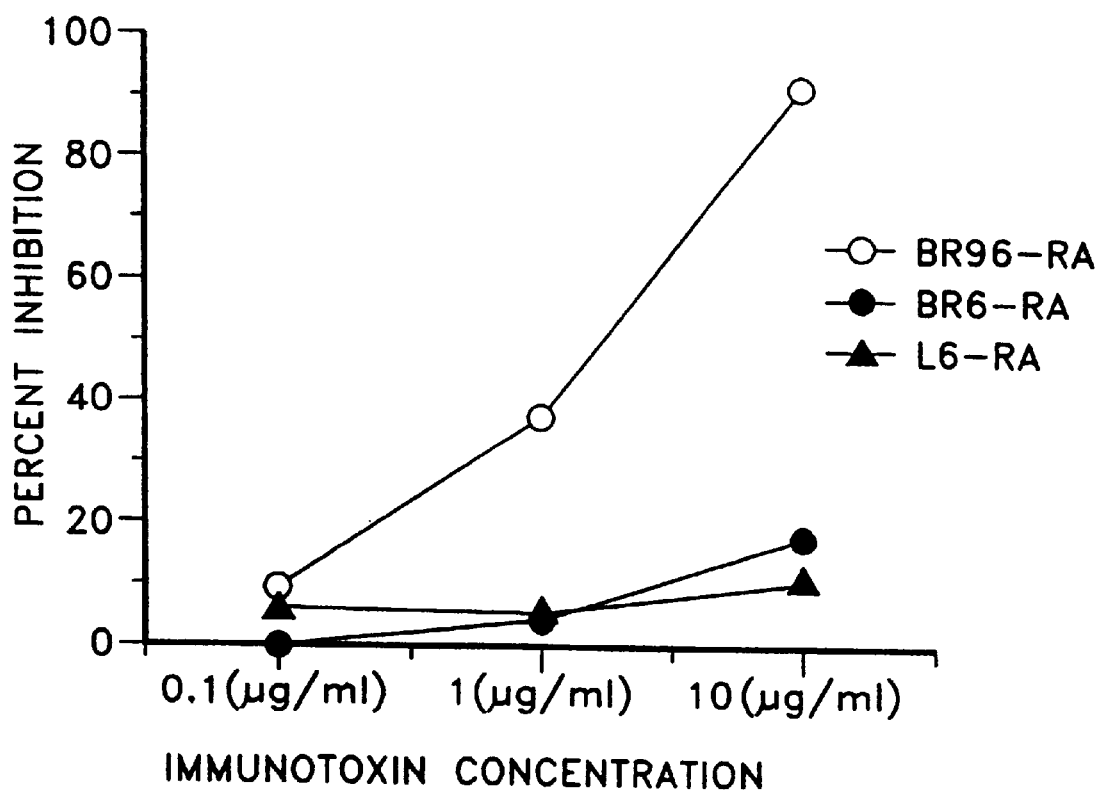
FIG. 4 depicts the percent inhibition of thymidine incorporation into the DNA of C colon carcinoma cells treated with a BR96-RA immunotoxin at varying concentrations as described in Example 3, infra. BR6-RA does not bind to the C cells; L6-RA binds to the C cells but does not internalize.
Figure 5:
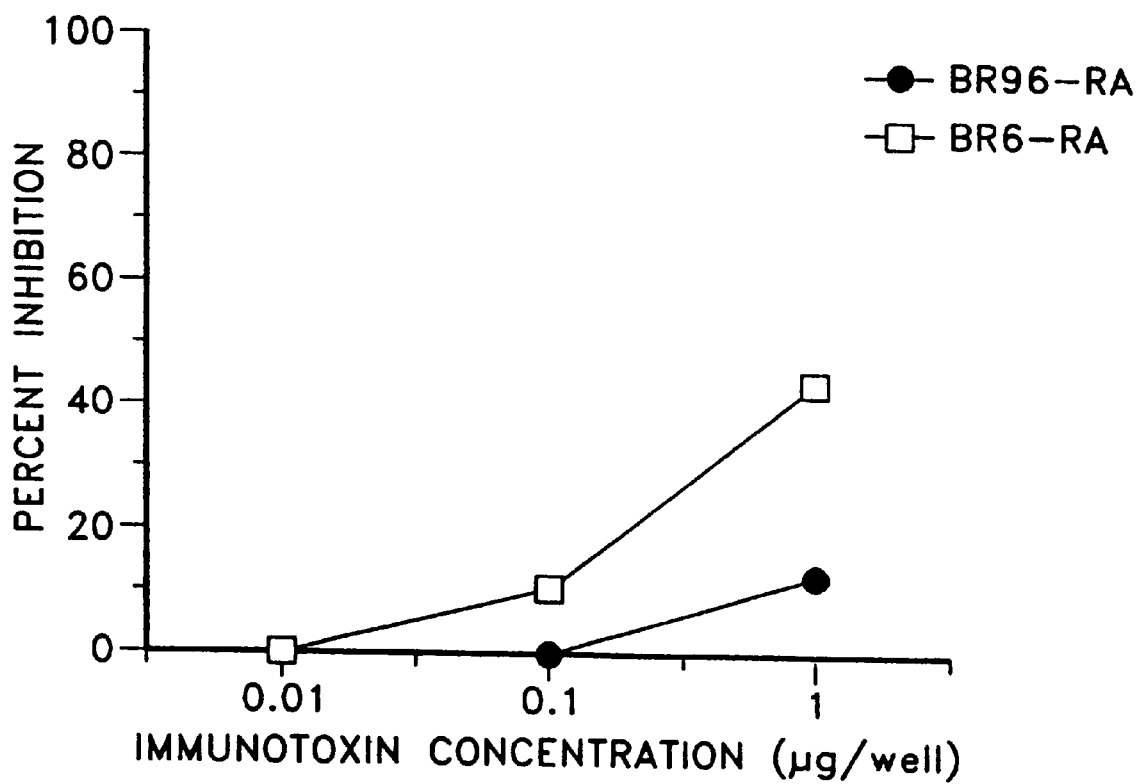
FIG. 5 depicts the percent inhibition of thymidine incorporation into the DNA of 3347 colon carcinoma cells treated with a BR96-RA immunotoxin at varying concentrations as described in Example 3, infra. BR96 does not bind to these cells while BR6 does.

FIG. 1 depicts the percent inhibition of thymidine incorporation by cells from the 3396 breast carcinoma cell line caused by internalization of BR96-RA. Similar results were obtained with the 2707 lung carcinoma cell line (FIG. 2) and C colon carcinoma cell line (see FIG. 4). The BR96-RA was not internalized by HCT 116 cell line (ATCC No. CCL 247), a human colon carcinoma cell line that does not bind BR96 (see FIG. 3). FIG. 5 shows no internalization of BR96-RA on 3347, a colon carcinoma cell line to which BR96 does not bind; BR6-RA, on the other hand, which binds to the 3347 cells, does internalize. This study, therefore, demonstrated not only internalization of the BR96 antibody but the selectivity of the internalization of the BR96 antibody for antigen positive carcinoma cells.

EXAMPLE 4
Cytotoxicity of Unmodified BR96 Monoclonal Antibody

Three types of experiments were performed to follow up on the unexpected observation that monoclonal antibody BR96 appeared to be cytotoxic by itself (i.e., in unmodified state) when tested in a FACS assay. So as to avoid an effect of complement in serum, all sera used were heat inactivated (56° C. for 30 min); in addition, some of the experiments with FACS analysis (as described below) were performed on cells which were grown in serum-free medium and tested in the absence of serum.

Figure 6:
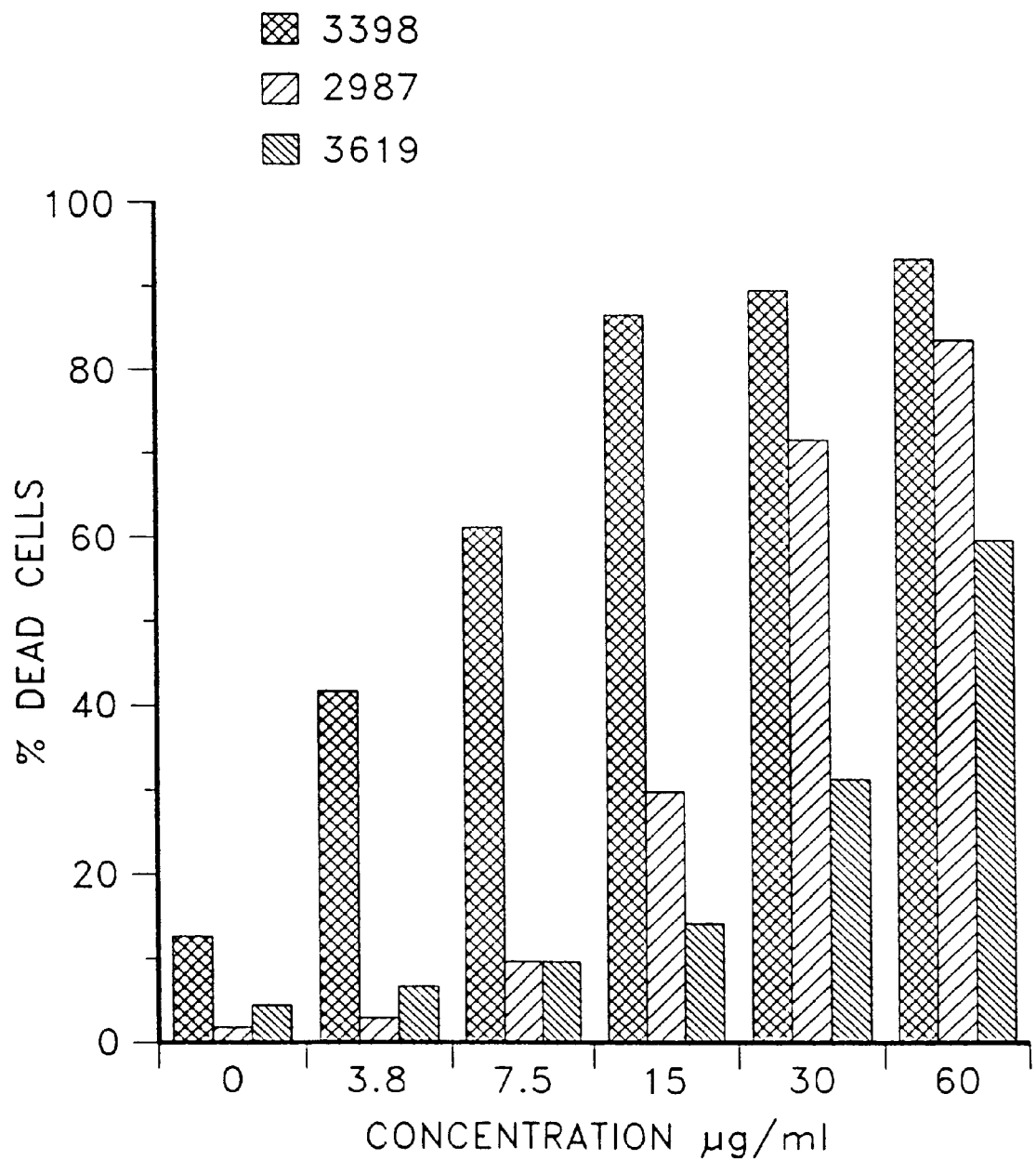
FIG. 6 depicts the results of FACS analysis of the cytotoxicity of propidium iodide stained 3396 breast carcinoma cells, 2987 lung carcinoma cells and 3619 colon carcinoma cells, as described in Example 4, infra.

First, living suspended cells from a variety of antigen positive carcinoma lines (3396, 2987, 3619) were treated with monoclonal antibody BR96. Cells ($5 \times 10^5$) were incubated on ice for 30 min with 100 μl of BR96 or control monoclonal antibody at a concentration of 60, 30, 15, 7.5 and 3.8 μg/ml in culture medium (IMDM, 15% FBS). After washing the cells twice with culture medium, the cells were suspended in 500 μl medium and stained by adding the dye propidium iodide which stains dead cells [Krishan, *Cell Biol.* 66:188 (1975); and Yeh, *J. Immunol. Methods*, 43:269 (1981)]. Out of a 1 mg/ml stock solution (in 70% alcohol) 5 μl dye was added to cell samples, incubated on ice for 15 min, washed once and finally suspended in 500 μl medium. The cells were evaluated on a Coulter Epics C FACS, with dead cells being identified by their red fluorescence. The analysis was done on a two-parameter display with log forward lightscatter in the horizontal and log red fluorescence in the vertical display. Computations of cell size versus cell viability were obtained by applying the Coulter Epics C Quadstat program. Tumor cells which could bind BR96 as well as tumor cells not binding BR96 were studied in parallel. The results are shown in FIG. 6. FIG. 6 demonstrates that incubation of cells from any of three antigen-positive carcinomas with BR96 rapidly killed them. Untreated or antigen-negative cells were not killed.

Figure 7:
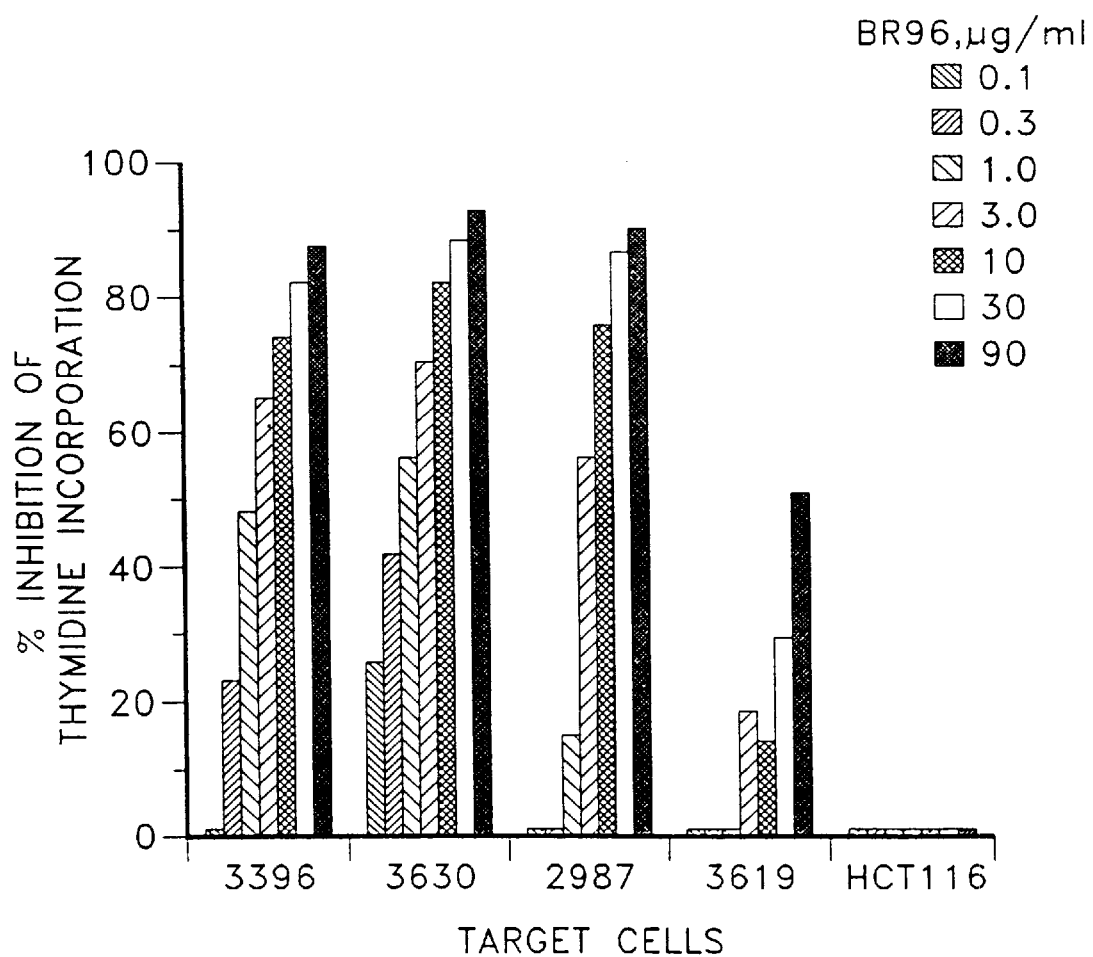
FIG. 7 depicts the effects of BR96 on cell proliferation of various cell lines as described in Example 4, infra.

Second, tumor cells (3396, 3630, 2987, 3619 and HCT 116) were exposed to BR96 (or the control monoclonal antibody) for 18 h at 37° C. In a 96-well microtiter plate at $3 \times 10^3$ cells/well in 150 μl of IMDM medium containing FBS for 66 h after which 50 μl of $^3$[H]-thymidine was added at 1 μCi/well and the plate was incubated for another 6 h at 37° C. Subsequently, it was frozen at −70° C. for at least 1 h and thawed in a gel dryer for 15 min, and the cells harvested onto glass fiber filters. The tritiated thymidine assay was then performed as described in the preceding example, except that the cells and antibodies were incubated at 37° C. FIG. 7 illustrates the results. BR96 caused an inhibition of [$^3$H]thymidine incorporation into antigen-positive cell lines, and this effect was dose dependent. The antigen-negative cell line HCT116 was not affected by any concentration of BR96 examined.

Figure 8:
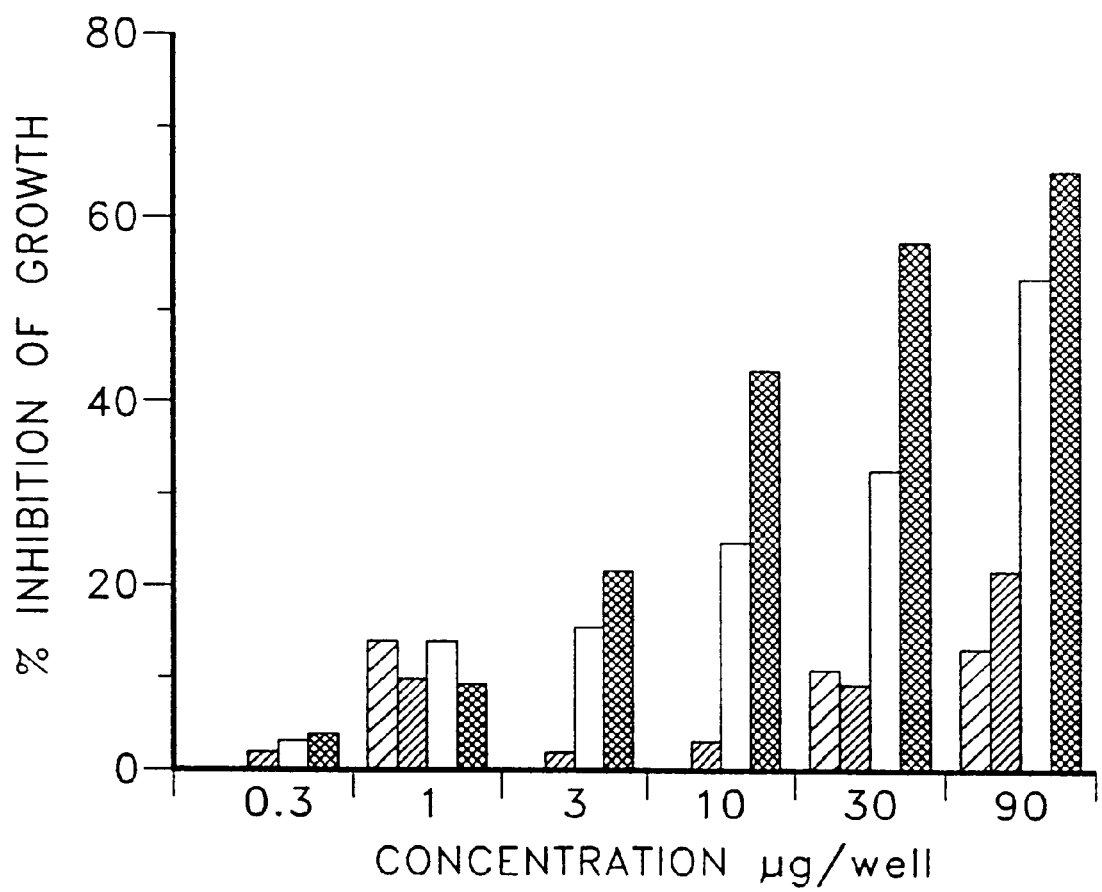
FIG. 8 illustrates the effect of BR96 on cell growth of various cell lines, measured by a staining method as described in Example 4, infra.

Third, using a modification of a procedure described by Linsley et al. [Linsley, et al., "Identification and characterization of cellular receptors for growth regulator, Oncostatin M", *J. Biol. Chem.* 264:4282–4289 (1989)] a growth inhibition assay was performed. Cells from four different cell lines (HCT116, 2987, 3396 and 3630) were seeded ($3 \times 10^3$) in a volume of 0.1 ml of IMDM with 15% fetal bovine serum (FBS) in 96-well microtiter plates and allowed to attach for 3 h at 37° C. Various concentrations of whole BR96 monoclonal were then added in a volume of 0.1 ml, after which incubation at 37° C. was continued for 72 h. Subsequently, the culture medium was removed and the cells were stained by crystal violet (0.1%, in 20% methanol) for 30 min. and washed three times with PBS. The bound dye was eluted by the addition of 0.1 ml of a solution of 0.1 M sodium citrate, pH 4.2, in 50% ethanol. Samples were assayed in triplicate on an ELISA reader measuring the absorbance in the presence of BR96 with the absorbance in untreated samples. The results of this procedure are expressed as percentage inhibition of cell growth. FIG. 8 illustrates the results. The results of this assay were in agreement with those presented above for the thymidine incorporation assay (FIG. 7).

EXAMPLE 5
Antibody-Dependent Cellular Cytotoxicity Activity of BR96 Antibody

Determination of antibody-dependent cellular cytotoxicity activity of BR96 monoclonal antibody was performed as described by Hellstrom et al., *Proc. Natl. Acad. Sci. (USA)* 82:1499–1502 (1985). Briefly, a short-term $^{51}$Cr-release test that measures the release of $^{51}$Cr as described by Cerrotini et al., *Adv. Immunol.* 18:67–132 (1974) was used as evidence of tumor-cell lysis (cytotoxicity). Peripheral blood lymphocytes from healthy human subjects were separated on Ficoll-Hypaque [Hellstrom et al., *Int. J. Cancer* 27:281–285 (1981)] to provide effector cells equal to 5% natural killer cell reactivity against SK-MEL-28 cells (ATCC No. HTB 72); $10^6$ cells were labeled by incubation with 100 μCi (1 Ci=37 Gbq) of $^{51}$Cr for 2 h at 37° C., after which they were washed three times and resuspended in medium. The labeled cells were seeded ($2 \times 10^4$ cells per well in 20 μl) into Microtiter V-bottom plates (Dynatech Laboratories, Alexandria, Va.). Purified antibody BR96 (10 μg/ml, 1 μg/ml, and 0.1 μg/ml) was then added, followed by $2 \times 10^5$ lymphocytes per well in 100 μl. The mixtures were incubated for 2 to 4 h after which the plates were centrifuged at 400×g. The supernatants were removed and the radioactivity in 100 μl samples was measured with a gamma-counter. There were two replicates per group; the variation between replicates was less than 10%. Several "criss-cross" experiments were done, in which lung (or colon) carcinoma and melanoma targets were tested in parallel with monoclonal antibody BR96 and with the antimelanoma monoclonal antibody MG-22 [Hellstrom et al., *Proc. Natl. Acad. Sci. USA*, 82:1499–1502 (1985)] which do not bind to most carcinoma cells. Controls included the incubation of target cells alone or with either lymphocytes or monoclonal antibody separately.

Spontaneous release was defined as the counts per minute (cpm) released into the medium from target cells exposed to neither antibodies nor lymphocytes, and total release, as the number of counts released from target cells that were osmotically lysed at the end of the assay. Percent cytotoxicity was calculated as:

$$\frac{\text{experimental group release} - \text{spontaneous release}}{\text{total release} - \text{spontaneous release}} \times 100$$

Effector cells were characterized by assessing their sensitivity to incubation with anti-serum to the Leu-11b surface marker and guinea pig complement, using procedures described by Hellstrom et al., in *Monoclonal Antibodies and Cancer Therapy*, UCLA Symposia on Molecular and Cellular Biology, New Series, eds. Reisfeld & Sell, Liss, New York, Vol 27, pp. 149–164 (1985), incorporated herein by reference. This was done to measure the expression of the Leu-11b marker, which characterizes natural killer (NK) cells and is expressed by lymphocytes mediating antibody-dependent cellular cytotoxicity against human melanoma cells in the presence of monoclonal antibody BR96. The cytotoxicity by effector cells alone ("natural killer effect") was subtracted from the data provided in FIG. 9.

Figure 9:
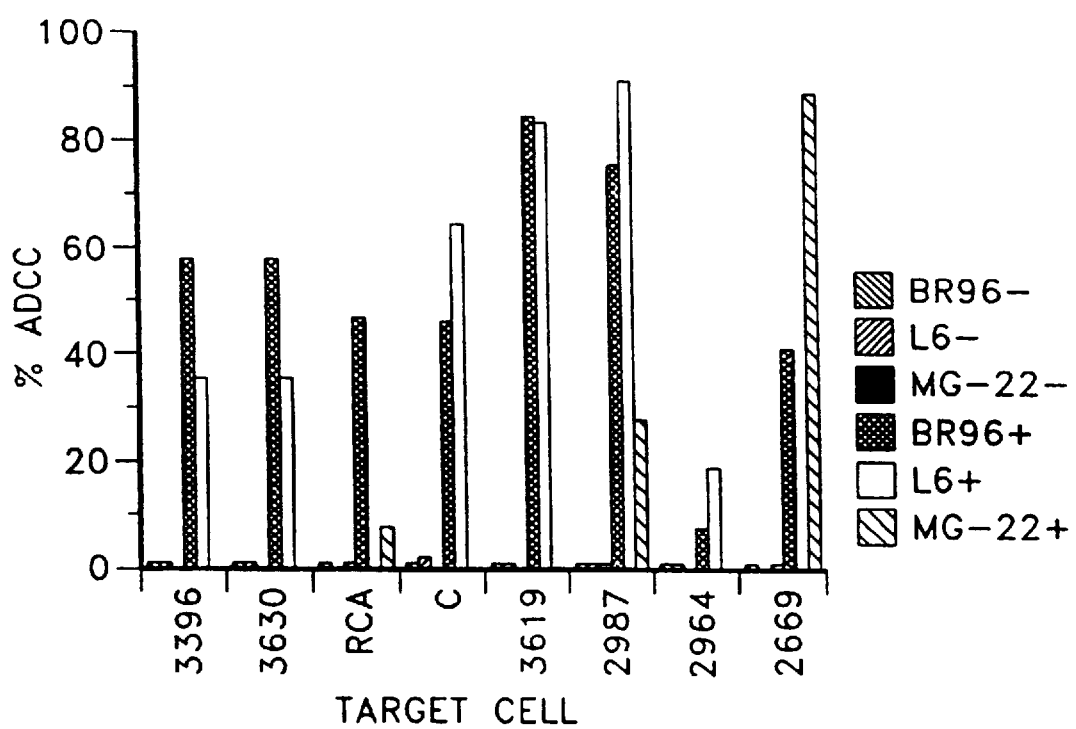
FIG. 9 illustrates the results of tests to determine antibody-dependent cellular cytotoxicity activity of BR96 as described in Example 5, infra.

The results shown in FIG. 9 for an antibody concentration of 10 μg/ml indicate that BR96 mediates antibody-dependent cellular cytotoxicity activity if present in sufficient concentrations and if the target cells express sufficient concentrations of the epitope. The antibody-dependent cellular cytotoxicity activity can be seen at antibody concentrations lower than those at which the antibody is cytotoxic by itself (usually around 20 μg/ml). When antibody BR96 was used alone as a control it produced 0% killing at the concentrations tested and using the $^{51}$Cr assay. antibody-dependent cellular cytotoxicity activity was only found with BR96 antibody-binding cell lines. Thus, cells from five different carcinoma lines, which all bound BR96, were killed via antibody-dependent cellular cytotoxicity at monoclonal antibody concentrations down to 0.1 μg/ml, while cells from a sixth line, 2964, which did not bind BR96, were not killed. The requirement for antibody binding to obtain antibody-dependent cellular cytotoxicity was further demonstrated by the fact that both of the two carcinomas which could bind a different antibody, L6 (lines 3619 and 2987), were killed by L6 via antibody-dependent cellular cytotoxicity, while the others were not. Under the conditions of the assay, BR96 alone caused the release of only 1% of the label, even when tested at a concentration of 10 μg/ml.

EXAMPLE 6

Ability of BR96 to Mediate Complement-Mediated Cytotoxicity (Complement-Dependent Cytotoxicity)

Tests to evaluate the ability of monoclonal antibody BR96 to kill tumor cells in the presence of human serum as a source of complement (complement-mediated cytotoxicity or complement-dependent cytotoxicity) were performed similarly to those for the antibody-dependent cellular cytotoxicity tests described in Example 5, supra, except that 100 μl of human serum from normal human subjects as the source of complement diluted 1:3 to 1:6 was added per microtest well in place of a suspension of effector cells.

Figure 10:
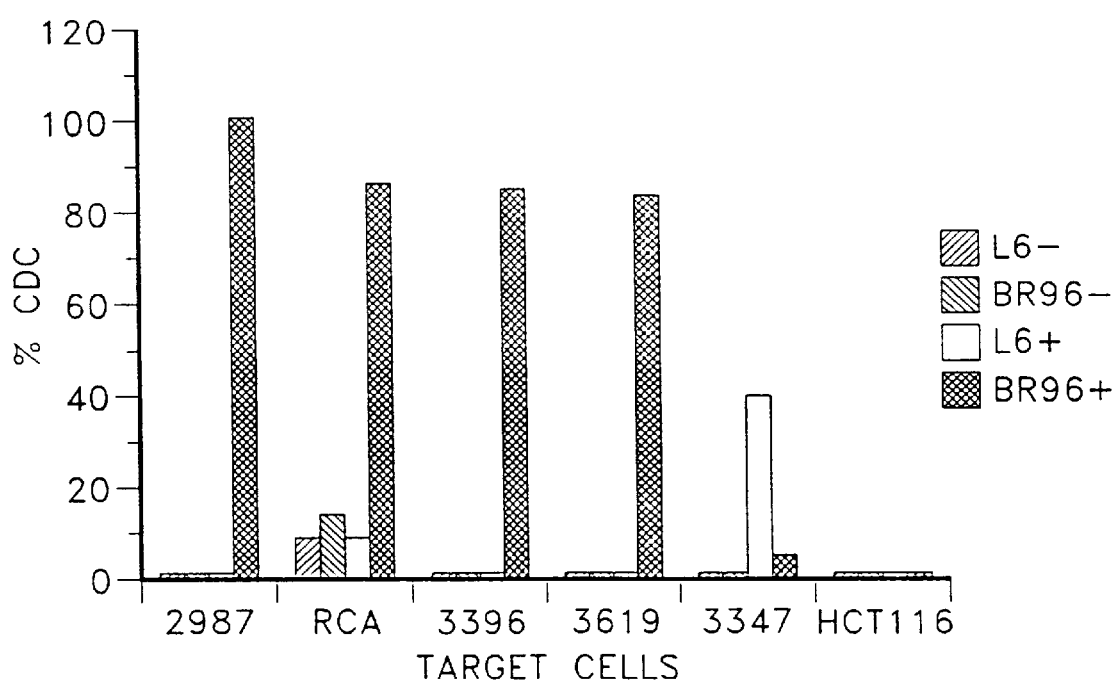
FIG. 10 describes the results of tests to determine complement-dependent cytotoxicity activity of BR96 as described in Example 6, infra.

As shown in FIG. 10, complement-dependent cytotoxicity against cells binding BR96 was seen at an antibody concentration of 0.1–5.0 μg/ml, while there was no complement-dependent cytotoxicity against the BR96 antigen-negative lines HCT116 and 3347. The 3347 cells could, however, be killed when using the L6 monoclonal antibody, which binds to these cells. Controls were always included in which BR96 was tested in the absence of complement. No killing by BR96 alone was detected by the $^{51}Cr$ release assay. These data show that BR96 gave a cytotoxic effect in the presence of human serum at concentrations where it is not cytotoxic by itself. (Control antibody gave no complement-dependent cytotoxicity).

EXAMPLE 7

Determination of Reactivity of BR96 to Glycolipids and Glycoproteins

Figure 11:
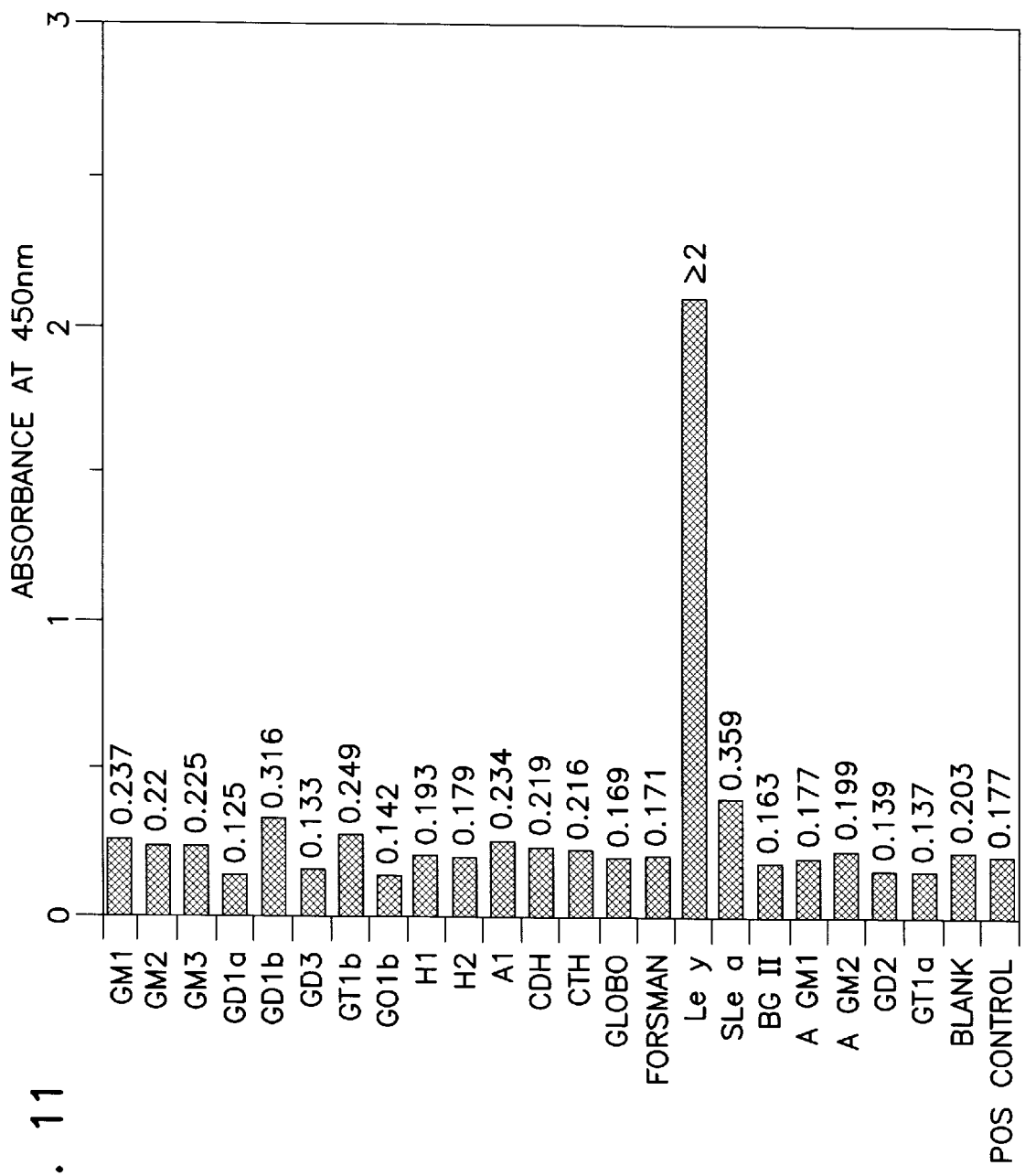
FIG. 11 is a bar graph of the results of testing the reactivity of BR96 against glycolipids as described in Example 7, infra.
Figure 12:
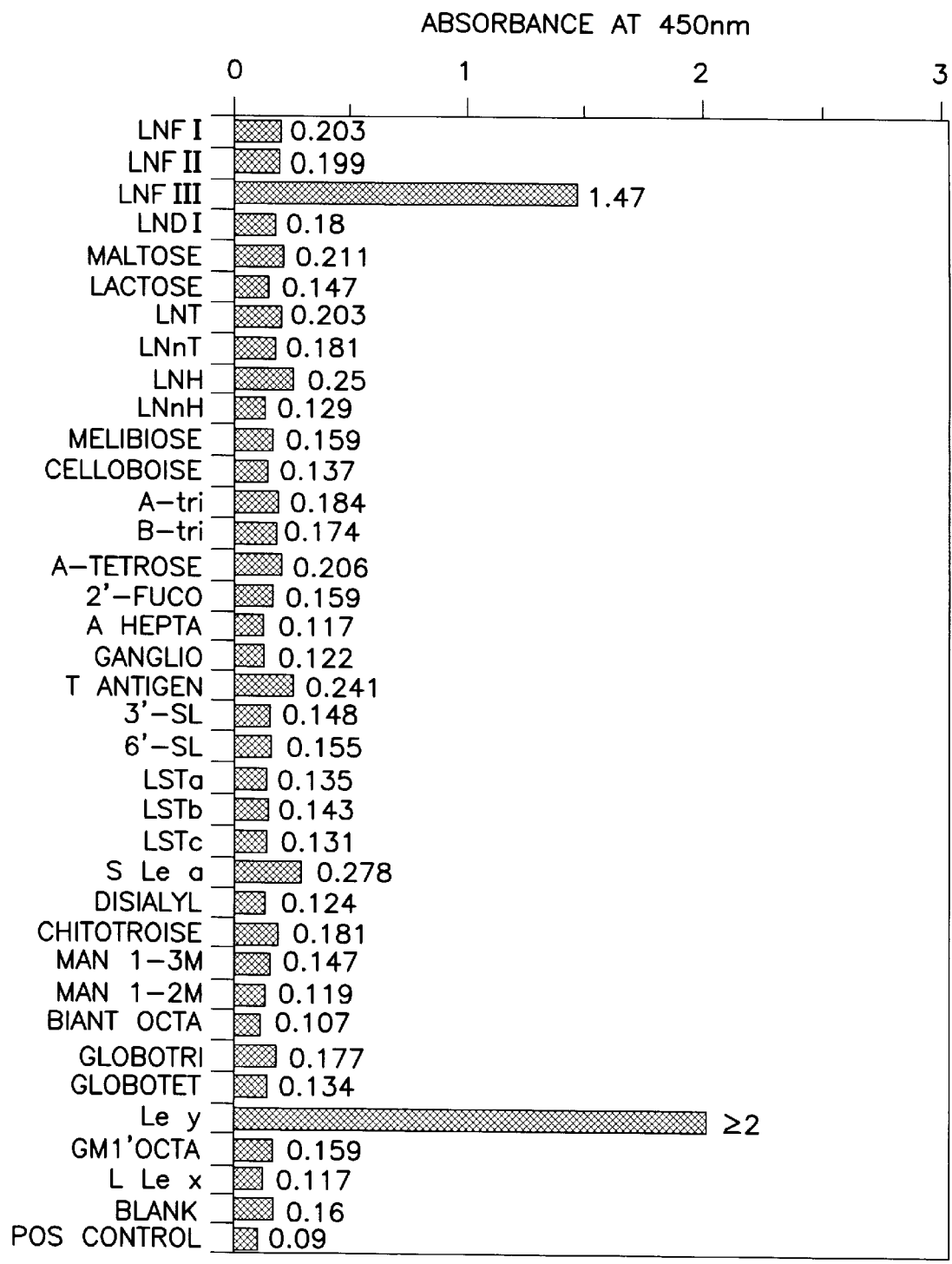
FIG. 12 is a bar graph of the results of testing the reactivity of BR96 against neoglycoproteins as described in Example 7, infra.

BR96 antibody was tested for reactivity to a variety of immobilized glycolipid antigens having known carbohydrate structures and synthetic glycoproteins (so called "neoglycoproteins") using an ELISA assay in which purified glycolipids and glycoproteins and antibody were used in excess (Dr. John Magnani, Biocarb, Gaithersburg, Md.; Lloyd et al., *Immunogenetics* 17: 537–541 (1983)). Glycolipids were dried from methanol in microtiter wells at 100 ng/well. Synthetic glycoproteins were coated on the surface of the wells by incubation of glycoprotein diluted to 200 ng in phosphate buffered saline (PBS), at pH 7.4/well. Purified BR96 was assayed at a concentration of 10 μg/ml in 0.01 M Tris-HCl, pH 7.4, containing 1% BSA containing antibodies from ascites were assayed at a dilution of 1:100 in the same buffer. At these high concentrations most binding interactions are readily detected. Absorbance values were calculated as the average of duplicate wells. The results of this analysis are summarized in FIGS. 11 and 12 showing that BR96 reacted with $Le^y$ and Lex determinant.

These findings indicate that BR96 can bind to a variant form of the Lewis Y (Fuc α1-2Galβ1-4(Fucα1-3)GlcNAc) antigen and that fucose α1-3 attached to GlcNAc forms a portion of the $Le^y$-related epitope recognized by BR96. The high tumor specificity of BR96 and ability to internalize (not previously described for monoclonal antibodies reactive with the other $Le^y$ determinant) suggests that the antibody recognizes a complex epitope, a portion of which includes at least a part of a $Le^y$ determinant.

EXAMPLE 8

Preparation and Characterization of BR96 F(ab')$_2$ Fragments

Murine BR96 (IgG$_3$) was purified by Protein A affinity chromatography from murine ascites fluid. Briefly, delipidated ascites was passed over a column containing a matrix of immobilized Protein A (RepliGen Corp., Cambridge, Mass.) previously equilibrated with 1 M potassium phosphate, pH 8.0. Following the passage of ascites, the column was washed with equilibration buffer until no further protein was spectrophotometrically detected. The bound BR96 was then eluted from the column using 0.1 M citrate buffer, pH 3.0. Immediately after elution, the eluate was neutralized with 1.0 M Tris buffer, pH 9.0, until the pH was approximately 7.0. The monoclonal antibody was then dialyzed into PBS and concentrated prior to storage or use.

F(ab')$_2$ fragments were then generated by digesting purified BR96 monoclonal antibody with pepsin according to Lamoyi, "Preparation of F(ab')$_2$ Fragments from Mouse IgG of Various Subclasses", *Meth. Enzymol.* 121: 652–663 (1986). Residual whole antibody and Fc fragments were adsorbed from the reaction mixture by passage over a protein A affinity column. The resulting F(ab')$_2$ fragment preparations were dialyzed extensively against PBS and sterile filtered.

The BR96 F(ab')$_2$ fragments preparations were characterized by gel permeation HPLC, SDS-PAGE and by ELISA on the human breast tumor line 3396 (Bristol-Myers Squibb Co., Seattle, Wash.). Gel permeation HPLC was used to assess the molecular sizes of the proteins comprising the F(ab')$_2$ preparation. Reproducible chromatograms from different preparations indicated that 75–80% of the protein was F(ab')$_2$. No protein was detected at the positions representing higher molecular weight material, such as whole BR96 or protein aggregates. The remaining 20–25% of the protein eluted at positions corresponding to inactivated pepsin and to other smaller non-protein A-binding digestion products.

Nonreducing and reducing SDS-PAGE was used to examine the denatured molecular sizes and structural arrangement of the proteins in the F(ab')$_2$ preparations. A single major band at the position of F(ab')$_2$ (approximately 100 kdal) was typically observed, with no visible contaminating whole monoclonal antibody band (160 kdal). Lower molecular weight bands (i.e. less than 100 kdal) representing inactivated pepsin and small digestion products were minimal. Under reducing conditions the expected results were obtained with the only major bands occurring as a doublet at approximately 25 kdal representing the light chain and the remaining fragmented portion of the heavy chain. No whole heavy chain band was observed.

Figure 13:
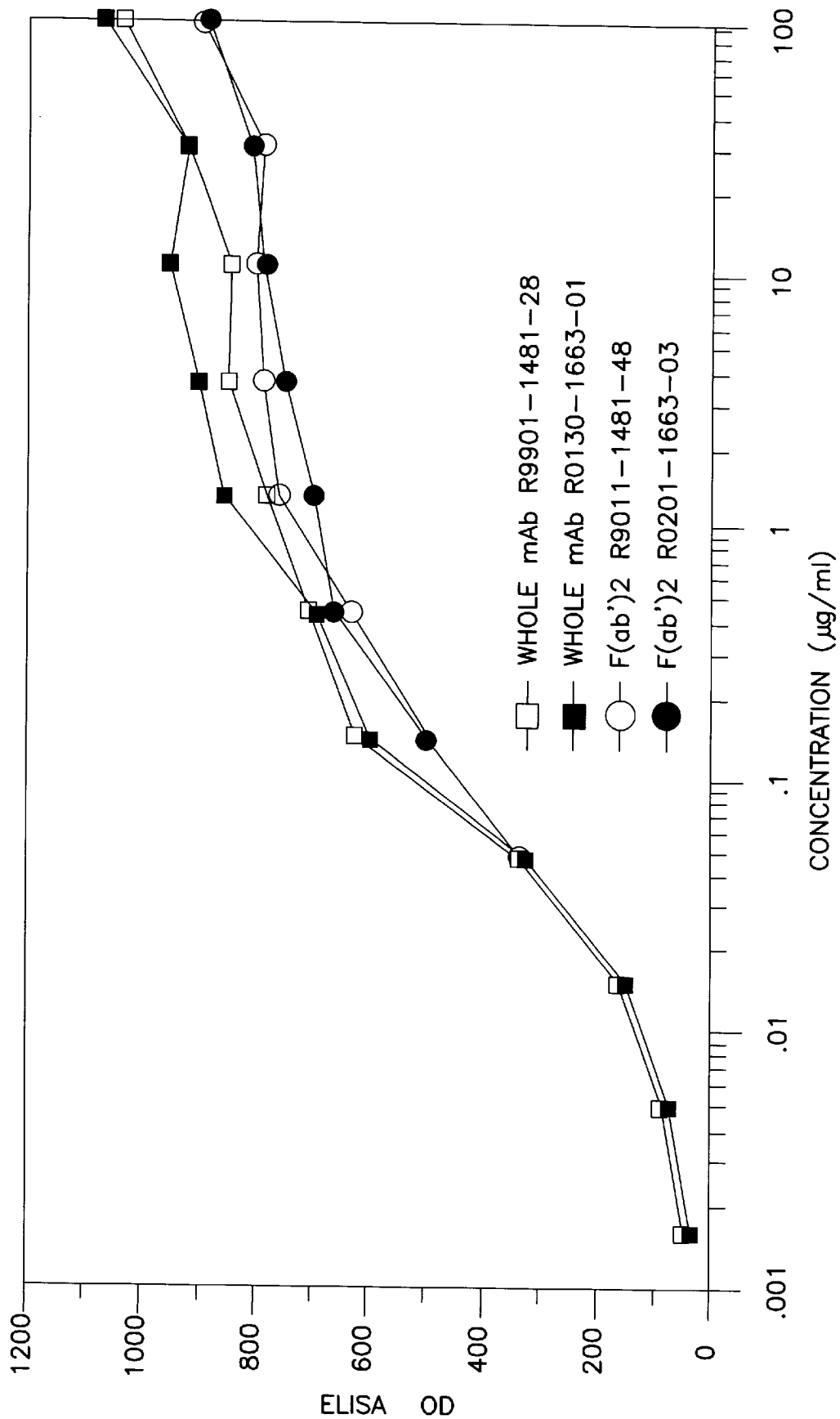
FIG. 13 is a graph of the binding activity of BR96 F(ab')$_2$ fragments compared to that of whole BR96 monoclonal antibody in an ELISA using goat anti-K light chain detecting reagent, as described in Example 8, infra.
Figure 14:
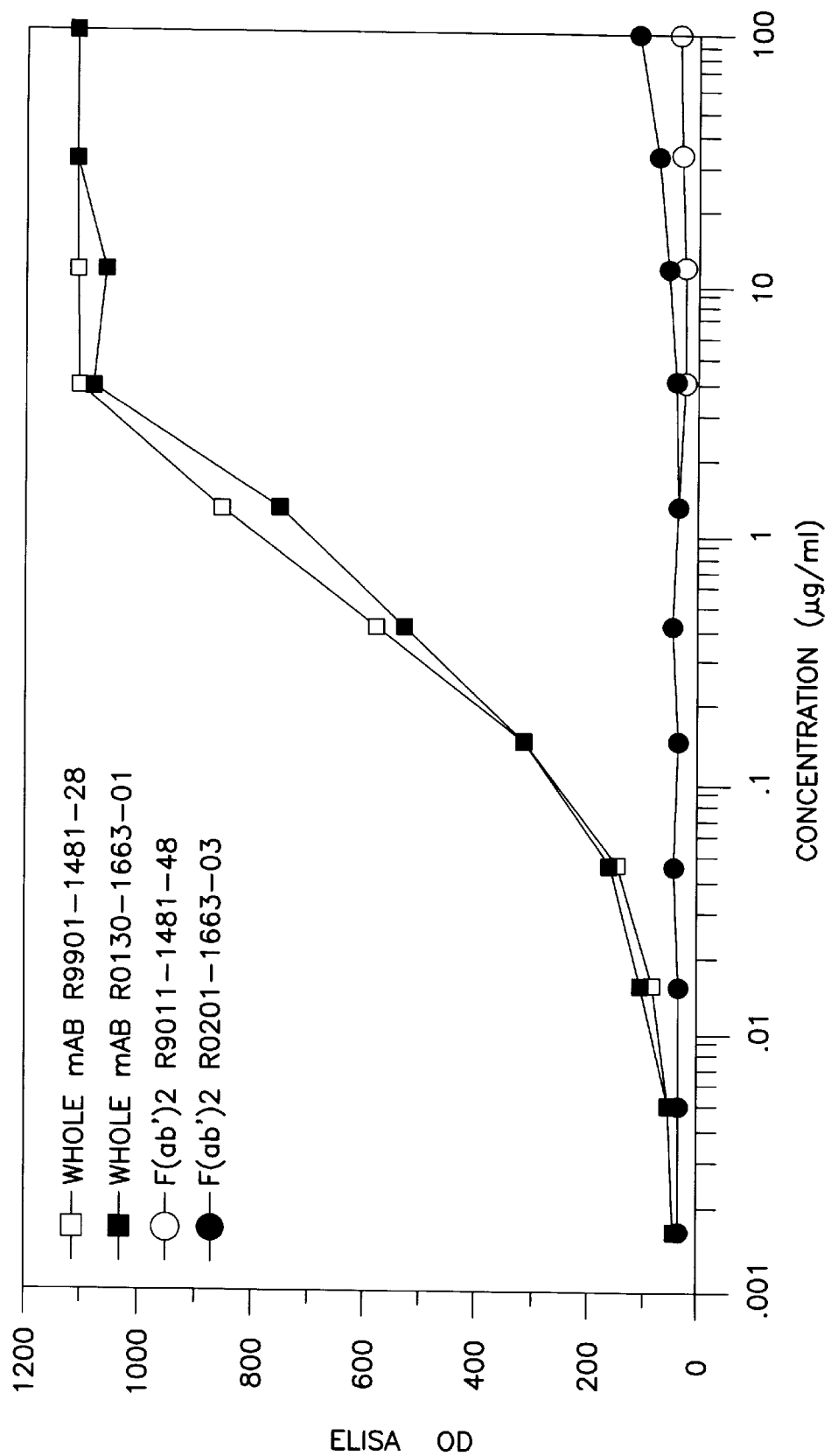
FIG. 14 is a graph of the binding activity of BR96 F(ab')$_2$ fragments as compared to that of whole BR96 monoclonal antibody in an ELISA using peroxidase conjugated protein A detecting reagent, as described in Example 8, infra.

Functional (binding) activity of the BR96 F(ab')$_2$ fragments was compared to that of whole BR96 in an ELISA with 3396 cells supplying the antigen. Binding of BR96 whole antibody or F(ab')$_2$ fragments to the cells was detected with an HRP-conjugated goat anti-murine K light chain reagent as shown in FIG. 13. On a duplicate plate, binding of whole BR96 was distinguished from binding of F(ab')$_2$ fragments by using HRP-conjugated protein A which binds to the whole antibody but not the F(ab')$_2$ fragments (FIG. 14).

These results indicate that BR96 F(ab')$_2$ (lot R0201-1663-03, lot 2) contained a trace amount of whole BR96 antibody. The level of contaminating whole antibody can be estimated to be approximately 8 trifold dilutions away from the amount of F(ab')$_2$ present, or about 0.01%. The other F(ab')$_2$ preparation (lot R9011-1481-48, lot 1) showed no detectable level of contaminating whole BR96, indicating that any effect of BR96 can be explained by binding of the Fab region and not the Fc region.

In summary, the BR96 F(ab')$_2$ preparations appear to be completely free of contaminating whole BR96 IgG by HPLC and by SDS-PAGE. In only one instance, when a very sensitive ELISA method was used were detectable levels of contaminating whole BR96 antibody found and this represented only approximately 0.01% by weight compared to the amount of F(ab')$_2$ fragments present.

EXAMPLE 9

Preparation and Characterization of Chimeric BR96 Antibody (ChiBR96)

The murine/human chimeric BR96 antibody of the invention ("ChiBR96") was produced using a two-step homologous recombination protocol as described by Fell et al., in *Proc. Natl. Acad. Sci. USA* 86: 8507–8511 (1989) and in co-pending patent application by Fell and Folger-Bruce, U.S. Ser. No. 243,873, filed Sep. 14, 1988, and Ser. No. 468,035, filed Jan. 22, 1990, and assigned to the same assignee as the present application; the disclosures of all of these documents are incorporated in their entirety by reference herein.

Human Heavy Chain DNA Transfection

Figure 15:
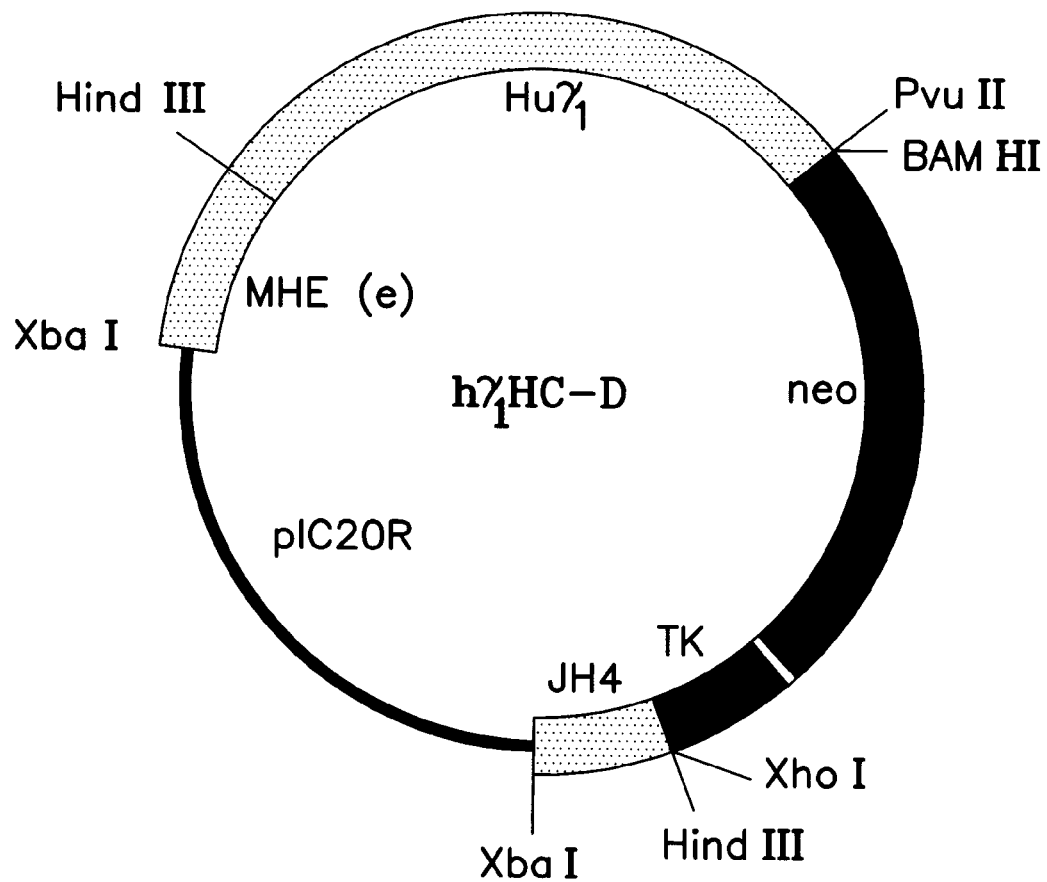
FIG. 15 is a diagram of vector phγ$_1$HC-D used in the electroporation procedure, as described in Example 9, infra.

The murine hybridoma cell line BR96, ATCC No. HB10036, obtained as described above was transfected ($8\times10^6$ cells) with hγ1/HC-D (deposited at Agricultural Research Service Culture Collection, Peoria, Ill., NRRL No. B 18599) (FIG. 15) by electroporation (Gene Pulser; Biorad Laboratories, Richmond, Calif.) at 250 V, 960 μFd capacitance setting, in isotonic phosphate buffered saline (PBS) and 30 μg/ml of the purified 6.2 kb XbaI restricted fragment of the vector hgγ1HC-D. After 48 hr cells were seeded in 96-well plates at $10^4$ cells/well. Selection for Neo$^R$ was carried out in IMDM medium (GIBCO, Grand Island, N.Y.) containing 10% (vol/vol) fetal bovine serum (FBS) and the antibiotic aminoglycoside G418 (GIBCO) at 2.0 mg/ml.

Detection of Secreted Human IgG (Hu γ1) Antibody by ELISA

Culture supernatants were screened using a sandwich ELISA assay 2 weeks after transfection. Goat anti-human IgG, Fc specific (CALTAG, San Francisco, Calif.) was used as the capture antibody and goat anti-human IgG, Fc specific conjugated to horseradish peroxidase HRPO, (CALTAG) was the antibody used to detect bound human IgG. Cells from the HuIgG positive wells were subcloned by dilution and dilution clones were screened by ELISA to detect human IgGγ1 by the previously described method. The clones containing human IgGγ1 were also screened by ELISA to detect murine IgG3 heavy chain. Goat anti-mouse IgG3 (Southern Biotechnology Assoc., Inc., Birmingham, Ala.) was used as the capture antibody and goat anti-mouse conjugated to HRPO (Southern Biotechnology Assoc., Inc.) was the antibody used to detect the mouse IgG3.

One of the human IgGγ1 positive murine IgG3 negative (Huγ1$^+$, MuG3$^-$) clones was chosen and designated Chi-HBR96. This heavy chain chimeric hybridoma cell line, ChiHBR96 was characterized for antigen specificity on MCF-7 cells and for expression levels by a quantitative ELISA for human IgG expression on MCF7 cells. The cell line ChiHBR96 expressed approximately 20 μg/ml of antigen-specific human IgG antibody.

Light Chain DNA Transfection

Figure 16:
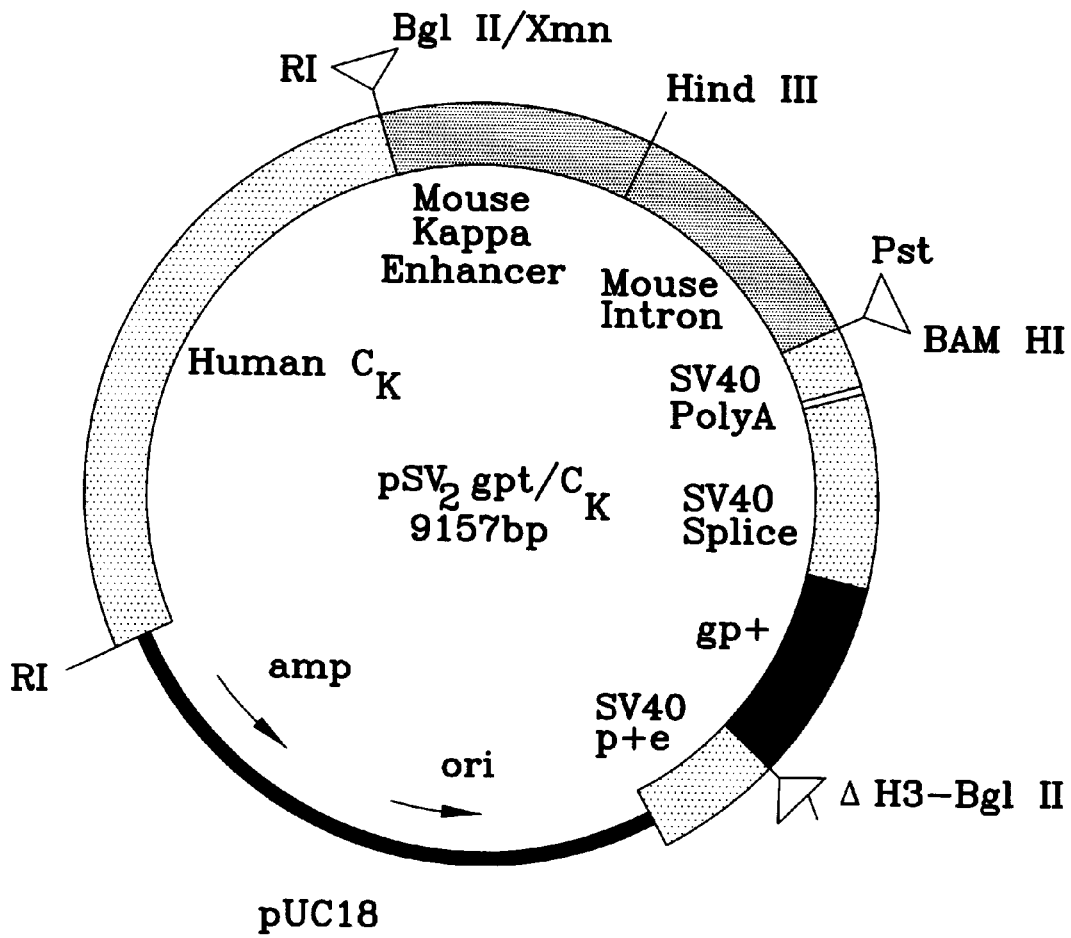
FIG. 16 is a diagram of vector pSV$_2$gpt/C$_K$ used in the electroporation procedure, as described in Example 9, infra.

The ChiHBR96 hybridoma ($8\times10^6$ cells) was transfected by electroporation as described above but using 30 μg/ml of the human light chain recombination vector pSV$_2$gpt/C$_K$ (NRRL No. B 18507) containing the human light chain K immunoglobulin sequence shown in FIG. 16, linearized with HindIII. After 48 hr cells were seeded in 96-well plates at $10^4$ cells/well. Selection for gpt was carried out in IMDM medium containing 10% (vol/vol) FBS, 15 μg/ml hypoxanthine, 250 μg/ml xanthine and 2.25 μg/ml mycophenolic acid (MA).

Detection of Secreted Human Kappa (Hu K) Antibody by ELISA

Culture supernatants were screened using a sandwich ELISA assay as described above, 2 weeks after transfection. Goat α-human K (CALTAG) was the capture antibody and goat anti-human K HRPO (CALTAG) was the antibody used to detect bound human K. Wells containing human K antibody were subcloned by dilution and the clones were screened by ELISA to detect human K or murine K chain. Goat anti-mouse K (Fisher Scientific, Pittsburgh, Pa.) was used as the capture antibody and goat anti-mouse K conjugated to HRPO (Fisher Scientific) was the antibody used to detect the presence of the mouse K chain. One of the human K positive, murine K negative clones (HuK$^+$, MuK$^-$) was chosen to analyze antigen specificity on MCF-7 cells and for expression levels by a quantitative ELISA for human IgG expression on MCF-7 cells. A cell line that was antigen specific for MCF-7 cells and HuIgG$^+$, MuIgG3$^-$, HuK$^+$, MuK$^-$ was chosen and designated Chimeric BR96 (ChiBR96).

The original expression of the heavy and light chain antigen specific chimeric BR96 (ChiBR96) antibody was approximately 25 μg/ml. Through four sequential rounds of cloning the line in soft agarose with a rabbit α HuIgG antibody overlay to detect cells secreting the highest amount of chimeric antibody [Coffino et al., *J. Cell. Physiol.* 79: 429–440 (1972)], a hybridoma cell line (ChiBR96) was obtained secreting approximately 130 μg/ml of chimeric antibody. Hybridoma ChiBR96 was deposited with the ATCC on May 23, 1990, and there provided with the deposit number, ATCC No. HB 10460.

Binding of ChiBR96

The relative affinity of the ChiBR96 antibody and murine BR96 antibody of the invention for the tumor associated antigen on MCF-7 cells was determined by an ELISA competition binding assay [Hellstrom et al., *Cancer Res.* 50: 2449–2454 (1990)]. Briefly, adherent antigen bearing cell line MCF-7 was plated in a 96-well microtiter dish at $3\times10^4$ cells/well and allowed to grow to confluency for about 3–4 days. The growth media was discarded and the cells are fixed with 0.5% glutaraldehyde in PBS (Sigma Chemical Co., St. Louis, Mo.), at 100 μl/well for 30 min. The glutaraldehyde was discarded and the plate was washed gently with PBS three times. The plate was then blocked with binding buffer (0.1% BSA in DMEM) 200 μl/well for 1 hr or was stored indefinitely at −20° C. Binding buffer was discarded and samples and standards were added to the wells. The plates were covered and incubated overnight at 4° C. Samples and standards were discarded and the plates were washed three times with PBS. HRP-conjugate diluted in 1% horse serum in PBS was added to wells, 100 μl/well and incubated for 1 hr at 37° C. The ELISA was developed with 3,3',5,5'-tetramethyl benzidine (TMB) chromagen (Genetic Systems, Seattle, Wash.) in a citrate buffer. Color development was arrested with 3N H$_2$SO$_4$ and the plate was read on a Titertek Microplate reader at 450 nm. This assay determined how well 0.3 μg/ml of biotinylated ChiBR96 antibody competes with either unlabeled ChiBR96 or unlabeled murine BR96 monoclonal antibody for the antigen. The bound biotinylated ChiBR96 antibody was detected with avidin-HRPO and developed with standard ELISA reagents.

Figure 17:
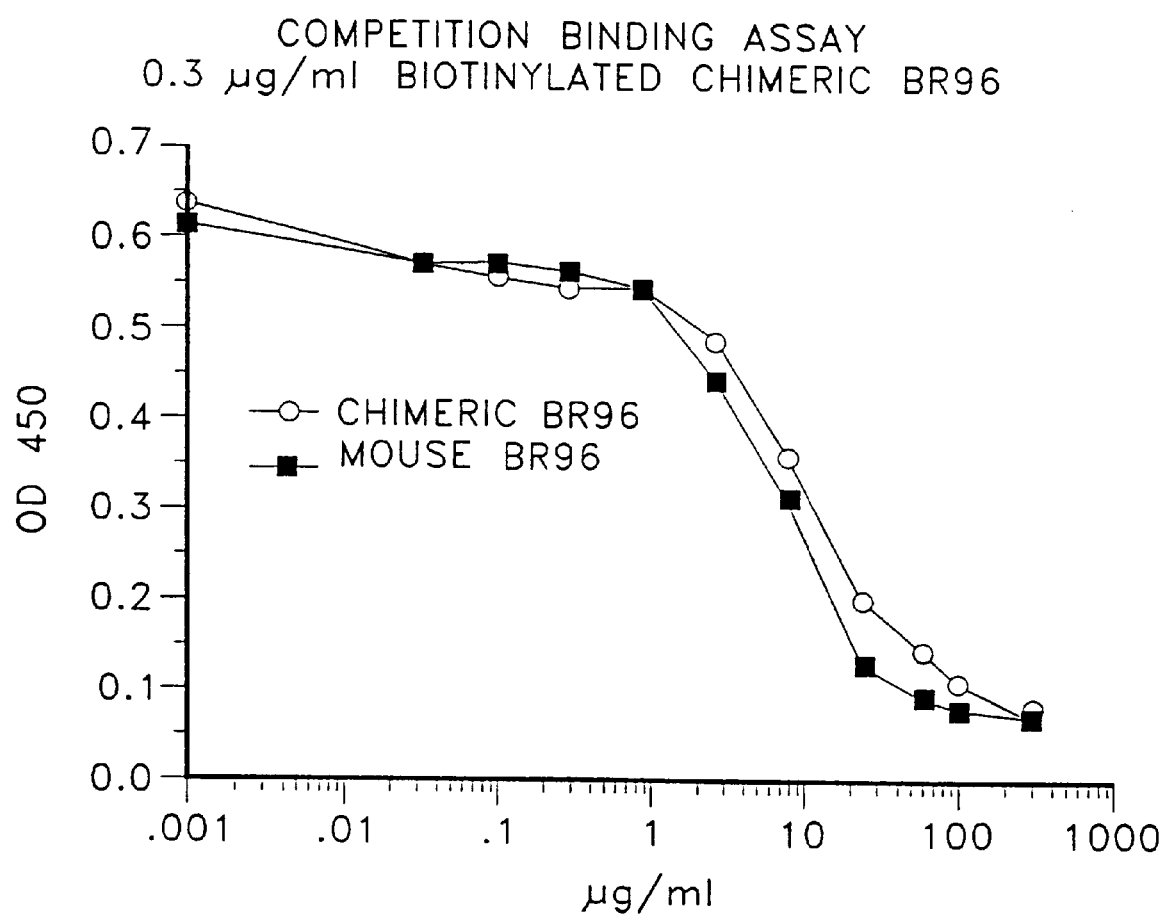
FIG. 17 is a graph depicting the results of the competition binding assay comparing the binding of the murine BR96 monoclonal antibody of the invention with binding of the chimeric BR96 antibody of the invention, as described in Example 9, infra.

As shown in FIG. 17, the overlap of the two binding curves indicates that the two antibodies have the same specificity and relative affinity for the tumor antigen.

EXAMPLE 10

Characterization of the ChiBR96 Antibody and BR96 F(ab')$_2$ Fragments

Cytotoxicity of Unmodified ChiBR96 and BR96 F(ab')$_2$ Fragments

Living suspended cells from the BR96 antigen positive carcinoma lines 3396, 2987 and MCF-7, were treated with ChiBR96 and BR96 F(ab')$_2$ fragments prepared as described in Examples 8 and 9, above, to determine cytotoxicity of these antibodies as compared to the BR96 monoclonal antibody of the invention. The cytotoxicity tests were performed by FACS assay as described above in Example 4. The results of these experiments are shown in FIGS. 18–20 as percentage dead cells vs. antibody concentration in μg/ml.

Figure 18:
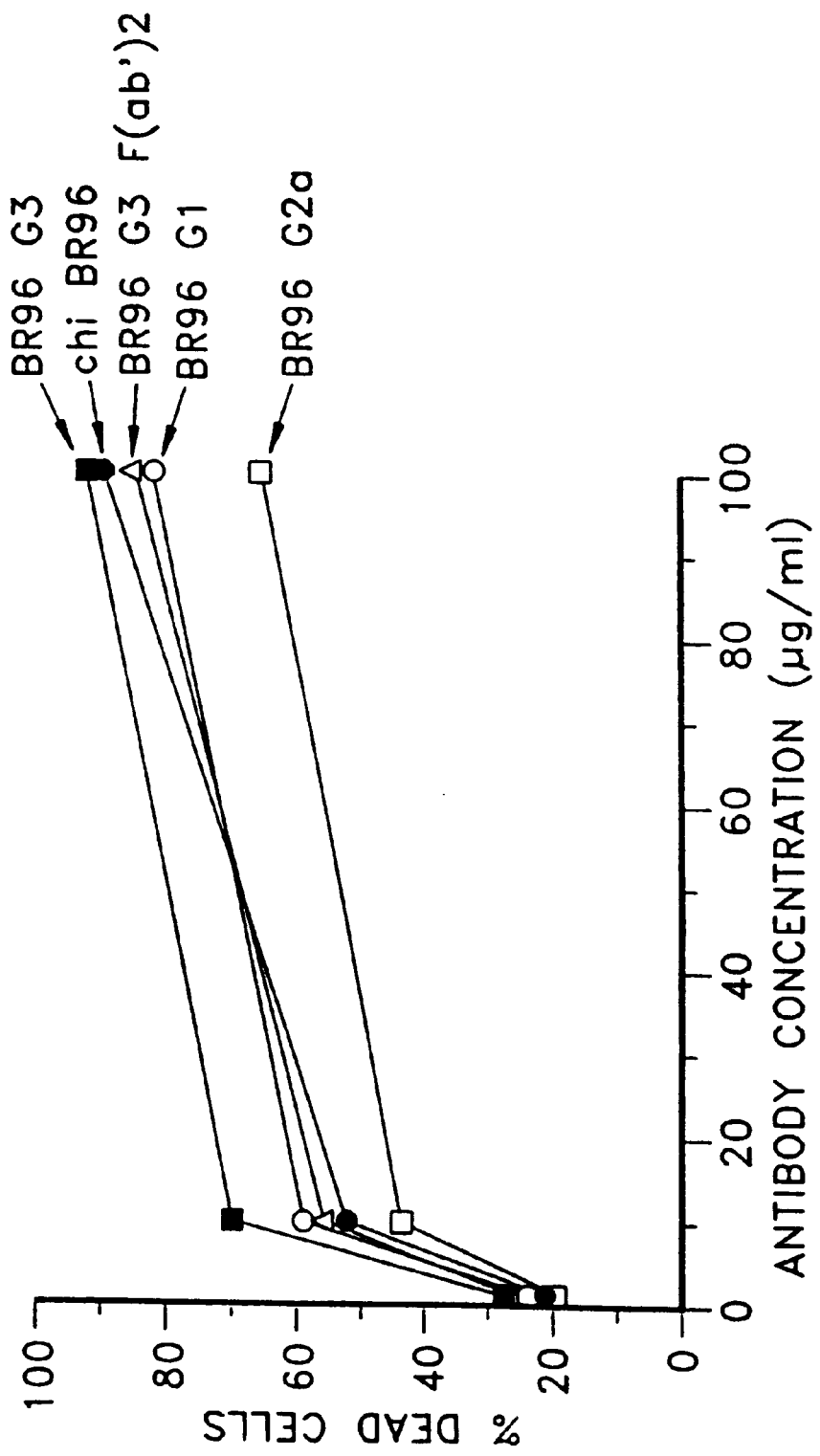
FIG. 18 depicts the results of FACS analysis of the cytotoxicity of the antibodies of the invention on 3396 breast carcinoma cells as described in Example 10, infra.
Figure 19:
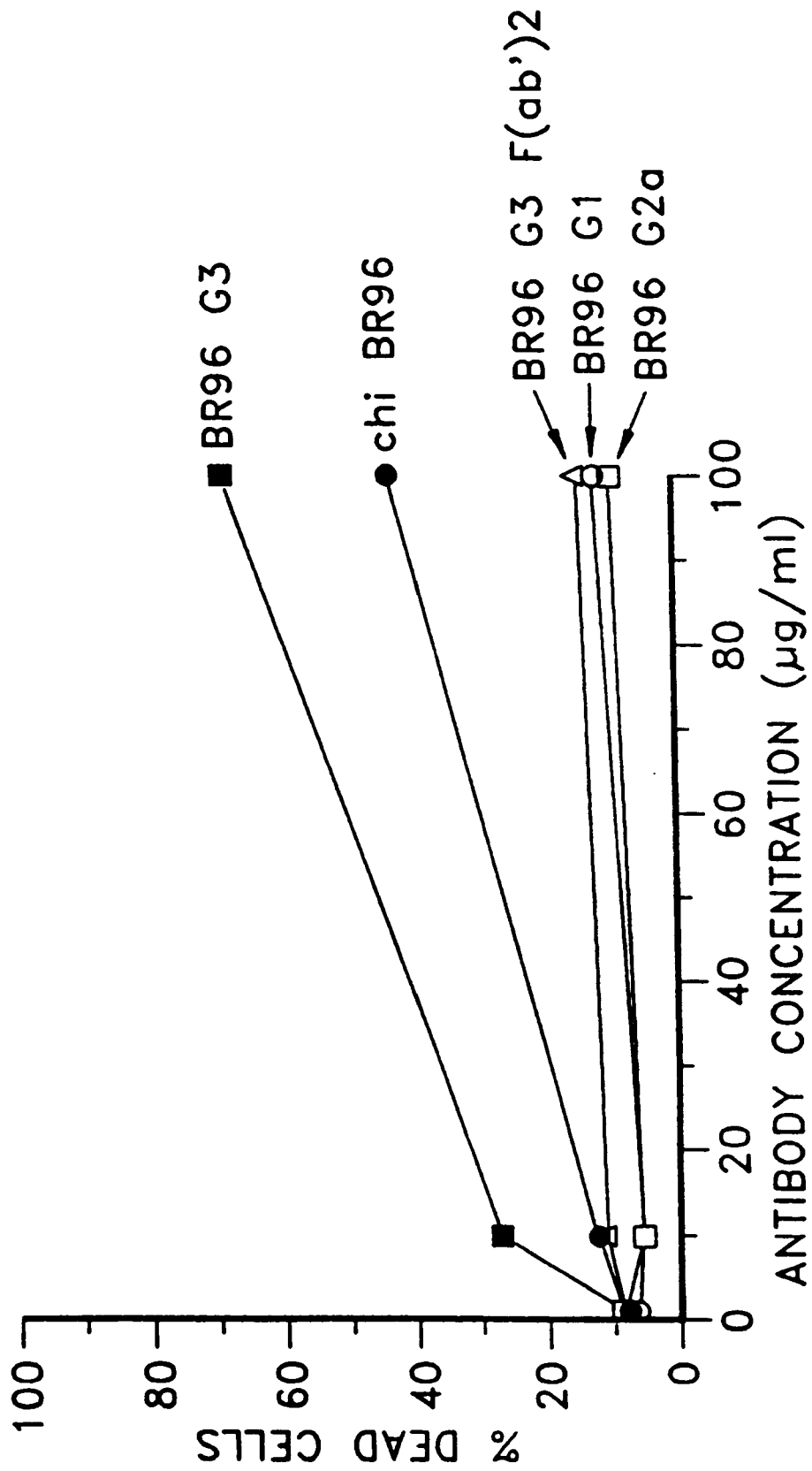
FIG. 19 depicts the results of FACS analysis of the cytotoxicity of the antibodies of the invention on 2987 human lung adenocarcinoma cells as described in Example 10, infra.
Figure 20:
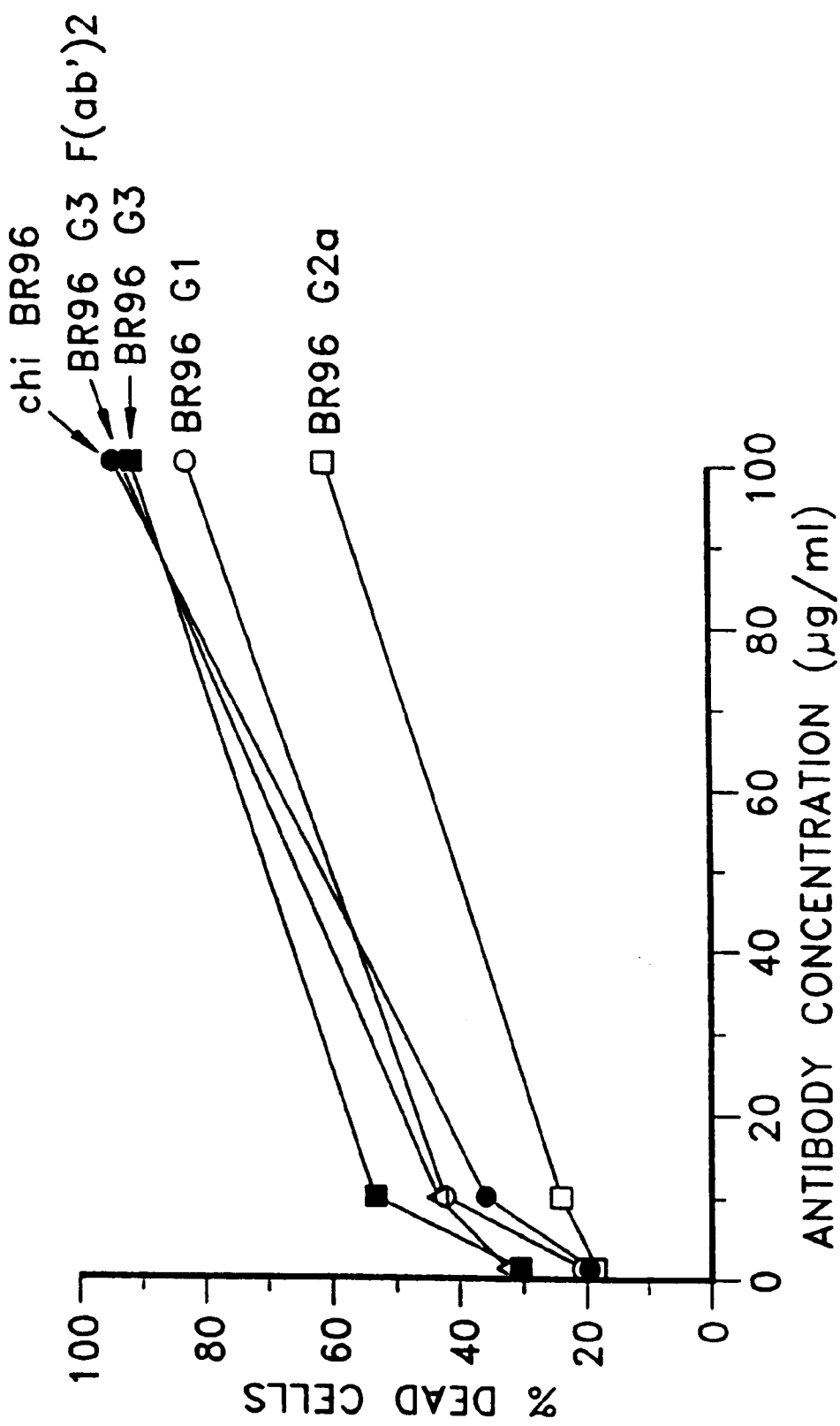
FIG. 20 depicts the results of FACS analysis of the cytotoxicity of the antibodies of the invention on MCF-7 cells as described in Example 10, infra.

FIGS. 18 and 20 show that the chimeric BR96 antibody and F(ab')$_2$ fragments of BR96 IgG3 are similar to BR96 monoclonal antibody with respect to cytotoxicity to 3396 and MCF-7 cells. FIG. 19 demonstrates that the cytotoxic effect on 2987 cells is much lower than on the other breast carcinoma cells (FIGS. 18 and 20). These results suggest that a higher binding ratio (Table 2) is important for killing by these antibodies and/or that different tumor cells might have different sensitivity to killing by these antibodies. These results illustrate that the ChiBR96 antibody and the F(ab')$_2$ fragments are cytotoxic by themselves, i.e. in unconjugated form, and also illustrate that the cytotoxicity of the BR96 antibodies is not dependent on the Fc region.

Internalization of ChiBR96

The internalization of the ChiBR96 antibody within carcinoma cells was evaluated in comparison to internalization of the BR96 monoclonal antibody. The antibodies were conjugated to ricin A chain toxin to form immunotoxins ChiBR96-RA (1–4 Ricin A chains per antibody molecule) and BR96-RA (1–2 Ricin A chains per antibody molecule) and internalization by carcinoma cell lines 3396 and 3630 was measured using a thymidine uptake inhibition assay, as described in Example 3, above.

Figure 21:
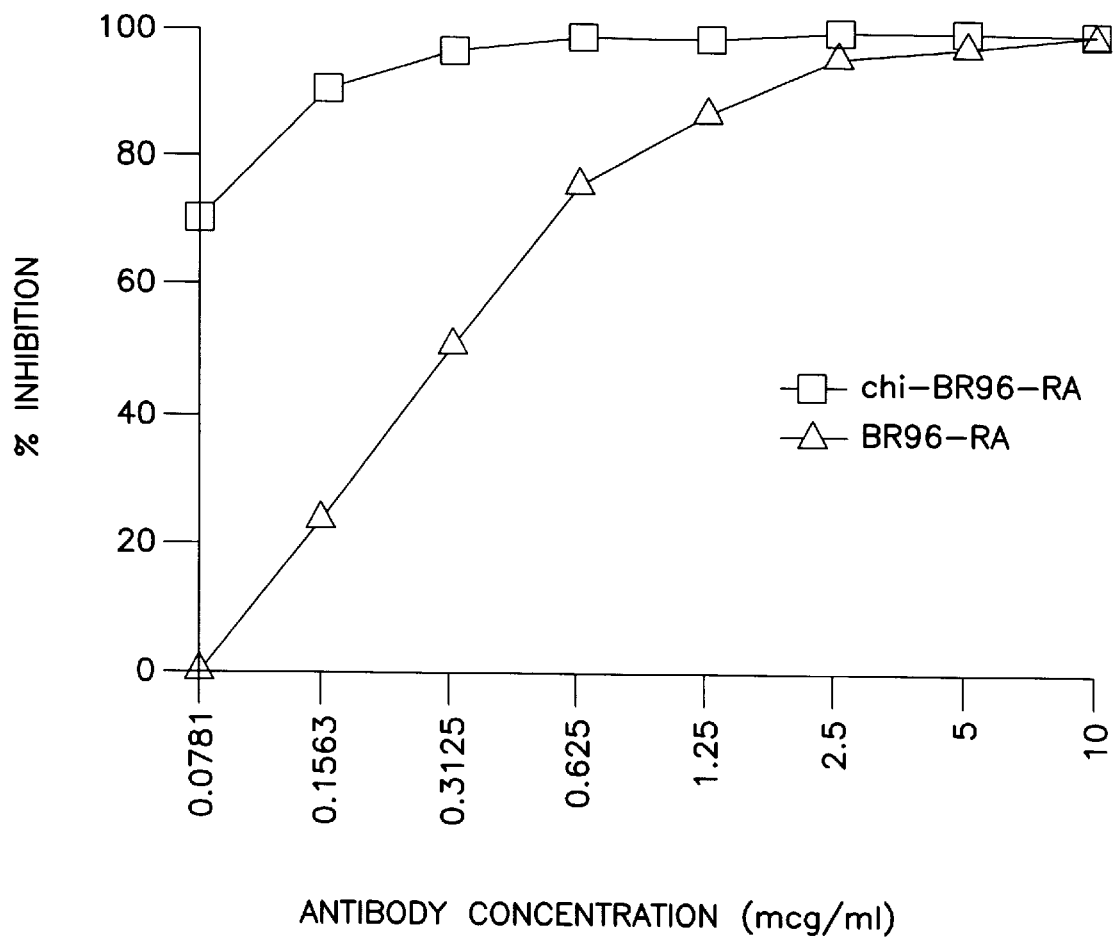
FIG. 21 depicts the percent inhibition of thymidine incorporation into the DNA of 3396 breast carcinoma cells treated with a murine BR96-RA immunotoxin and chimeric (Chi) BR96-RA at varying concentrations as described in Example 10, infra.
Figure 22:
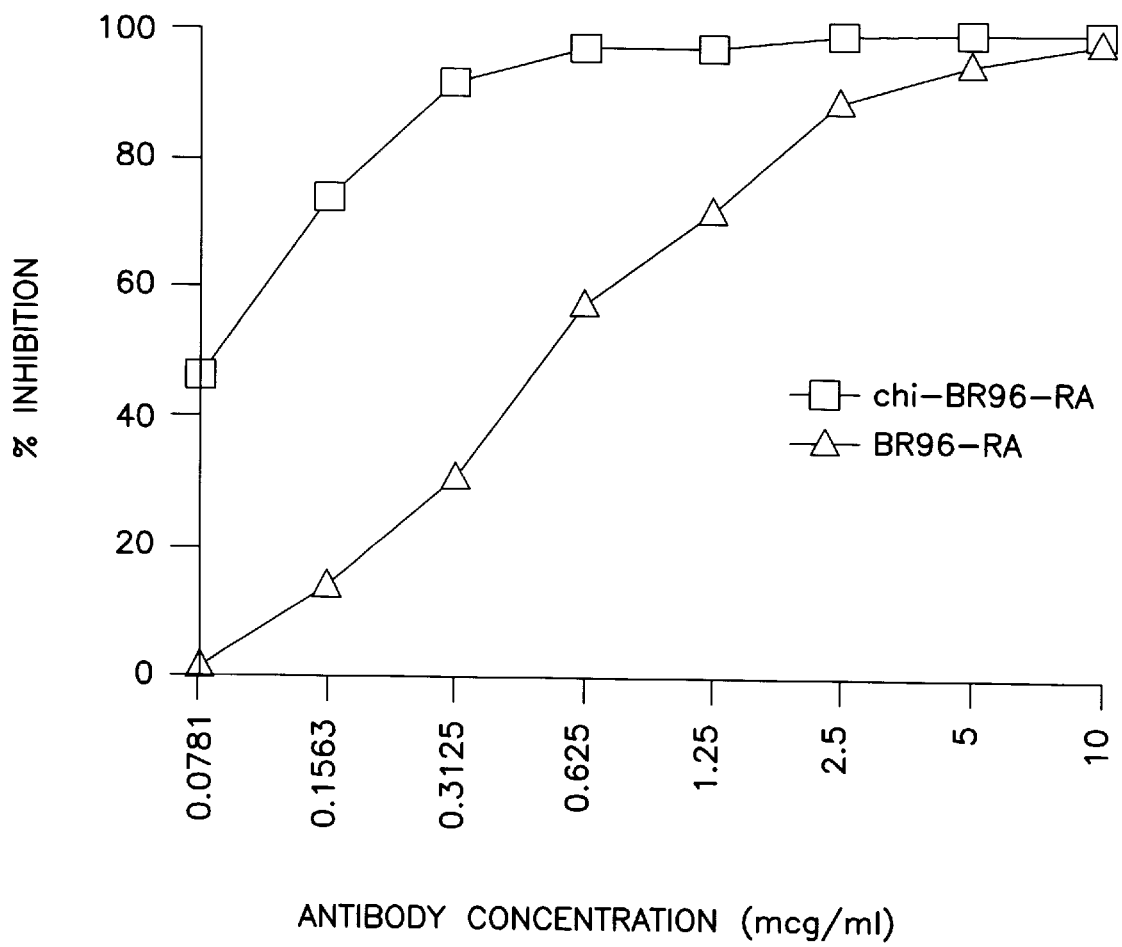
FIG. 22 depicts the percent inhibition of thymidine incorporation into the DNA of 3630 breast carcinoma cells treated with a murine BR96-RA immunotoxin and ChiBR96-RA at varying concentrations, as described in Example 10, infra.

Graphs of the percent inhibition of thymidine incorporation vs. immunotoxin concentration for each cell line tested are shown in FIGS. 21 and 22. FIG. 21 depicts the percent inhibition of thymidine incorporation by cells from the 3396 breast carcinoma cell line caused by internalization of ChiBR96-RA and BR96-RA. As shown in the graph, ChiBR96 is internalized similarly to BR96, and appears to be at least as efficient as BR96 at killing tumor cells. Similar results were obtained with the 3630 breast carcinoma cell line (FIG. 22).

Antibody-dependent cellular cytotoxicity Activity of ChiBR96 Antibody

Determination of antibody-dependent cellular cytotoxicity activity of ChiBR96 was conducted as described in Example 5, above using the following cell lines: breast cancer lines 3396, 3630 and 3680 (Bristol-Myers Squibb Co., Seattle, Wash.) and MCF-7 (ATCC No. HTB22); ovarian cancer line 3633-3 (Bristol-Myers Squibb Co., Seattle, Wash.); and lung cancer lines 2987; 3655-3 and 2981 (Bristol-Myers Squibb Co., Seattle, Wash.). The results are shown in Table 3 for various antibody concentrations.

TABLE 3 antibody-dependent cellular cytotoxicity Activity of Chi-BR96

| Cell Lines | Antibody | NK | 10 | 1 | 0.1 | 0.01 | 0.001 |
|---|---|---|---|---|---|---|---|
| Breast Cancer | BR96 | 28 | 86 | 74 | 59 | 27 | 25 |
| 3396 | ChiBR96 |  | 88 | 79 | 60 | 34 | 26 |
| MCF-7 | BR96 | 16 | 16 | 82 | 69 | 54 | 15 |
|  | ChiBR96 |  | 90 | 82 | 57 | 25 | 17 |
| MCF-7 | BR96 | 22 | 73 | 69 | 48 | 22 | 22 |
|  | ChiBR96 |  | 76 | 70 | 57 | 33 | 26 |
| 3630 | BR96 | 30 | 69 | 64 | 42 | 30 | 34 |
|  | ChiBR96 |  | 69 | 56 | 42 | 36 | 36 |
| 3680 | BR96 | 13 | 73 | 67 | 58 | 34 | 38 |
|  | ChiBR96 |  | 70 | 71 | 61 | 39 | 30 |
| Ovarian Cancer | BR96 | 20 | 92 | 90 | 64 | 28 | 23 |
| 3633-3 | ChiBR96 |  | 88 | 88 | 54 | 43 | 29 |
| Lung Cancer | BR96 | 11 | 51 | 57 | 41 | 9 | 7 |
| 2987 | ChiBR96 |  | 69 | 65 | 51 | 28 | 15 |
| 3655-3 | BR96 | 4 | 49 | 37 | 0 | 0 | 0 |
|  | ChiBR96 |  | 39 | 35 | 12 | 6 | 5 |
| 2981 | BR96 | 3 | 4 | 3 | 3 | 4 | 5 |
|  | ChiBR96 |  | 5 | 4 | 3 | 4 | 4 |

The results shown in Table 3 for various antibody concentrations indicate that ChiBR96 mediates antibody-dependent cellular cytotoxicity activity to a similar extent as BR96. The antibody-dependent cellular cytotoxicity activity can be seen at antibody concentrations lower than those at which the ChiBR96 antibody is cytotoxic by itself. When antibody BR96 was used alone as a control it produced 0% killing at the concentrations tested. antibody-dependent cellular cytotoxicity activity was only found with the BR96 antibody-binding cell lines.

Ability of ChiBR96 to Mediate Complement-Mediated Cytotoxicity

Determination of the ability of ChiBR96 to kill tumor cells in the presence of human serum as a source of complement (complement-dependent cytotoxicity) were performed as described in Example 6, using breast cell lines 3396; MCF-7, 3630 and 3680; ovarian cancer cell line 3633-3; and lung cancer cell lines 3655-3, 2987 and 2981. Table 4 presents the results.

TABLE 4 complement-dependent cytotoxicity Activity of ChiBR96

| Cell Lines | Antibody | 10 | 1 | 0.1 | 0.01 |
|---|---|---|---|---|---|
| Breast Cancer | BR96 | 100 | 99 | 78 | 13 |
| 3396 | ChiBR96 | 86 | 92 | 13 | 2 |
| MCF-7 | BR96 | 94 | 100 | 63 | 2 |
|  | ChiBR96 | 92 | 83 | 1 | 0 |
| 3630 | BR96 | 94 | 100 | 82 | 9 |
|  | ChiBR96 | 86 | 86 | 33 | 9 |
| 3680 | BR96 | 100 | 100 | 19 | 7 |
|  | ChiBR96 | 87 | 100 | 5 | 9 |
| Ovarian Cancer | BR96 | 98 | 98 | 21 | 0 |
| 3633-3 | ChiBR96 | 100 | 100 | 26 | 1 |
| Lung Cancer | BR96 | 91 | 22 | 0 | 0 |
| 3655-3 | ChiBR96 | 46 | 3 | 0 | 0 |
| 2987 | BR96 | 100 | 100 | 1 | 0 |
|  | ChiBR96 | 100 | 43 | 0 | 0 |
| 2981 | BR96 | 0 | 3 | 3 | 2 |
|  | ChiBR96 | 1 | 1 | 2 | 10 |

As shown in Table 4, ChiBR96 gave a cytotoxic effect (complement-dependent cytotoxicity) similar to that of BR96, in the presence of human serum containing complement. BR96 and ChiBR96 were not cytotoxic in any concentration. Human serum was also not cytotoxic.

The above results demonstrate that the whole BR96 antibody and chimeric antibody of the invention are internalized within carcinoma cells to which they bind, are cytotoxic alone in unmodified form and have antibody-dependent cellular cytotoxicity and complement-dependent cytotoxicity activity for cells expressing a higher amount of epitopes.

EXAMPLE 11

Evaluation of BR96 Antibodies In Vivo

The therapeutic potential of the unmodified BR96 antibody of the invention for treatment of tumors was examined in a series of experiments using human tumor xenografts in nude mice. In addition, certain parameters were examined that might influence the efficacy of BR96 as an antitumor agent. These parameters include level of antigen expression on the target tumor line, time from tumor implantation to initiation of therapy and effects of dose.

In all the in vivo experiments of this example, the required number of Balb/c nu/nu mice (Harlan Sprague Dawley, Indianapolis, Ind.) were implanted with either the human lung adenocarcinoma cell line H2987 or H2707 tumor line. Cells from these tumor lines were grown in vitro, harvested, washed and resuspended in PBS prior to subcutaneous (s.c.) implantation of 10 million cells into the rear flank of each mouse. These groups of mice were then randomized and separated into smaller equal groups of 8 or 10 mice each.

To increase the chance of observing any antitumor effects of BR96 while still requiring the antibody to actually localize to the tumor implant site for any effect to occur, therapy was initiated 24 hours after tumor implantation on day 2. Both the BR96 and control monoclonal antibodies were administered at the same dose and schedule, although initiation of therapy in some cases varied. The treatment dose was administered in 0.2 ml PBS intravenously (i.v.) through the tail vein of the mouse. Normally the schedule was once every three days for five injections (Q3DX5). However, two extra injections were given on days 19 and 21 after H2987 tumor implantation in the initial experiment.

Antitumor Effects of BR96 Antibody in 2987 and 2707 Tumors

Tumor volumes were determined for each animal weekly with measurement usually beginning on the eighth day after implantation. Tumor volumes were calculated from the measurements of tumor length and perpendicular width using the formula:

Tumor Volume=longest length×(perpendicular width squared/2)

Group mean values were then calculated and plotted against time after tumor implantation.

Figure 23:
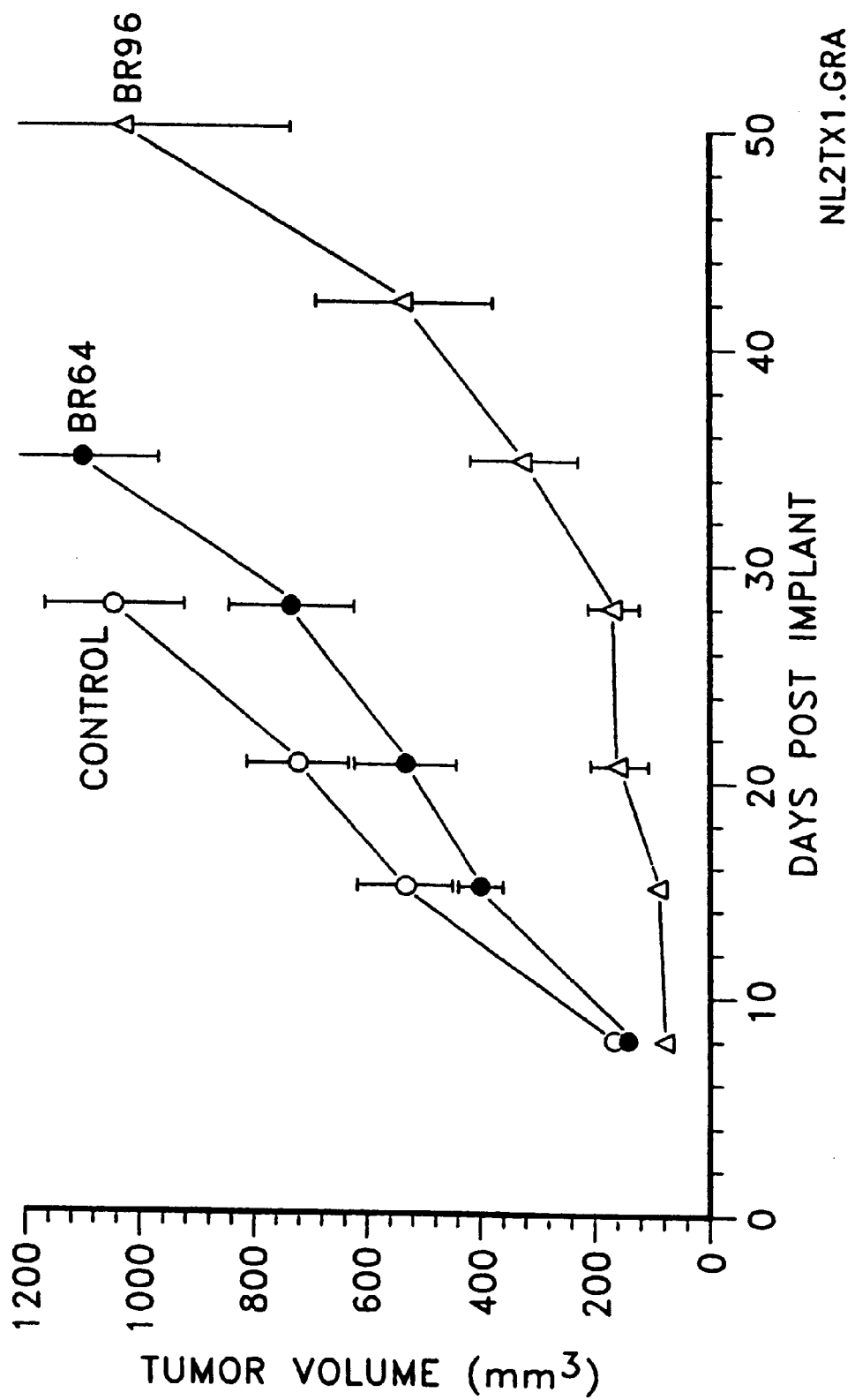
FIG. 23 is a graph depicting the antitumor effects of unmodified BR96 on the tumor cell line H2987, as described in Example 11, infra.

In the initial experiment depicted in FIG. 23 treatment with BR96 resulted in highly significant anti-tumor effects against the H2987 cell line. BR64, which also binds and is internalized by these cells, was used as a negative control, and showed little if any effect compared to the PBS treated controls.

Table 5 summarizes the effects on the individual tumors at the end of treatment in this first experiment.

TABLE 5

Effects of Treatment with Unmodified BR96 Initiated At Different Times After H2987 Implantation
EXPERIMENT 1
DAY 28

| GROUP | MAb | TUMOR RESPONSE | | | PRO-GRESSION |
|---|---|---|---|---|---|
| | | COMPLETE | PARTIAL | STABLE | |
| 1 | BR96 | 2 | 0 | 3 | 5 |
| 2 | BR64 | 0 | 0 | 1 | 9 |
| 3 | PBS | 0 | 0 | 0 | 10 |

Only treatment with BR96 antibody resulted in complete absence of tumor. Two animals in this group were tumor free and an additional 3 animals showed cessation of growth of their tumors following treatment with BR96 antibody. The two mice showing no signs of tumor remained tumor free throughout the course of the experiment.

Antitumor Effects of BR96 Antibody on Established Tumors

One of the ultimate goals of tumor therapy is the effective treatment of established and growing tumors. To examine whether BR96 could have an antitumor effect on established tumors the H2987 or H2707 lung adenocarcinoma tumor lines were used as xenografts in nude mice. Because both of these tumor lines result in palpable tumors eight days after administration of 10 million cells s.c., delaying initiation of treatment provided a method to examine antitumor effects on established tumors.

Therefore, to further examine the efficacy of unmodified BR96, several experiments were performed where treatment was withheld for either 5 or 8 days following s.c. tumor implantation. The delay in treatment initiation allowed the tumor cells to become established tumors. This results in an animal model that is more difficult to treat but resembles the clinical situation in a more realistic manner.

The treatment protocol is summarized in Table 6. Three groups of 10 mice each were treated with BR96 antibody initiated at different times as described in this Table. Control mice received either FA6 or PBS beginning on DAY 2. FA6 is a murine IgG$_3$ directed against a bacterial antigen not found in mammalian species, and acted as an isotype matched nonbinding negative control monoclonal antibody.

TABLE 6

Effects of Treatment With Unmodified BR96
Initiated at Different Times After H2987 or
H2707 Implantation
TREATMENT PROTOCOL

| GROUP | MAb | SCHEDULE/ROUTE | DOSE | DAYS INJECTED |
|---|---|---|---|---|
| 1 | BR96 | Q3D × 5 i.v. | 1 mg | 2, 5, 8, 11, 14 |
| 2 | BR96 | Q3D × 5 i.v. | 1 mg | 5, 8, 11, 14, 17 |
| 3 | BR96 | Q3D × 5 i.v. | 1 mg | 8, 11, 14, 17, 20 |
| 4 | FA6 | Q3D × 5 i.v. | 1 mg | 2, 5, 8, 11, 14 |
| 5 | PBS | Q3D × 5 i.v. | 0.2 ml | 2, 5, 8, 11, 14 |

Figure 24:
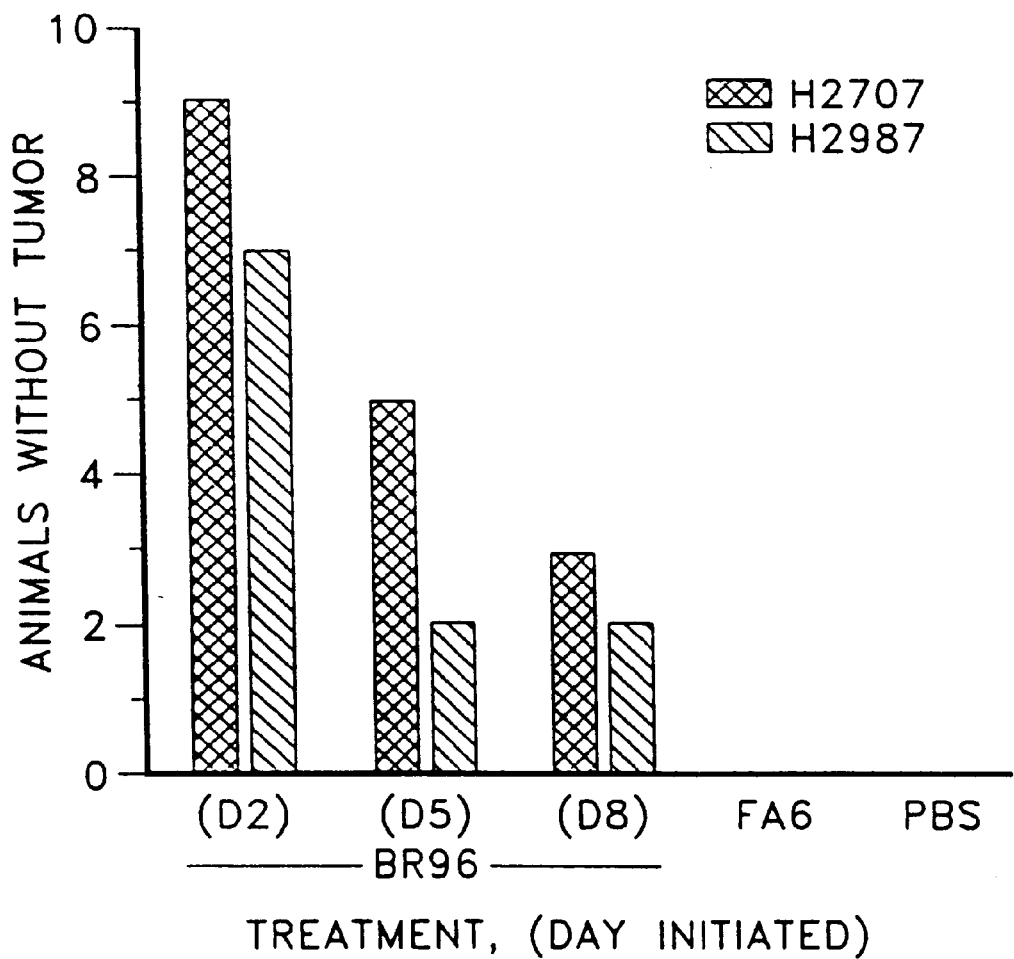
FIG. 24 is a bar graph illustrating the absence of tumors at the end of treatment for animals treated with BR96, as described in Example 11, infra.

The results of this treatment protocol for both H2987 and H2707 tumor cell lines are shown in FIG. 24, where the number of animals without tumors versus when initiation of treatment after tumor implantation occurred are plotted. Absence of tumor, as defined by the absence of a palpable tumor, was assessed at the end of treatment for each group. The day used for the determination of tumor absence varied since treatment was initiated at different times post tumor implant. Early initiation of treatment was clearly more effective and efficacy decrease as onset of treatment increased from time of tumor implant. Since delay in initiation of treatment allows greater growth and establishment of the tumor, decreased efficacy at later treatment initiation times reflects the increasing difficulty of treating larger and more established tumors.

These results demonstrate that BR96 has antitumor effects against two different tumor cell lines. Antitumor effects were only observed in the three groups treated with BR96 antibody while those animals treated with either the control FA6 or PBS showed no antitumor effects.

It is significant that the differences in efficacy with more established tumors are greater with the higher antigen expressing tumor line, H2707. The observation that H2707 has a greater response to BR96 therapy than H2987 is consistent with the assumption that the amount of antigen expressed by a tumor cell may influence the efficacy of BR96 treatment. From the data above it is clear that BR96 has antitumor effects against staged tumors.

Dose Effects of BR96 Antibody

Figure 25:
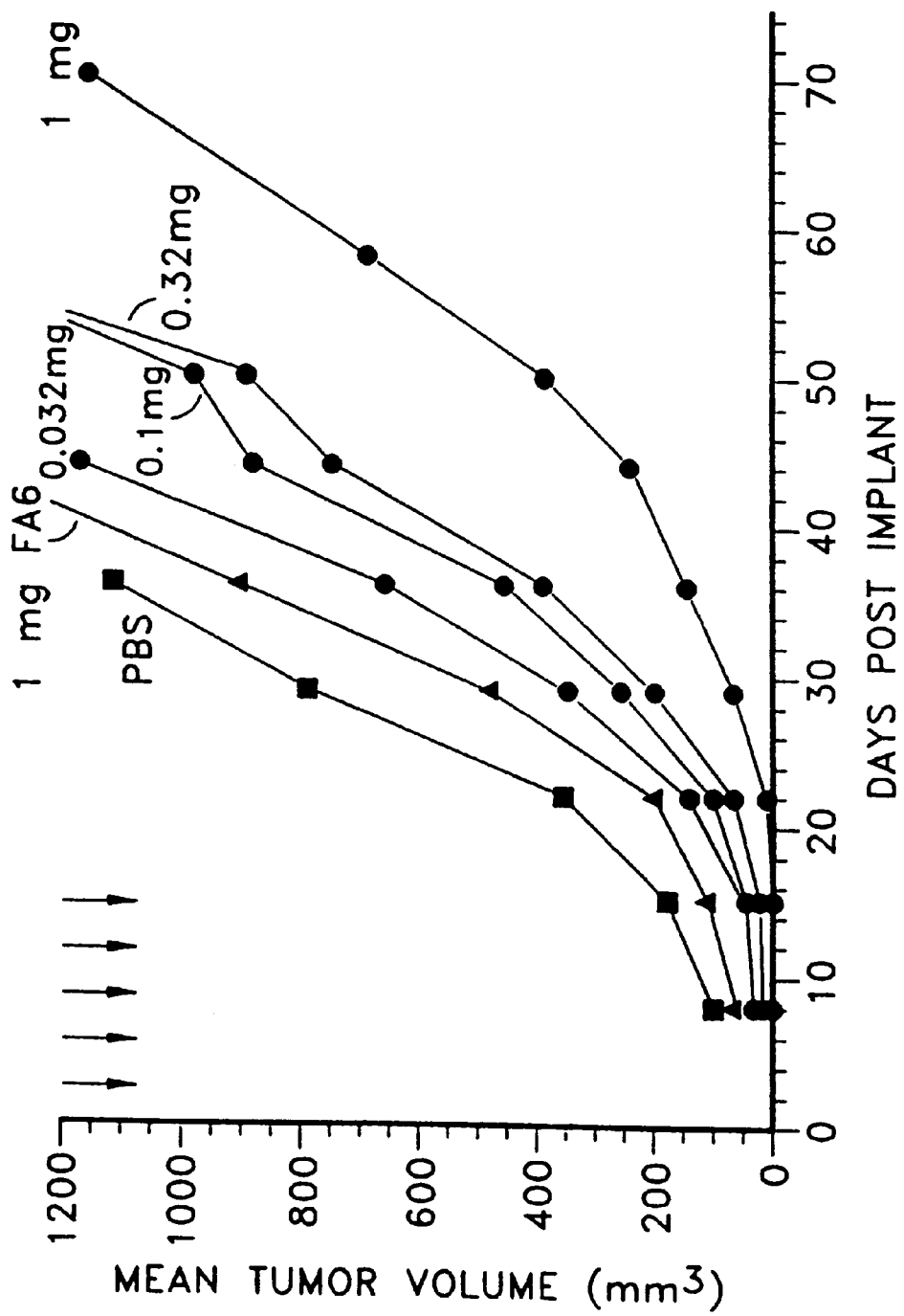
FIG. 25 depicts the dose effects of BR96 antibody after implantation of H2707 cells, as determined by tumor volume, as described in Example 11, infra.

In another experiment, the dose effects of BR96 against the H2707 tumor line were examined. In this experiment, ER96 was administered in decreasing half log amounts from 1 mg/dose to 0.032 mg/dose. The mean tumor volumes versus time post tumor implant of the groups are presented in FIG. 25. The control treated animals were given only the highest dose of monoclonal antibody, 1 mg/dose FA6. These control animals showed no antitumor effects while there was a dose dependent response when BR96 antibody was administered over the chosen dose range.

Antitumor Effects of F(ab')$_2$ Fragment and Chimeric BR96

Figure 26:
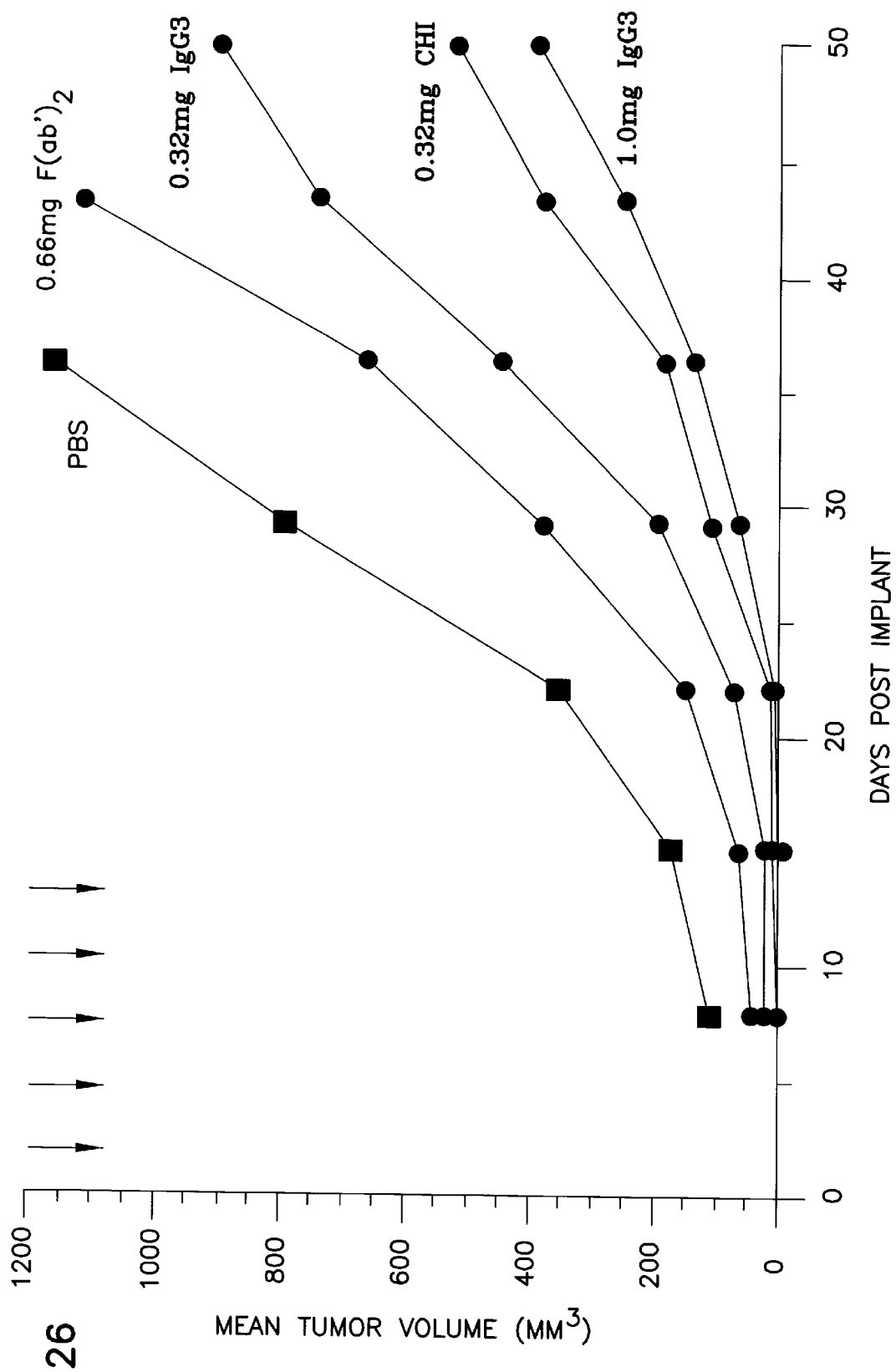
FIG. 26 illustrates the effects of treatment with F(ab')$_2$ fragments and chimeric BR96 after implantation of 2707 cells as determined by tumor volume, as described in Example 11, infra.

In addition, antitumor effects of the F(ab')$_2$ BR96 fragment were examined to determine if the antitumor effects seen in vivo were due to the Fc portion or if actual binding to the tumor with its subsequent internalization was sufficient for cell death, as indicated by in vitro assays. The dose of F(ab')$_2$ fragment was 0.66 mg/dose using the same schedule as the whole BR96. This dose corresponds to an approximate molar equivalent of binding regions compared to the 1.0 mg/dose whole IgG$_3$ BR96. Mean tumor volume values versus time post tumor implantation for this group treated with the antibody fragment are shown in FIG. 26. There were clearly some antitumor effects although the effects were not as strong as with whole antibody. These effects were most pronounced at the earlier time points during and immediately following treatment.

Chimeric BR96 was also examined for antitumor effects in this experiment. An intermediate dose of 0.32 mg/dose for the chimeric monoclonal antibody was chosen. The mean tumor volume values for this group of mice is also shown in FIG. 26. Treatment with chimeric antibody BR96 was more efficacious than a comparable dose of the murine BR96 IgG$_3$. This is further demonstrated in FIG. 27 which shows that 6 of the 8 mice treated with chimeric BR96 were free of palpable tumors at the end of treatment.

Figure 27:
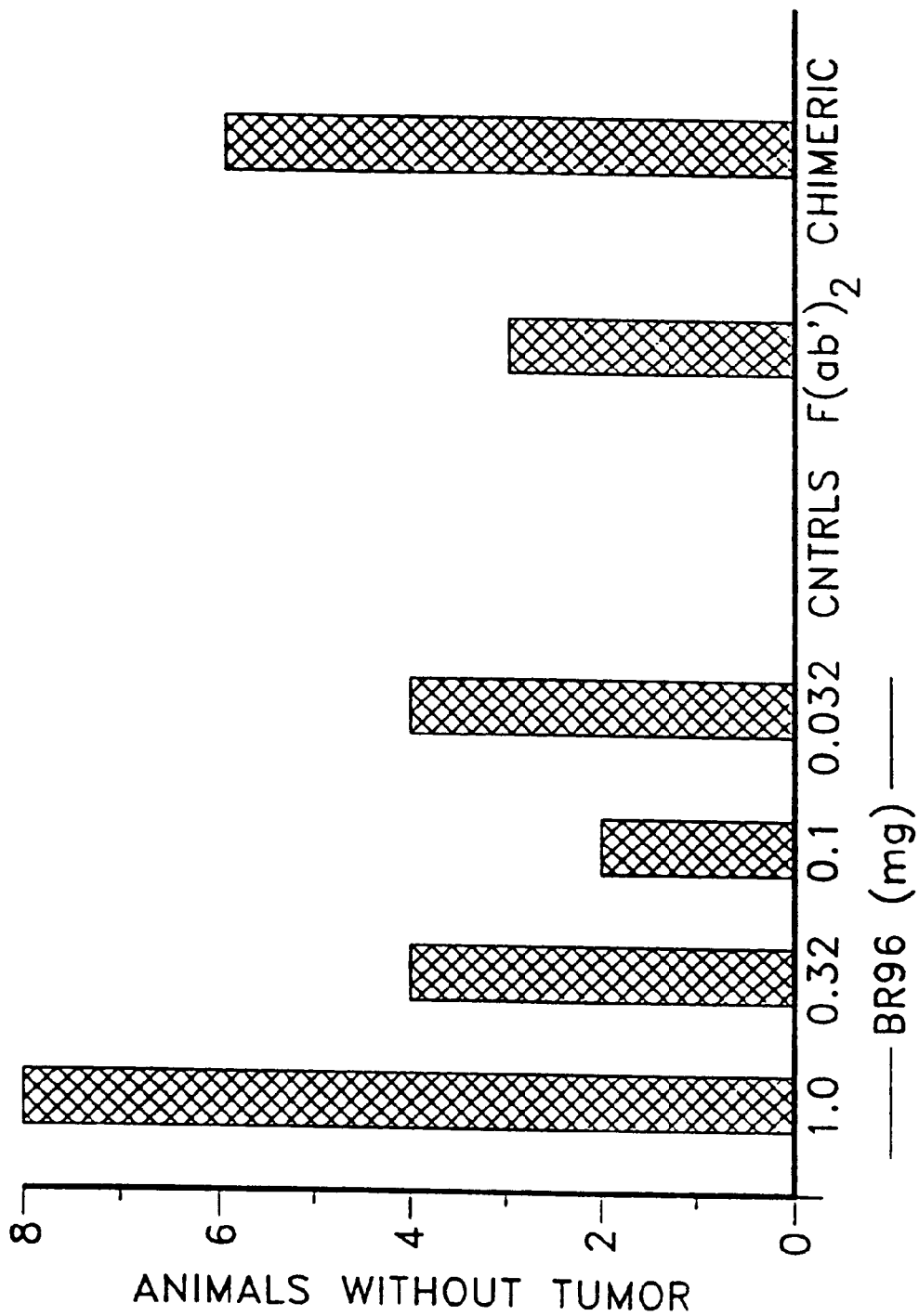
FIG. 27 illustrates the absence of tumors after treatment with various doses of BR96 antibody, as compared to the effects of F(ab')$_2$ fragments and chimeric BR96, as described in Example 11, infra.

Examination of the individual tumors depicted in FIG. 27 shows that at completion of treatment a clear dose effect was evident by the number of animals without tumors after treatment with decreasing amounts of whole IgG3 BR96 antibody from 1.0 to 0.1 mg/dose. Surprisingly, treatment with 0.032 mg/dose resulted in an antitumor effect similar to the 0.32 mg/dose. This may reflect that the level of cells killed in the tumor from the treatment was very close to the minimum amount necessary for the tumor to continue to grow.

Three of the eight animals treated with the F(ab')$_2$ fragment were free of palpable tumors after treatment. Therefore the Fc portion is not entirely necessary for the antibody to have antitumor effects in vivo although it should enhance the tumorcidal properties of BR96, particularly in immunocompetent animals.

The above results demonstrate that unmodified BR96 antibodies are effective antitumor agents against tumor lines in vivo. Moreover, the BR96 antibodies have an effect on staged or established growing tumors. There is an indication that higher antigen density on the tumor line may increase the ability of BR96 to kill these cells. It has been shown that any of the forms of the monoclonal antibody, i.e., chimeric, murine whole IgG$_3$ or F(ab')$_2$ fragments, are effective as antitumor agents. Earlier treatment and higher doses are preferred.

EXAMPLE 12

Localization and Biodistribution of BR96 Antibodies

Radioiodinated BR96 monoclonal antibodies administered at doses used in the therapy experiments described above in Example 11 were used to determine biodistribution characteristics. Specifically, the whole IgG$_3$ BR96, chimeric or F(ab')$_2$ fragments together with the appropriate control (whole monoclonal antibody FA6, chimeric 96.5 and 96.5 F(ab')$_2$, respectively) were used to localize in the tumor and various other organs.

Prior to the localization experiments, animals were injected with tumor cells as described above in Example 11, for the therapy studies. However, the tumors were allowed to grow in the animals for approximately 2 weeks. At this time, 100 μg of BR96 antibody or fragment was radiolabeled with $^{125}$I using 10 μg Iodogen for 10 minutes at room temperature as directed by the manufacturer. Control antibody or fragments were labeled with $^{131}$I using the same method. These radioiodinated antibodies were diluted with the appropriate unlabeled antibodies to reach the doses used in the therapy experiments. Both the specific and nonspecific antibodies were then mixed and administered together, i.v., through the tail vein of the mouse. At selected times mice were randomly pulled from the group, anesthetized, bled through the orbital plexus and sacrificed. Various tissues were removed, weighed and counted on a gamma counter capable of differentiating between the two radioisotopes of iodine. From this data, percent injected dose and percent injected dose per gram were calculated.

The accumulated data from the 24 post administration time point in the localization experiments are summarized in Table 7.

TABLE 7

Summary of Biodistribution Experiments

| ANTIBODY | DOSE (mg) | TUMOR CELL | % INJECTED DOSE/GRAM 24 HRS. POST ADMINISTRATION |       |       |        |        |      |
|----------|-----------|------------|-------|-------|-------|--------|--------|------|
|          |           |            | BLOOD | TUMOR | LIVER | SPLEEN | KIDNEY | LUNG |
| 1) BR96-G$_3$ | 1.0 | H2987 | 10.2 | 6.8 | 2.2 | 1.9 | 3.4 | 4.7 |
| FA6 | 1.0 |  | 6.3 | 2.1 | 2.1 | 1.6 | 2.4 | 3.2 |
| 2) BR96-G$_3$ | 0.3 | H2707 | 9.0 | 7.0 | 1.8 | 1.6 | 2.7 | 3.7 |

TABLE 7-continued

Summary of Biodistribution Experiments

| DOSE | | | % INJECTED DOSE/GRAM 24 HRS. POST ADMINISTRATION | | | | | |
|---|---|---|---|---|---|---|---|---|
| ANTIBODY | (mg) | CELL | BLOOD | TUMOR | LIVER | SPLEEN | KIDNEY | LUNG |
| FA6 | 0.3 | | 5.9 | 2.7 | 2.0 | 1.8 | 2.2 | 2.8 |
| 3) ChiBR96 | 0.32 | H2707 | 7.2 | 8.2 | 1.4 | 1.6 | 2.0 | 3.5 |
| Chi96.5 | 0.32 | | 7.5 | 2.3 | 1.8 | 1.6 | 1.9 | 3.5 |
| 4) F(ab')$_2$ | | | | | | | | |
| BR96 | 0.65 | H2707 | <0.3 | <0.3 | <0.3 | <0.3 | <0.3 | <0.3 |
| 96.5 | 0.65 | | <0.3 | <0.3 | <0.3 | <0.3 | <0.3 | <0.3 |

The only tissue showing significant differences between specific and nonspecific antibody is the tumor. All other tissues examined show approximately equal uptake between the specific and nonspecific antibodies. One possible exception is the lower blood levels for the nonspecific antibody, FA6. This indicates accelerated blood clearance of this antibody. However, the difference between the specific and nonspecific antibody in the tumor is greater than the difference in blood levels between the FA6 and BR96 antibodies.

The data in Table 7 also demonstrate that the percent of the dose present in a particular organ is constant regardless of the dose administered. This would therefore indicate there is quantitatively more antibody present at the tumor site when higher doses are administered. In addition, there are no apparent differences between the two tumor lines with respect to specific vs nonspecific uptake.

Table 7 also demonstrates that the F(ab')$_2$ was cleared from the animal at a much faster rate than either the IgG$_3$ or chimeric BR96. This could explain the reduction in efficacy of the fragment compared to whole antibody in the therapeutic experiments. Any antitumor effects from the fragment must therefore be rapid and occur during the short time span prior to being cleared.

ChiBR96 localized at a comparable level to the IgG$_3$ BR96. Higher amounts were present only in the tumor compared to the control chimeric antibody. This suggests that any increase in efficacy of the chimeric antibody compared to the murine BR96 IgG$_3$ is due to the human constant region substitution. Of equal importance, the human constant region substitution does not appear to affect the ability of the chimeric antibody to localize to the tumor or adversely affect its biodistribution.

In summary, the IgG$_3$ and chimeric forms of BR96 are capable of specifically localizing to the tumor site. Moreover, both localization and therapeutic effects have been shown in these preliminary experiments at comparable doses. Indirect evidence of localization of the F(ab')$_2$ fragments was shown by the antitumor activity of the fragments in the therapy experiments. This activity must occur before 24 hours.

EXAMPLE 13

Preparation and Cytotoxicity of Chimeric Monoclonal Antibody F(ab')$_2$ and Fab' Fragments Conjugated to Pseudomonas Exotoxin Cell-specific cytotoxic reagents were prepared by chemically combining the chimeric antibody BR96 (ChiBR96) with Pseudomonas exotoxin A (PE) using either native PE or a truncated form (LysPE40) devoid of the cell recognition region (Domain I). A variety of chimeric BR96-immunotoxins were constructed by chemical conjugation of PE and LysPE40 with Fab' or F(ab')$_2$ enzymatic digest products, or BR96 antibody, by thiolation with 2-iminothiolane or by direct attachment to intact BR96 antibody by reduction with DTT as described below.

Reagents

Succinimidyl 4-(N-maleimido-methyl) cyclohexane 1-carboxylate (SMCC) and 2-iminothiolane (2-IT) were purchased from the Pierce Chemical Corporation (Rockford, Ill.). Soluble pepsin was purchased from Sigma Chemical Co. (St. Louis, Mo.). Na[$^{125}$I] and [$^3$H]-leucine were purchased from New England Nuclear (Boston, Mass.). Native PE was purchased from Berna Products (Coral Gables, Fla.). Mono Q columns were purchased from Pharmacia (Uppsala, Sweden). TSK-3000 columns were purchased from TosoHaas, Inc. (Philadelphia, Pa.). Immunoblots were performed using mouse (anti-id BR96) and rabbit (anti-PE) ABC kits (Vector Laboratories, Burlingame, Calif.). Rabbit polyclonal anti-PE antibody and mouse anti-PE monoclonal antibody M40/1 were supplied by Drs. Ira Pastan and David FitzGerald, National Institutes of Health (Bethesda, Md.). Anti-idiotypic BR96 antibody 757-4-1 was prepared using the BR96 antibody of the invention and standard procedures for preparing anti-id antibodies [see, Kahn et al., Cancer Res. 49: 3159–3162 (1989) and Hellstrom et al., Cancer Res. 50: 2449–2454 (1990)] by Dr. Bruce Mixan, Bristol-Myers Squibb (Seattle, Wash.)].

Cell Culture and Plasmids

Figure 36:
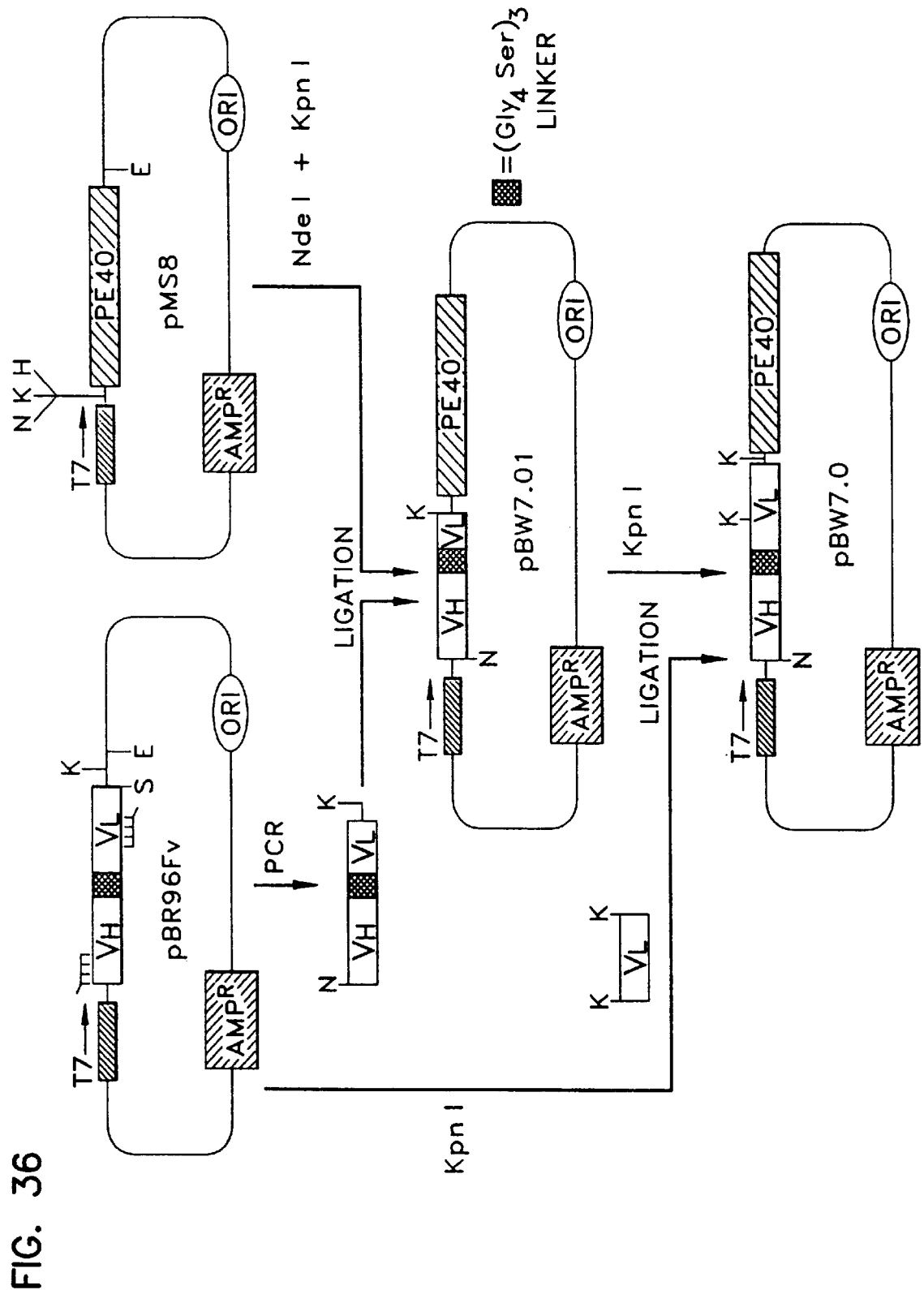
FIG. 36 is a schematic illustration of the construction of expression plasmid pBW 7.0 encoding BR96 sFv-PE40 as described in Example 14, infra (E, Eco RI; H, Hind III; K, KPNI; N, NDe I; S, Sal I; (Gly$_4$Ser)$_3$ represents a 15 amino acid linker).

All cells were cultured in RPMI 1640 supplemented with 10% fetal bovine serum, except L929, which was cultured in DMEM supplemented with 10% fetal bovine serum. Plasmid pMS8 (FIG. 36), which encodes the gene for LysPE40 under control of the T7 promoter, was constructed by Dr. Clay Siegall (provided by Dr. Ira Pastan, NIH, Bethesda, Md.) from the vector pVC85 [Kondo et al., J. Biol. Chem. 263: 7470–7475 (1988)] by inserting at the amino terminus a lysine residue and also inserting a multiple cloning site.

Expression and Purification of LysPE40

The plasmid pMS8 encoding LysPE40 was transformed into E. coli BL21 (λDE3) cells and cells were cultured in Super Broth (Digene, Inc., Silver Spring, Md.) containing 75 μg of ampicillin per ml at 37° C. When absorbance at 650 was 2.0 or greater, isopropyl 1-thio-β-D-galactopyranoside was added (1 mM) and cells were harvested 90 minutes later. The bacteria were washed in sucrose buffer (20% sucrose, 30 mM Tris-HCl (pH 7.4), 1 mM EDTA), and osmotically shocked in ice-cold H$_2$O to isolate the periplasm. LysPE40 protein was purified from the periplasm by successive anion-exchange and gel-filtration chromatographies using a Pharmacia fast protein liquid chromatography (FPLC) system as described previously [Batra et al., *Proc. Natl. Acad. Sci. USA* 86: 8545–8549 (1989) and Siegall et al., *Proc. Natl. Acad. Sci. USA* 85: 9738–9742 (1988)].

Generation of BR96 F(ab')$_2$ and Fab' Fragments

F(ab')$_2$ fragments were generated from ChiBR96 (4 mg/ml) by pepsin digestion (25 μg/ml in 0.1 M citrate buffer, pH 4.0, [Parham, in Handbook of Experimental Immunology, Weir, Ed., Blackwell Scientific Publishers, p. 1–23 (1986)]. After 6 hours incubation at 37° C., digestion was terminated by adjusting the pH to 7.2 with PBS. Purity of the digest preparation was 90–95% F(ab')$_2$ determined by SDS-PAGE (4–20% gradient gels) and Coomassie blue staining.

Fab' was prepared from the ChiBR96 F(ab')$_2$ by reduction with cysteine to break the remaining interchain disulfide bonds [Parham et al., supra]. Briefly, F(ab')$_2$ molecules (2–4 mg/ml) in 0.1 M Tris-HCl (pH 7.5) were incubated at 37° C. for 2 hours with cysteine (0.01 M final concentration). Free sulfhydryl groups on the Fab' molecule were alkylated with 0.02 M iodoacetamide (CalBiochem, San Diego, Calif.) for 30 minutes at room temperature to prevent recombination of the Fab' to F(ab')$_2$. The reaction mixture was dialyzed against PBS. Purity was greater than 85% as assessed by SDS-PAGE.

Immunotoxin Construction and Purification

Chimeric BR96 (6–10 mg/ml) was thiolated by addition of a 3-fold molar excess of 2-iminothiolane (2-IT) in 0.2 M sodium phosphate (pH 8.0), 1 mM EDTA for 1 hour at 37° C. [Batra et al., *Proc. Natl. Acad. Sci. USA* 86: 8545–8549 (1989)], which introduces sulfhydryl groups by reaction of 2-iminothiolate with primary amines. Unreacted 2-IT was removed by PD-10 column chromatography (Pharmacia). Alternatively, free thiol groups were generated by reduction with dithiothreitol (DTT). Chimeric BR96 was incubated with a 20-fold molar excess of DTT for 2.5 hours at 42° C. Excess DTT was removed by overnight dialysis against PBS under nitrogen. The number of thiol groups on the monoclonal antibody was determined by DTNB reduction (Ellman's reagent, Sigma Chem. Co.) as described by Deakin et al., *Biochem. J.* 89: 296–304 (1963), incorporated by reference herein. This procedure routinely gave 4 thiol groups per BR96 antibody, with no reduction in antibody binding reactivity or protein concentration. The procedure was not used with F (ab')$_2$ or Fab' fragments.

Thiolated BR96 antibody was condensed with maleimide-modified PE or LysPE40. A non-cleavable maleimide group was attached to lysine residues on the toxin (PE or LysPE40; 6–8 mg/ml) by mixing with 3-fold molar excess of SMCC in 0.2 M sodium phosphate (pH 7.0), 1 mM EDTA at room temperature for 30 minutes and purified on a PD-10 column. Modified toxin and thiolated antibody were mixed in a 4:1 molar ratio and incubated at room temperature for 14–16 hours to allow a thioether linkage to form. Immunotoxins were purified by anion-exchange (Mono Q) to remove unreacted antibody and gel-filtration chromatography (TSK-3000) to remove unconjugated toxin as previously described by Kondo et al., *J. Biol. Chem.* 263: 9470–9475 (1988); and Batra et al., *Proc. Natl. Acad. Sci. USA* 86: 8545–8549 (1989), all incorporated by reference herein.

Figure 28:
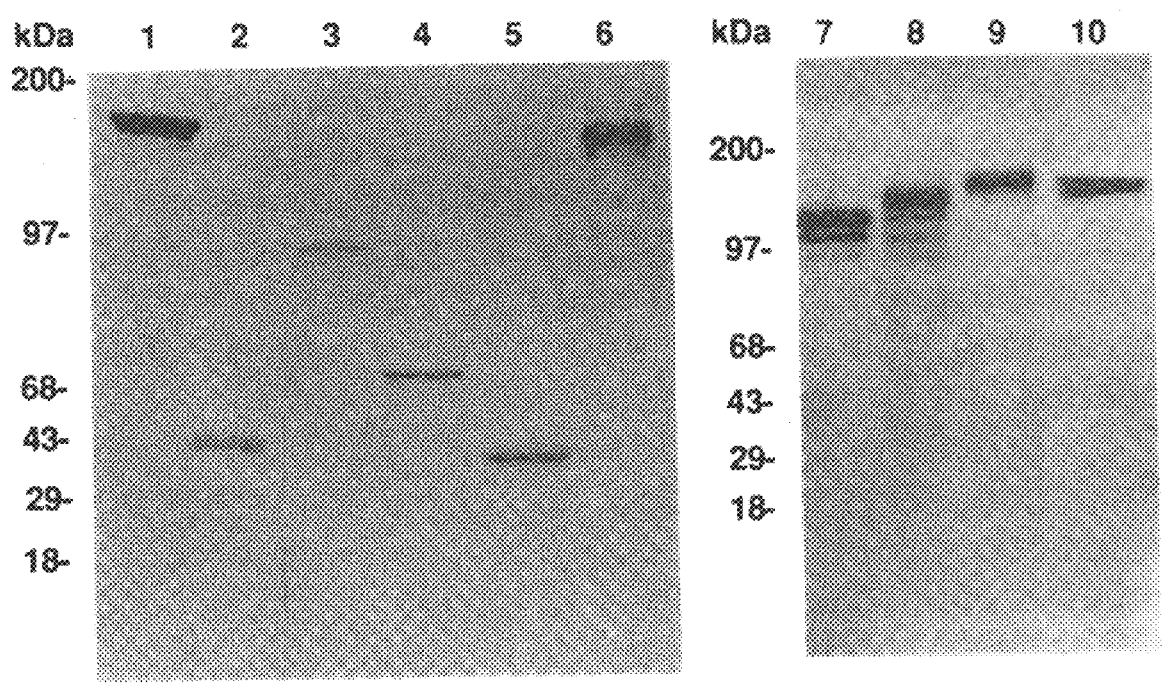
FIG. 28 is a photograph of the gel obtained from non-reducing SDS-PAGE analysis of conjugated and unconjugated ChiBR96 IgG, Fab' and F(ab')$_2$ immunotoxins as described in Example 13, infra (Lane 1: ChiBR96 IgG; Lane 2: ChiBR96 Fab'; Lane 3: ChiBR96 Fab'-LysPE40; Lane 4: Native PE; Lane 5: LysPE40; Lane 6:ChiBR96 IgG-LysPE40; Lane 7:ChiBR96(Fab')$_2$; Lane 8: ChiBR96 F(ab')$_2$-LysPE40; Lane 9:ChiBR96 IgG-LysPE40; Lane 10:ChiBR96 IgG).

Chimeric BR96 IgG-LysPE40 (190 kDa), Fab'-LysPE40 (96 kDa) and F(ab')$_2$-LysPE40 (145 kDa) conjugates were additionally analyzed by non-reducing SDS-polyacrylamide gel electrophoresis (SDS-PAGE) to determine the size of the native conjugate (FIG. 28). From the Coomassie blue stained gels, it was determined that there was less than 5% unconjugated antibody after purification.

Binding Studies

For competition binding studies, L2987 cells (Bristol-Myers Squibb Co., Seattle, Wash.) were removed from monolayer culture using 0.2% trypsin and washed with RPMI 1640 containing 2% FCS (wash buffer). Cell suspensions (1.0×10$^6$ cells/0.1 ml) were incubated with 0.1 ml fluorescein isothiocyanate (FITC)-labeled ChiBR96 (13.3 μg/ml final concentration) and 0.1 ml of diluted antibody or immunotoxin at 4° C. for 1 hour, washed, and the amount of cell-bound FITC labeled-ChiBR96 was quantified on an EPICS V model 753 Flow Cytometer (Coulter Corp., Hialeah, Fla.).

For direct binding studies, two-fold serially diluted immunotoxins or antibody was incubated for 1 hour at 4° C. in 0.2 ml wash buffer containing 1×10$^6$ L2987 cells. Cells were washed and then incubated in wash buffer containing 1:40 diluted FITC labelled goat anti-human kappa antibody (Bethyl Labs, Montgomery, Tex.) for an additional 30 min at 4° C. to quantitate cell-bound antibody. Cells were washed and analyzed for cell surface fluorescence on a flow cytometer to determine the amount of immunotoxin or antibody remaining on the cell surface.

Two methods were used to determine whether there was an alteration in antibody binding activity after conjugation to PE or LysPE40. Competition binding analysis showed that both immunotoxins competed with FITC-labeled ChiBR96 as efficiently as unconjugated ChiBR96 antibody (FIG. 29), indicating that binding affinity for the BR96 antigen was not perturbed after chemical conjugation. Similar results were obtained using the direct binding assay for both PE and LysPE40 conjugates.

Figure 29:
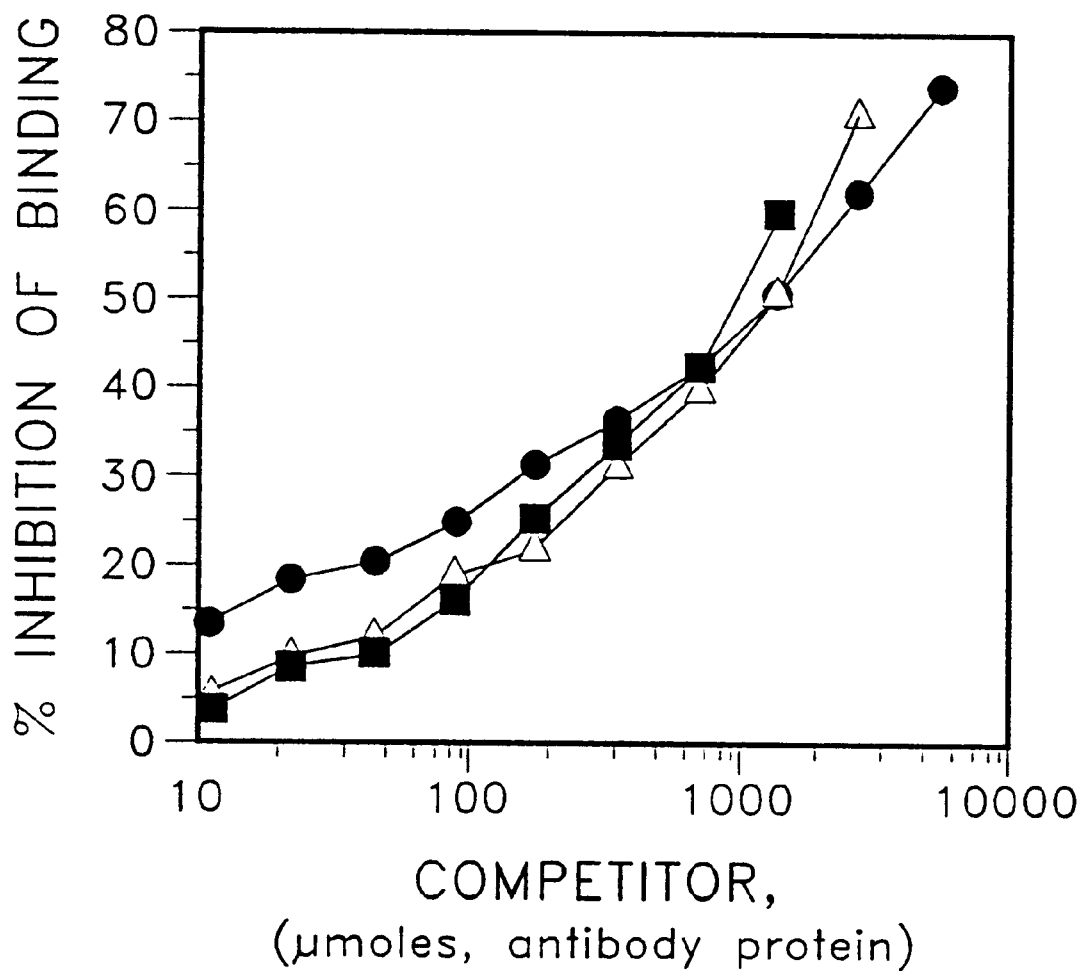
FIG. 29 is a graph depicting the results of competition of ChiBR96-PE and ChiBR96-LysPE40 binding as described in Example 13, infra (ChiBR96 (closed circle); ChiBR96-PE (closed square); ChiBR96-LysPE40 (open triangle)).
Figure 30A:
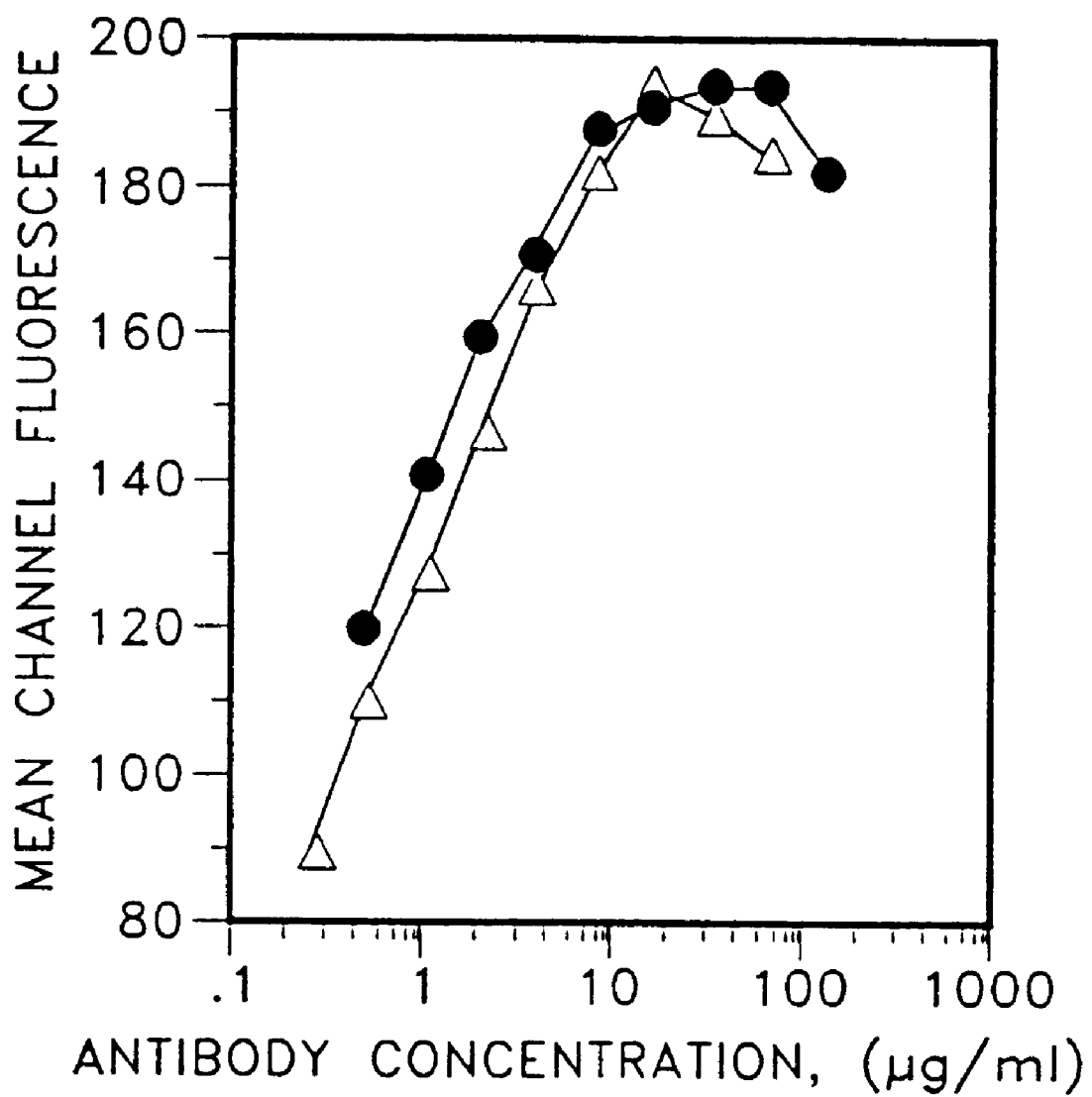
FIGS. 30A, B, C are graphs of the direct binding of intact ChiBR96-LysPE40, F(ab')$_2$-LysPE40 and Fab'-LysPE40 to L2987 cells, as described in Example 13, infra (ChiBR96 (closed circle); ChiBR96-LysPE40 (open triangle); ChiBR96 F(ab')$_2$ (open square); ChiBR96 F(ab')$_2$-LysPE40 (closed circle); ChiBR96 Fab' (open circle); ChiBR96 Fab'-LysPE40 (open circle)).
Figure 30B:
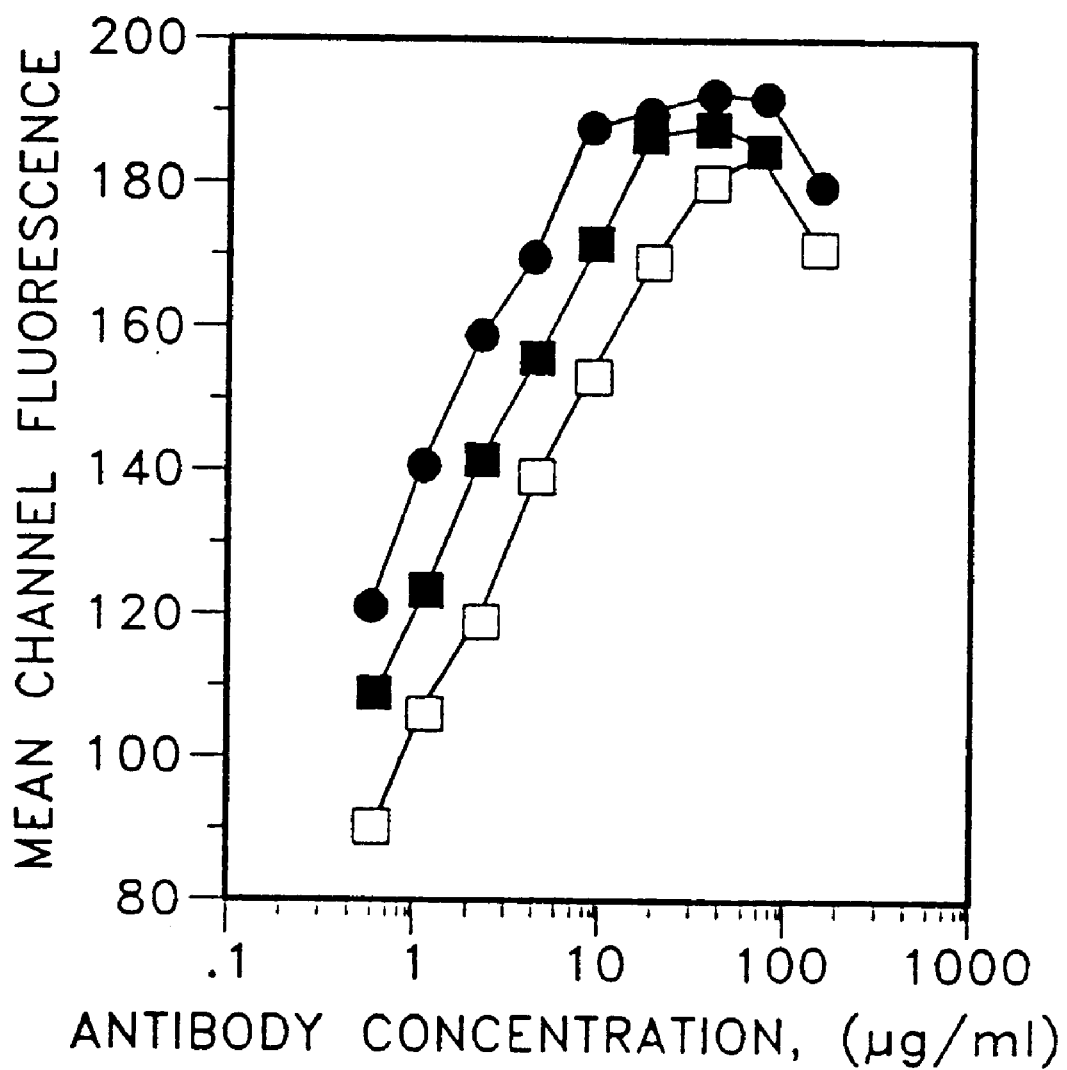
Figure 30C:
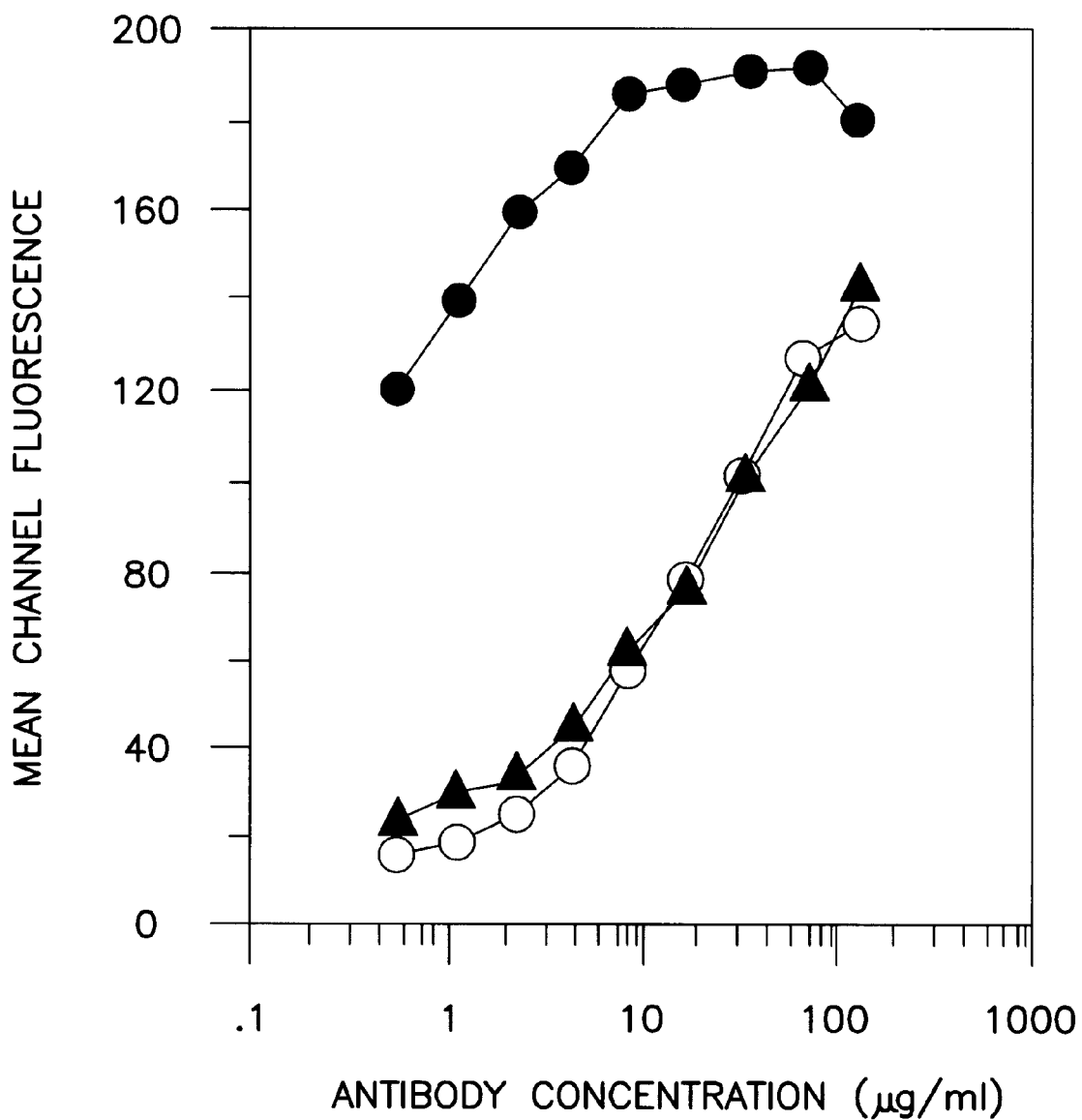

Binding activities of LysPE40 conjugated and unconjugated IgG, F(ab')$_2$ and Fab' were also compared by direct binding to L2987 tumor cells. Cell-bound antibody protein was quantitated using FITC-labeled goat anti-human kappa light chain antibody. Binding of the LysPE40 immunotoxin was similar to that obtained using unconjugated ChiBR96 antibody (FIG. 30A) and agreed with results obtained using the competition binding assay (FIG. 29). FIG. 30B compares the binding activity of intact IgG to F(ab')$_2$ and F(ab')$_2$-LysPE40. There was no loss in immunoreactivity with the F(ab')$_2$ and F(ab')$_2$-immunotoxin as compared to ChiBR96 IgG. Conjugation of PE40 to Fab' did not affect immunoreactivity (FIG. 30C), however, binding of the Fab' was significantly decreased as compared to intact IgG (FIG. 30C), most likely because of the monovalency of the Fab' molecule.

Antigenic Modulation and Internalization

Modulation of intact ChiBR96, F(ab')$_2$ or Fab' immunotoxins was assayed on L2987 cells propagated as 90–95% confluent monolayer cultures in 96 well microtiter plates as described above. Target cells were pulsed for 1 hour at 4° C. with 0.1 ml of two-fold serially diluted immunotoxin ranging from 5–800×10$^{-7}$ M antibody protein in binding buffer. Monolayer cultures were washed free from unbound material using growth medium and individual plates were incubated in complete medium under either non-modulating (4° C.) or modulating (37° C.) conditions.

The amount of membrane-associated immunotoxin bound to target cell populations at each time point shown in FIG. 31 was quantified using [$^{125}$I]M40/1 (anti-PE) antibody (provided by Dr. D. Fitzgerald, NCI, Bethesda, Md., [Ogata et al., *Inf. and Immun.* 59: 407–414 (1991)]). Epitope mapping of M40/1 antibody determined that it binds to a 44 amino acid region in the PE domain II [Ogata et al., supra]. Monoclonal antibody M40/1 was radioiodinated using Na[$^{125}$I] (New England Nuclear, Boston, Mass.) and chloramine T (Kodak Chemical Co., Rochester, N.Y.) as described by McConahey and Dixon, *Arch. Allergy Appl.* 29: 185–188 (1966), incorporated by reference herein. Radio-iodinated M40/1 was separated from unbound iodine by PD10 column chromatography (Pharmacia). Specific activities ranged from 2 to $5 \times 10^5$ CPM/μg.

At various times during incubation at 37° C. or 4° C., a triplicate set of wells were twice washed with wash buffer and pulse-labeled with 0.1 ml [$^{125}$I]-labeled M40/1 antibody (0.5 μg/ml in wash buffer containing 0.2% sodium azide) to determine membrane bound conjugate. After 15 minutes, monolayers were washed free of unbound label, and cell-bound cpm was determined by solubilization of the cell monolayer with 0.5 N NaOH. Cell-bound radioactivity was determined using a LKB model 1272 gamma counter. Non-specific binding was determined by incubation of target cells with a similar concentration of unconjugated ChiBR96. In certain experiments, unconjugated PE was used to determine background binding levels. [$^{125}$I]-labeled M40/1 antibody did not react with membrane bound antibody or PE.

Figure 31A:
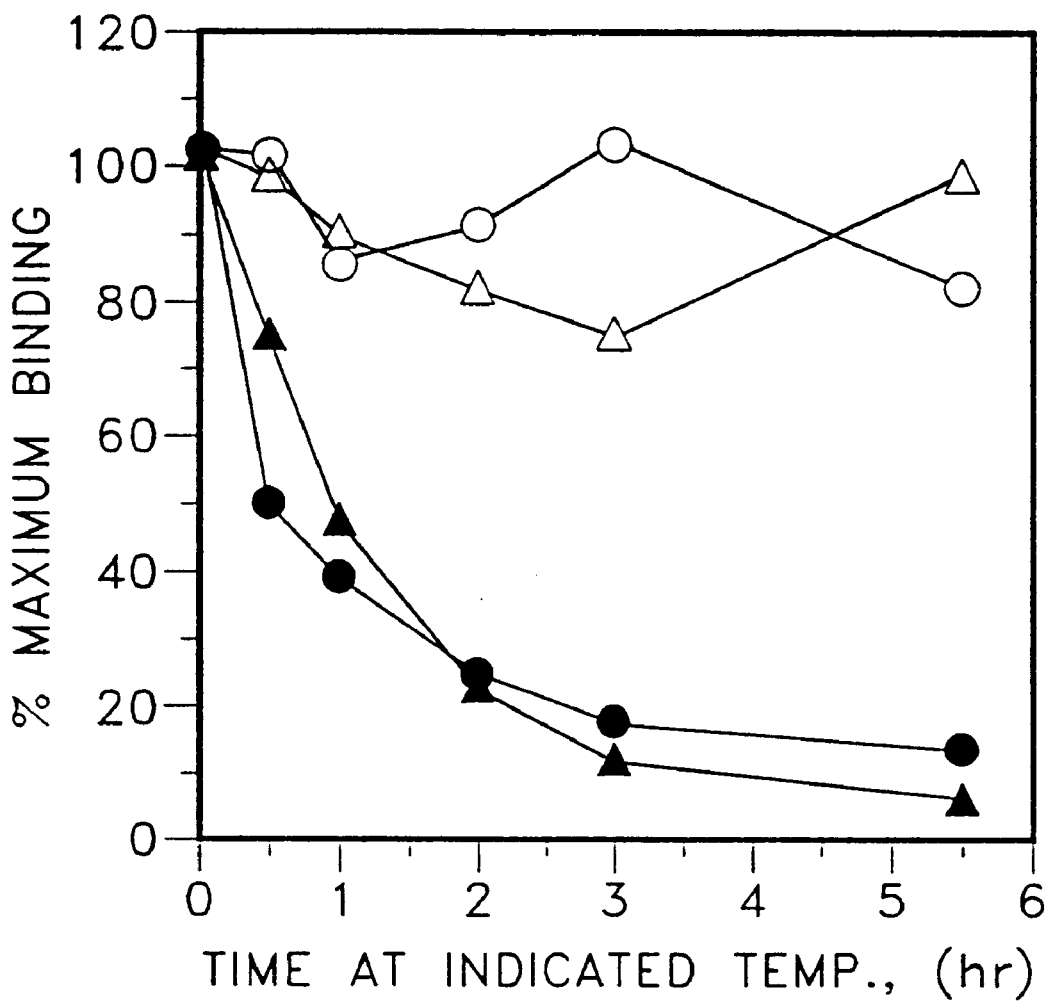
FIGS. 31A and B are graphs showing the determination of endocytosis of cell-surface immunotoxin after modulation with ChiBR96-PE or ChiBR96-LysPE40 immunotoxins as described in Example 13, infra (31A: loss of cell surface immunotoxin under modulating and non-modulating conditions; 31B: internalization of cell-bound immunotoxin using immunotoxin plus radiolabeled M-40/1 complex; ChiBR96-PE coated cells were incubated at 4° C. (open circle) or 37° C. (closed circle); ChiBR96-LysPE40 coated cells were incubated at 4° C. (open triangle) or 37° C. (closed triangle).

The ability of ChiBR96-PE and ChiBR96-LysPE40 to induce antigenic modulation was initially measured by determining the loss of immunotoxin from the cell surface membrane (FIG. 31). There was no difference in modulation kinetics between PE or LysPE40 immunotoxins with approximately 50% of the original cell-bound immunotoxin modulated from the surface membrane 30 minutes after warming to 37° C. Cells incubated under conditions which do not allow antigenic modulation (4° C.), showed essentially no loss of cell surface toxin within 6 hours (FIG. 31A).

Figure 31B:
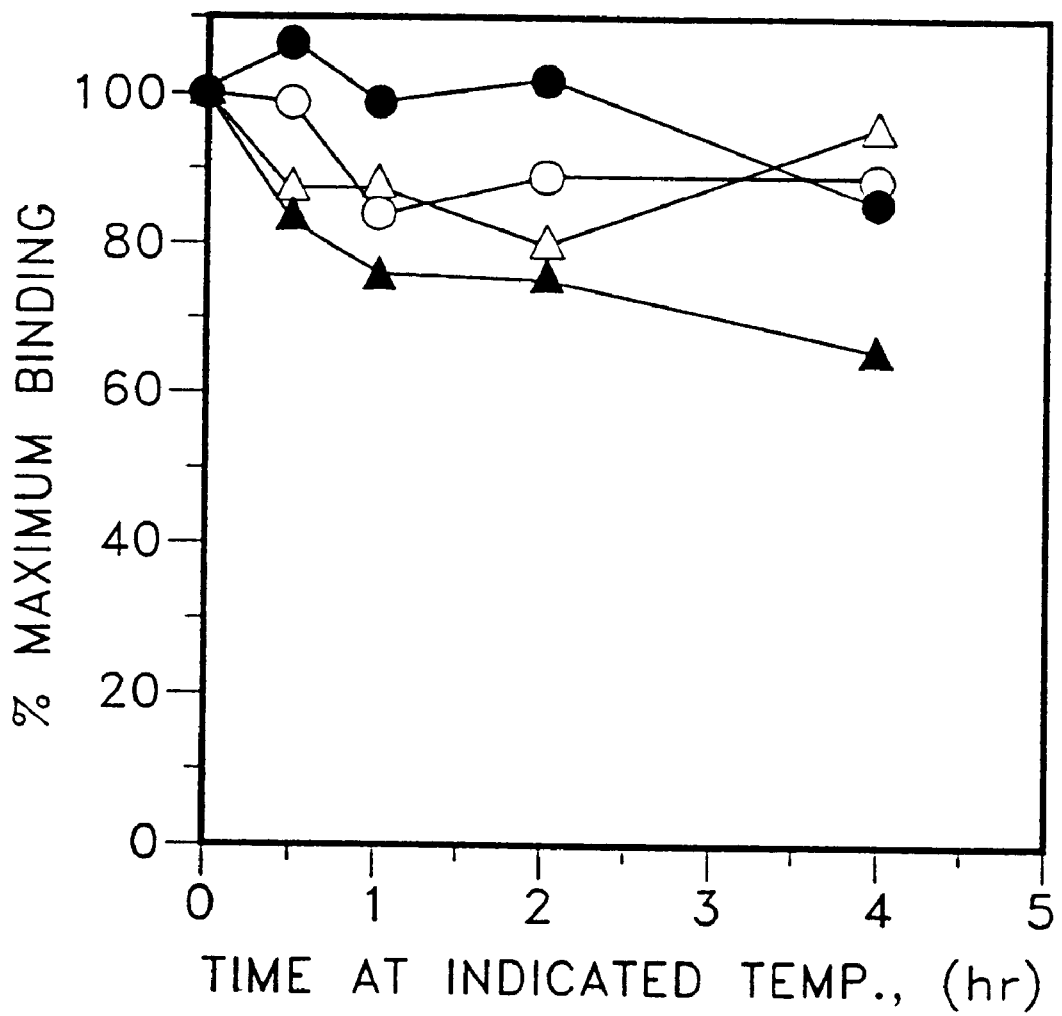

In order to confirm that the loss of cell-surface immunotoxin was due to endocytosis, cells were incubated with a [$^{125}$I]-labeled immunotoxin complex for 1 hour at 4° C. to permit binding, washed and were subsequently modulated at 37° C. As shown in FIG. 31B, essentially all the radiolabeled immunotoxin remained cell-associated, despite the concomitant loss from the cell-surface membrane (FIG. 31A). These findings confirm that most if not all of the membrane-associated BR96 immunotoxins were rapidly internalized, and that internalization rates were similar for PE and LysPE40 immunotoxins.

The capacity of ChiBR96 F(ab')$_2$-LysPE40 and Fab'-LysPE40 immunotoxins to internalize was also determined by measuring the loss of cell-surface immunotoxin using radiolabeled anti-PE antibody. Essentially all of the ChiBR96 immunotoxins were completely internalized after 4.5 hours including the Fab'-immunotoxin (Table 8). However, rate differences were observed. At 2.5 hours, when 76% of the intact IgG toxin and 72% of the F(ab')$_2$ were internalized, only 12% of the Fab' immunotoxin was internalized. Therefore, both IgG, F(ab')$_2$ and Fab'-LysPE40 immunotoxins were modulated from the cell surface membrane, but at different rates.

TABLE 8

Internalization of BR-96-Immunotoxins
from the Cell Surface Membrane of L2987 Cells

| | % INTERNALIZATION | |
|---|---|---|
| | 2.5 hr | 4.5 hr |
| BR-96-LysPE40 | 74.0 | 85.0 |
| F9(ab')$_2$-LysPE40 | 72.0 | 91.6 |
| Fab'-PE40 | 12.0 | 89.6 |

Inhibition of Protein Synthesis Assay

Cytotoxicity of various forms of ChiBR96 antibody conjugated to LysPE40 against tumor cells was determined by measuring inhibition of protein synthesis as follows: Tumor cells ($1 \times 10^5$ cells/ml) in growth media were added to 96 well flat bottom tissue culture plates (0.1 ml/well) and incubated at 37° C. for 16 hours. Dilutions of toxin or toxin-conjugates were made in growth media and 0.1 ml added to each well (3 wells/dilution) for 1 hour or 20 hours at 37° C. After the appropriate incubation time, unreacted material was removed by washing the monolayer with growth media. Cells were incubated in 0.2 ml growth media for a total of 20 hours and pulse-labeled with [$^3$H]-leucine (1 μCi/well) for an additional 4 hours at 37° C. The cells were lysed by freezing, thawing at 37° C. and harvested using a Tomtec cell harvester (Orange, Conn.). Cellular protein labeled with [$^3$H]-leucine was determined by counting the radioisotope using a LKB Beta Plate (LKB, Piscataway, N.J.) liquid scintillation counter.

Analysis of Competition of Immunotoxin Cytotoxic Activity

Chimeric BR96-PE40 was added at 0.8, 4 and 20 pM concentrations to MCF-7 cells in the presence or absence of 50 μg (333 pM) ChiBR96 antibody. Cytotoxicity was determined as described in the inhibition of protein synthesis assay as described above.

In vitro Cytotoxicity of Intact IgG-PE Immunotoxins

The in vitro cytotoxic activity of the immunotoxins against cancer cells was assayed by comparing inhibition of protein synthesis on antigen positive and antigen negative cells (Table 9). BR96 antigen-positive cell lines MCF-7, L2987, and RCA were the most sensitive to ChiBR96-PE with EC$_{50}$ values of 0.14, 0.28, and 1.4 pM, respectively. The immunotoxin was also more inhibitory than native PE which had EC$_{50}$ values of 200, 140 and 380 pM. When tested on antigen-negative cell lines, little difference in EC$_{50}$ values between PE and the immunotoxin was observed. Specificity, (antibody-directed cell-killing), must take into account the different sensitivities of the various cell lines to native PE. Thus, the ChiBR96 immunotoxins were 100–500 fold more potent than native PE against antigen-positive cell lines.

TABLE 9

Cytotoxicity of ChiBR96-PE on Human Tumor Cells

| | | | EC$_{50}$, pM | | |
|---|---|---|---|---|---|
| Cell Line | Type | BR96 Antigen | DTT Reduced ChiBR96-PE | 2-IT-Treated ChiBR96-PE | Native PE |
| MCF-7[1] | Breast | + | 0.10 | 0.14 | 200.0 |
| L2987 | Lung Ca. | + | 0.25 | 0.28 | 140.0 |
| RCA | Colon Ca. | + | 1.2 | 1.4 | 380.0 |
| A2780 | Ovarian Ca. | − | 23.0 | 23.0 | 60.0 |
| L929 | Mouse Fblst | − | 13.5 | 14.0 | 3.0 |
| KB[2] | Epidermoid | − | 220.0 | 231.0 | 227.0 |

[1]ATCC No. HTB 22
[2]ATCC No. CCL 17
EC$_{50}$ represents the amount of immunotoxin or toxin required to inhibit 50% of the protein synthesis as determined by [$^3$H]-leucine incorporation in cellular protein. (BR96 antigen + = Epitope density of > $1 \times 10^4$ molecules/cell).

Cytotoxicity of ChiBR96 Mab and Enzymatic Fragments Linked to LysPE40 Against MCF-7 Cells Smaller immunotoxin molecules may be beneficial in tumor penetration, therefore, the cytotoxic activity of ChiBR96 as Fab', F(ab')2 fragments and as an IgG linked to LysPE40 was compared (Table 10). As with the ChiBR96-

Figure 32:
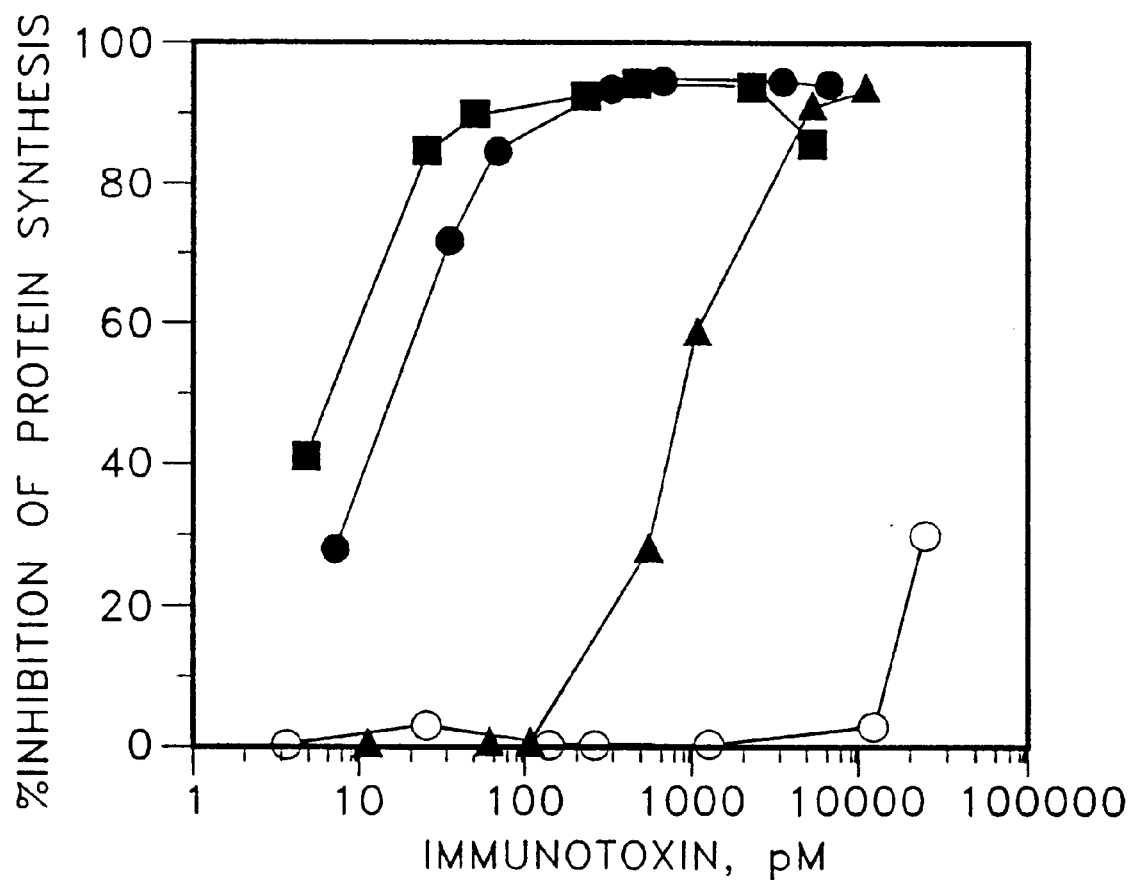
FIG. 32 is a graph of the cytotoxic effects of various ChiBR96 forms conjugated to LysPE40 against MCF-7 cells as described in Example 13, infra (ChiBR96-PE40 (closed square); ChiBR96 F(ab')$_2$-PE40 (closed circle); ChiBR96 Fab'-PE40 (closed triangle); PE40 open circle).

PE immunotoxin (Table 9), MCF-7 and L2987 cells were the most sensitive cell lines tested. The IgG and F(ab')$_2$-LysPE40 molecules showed similar cytotoxic activity against MCF-7 cells (EC$_{50}$=8–14 pM) while the Fab'-LysPE40 conjugate was much less active (EC$_{50}$=780 pM) (FIG. 32). Specificity of protein synthesis inhibition activity of Fab' and F(ab')$_2$ conjugates was also preserved, with little or no inhibitory activity observed against the antigen-negative cell lines A2780.

TABLE 10

Cytotoxicity of 2-iminothiolane Substituted Chimeric BR96-PE40 on Human Tumor Cells

| Cell Line | Type | BR96 Antigen | BR96 PE40 | F(ab')$_2$-PE40 | Fab'-PE40 | PE40 |
|---|---|---|---|---|---|---|
| MCF-7 | Breast Ca. | ++ | 8 | 14 | 780 | 15,000 |
| L2987 | Lung Ca. | + | 37 | 70 | 2700 | 17,500 |
| RCA | Colon Ca. | + | 84 | 110 | 5000 | 15,000 |
| A2780 | Ovarian Ca. | − | 650 | 2500 | 11,000 | 15,000 |
| KB | Epidermoid Ca | − | >5000 | N.D. | N.D. | >25,000 |

EC$_{50}$ is described in Table 8 legend. N.D. = not determined.

Specificity of Growth Inhibition By ChiBR96-LysPE40

Figure 33:
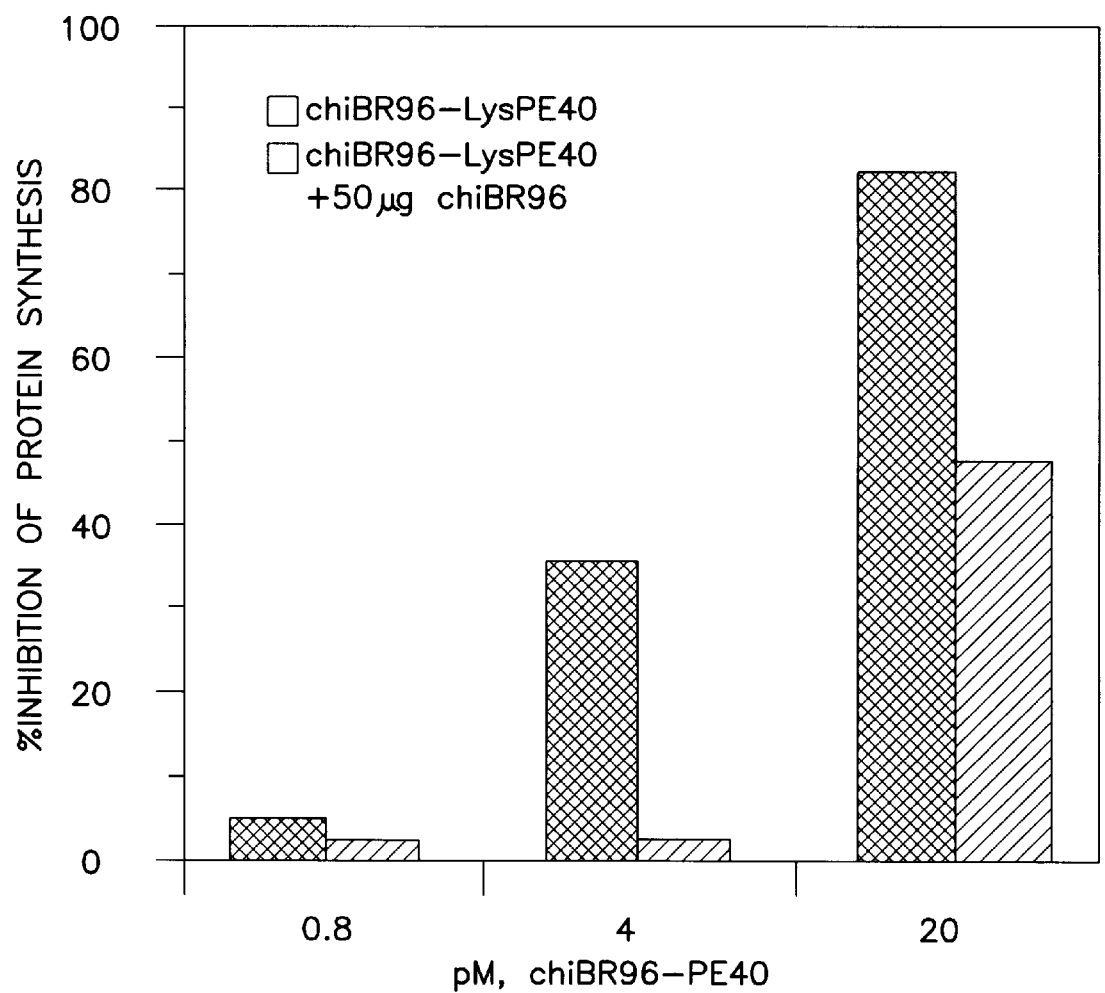
FIG. 33 is a bar graph depicting the results of competition analysis of ChiBR96-PE40 cytotoxic activity against MCF-7 cells as described in Example 13, infra.

Specificity was confirmed by abrogating the protein synthesis inhibition by ChiBR96-LysPE40 with unconjugated ChiBR96. Addition of excess ChiBR96 antibody (50 μg) with ChiBR96-LysPE40 immunotoxin, resulted in a decrease of in vitro potency (FIG. 33). At 20 pM of ChiBR96-LysPE40, approximately 50% of its cytotoxic effect was blocked by the addition of excess unconjugated antibody, while at 4 pM, the excess ChiBR96 completely blocked the cytotoxic activity of ChiBR96-LysPE40.

Kinetics of Cytotoxicity of ChiBR96 Immunotoxins and Native PE

In part, the effectiveness of immunotoxins may depend on the rate of internalization after binding to antigen-positive cells. To determine the cytotoxic activity of ChiBR96-PE, ChiBR96-LysPE40 and PE, a time course analysis was performed where cells were incubated with toxin for up to 20 hours as described above.

Figure 34A:
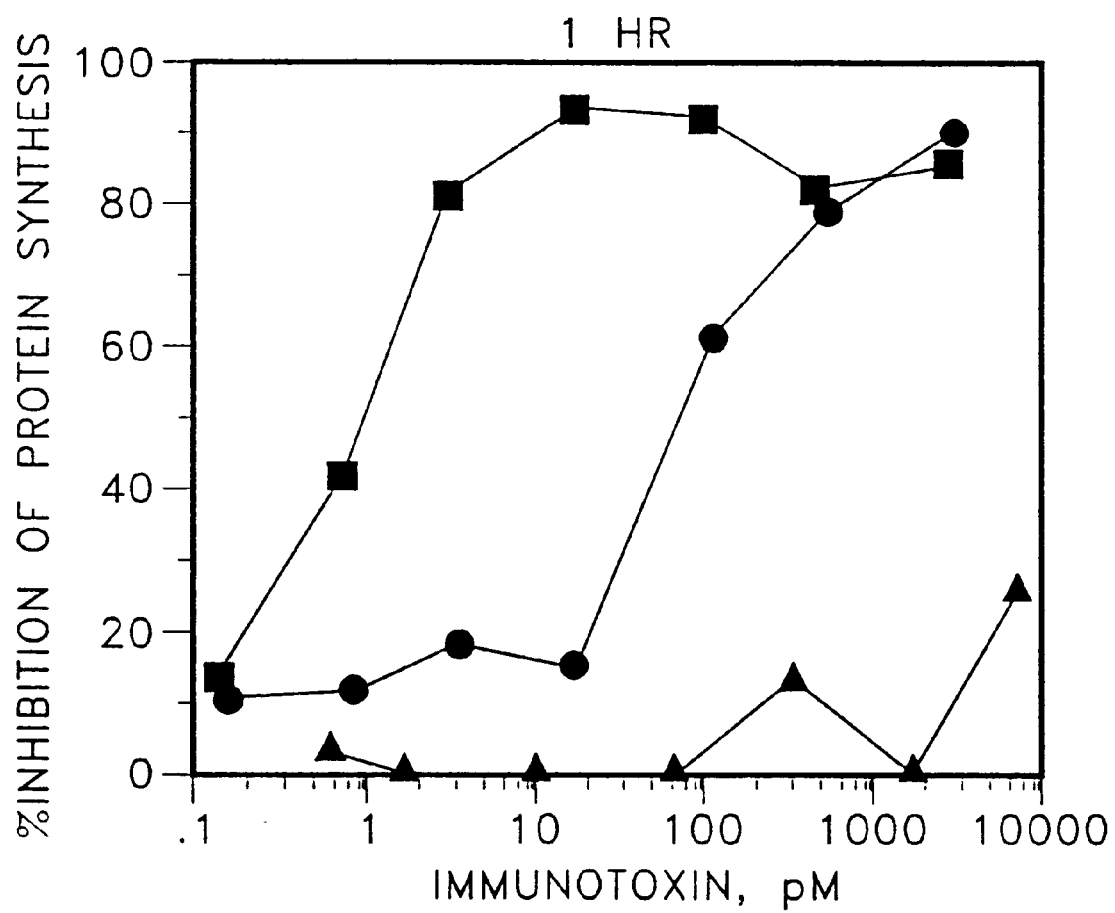
FIGS. 34A and B are graphs showing the results of protein synthesis inhibition analysis of ChiBR96-(PE/LysPE40) vs. PE against MCF-7 cells as described in Example 13, infra (34A: 1 hr; 34B: 20hr; ChiBR96-PE (closed square); BR96-PE40 (closed circle); PE (closed triangle).
Figure 34B:
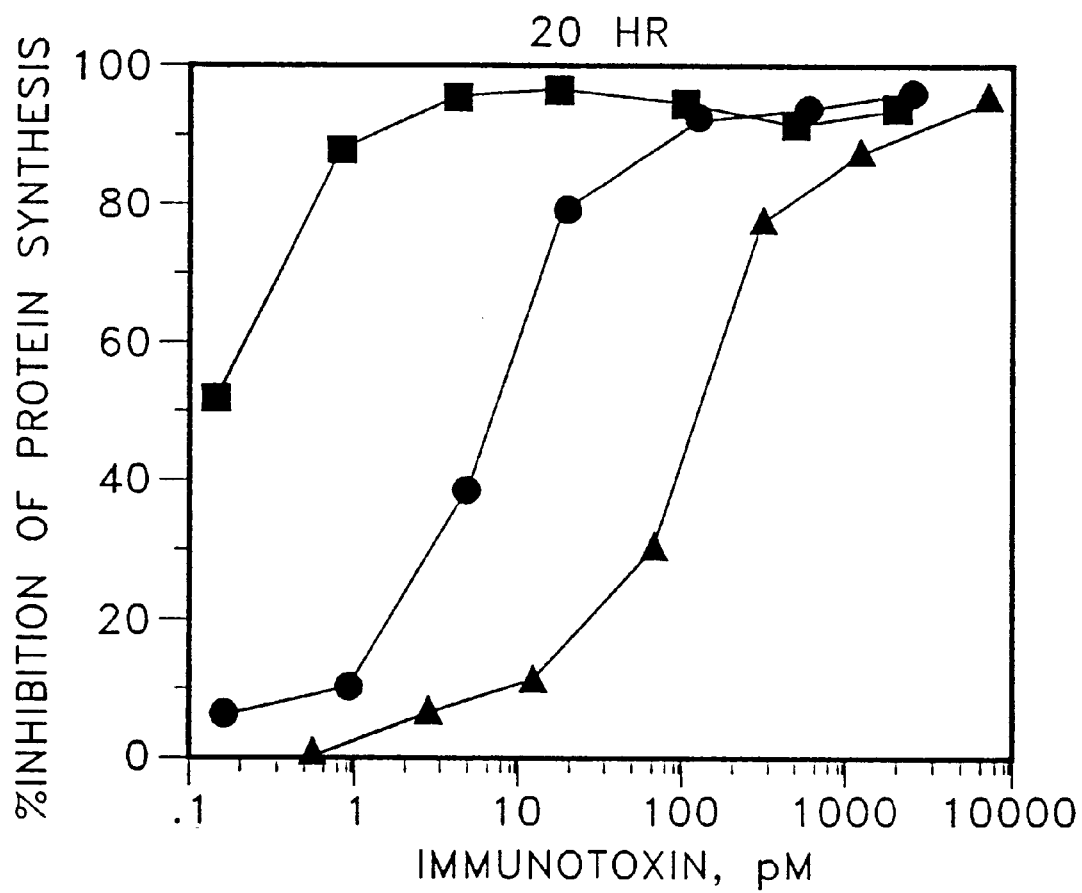

After 1 hour incubation, MCF-7 cells were sensitive to ChiBR96-PE and ChiBR96-LysPE40 (EC$_{50}$ values of 1 and 60 pm, respectively) but not to the native toxin (EC$_{50}$>10,000 pM). After 20 hours MCF-7 cells were slightly more sensitive to ChiBR96-PE and ChiBR96-PE40, but much more sensitive to PE; EC$_{50}$=200 pM (FIG. 34). This assay was repeated at 2, 4, and 6 hour time points. At each time point, PE was considerably less cytotoxic against MCF-7 cells than ChiBR96-immunotoxins. This may be due in part to the mechanism by which the toxin molecule is delivered to target cells.

This example demonstrates the production of immunotoxins containing the carcinoma-associated monoclonal antibody ChiBR96 and Pseudomonas exotoxin A. The antibody was used in forms including native IgG, reduced IgG, F(ab')$_2$ and Fab'. The toxin component of the immunotoxin was either native PE or LysPE40, a truncated form containing a genetically modified amino terminus that includes a lysine residue for conjugation purposes. Chimeric BR96-toxin conjugates were found to be cytotoxic to cells which display Lewis Y, a determinant recognized by the BR96 monoclonal antibody of the invention. The most cytotoxic of the conjugates produced was ChiBR96-PE which was 1000-fold more potent than PE itself against MCF-7 breast carcinoma cells. Chimeric BR96-LysPE40 was also extremely cytotoxic towards BR96 antigen positive cells (1000-fold more potent than LysPE40). Both ChiBR96-PE and ChiBR96-LysPE40 were produced using two procedures which generated sulfhydryl groups on the antibody, by mild reduction of the antibody or by derivatizing the antibody with 2-iminothiolane. The former procedure produced a greater yield of conjugate, but conjugates produced by both procedures resulted in chimeric molecules of identical activities.

Chimeric BR96-PE and ChiBR96-LysPE40 were almost fully active with 1 hour incubation, while PE was relatively inactive (FIG. 34). With continued incubation, ChiBR96-immunotoxins increase cytotoxic activity only slightly while PE becomes cytotoxic to the MCF-7 cells at later time points. This rapid efficacy of ChiBR96-immunotoxins is evidence of the utility of ChiBR96 in targeting cell populations for killing.

The binding and internalization activities of ChiBR96-immunotoxins were also examined. Immunoconjugates prepared with intact IgG or its F(ab')$_2$ or Fab' enzymatic digest products were not affected in terms of binding by chemical conjugation to LysPE40 (FIG. 30) or PE. Differences in binding activity between Fab' and F(ab')$_2$ or IgG conjugates may be attributed to differences in avidity due to the monovalence of the Fab' molecule. We also cannot exclude the possibility that enzymatic digestion used to generate the Fab' fragments contributed to the decreased avidity. Of most interest was the comparison between ChiBR96-LysPE40 and the enzymatic fragment immunotoxins ChiBR96 F(ab')$_2$-LysPE40 and ChiBR96 Fab'-LysPE40. This finding is also reflected in the cytotoxicity data (Table 10).

The results presented in this example demonstrate that both intact PE and LysPE40 immunotoxins as well as F(ab')$_2$ and Fab' immunotoxins demonstrate cytotoxic activity in vitro.

EXAMPLE 14

Preparation of Single-Chain BR96 sFv-PE40 Immunotoxin

This example describes the preparation and characterization of cytotoxicity of a single-chain immunotoxin, BR96 sFV-PE40, consisting of the cloned heavy and light chain Fv portions of the BR96 monoclonal antibody of the invention linked to PE40. Q Sepharose was purchased from Pharmacia (Uppsala, Sweden). TSK-3000 columns were purchased from TosoHaas, Inc. (Philadelphia, Pa.). Immunoblots were performed using mouse anti-idiotypic BR96 antibody 757-4-1 as described above in Example 13, and ABC immunoblot kits (Vector Laboratories, Burlingame, Calif.). Chloramine T was purchased from Sigma Chemical Co. (St. Louis, Mo.). MCF-7 human breast carcinoma cells were originally obtained from the ATCC (Rockville, Md.) and have been maintained by Bristol-Myers Squibb Company, Seattle, Wash. RCA colon carcinoma cells were obtained from M. Brattain, Baylor University, Texas. L2987 lung adenocarcinoma cells were obtained from Dr. I. Hellstrom, Bristol-Myers Squibb Co., Seattle, Wash. A2780 ovarian carcinoma cells were obtained from K. Scanlon, NIH, Bethesda, Md., and KB epidermoid carcinoma cells were obtained from Dr. Ira Pastan, NIH, Bethesda, Md. Cells were cultured in RPMI 1640 supplemented with 10% fetal bovine serum.

Construction of BR96 sFv-PE40

In order to produce a single-chain recombinant immunotoxin, the Fv domains of the light and heavy chains of BR96 IgG were isolated from plasmid pBR96 Fv (FIG. 36) containing the BR96 Fv sequences using PCR amplification.

Identification of Primers for PCR Amplification

Two sets of PCR primers:

Primer 1: 5'-GCTAGACATATGGAGGTGCAGCTGGT GGAGTCT-3' (SEQ ID NO: 1) and primer 2: 5'-GCT GTGGAGACTGGCCTGGTTTCTGCAGGTACC-3' (SEQ ID NO:2) were devised for the amplification of the $V_L$ and $V_H$ of murine chimeric BR96 monoclonal antibody. The $V_L$ and $V_H$-5' PCR primers were based on the N-terminal amino acid sequence of the BR96 light and heavy chains (FIG. 35, SEQ ID NO:3), respectively, while the 3' primers were designed according to the frequency of the most common nucleotide at each position of joining (J)-region segments after alignment of $V_H$ and $V_k$ genes [Kabat et al., in Sequences of Proteins Of Immunological Interest, U.S. Dept. Health and Human Services, Washington, D.C. (1987)]. The $V_L$-5' primer was comprised of 24 nucleotides encoding the N-terminal amino acids of the variable light chain and a Hind III site 5' to these nucleotides while the $V_L$-3' primer consisted of 22 nucleotides which were complementary to the J region of mouse kappa light chain mRNA and a Sph I site 5' to these nucleotides. The $V_H$-5' primer contained 30 nucleotides encoding the N-terminal amino acids of the heavy chain and an Eco RI site 5' to these nucleotides while the $V_H$-3' primer contained 22 nucleotides with J region complimentarily and a BamHI site 5' to these nucleotides. In designing each primer, additional nucleotides were incorporated at the 5' end in order to optimize restriction site digestion and subsequent cloning of the PCR reaction products. The 5' PCR primer (primer 1) was designed to encode a unique Nde I restriction site.

RNA Isolation, cDNA Synthesis and Amplification

RNA was prepared from about $1\times10^8$ BR96 hybridoma cells grown in IMDM supplemented with 10% fetal calf serum (FCS). Total RNA was used for first strand cDNA synthesis using random hexamers at 23° C. for 10 minutes in a 20 μl reaction mixture containing 1 μg of total RNA, 4 mM $MgCl_2$, 1 mM of each dNTP, 1 unit of RNAase inhibitor (recombinant RNAase inhibitor originally isolated from human placenta, Perkin-Elmer/Cetus, Norwalk, Conn.), 1×PCR buffer (10×PCR Reaction buffer=500 nM KCl, 100 mM Tris-HCl, pH 8.3), 2.5 μM random hexanucleotide (Perkin-Elmer/Cetus) and 2.5 units of reverse transcriptase (cloned Moloney murine leukemia virus [M-MLV] reverse transcriptase, 2.5 units/μl from Perkin-Elmer/Cetus). Subsequent to hexameric primer extension with reverse transcriptase, the reaction mixtures were incubated successively in a thermal cycler (Eppendorf MicroCycler) at 42° C. for 15 minutes, 99° C. for 5 minutes and 5° C. for 5 minutes. Amplification of $V_L$ and $V_H$ cDNAs was performed with 35 cycles of PCR using reagents according to manufacturer's instructions (GeneAmp RNA-PCR, Perkin-Elmer/Cetus) in two separate tubes with 0.15 μM each of either $V_L$-5' and $V_L$-3 or $V_H$-5' and $V_H$-3' primers. Each PCR cycle consisted of denaturation at 95° C. for 1 minute followed by annealing and extension at 60° C. for 1 minute. In order to fully extend all cDNAs, a single held extension was performed at 60° C. for 7 minutes.

Cloning of Amplified cDNA

The amplified PCR products were purified on ion-exchange mini-columns (Elutip-D, Schleicher & Schuell, Keene, N.H.), concentrated by ethanol precipitation and digested with either EcoRI and BamHI ($V_H$ gene) or Hind III and Sph I ($V_L$ gene). Subsequently, the digested PCR reaction products were further purified on 1.5% agarose gels (SeaKem, FMC Corp. Rockland, Me.) and the $V_H$ or $V_L$ gene fragments separately cloned into pEV3-SM2 [Crowl et al., Gene 38: 31–38 (1985)] digested with either EcoRI and BamHI or with Hind III and Sph I respectively. Clones containing V gene inserts were identified by colony hybridization using either random-primed radiolabeled $V_L$ or $V_H$ cDNA fragments as probes. The nucleotide sequence was then determined for several cloned $V_L$ or $V_H$ cDNA inserts, employing primers based upstream within the lambda $P_L$ promoter or downstream of Sal I within pBR322 sequences.

Construction of Plasmid pBW 7.0

Starting with the BR96 sFv sequence encoded by plasmid pBR96Fv (FIG. 35, prepared by Dr. McAndrew, Bristol-Myers Squibb Co.) a 550 bp sequence corresponding to the variable heavy and variable light chains connected with a synthetic $(Gly_4Ser)_3$ hinge region up to the Kpn I restriction site in the light chain, was used to PCR-amplify with primer 1 and primer 2 described above. After PCR-amplification and digestion with Nde I and Kpn I the 550 bp Nde I-Kpn I fragment was ligated into a 4220 bp Nde I-Kpn I vector fragment prepared from plasmid pMS8 described above, (supplied by Dr. Ira Pastan, NIH, Bethesda, Md.), which encodes the gene for PE40 under the transcriptional control of the T7 promoter [Studier et al., J. Mol. Biol. 189: 113–130 (1986)]. The product of this ligation was an intermediate vector designated pBW 7.01 (FIG. 35). Subsequently, the 227 bp Kpn I fragment from pBR96 Fv was subcloned into the unique Kpn I site of pBW 7.01. The resulting plasmid pBW 7.0 (FIG. 36), encoding the BR96 sFv-PE40 gene fusion, was confirmed by DNA sequence analysis.

Expression and Purification of BR96 sFv-PE40

The plasmid pBW 7.0 encoding BR96 sFv-PE40 obtained as described above was transformed into E. coli BL21 (λ DE3) cells cultured in Super Broth (Digene, Inc., Silver Springs, Md.) containing 75 μg of ampicillin per ml at 37° C. When absorbance at 650 nm reached 1.0, isopropyl 1-thiol-B-D-galactopyranoside (IPTG) was added to a final concentration of 1 mM, and cells were harvested 90 minutes later. Upon induction with IPTG, the E. coli cells transformed with pBW 7.0 expressed large amounts of fusion protein that was localized to the inclusion bodies. The bacteria were washed in sucrose buffer (20% sucrose, 30 mM Tris-HCl (pH 7.4), 1 mM EDTA) and were osmotically shocked in ice-cold $H_2O$ to isolate the periplasm. Subsequently, inclusion bodies were isolated away from the spheroplast membrane proteins by extensive treatment with Tergitol (Sigma) to remove excess bacterial proteins, followed by denaturation in 7 M guanidine-HCl (pH 7.4), refolding in PBS supplemented with 0.4 M L-Arginine and extensive dialysis against 0.02 M Tris, pH 7.4. Protein was purified using anion-exchange on a Q-Sepharose column and fractions containing BR96 sFv-PE40 were then pooled and separated by gel-filtration (on a TSK-3000 column) chromatographies with a Pharmacia fast protein liquid chromatograph (FLPC) system as described by Siegall et al., Proc. Natl. Acad. Sci. USA 85: 9738–9742 (1988).

Figure 37A:
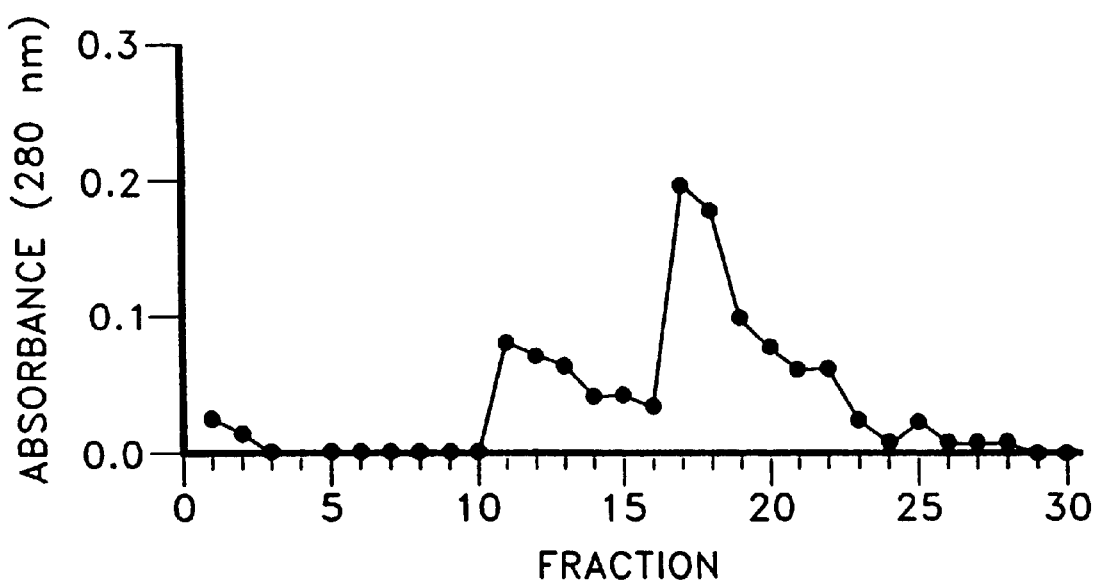
FIGS. 37A, B, C illustrate the purification of BR96 sFv-PE40 by gel filtration as described in Example 14, infra (FIG. 37A: profile of gel filtration column chromatography of renatured BR96 sFv-PE40 after initial purification over Q-Sepharose.
Figure 37B:
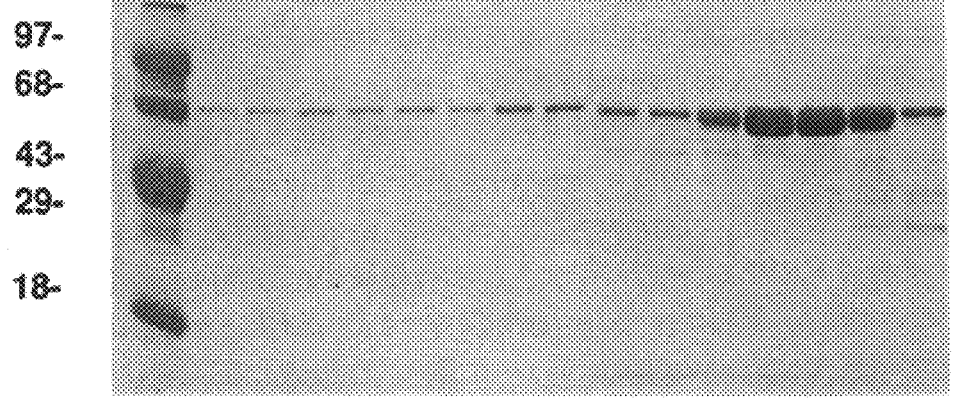
FIG. 37B: 12% denaturing SDS-polyacrylamide gel stained with Coomassie brilliant blue.
Figure 37C:
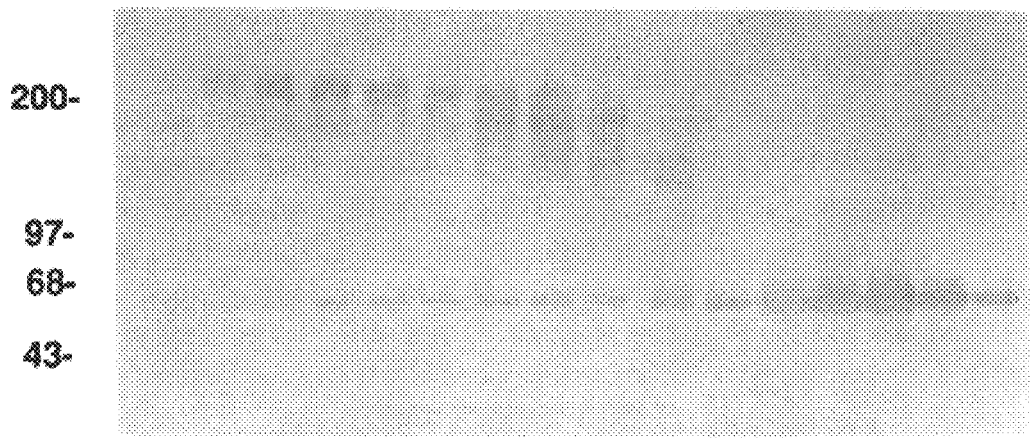
FIG. 37C: immunoblot of a 4–12% non-denaturing SDS-polyacrylamide gel probed with BR96 anti-idiotypic antibody; lanes 1–15 correspond to fractions 7–21 on the gel filtration profile shown in FIG. 37A; lane M represents molecular weight marker proteins in kilodaltons. Molecular weight standards correspond to 670 kDa, 158 kDa, 44 kDa and 17 kDa eluted in fractions 10, 15, 21 and 30, respectively).

The chromatographic profile of the size exclusion column indicated the presence of two major species (FIG. 37A). The first species eluted between gel filtration standards of 660 kD and 158 kD and represents an aggregated form of the recombinant protein (fractions 9–14). The second species (fractions 15–21) represents the 67 kDa monomeric form of BR96 sFv-PE40 which, as expected, eluted between the 158 kDa and 44 kDa standards. These results were confirmed by reducing (FIG. 37B) and non-reducing SDS-PAGE analysis (FIG. 37C). Whereas FIG. 37B shows the purification profile based on Coomassie staining, FIG. 37C shows immunoblot analysis using anti-idiotypic BR96 antibody. The above data demonstrate that purification yielded two forms of recombinant protein, monomers and aggregates.

Direct Lewis Y Determinant Binding ELISA

Because BR96 sFv-PE40 is monovalent it provides only one antigen-binding site per molecule. In order to test the relative binding activities of monovalent BR96 sFv-PE40 compared to the bivalent BR96 antibody, a direct binding assay was performed in which purified Lewis Y was coated on ELISA plates and the recombinant BR96 sFv-PE40 molecule was compared, in its ability to bind to the antigen, with several antibodies and antibody fragments. Lewis-Y (ChemBiomed, Alberta, Canada) was diluted to 0.2 μg/ml in Coating Buffer (100 mM sodium carbonate/bicarbonate, pH 9.4) prior to coating Dynatech Immunon II plates and incubating for 16 hours at 4° C. Excess antigen was removed and the plates were blocked with PTB buffer (PBS containing 0.05% Tween 20 and 1% BSA) for 1 hour at room temperature followed by 3 washes with PTB. The antibody samples were serially diluted in PTB to a final concentration ranging from 1.25 μg/ml to 80 μg/ml and incubated overnight at 4° C. on the plate in a volume of 50 μl/well. The plates were washed 3 times with PTB buffer and each well was incubated with 100 μl/well of biotinylated BR96 anti-idiotypic antibodies (2.56 μg/ml) in PTB for 1 hour at room temperature. The plates were then washed 4 additional times with PTB. Alkaline phosphatase-conjugated streptavidin (Kirkegaard & Perry Labs, Gaithersburg, Md.) was added to each well (100 μl of 0.5 μg/ml in PBS containing 1% BSA) and incubated for 1 hour at 37° C. Plates were washed 3 times with PTB and 3 times with phosphatase buffer (75 M Tris, 0.1 M NaCl, 5 mM $MgCl_2$, pH 9.4) and reacted with p-nitrophenyl phosphate (1 mM in phosphatase buffer) for 30 to 60 minutes at 37° C. The reaction was stopped by the addition of 2 N NaOH. The plates were read at 405 nm on a Molecular Device, Inc. (Menlo Park, Calif.) microplate Reader.

Figure 38:
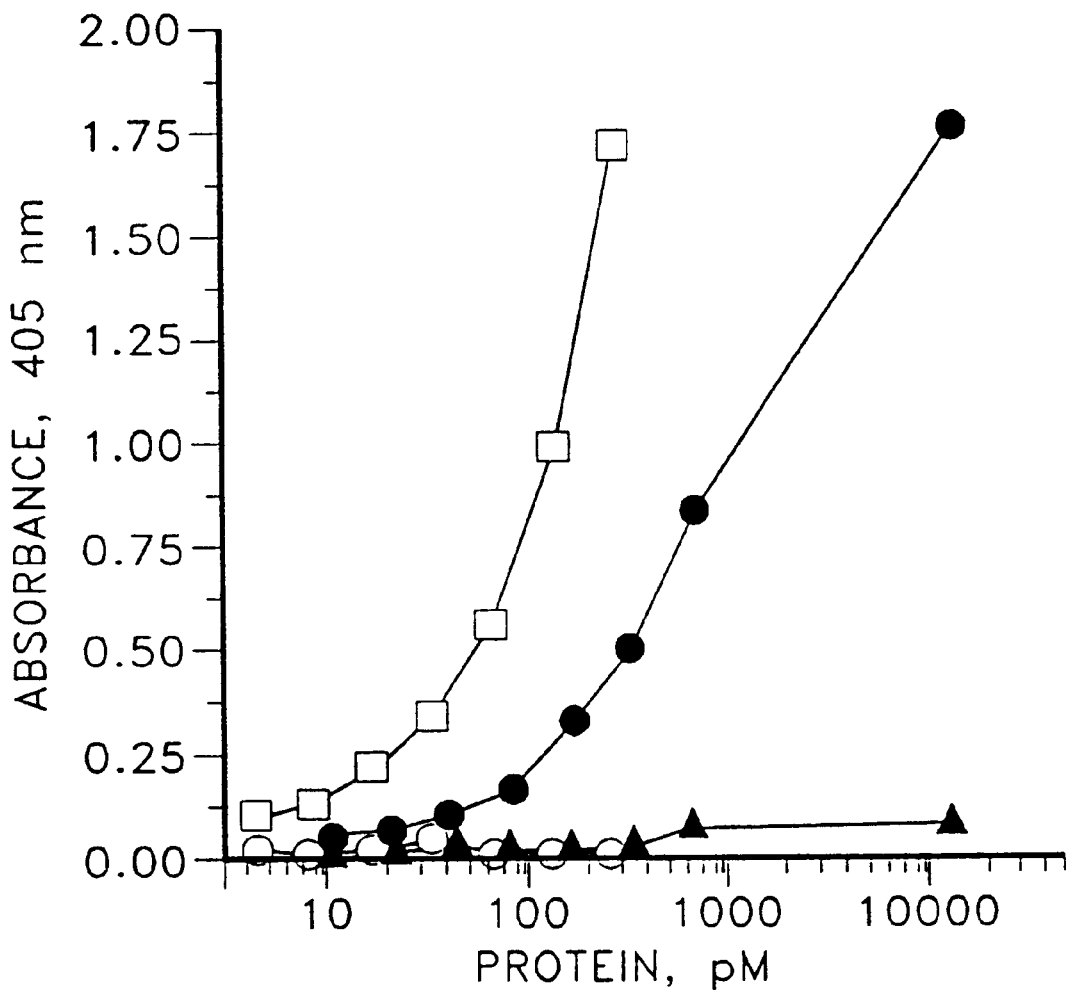
FIG. 38 is a graph depicting the results of a direct binding assay on ELISA plates coated with Lewis-Y antigen and probed with BR96 anti-idiotype antibody, and comparing the binding of BR96 IgG (open square), BR96 sFv-PE40 monomers (closed circle), BR96 sFv-PE40 aggregates (closed triangle) and L6 IgG (open circle), as described in Example 14, infra.

In comparison with BR96 IgG, monomeric BR96 sFv-PE40 bound approximately 5-fold less well (FIG. 38). In contrast, the aggregated form of BR96 sFv-PE40 was unable to bind to the Lewis-Y determinant. L6 IgG, an antibody that does not bind the BR96 antigen, was used as a negative control.

In addition, the competitive binding ability of BR96 sFv-PE40 was compared with BR96 IgG. Microtiter plates were coated with Lewis-Y antigen as described above. Antibody samples were diluted in PBS containing 1% BSA to final concentrations ranging from 1.36 μg/ml to 175 μg/ml. $^{125}$I-BR96 IgG was added to each sample (5 μCi/ml) along with antibody competitor to a final volume of 100 μl. The entire mixture of radiolabeled BR96 IgG and antibody competitor were added to the Lewis-Y coated plates and incubated for 2 hours at 37° C. The plates were washed five times with PBS containing 0.05% Tween-20 and the wells counted on a gamma counter. This assay, which also used Lewis-Y coated plates, measured the amount of bound radioiodinated BR96 IgG when compared with various amounts of BR96 sFv-PE40 or BR96 IgG.

Figure 39:
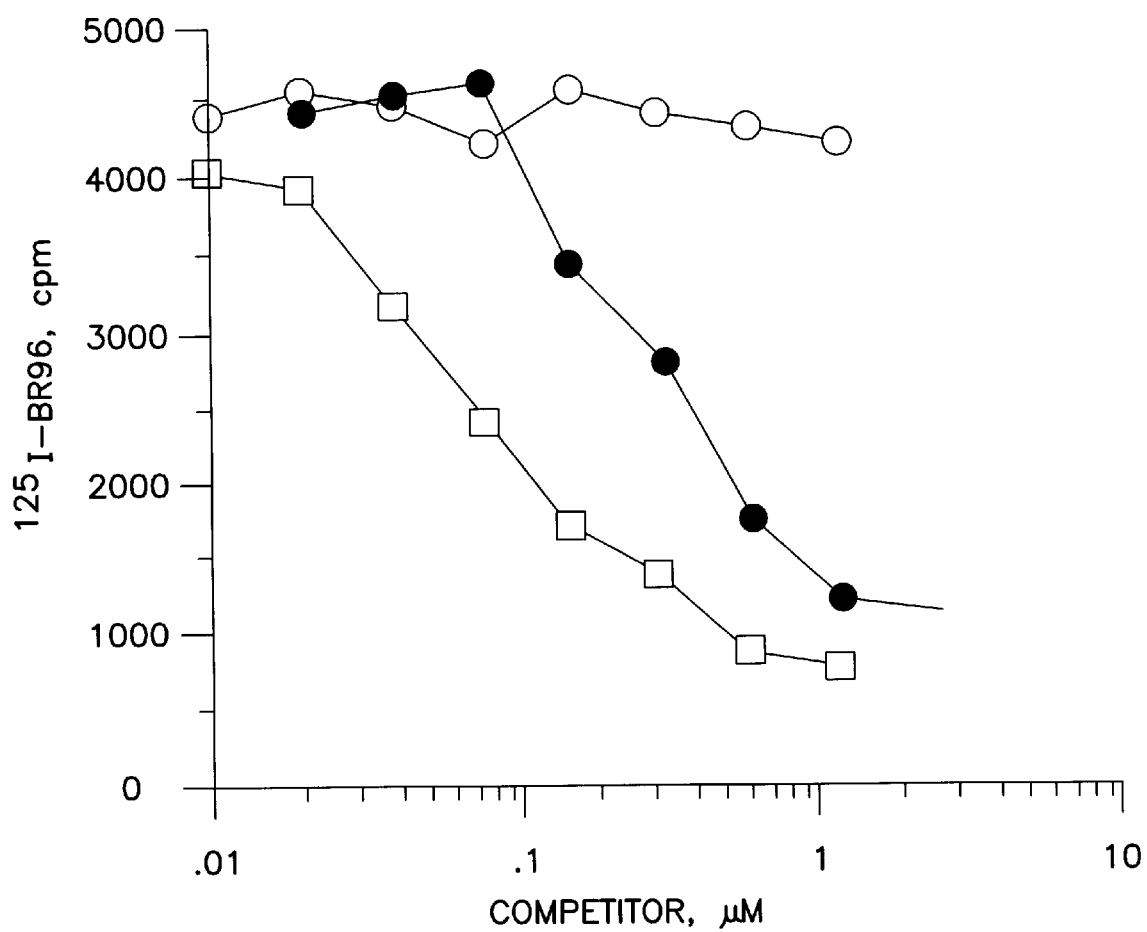
FIG. 39 is a graph showing the results of binding analysis of BR96 sFv-PE40, with competition of $^{125}$I-labeled BR96

The results of the competitive binding assay were that BR96 sFv-PE40 competed 5-fold less well than BR96 IgG (FIG. 39) which correlates with the direct binding data in FIG. 38. The addition of L6 IgG, which did not compete for binding, demonstrates the specificity of this assay.

Cytotoxicity of BR96 sFv-PE40 Against Cancer Cells

To determine the cytotoxic potential of monomeric BR96 sFv-PE40 the effect of the single-chain immunotoxin was compared to that of the chemical conjugate, ChiBR96-LysPE40 on MCF-7 breast carcinoma cells measured as inhibition of protein synthesis (FIG. 40). Determination of inhibition of protein synthesis was as follows:

All cell lines were cultured as monolayers at 37° C. in RPMI 1640 supplemented with 10% fetal bovine serum, 2 mM L-glutamine and 50 units/ml penicillin/streptomycin. Tumor cells were plated onto 96-well flat bottom tissue culture plates ($1 \times 10^4$ cells/well) and kept at 37° C. for 16 hours. Dilutions of immunotoxin were made in growth media and 0.1 ml added to each well for 20 hours at 37° C. Each dilution was done in triplicate. The cells were pulsed with [$^3$H]-leucine (1 μCi/well) for an additional 4 hours at 37° C. The cells were lysed by freeze-thawing and harvested using a Tomtec cell harvester (Orange, Conn.). Incorporation of [$^3$H]-leucine was determined by a LKB Beta-Plate liquid scintillation counter.

For competition experiments, tumor cells were prepared as described above. BR96 IgG or, as a control, L6 IgG was diluted to 100 μg/ml in growth media before addition to the cell monolayer (0.1 ml/well). After incubation at 37° C. for 1 hour, dilutions of BR96 sFv-PE40 were added, incubated an additional hour, cell supernatants were removed, and cells were washed with complete RPMI growth media. Growth media (0.2 ml) was added to each well, cells were incubated at 37° C. for 20 hours and were labelled with [$^3$H]-leucine as described above. The results indicate that the single-chain immunotoxin was 3-fold more potent than the conjugate, with $ID_{50}$ values of 4 and 12 pM, respectively.

Next, in order to correlate the cytotoxicity with the presence of the BR96 antigen, the relative antigen density was determined on five tumor cell lines by FACS analysis (FIG. 41). Assays were performed by fluorescence as described by Hellstrom et al., Cancer Res. 50: 2183–2190 (1990). Briefly, target cells were harvested in logarithmic phase with EDTA (0.02%) in calcium- and magnesium-free PBS. The cells were washed twice in PBS containing 1% BSA and resuspended to $1 \times 10^7$ cells/ml in PBS containing 1% BSA and 0.02% $NaN_3$. Cells (0.1 ml) were mixed with BR96 or a human IgG control (0.2 ml at 50 μg/ml) and incubated for 45 minutes at 4° C. The cells were washed 2 times and resuspended in 0.1 ml of an appropriate concentration of FITC labelled rabbit anti-human IgG (Cappel, Malvern, Pa.). Cells were incubated for 30 minutes at 4° C., washed 2 times in PBS containing 0.02% $NaN_3$ and analyzed on a Coulter EPICS 753 fluorescence-activated cell sorter. Data are expressed as the fluorescence intensity of cells reacted with BR96 minus cells reacted with control antibody. On a logarithmic scale, 25 units of fluorescence intensity represents a doubling of antigen density. FACS analysis of a non-specific human IgG antibody was performed for each cell line to determine non-specific fluorescence and a fluorescence intensity was calculated (Table 11).

TABLE 11

Cytotoxicity of BR96 sFv-PE40 on Various Cell Lines

| Cell Line | Cancer Type | BR96 Fluorescence Intensity | $ID_{50}$ ng/ml | (pM) |
| --- | --- | --- | --- | --- |
| MCF-7 | Breast | 177.8 | 0.3 | (4.4) |
| L2987 | Lung | 172.8 | 5.0 | (75) |
| RCA | Colon | 138.5 | 8.0 | (119) |

TABLE 11-continued

Cytotoxicity of BR96 sFv-PE40 on Various Cell Lines

| Cell Line | Cancer Type | BR96 Fluorescence Intensity | ID$_{50}$ ng/ml | (pM) |
|---|---|---|---|---|
| A2780 | Ovarian | 103.2 | 50.0 | (750) |
| KB | Epidermoid | 33.6 | 500.0 | (7,462) |

ID$_{50}$ is the amount of BR96 sFv-PE40 required to inhibit 50% of protein synthesis as determined by [$^3$H]-leucine incorporation.
BR96 Fluorescence intensity is the specific BR96 fluorescence intensity minus non-specific human IgG fluorescence.

When the cytotoxic potential of BR96 sFv-PE40 was tested on the cell lines, it was found that inhibition of protein synthesis correlated with BR96 antigen density (Table 11). For example, MCF-7 cells were the most sensitive to BR96 sFv-PE40 (ID$_{50}$ of 4.4 pM) of the cell lines tested. In contrast, KB cells which display negligible amounts of the BR96 antigen were much less sensitive to BR96 sFv-PE40 (ID$_{50}$ of 7,462 pM). The cytotoxic activity of monomeric and aggregated BR96 sFv-PE40 was also compared, and the monomer was demonstrated to be approximately 50–60 times more effective at inhibiting protein synthesis than the aggregate population with ID$_{50}$ values on L2987 cells of 75 pM and 2920 pM, respectively.

The competitive cytotoxicity experiments were conducted to confirm the specificity of the immunotoxin for its antigen binding site (FIG. 42). The cytotoxic effect of BR96 sFv-PE40 is due to specific antigen binding, because the effect is severely reduced by excess BR96 IgG, but not by L6 IgG, which does not recognize the BR96 antigen.

Comparative Blood-Level Lifetime Analysis of BR96-Immunotoxins

BR96 sFv-PE40 is approximately one-third the size of the immunotoxin conjugate, ChiBR96-LysPE40. Because protein size can affect biological kinetics, the difference in blood half-life between BR96 sFv-PE40 and ChiBR96-LysPE40 was measured. Both immunotoxins were radioiodinated and administered to athymic mice via their tail vein using the following procedures.

BR96 sFv-PE40 and ChiBR96-LysPE40 were labelled with Na $^{125}$I using Chloramine T [McConahey et al., Arch. Allergy Appl. 29: 185–188 (1966)]. Each reaction contained 100 μg of immunotoxin in PBS, 1 μCi of Na$^{125}$I, and 10 ng/ml chloramine T in a total reaction volume of 100 μl.

After a five minute incubation at room temperature, the reaction was terminated by addition of 20 ng/ml Na-metabisulfide. The free Na$^{125}$I was separated from the radiolabeled immunotoxin by gel filtration through PD-10 columns (Pharmacia). The specific activity of both immunotoxins was approximately 10 μCi/μg.

Female athymic mice (nu/nu) were purchased from Harlan Sprague Dawley (Indianapolis, Ind.) at 4–6 weeks of age. The animals were intravenously injected via the tail vein with 10 μCi of $^{125}$I-BR96 sFv-PE40 or $^{125}$I-ChiBR96-LysPE40. The animal (2–4/data point) were sacrificed at various time points and the blood was collected and counted in a gamma counter. The percent (%) ID for the blood was determined as (CPM detected/CPM injected)×100. ID/ml was calculated assuming a 1.6 ml total blood volume. Results are shown in Table 12.

TABLE 12

Single-Chain Immunotoxin vs. Chemical Conjugate Immunotoxin Comparative Blood Level Analysis

| Time | BR96 sFv-PE40 % ID/ml Blood | ChiBR96-LysPE40 % ID/ml Blood |
|---|---|---|
| 5 minutes | 49.8 | 57.5 |
| 15 minutes | 43.3 | 54.8 |
| 30 minutes | 28.2 | 46.3 |
| 60 minutes | 15.5 | 41.5 |
| 2 hours | 8.6 | 23.4 |
| 4 hours | 5.2 | 22.0 |
| 6 hours | 2.5 | 20.5 |
| 24 hours | 0.2 | 7.2 |
| 48 hours | 0.1 | 3.6 |

BR96 sFv-PE40 clears from the blood faster than ChiBR96-LysPE40. The estimated half-life in the blood for the single-chain immunotoxin is approximately 30 minutes as compared to almost 2 hours for the chimeric BR96 immunotoxin conjugate. In this experiment, the measurement of $^{125}$I-labelled BR96 immunotoxin in the blood determined how much of the molecule was present.

In order to measure the amount of detectable single-chain immunotoxin that was biologically active, the blood was assayed for BR96 sFv-PE40 directed cytotoxic activity at the various times indicated in Table 12.

The results in this Example provide an expression plasmid for the production of a single-chain immunotoxin composed of the carcinoma-reactive antibody of the invention, BR96 and a truncated form of Pseudomonas exotoxin. The chimeric molecule, BR96 sFv-PE40, purified from E. coli exists in both a monomeric and an aggregated form. The specificity of the monomeric BR96 sFv-PE40 for its antigen was confirmed through a competition analysis with BR96 IgG. The FACS analysis of five different cell lines demonstrates the distribution of the BR96 antigen, and the cytotoxic potential of BR96 sFv-PE40 was correlated with the relative number of antigen expressed on the surface of the target cells. BR96 sFv-PE40 is extremely potent against cancer cells displaying the BR96 antigen, with MCF-7 cells being the most sensitive cell line examined. BR96 sFv-PE40 was shown to be more potent than the BR96 IgG chemical conjugate against the tumor cell lines tested. To assess the potential anti-tumor activity of BR96 sFv-PE40, the chimeric toxin was intravenously administered to mice and found to have a serum half-life of 30 minutes, as compared to that of ChiBR96-LysPE40, which was almost 2 hours. It may be an advantage that the single-chain immunotoxin is cleared so rapidly from the blood. The immunotoxin molecules are stable and retain biological activity following administration into animals.

EXAMPLE 15

In Vivo Effects of BR96 sFv-PE40

Anti-tumor Activity of BR96 sFv-PE40 Against Human Tumor Xenographs

L2987 and MCF-7 tumor fragments were implanted into female athymic mice (nu/nu) (Harlan Sprague Dawley, Indianapolis, Ind.) at 4–6 weeks of age. They were implanted with L2987 and MCF-7 tumor fragments from established tumor xenografts that were approximately 4 weeks old (800 cu mm). Tumor sections were implanted subcutaneously using a trocar onto the back hind quarter of the mice. Two weeks after implantation the animals were randomized and their tumors measured.

For the anti-tumor experiments, we only used animals that had tumors ranging from 50–100 cubic mm in size. The animals were intravenously injected via the tail vein with the BR96 sFv-PE40 immunotoxin according to the administration schedule indicated in FIGS. 43 and 44. Each treatment group consisted of five to ten animals.

Regression of MCF-7 breast carcinoma xenografts was observed with doses up to 0.75 mg/kg using administration schedules of Q4DX3 (FIG. 43). Using an administration schedule of Q2DX5, the L2987 lung tumors were observed to regress upon treatment with BR96 sFv-PE40 (FIG. 44). Complete regression of the tumor xenografts was observed at doses ranging from 0.375 mg/kg to 0.125 mg/kg.

The effect of the tumor xenografts was dose-dependent, as at lower doses the tumors were able to grow back after being regressed for a seven day period while at higher doses the complete regression lasted for over twenty days.

In untreated animals, the tumors grew rapidly and the animals were sacrificed approximately 30 days post implantation. No apparent toxicity was observed at the doses used in this experiment.

The tumor xenografts used in this study emanated from a small piece of a solid tumor excised from another animal. The tumor tissue was subcutaneously implanted and allowed to vascularize and grow before treatment was initiated. In this manner, the data presented herein demonstrate a tumor model of tumors found in humans.

EXAMPLE 16

Materials and Methods

Animals

Athymic mice and athymic Rowett rats (Harlan Sprague Dawley) were used in this study.

The binding of BR96 to normal rat tissues was similar to BR96 binding to normal human tissues, i.e., BR96 bound to cells in the esophagus, stomach, intestine and acinar cells of pancreas.

In contrast to rats, normal tissues from athymic mice did not bind BR96.

BR96-DOX

The conjugates were prepared by linking the DOX derivative maleimidocaproyl doxorubicin hydrazone to BR96 or control immunoglobulin (FIG. 45). For more detail, see Examples 20, 22 and 26.

Implanted Carcinoma Cells

L2987 lung carcinoma cells were selected in vitro for the ability to grow as multicellular spheroids. When injected IV into athymic mice or rats, tumors developed at various sites, including lymph nodes, lung, spleen, liver, brain, subcutaneously, and ascites was formed in some animals.

Athymic rats were transplanted subcutaneously with human lung adenocarcinoma L2987, colon carcinoma RCA, or breast carcinoma MCF7 and permitted to grow. Therapy (3 treatments 4 days apart) started 14 to 28 days after tumor transplantation when tumors were well established, i.e. when the tumors were 50 to 100 mm³ in size.

Administration of BR96 Into The Animals

Mice and rats were administed with BR96-DOX by three injections, each injection being about four days apart. Mice which were injected intraperitoneally (IP) were given 20 mg/kg of BR96-DOX. Mice which were injected intravenously were given 10 mg/kg of BR96. Intravenous (IV) injection involved less volume of BR96 because of the constraints of injection volume, namely, only 10 mg/kg was administrable by IV.

At the doses tested, there was no difference in the anti-tumor activity of BR96-DOX whether administered IP or IV.

Controls

One set of controls included untreated mice and mice that received (1) DOX (at doses optimized to produce maximal antitumor activity in each model); (2) unconjugated BR96; (3) mixtures of BR96 and DOX; and (4) DOX conjugated to either normal human IgG or the control MAb SN7. Doses of DOX and MAb are presented as mg/kg/infection.

Another set included rats using the protocol used in control mice.

Results of Treatment of Mice

Treatment with BR96-DOX consistently cured most mice bearing L2987 (FIG. 46A) or RCA (FIG. 46B) tumors. Further, mice treated with BR96-DOX exhibited complete and partial tumor regressions against MCF7 tumors (FIG. 46C). Complete tumor regression (CR) refers to a tumor that for a period of time is not palpable. Partial tumor regression (PR) means a decrease in tumor volume to $\leq 50\%$ of the initial tumor volume. Specifically, BR96-DOX cured 78% of the treated mice. In contrast, DOX alone was not active against established RCA tumors either in terms of tumor growth delay or regressions.

The MTD of free DOX (4 mg/kg administered as 3 injections 4 days apart) resulted in a delay in tumor growth and 25% cures. However, BR96-DOX given at a matching DOX dose (4 mg/kg DOX, 140 mg/kg BR96) cured 100% of the animals.

Figure 46A:
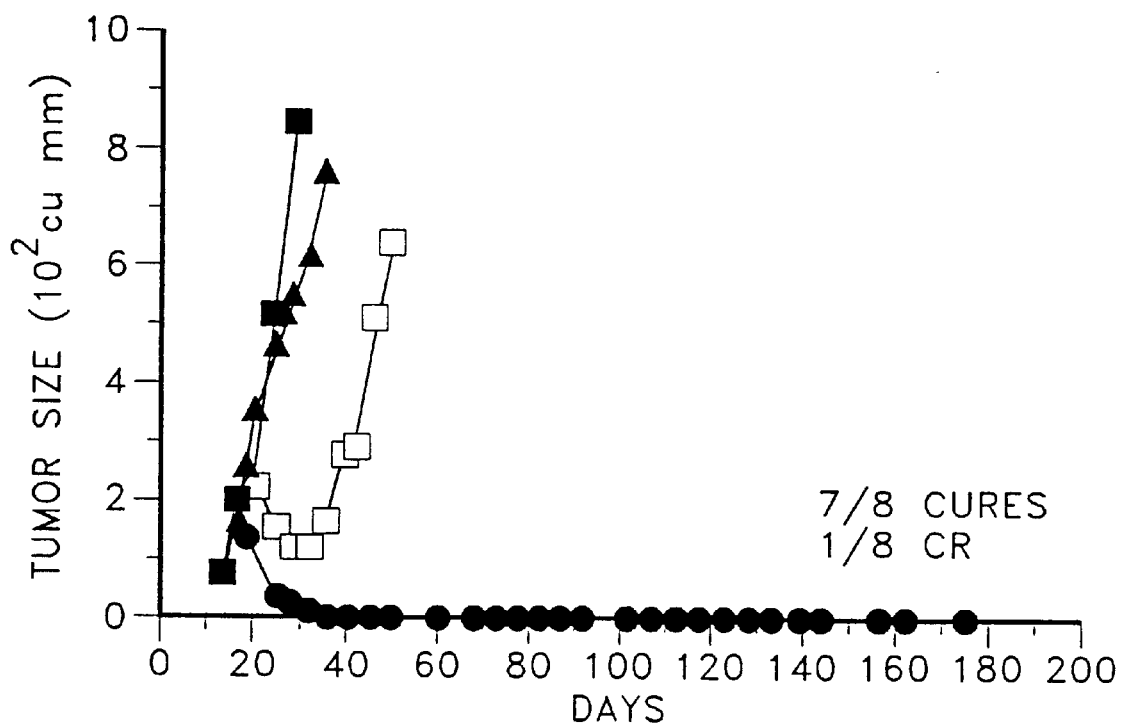
Figure 46B:
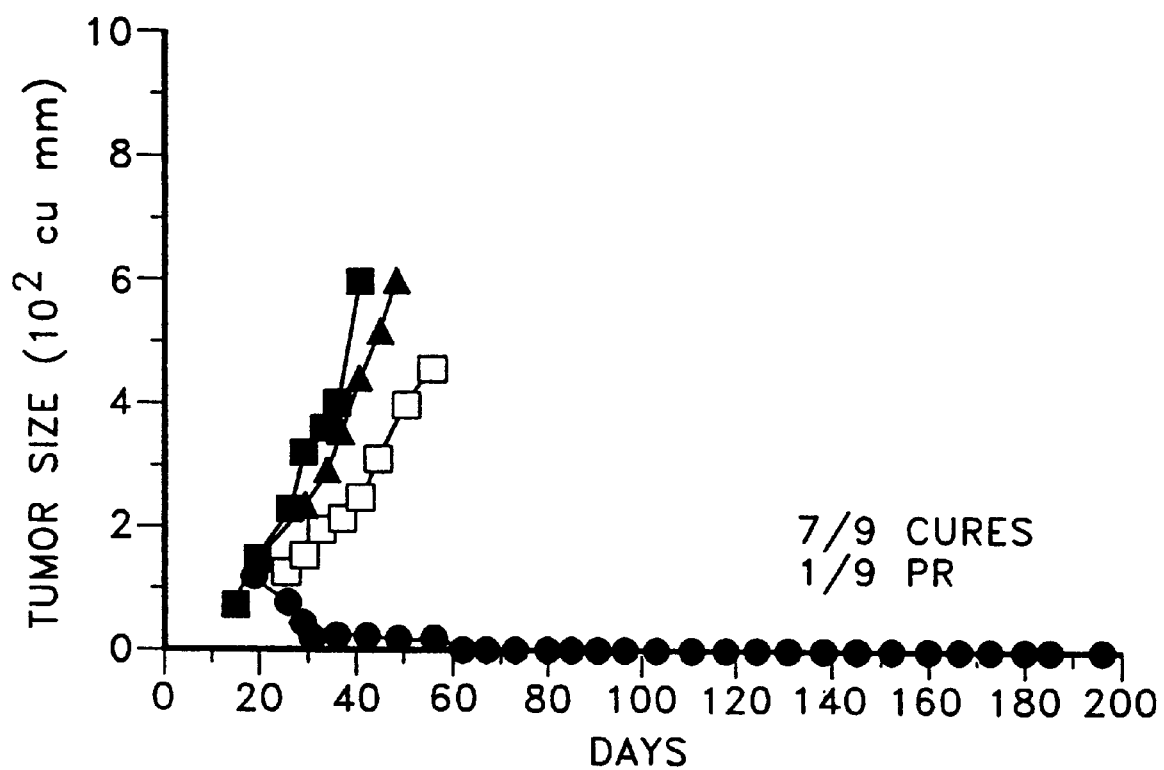
Figure 46C:
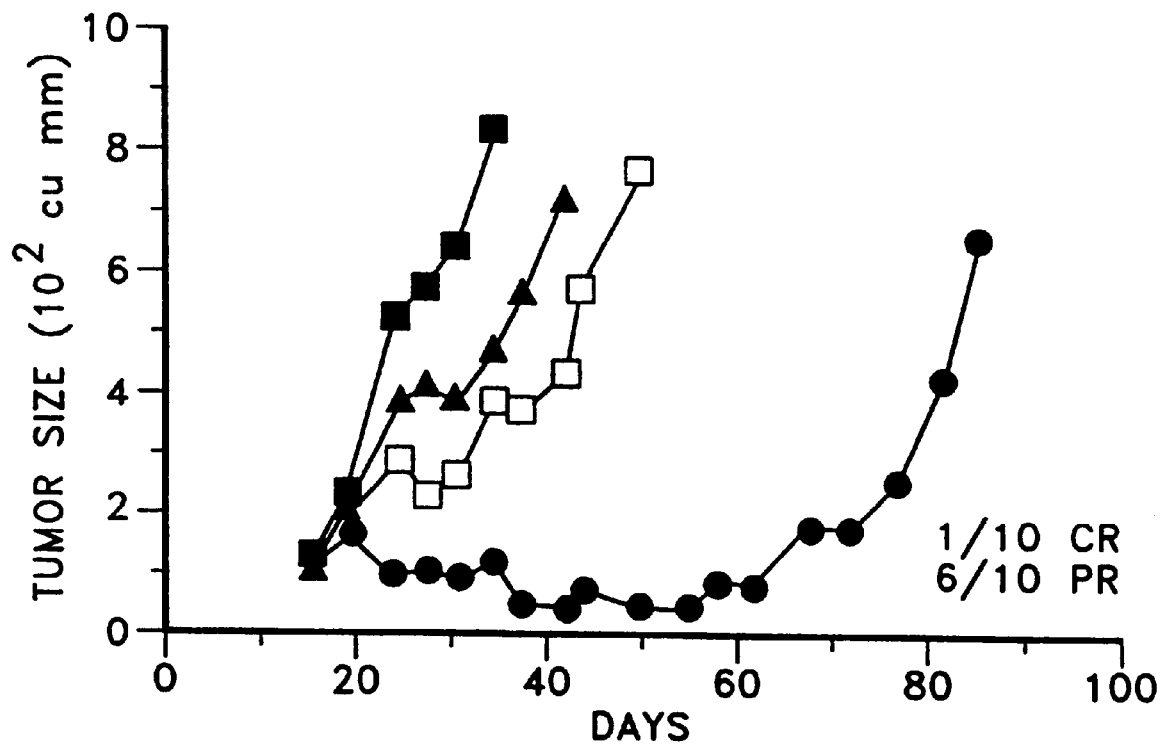

FIGS. 46A–D are line graphs showing the antigen-specific anti-tumor activity of BR96-DOX. FIG. 46A shows mice transplanted with L2987 lung tumor xenografts which have grown to about 50 to 100 mm³ at the initiation of therapy. Treatment with BR96-DOX consistently cured most mice bearing L2987 (FIG. 46A).

FIG. 46B shows mice transplanted with colon carcinoma RCA which have grown to tumor xenografts of about 50 to 100 mm³ at the initiation of therapy. Treatment with BR96-DOX consistently cured most mice bearing colon carcinoma RCA (FIG. 46B).

FIG. 46C shows the efficacy of BR96-DOX in mice transplanted with MCF7 tumors. These mice treated with BR96-DOX consistently exhibited complete and partial tumor regressions against MCF7 tumors (FIG. 46C).

Equivalent doses of non-binding IgG-DOX or SN7-DOX had no effect against these tumors. Although optimal doses of DOX delayed the growth of small L2987 tumors (50 to 100 mm³) and MCF7 tumors; regressions or cures were not observed.

Figure 46D:
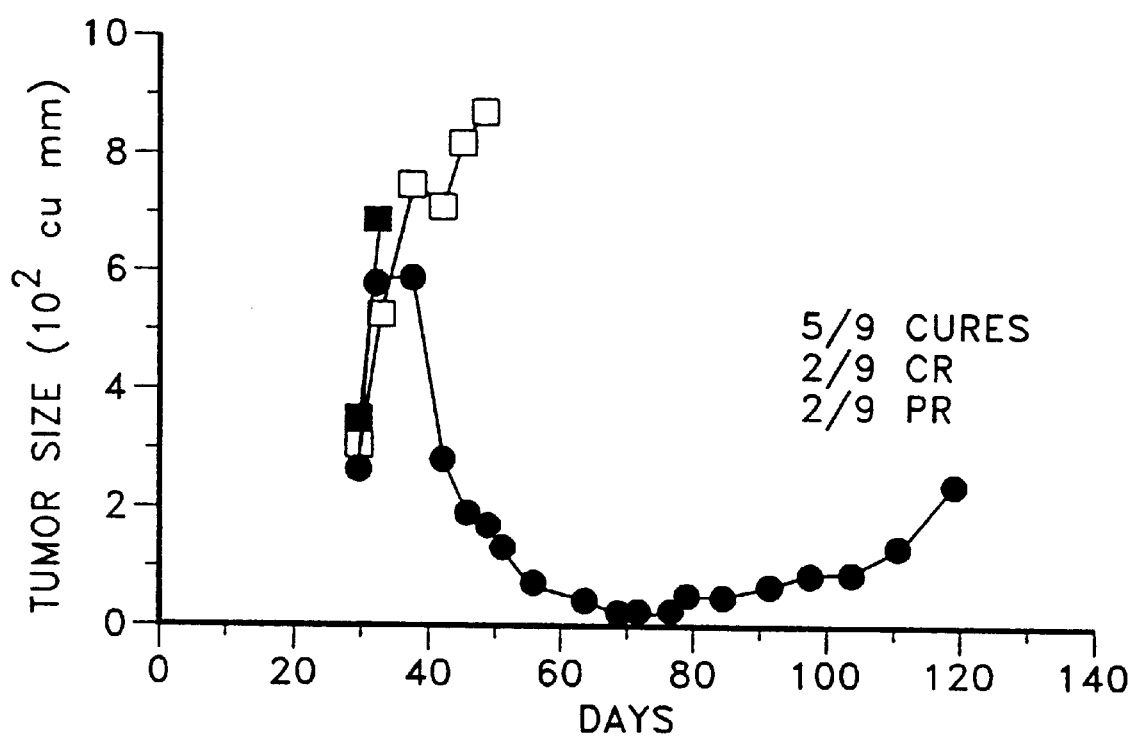

FIG. 46D shows mice transplanted with L2987 lung tumor xenografts which grew to about 250 to 800 mm³ at the initiation of therapy. Such mice which were treated with BR96-DOX also exhibited 56% cures, 22% complete and 22% partial regressions of lung tumors. In contrast, antitumor activity was not observed after treatment with an optimal dose of DOX.

FIG. 47 shows that BR96 is efficacious in curing athymic mice having large disseminated tumors.

Mice were inoculated IV with L2987 spheroids. Approximately twelve weeks later mice (14 mice/group) were selected for treatment with BR96 (8 mg/kg equivalent DOX administered as 3 injections 4 days apart) or DOX on the basis of visible tumor burden, i.e. therapy was delayed until mice displayed extensive disseminated disease, $\geq 0.5$ g of visible tumor burden.

The burden of disseminated disease in these animals was so far advanced that 50% of control animals died during the first 6 days of the experiment. The median survival time (MST) of the control group was 90 days and 100% of the mice were dead by day 102. Surviving mice were sacrificed 200 days after cell inoculation and sections of lung, lymph nodes, spleen, colon, jejunum, kidney, liver, brain, and heart were examined by histology.

Mice cured of L2987 or RCA tumors remained alive and tumor free for more than 1 year with no indication of side effects.

TABLE 13

Antitumor activity of BR96-DOX against established human tumor xenografts

| Treatment | Schedule | Dose (mg/kg/injection) | | | PERCENT TUMOR REGRESSIONS* | | | No. |
|---|---|---|---|---|---|---|---|---|
| | | DOX | MAb BR96* | Tumor | Cures | Complete | Partial | MICE |
| | | | | L2987 | | | | |
| BR96-DOX | q4d × 3+ | 20.0 | 689 | | 100 | 0 | 0 | 8 |
| | | 15.0 | 711 ± 36 | | 83.0 ± 0.8 | 3.3 ± 0.9 | 7.0 ± 0.9 | 29 |
| | | 10.0 | 513 ± 12 | | 83.0 ± 1.1 | 8.0 ± 0.7 | 2.0 ± 0.4 | 100 |
| | | 8.0 | 317 ± 3 | | 88.5 ± 0.1 | 3.7 ± 1.0 | 0 | 27 |
| | | 5.0 | 246 ± 5 | | 72.3 ± 2.2 | 17.9 ± 1.5 | 5.6 ± 0.7 | 117 |
| | | 2.5 | 109 ± 3 | | 30.4 ± 3.4 | 33.7 ± 2.4 | 21.3 ± 2.6 | 62 |
| | | 1.25 | 49 ± 1 | | 6.9 ± 0.9 | 11.6 ± 1.2 | 11.9 ± 2.1 | 44 |
| BR96-DOX | q1d × 1" | 30.0 | 1078 | | 50.0 | 50.0 | 0 | 10 |
| | | 25.0 | 930 | | 30.0 | 30.0 | 40.0 | 10 |
| | | 20.0 | 735 | | 60.0 | 20.0 | 10.0 | 10 |
| | | 15.0 | 540 | | 11.0 | 22.0 | 44.0 | 9 |
| IgG-DOX | q4d × 3 | 10.0 | 403 ± 5.2 | | 0 | 0 | 0 | 19 |
| | | 5.0 | 202 ± 3.2 | | 0 | 0 | 3.7 ± 1.0 | 27 |
| DOX | q4d × 3 | 8.0 | — | | 0 | 0 | 0.8 ± 0.8 | 125 |
| MAb BR96 | q4d × 3 | — | 400 | | 0 | 0 | 0 | 8 |
| | | — | 200 | | 0 | 0 | 0 | 8 |
| | | — | 100 | | 0 | 0 | 0 | 8 |
| BR96 + DOX | q4d × 3 | 8.0 | 400 | | 0 | 0 | 0 | 9 |
| | | 8.0 | 200 | | 0 | 0 | 0 | 9 |
| | | 8.0 | 100 | | 0 | 0 | 0 | 9 |
| | | | | RCA | | | | |
| BR96-DOX | q4d × 3 | 20.0 | 903 | | 100 | 0 | 0 | 10 |
| | | 15.0 | 625 | | 80.0 | 10.0 | 10.0 | 10 |
| | | 10.0 | 376 ± 5.4 | | 71.7 ± 0.9 | 0 | 10.7 ± 0.1 | 28 |
| | | 5.0 | 176 | | 11.0 | 22.0 | 11.0 | 9 |
| | | 2.5 | 90 | | 0 | 0 | 5.5 ± 1.3 | 18 |
| BR96-DOX | q7d × 3@ | 20.0 | 900 | | 100 | 0 | 0 | 10 |
| | | 15.0 | 625 | | 100 | 0 | 0 | 10 |
| | | 10.0 | 420 | | 80 | 10 | 0 | 10 |
| | | 5.0 | 210 | | 10 | 0 | 10 | 10 |
| IgG-DOX | q4d × 3 | 10.0 | 405 | | 0 | 0 | 0 | 10 |
| DOX | q4d × 3 | 8.0 | — | | 0 | 0 | 0 | 29 |
| DOX | q7d × 3 | 10.0 | — | | 0 | 0 | 0 | 10 |

*Mean ± SEM
+3 injections administered with a 4 day interval
"single injection
@3 injections administered with a 7 day interval Mice inoculated with L2987 spheroids and treated had an increased MST (MST of >200 days) relative to that of control mice (MST of 85 days) or mice treated with an optimal dose of DOX (MST of 140 days).

According to immunohistology, the degree of binding of BR96 to cells from these carcinoma lines was similar to that of biopsy material from human carcinomas of the same respective types (21).

Table 13 summarizes the tumor regression rates following treatment with various doses of (1) BR96-DOX, (2) DOX, and (3) mixtures of MAb and DOX against established L2987 and RCA tumor xenografts in mice.

BR96-DOX administered at equivalent DOX doses of ≧5 mg/kg (3 injections 4 days apart) produced long-term cures in 72 to 100% of mice (n=291) bearing L2987 tumors.

In the RCA colon tumor model, which was not sensitive to unconjugated DOX, BR96-DOX administered at equivalent DOX doses of ≧10 mg/kg (3 injections 4 days apart) cured 72 to 100% of mice (n=48).

BR96 administered at equivalent doses was not active against established tumors (either in terms of tumor growth delay or regressions) and the tumor growth delay produced by mixtures of BR96 and DOX was equivalent to that of DOX administered alone.

Contrary to our expectations, cells lacking BR96 expression were not detected after treatment with BR96-DOX. Also, cells obtained from tumors that grew back after BR96-DOX induced regression were as sensitive in vitro to DOX as the parental cell line.

The $IC_{50}$ (concentration required to produce 50% inhibition of $^3[H]$-thymidine incorporation) was 0.4±0.1 $\mu$M and 0.3±0.2 $\mu$M DOX for treatment and parental, respectively. These cells were also as sensitive to BR96-DOX as the parental cell line with $IC_{50}$ values of 2.7±0.5 $\mu$M and 2.6±0.8 $\mu$M equivalent DOX for parental and treated, respectively.

These data suggest that it may be possible to successfully retreat tumors with several rounds of BR96-DOX therapy.

The maximum tolerated dose (MTD) (equivalent DOX dose) of the BR96-DOX conjugate (administered as 3 injections 4 days apart) was 20 mg/kg administered intraperitoneally (IP). When administered intravenously (IV) the MTD was ≧10 mg/kg. This was the maximum dose that could be administered IV because of the constraints of injection volume.

At the doses tested, there was no difference in the antitumor activity of BR96-DOX whether administered IP or IV. At doses of BR96-DOX (Table 1) equivalent to ≧mg/kg of DOX (≧250 mg/kg BR96) more than 70% of treated animals were cured of established L2987 tumors.

In fact, the BR96-DOX (Table 13) equivalent to ≧5 mg/kg of DOX (>250 mg/kg BR96) more than 70% of treated animals were cured of established L2987 tumors. The BR96-DOX conjugate was active at doses as low as 1 mg/kg equivalent DOX. Therefore, the BR96-DOX conjugate was active at a dose equivalent to 1/20th of its MTD.

These data demonstrate the broad range of therapeutic doses which were achieved with BR96-DOX. The MTD of unconjugated DOX (8 mg/kg IV and 4 mg/kg IP) was lower than that of the BR96-DOX conjugate. Unconjugated DOX administered IV at the MTD produced a delay in tumor growth but no tumor regressions and if the dose was reduced to 50% of the MTD, DOX had no effect.

In contrast, activity equivalent to that of an optimal dose of DOX (8 mg/kg) was achieved at a dose of 1 mg/kg of BR96-DOX. The BR96-DOX conjugate produced antitumor activity comparable to that of an optimal dose of unconjugated DOX at 1/8th of the equivalent DOX dose. In summary, the BR96-DOX conjugate was more active, had a much broader range of therapeutic doses, and was more potent than unconjugated DOX.

Seven of the 8 surviving mice were free of detectable tumor (70% cures by combined life span and histologic examination).

The BR96-DOX conjugate demonstrated strong antitumor activity in all preclinical models evaluated. The efficacy and potency of BR96-DOX conjugates is likely due to several factors. The antigen to which BR96 binds is abundantly expressed at the tumor cell surface and active drug is released following antigen-specific binding and internalization of the conjugate into the acidic environment of lysosomes/endosomes.

Acid-labile immunoconjugates, in which a less stable disulfide linker was used, have been investigated previously (7,26). Although these conjugates were active in an antigen-specific manner, they had poor potency in vivo (7). The use of a more stable thioether linker, and a MAb with higher avidity and more rapid rates of internalization, improved the activity and potency of BR96-DOX conjugates and also increased the range of therapeutic doses.

We showed that administration of BR96-DOX conjugate at cumulative doses of at least 15 mg/kg DOX and 700 mg/kg MAb (equivalent to 45 mg/m² DOX and 2100 mg/m² MAb) resulted in greater than 70% cures of established lung tumors. This dose of MAb in mice is approximately equivalent to a cumulative dose of 3 g of MAb per patient and is only slightly higher than that required to achieve saturation of human carcinomas in patients given L6, another anticarcinoma MAb (G. Goodman, et al., *J. Clin. Oncol.*, 8, 1083 (1990)).

It would be clear to those skilled in the art that the optimal schedule for administering BR96-DOX will vary based upon the subject, the subject's height and weight, the severity of the disease.

The demonstration of tumor cures in animals in which BR96 binds to normal tissues highlights the fact that the appropriate combination of MAb, drug, and linker chemistry are critical aspects to successful antibody-directed therapy. The toxic effects of DOX are dose related and it is likely that increasing the intra-tumoral concentration of DOX will produce a significant increase in antitumor activity (S. K. Carter, *J. Natl. Cancer Inst.*, 55, 1265 (1975); R. C. Young, R. F. Ozols, C. E. Myers, *N. Eng. J. Med.*, 305, 139 (1981)).

BR96-DOX induced complete regressions and cures of xenografted human lung, breast and colon carcinomas growing subcutaneously in athymic mice and cured 70% of mice bearing extensive metastases of a human lung carcinoma.

Results of Treatment with Rats

The MTD of free DOX (4 mg/kg administered as 3 injections 4 days apart) resulted in a delay in tumor growth and 25% cures.

The MTD of free DOX (4 mg/kg administered as 3 injections 4 days apart) resulted in a delay in tumor growth and 25% cures. However, BR96-DOX given at a matching DOX dose (4 mg/kg DOX, 140 mg/kg BR96) cured 100% of the animals, and a dose equivalent to 2 mg/kg DOX (70 mg/kg BR96) cured 88% of the rats.

BR96-DOX given at a matching DOX dose (4 mg/kg DOX, 140 mg/kg BR96) cured 100% of the animals, and a dose equivalent to 2 mg/kg GOX (70 mg/kg BR96) cured 88% of the rats. Of the rats treated with BR96-DOX, 94% (15/16) remained alive and tumor free with no evidence of toxicity 150 days after the last dose of BR96-DOX.

It is surprising that BR96-DOX also cured 94% of athymic rats with subcutaneous human lung carcinoma, even though the rats, like humans, in contrast to mice, express the BR96 target antigen in some normal tissues.

The BR96-DOX conjugate demonstrated antigen-specific activity in vitro and was 8 to 25 fold more potent than non-binding (IgG-DOX or SN7-DOX) conjugates against carcinoma lines that expressed the BR96 antigen. BR96-DOX was much less active against cells that did not bind BR96.

Optimal doses of DOX 8 mg/kg) had no effect on the large disseminated tumors; the MST was 94 days and 100% of the mice were dead by day 140. In contrast, mice treated with BR96-DOX (8 mg/kg) had a MST of ≧200 days and 8 of the 10 animals survived for the duration of the experiment.

EXAMPLE 17

Conjugate of SPDP Thiolated Monoclonal Antibody BR64 with the Maleimidocaproylhydrazone of Adriamycin A solution of the BR64 antibody (25 mL, 10.37 mg/mL; determined by UV at 280 nm, 1.4 absorbance units equal 1 mg protein) was treated with SPDP solution in absolute ethanol (1.3 mL of 10 mmol solution). The solution was incubated for 1 hour at 31°–32° C., then chilled in ice and treated with a solution of DTT in phosphate buffered saline ("PBS") (1.3 mL of a 50 mmol solution). The solution was kept in ice for 1 hour then transferred to a dialysis tube and dialyzed three times against PBS (2 L per dialysis) for a period of at least 8 hours. After the dialysis, the concentration of protein was measured, as above, followed by a determination of molar concentration of free sulfhydryl groups by the Ellman method.

The thiolated protein (3 mL) was treated with an equivalent thiol molar amount of maleimidocaproylhydrazone of adriamycin, prepared as in Preparation 2, dissolved in dimethylformamide (DMF) (5 mg/mL, 0.131 mL) and the mixture was incubated at 4° C. for 24 hours. The solution was dialyzed three times against PBS (1000 mL) for a period of at least 8 hours. The solution was centrifuged and the supernatant was shaken for a few hours with Bio-beads™ SM-2 (non-polar neutral macroporous polystyrene polymer beads, Bio-Rad Laboratories, Richmond, Calif. 94804) and finally filtered through a Millex-GV (Millipore Corporation, Bedford, Mass. 01730) 0.22 µm filter unit. The overall average number of molecules of adriamycin per molecule of antibody ("MR") was determined by measuring the amount of adriamycin from the absorption at 495 nm ($\epsilon$=8030 cm$^{-1}$M$^{-1}$) and the amount of protein from the absorption at 280 nm, after correcting for the absorption of adriamycin at 280 nm according to the formula:

$$\text{Antibody (mg/mL)} = \frac{A_{280} - (0.724 \times A_{495})}{1.4}$$

The MR found for the product was 5.38; free adriamycin 0.14%; protein yield 60%.

EXAMPLE 18

Conjugate of SPDP Thiolated BR64 with the Maleimidocaproylhydrazone of Adriamycin A solution of the BR64 antibody (405 mL, 11.29 mg/mL) was stirred and treated with SPDP solution in absolute ethanol (22.3 mL of 10 mmol solution). The solution was incubated for 1 hour at 31°–32° C. while being gently shaken, then cooled in ice to 4° C., stirred and treated with a solution of DTT in PBS (22.3 mL of a 50 mmol solution). The solution was kept in ice for 1 hour then divided into 2 equal parts, each transferred to a dialysis tube and dialyzed six times against PBS (6 L per dialysis) for a period of at least 8 hours. After that the contents of the tubes were combined (400 mL) and the concentration of protein and free thiol groups was determined (molar ratio of —SH groups to protein is 8.5).

The solution of thiolated protein was stirred and treated with an equivalent thiol molar amount of maleimidocaproyl hydrazone of adriamycin dissolved in DMF (5 mg/mL, 35.7 mL) and the mixture was incubated at 4° C. for 24 hours. The solution was divided into 2 equal parts, transferred to dialysis tubes and dialyzed five times against PBS (6 L per dialysis) for a period of at least 8 hours. The contents of the dialysis tubes were combined, filtered through a 0.22µ cellulose acetate filter, and the filtrate was shaken for 24 hours with Bio-beads™ SM-2 (Bio-Rad Laboratories, Richmond, Calif. 94804). The solution was filtered through a 0.22µ cellulose acetate filter. The concentration of protein and adriamycin was determined (6.26 mg/mL and 162.4 µg/mL, respectively) yielding a molar ratio (MR) of 7.18. The protein yield was 77%. Unconjugated adriamycin present was 0.07%.

EXAMPLE 19

Conjugate of SPDP Thiolated SN7 with the Maleimidocaproylhydrazone of Adriamycin In a manner analogous to that described in Examples 17 and 18 monoclonal antibody SN7, an antibody which does not bind to the antigen recognized by BR64, was thiolated with SPDP and reacted with the maleimidocaproyl hydrazone of adriamycin to yield a conjugate with a molar ratio (MR) of 4. Protein yield was 51%. Unconjugated adriamycin present was 0.36%.

EXAMPLE 20

Conjugate of SPDP Thiolated ChiBR96 with the Maleimidocaproylydrazone of Adriamycin A solution of chimeric BR96 antibody, ChiBR96, (27.5 mL, 12.53 mg/mL) was treated with a 10 mM solution of SPDP in absolute ethanol (1.7 mL). The solution was incubated at 31° C. for 35 minutes, chilled in ice and treated with a 0.50 mM solution of DTT in PBS (1.7 mL) for 15 min at 4° C. The solution was transferred to a dialysis tube and dialyzed four times in PBS-0.1 M histidine buffer (4.5 L per dialysis) for a period of at least 8 hours. The amount of protein and molar concentration of thiol groups was determined (9.29 mg/mL and 2.06×10$^{-4}$ M, respectively). The solution (17 mL) was treated with an equivalent molar amount of the maleimidocaproylhydrazone of adriamycin in DMF (5 mg/mL, 0.59 mL) and the reaction mixture incubated at 4° C. for 24 hours. The reaction mixture was dialyzed three times, in the same buffer (4.5 L per dialysis), for at least 8 hours. The dialyzed solution was centrifuged and the supernatant shaken gently with Biobeads™ SM-2 (Bio-Rad Laboratories, Richmond, Calif. 94804) for a few hours at 4° C. The solution was centrifuged and the concentration of protein and adriamycin in the supernatant (19 mL) was determined (6.5 mg/mL and 67.86 µg/mL, respectively). The molar ratio of drug to protein is 2.9. Protein yield is 72% ; unconjugated adriamycin present is 1.2%.

EXAMPLE 21

Conjugate of Modified Bombesin with the Maleimidocaproylhydrazone of Adriamycin

Bombesin does not contain a free reactive sulfhydryl group which can be used to link the drug through the Michael Addition Receptor-containing linker. Thus, there was prepared a modified bombesin which contains an additional cysteine residue at the amino terminus of native bombesin. In addition, residue-3 of the native bombesin has been changed to a lysine residue. The modified bombesin, therefore, is designated "Cys$^0$-lys$^3$-bombesin".

Cys$^0$-lys$^3$-bombesin (11.3 mg) was dissolved in 1.1 mL of deionized water and adjusted to pH 7–7.5 with 10 µl 1.5 M Tris-HCl, pH 8.8 and then reacted with 0.45 mL maleimidocaproyl adriamycin hydrazone (15 mg/mL in deionized water) at ambient temperature for several hours. The reaction mixture was dialyzed against water overnight in dialysis tubing (molecular weight cutoff: 1000). The precipitate was removed by centrifugation (12,000× g) and the supernatant was saved. Adriamycin ("ADM") content of the bombesin-adriamycin conjugate was measured by diluting 1:50 in acetate buffer, pH 6.0. The adriamycin ("ADM") content was calculated using the formula:

$$[O.D._{495}/8030] \times 50 = ADM \text{ (M)}$$

For this preparation O.D.$_{495}$=0.116 thus the adriamycin content was 7.2×10$^{-4}$ M.

The product was chromatographed by HPLC using a C$_{18}$ (Beckman Instruments, Ultrasphere 5µ, 4.6 mm×25 cm) column. Buffer A: 10 mM NH$_4$OAc pH, 4.5; Buffer B: 90% acetronitrile/10% Buffer A. The column was equilibrated with 90% Buffer A/10% Buffer B and the chromatography conditions were: 90% buffer A/10% buffer B to 60% Buffer A/60% buffer B for 2 minutes, gradient to 50% buffer A/50% buffer B for 15 minutes. The product had a retention time of 9.3 minutes under these conditions.

EXAMPLE 22

A Conjugate of Iminothiolane Thiolated Chimeric BR96 and Maleimidocaproyl Hydrazone of Adriamycin Chimeric BR96 (15 mL, 9.05 mg/mL) was dialysed two times against 4 liters of 0.1 M sodium carbonate/bicarbonate buffer, pH 9.1. The antibody solution then was heated with iminothiolane (0.75 mL, 20 mM) at 32° C. for 45 minutes. The solution was then dialysed against 4 liters of sodium carbonate/bicarbonate buffer, pH 9.1 followed by dialysis against 4 liters of 0.0095 M-PBS-0.1 M L-histidine, pH 7.4. This solution had a molar ratio of —SH/protein of 1.35. The protein then was re-thiolated as described above to yield a solution with a molar ratio of —SH/protein of 5.0.

The maleimidocaproyl hydrazone of adriamycin (3.2 mg in 0.640 mL DMF) was added with stirring at 4° C. to the thiolated protein solution. The conjugate was incubated at 4° C. for 16 hrs then it was dialysed against 4 liters of 0.0095 M PBS-0.1 M L-histidine, pH 7.4. The dialysed conjugate was filtered through a 0.22$\mu$ cellulose acetate membrane into a sterile tube to which a small quantity (>5% (v/v)) of BioBeads™ SM-2 (Bio-Read Laboratories, Richmond, Calif. 94804) were added. After 24 hrs of gentle agitation, the beads were filtered off and the conjugate was frozen in liquid nitrogen and stored at −80° C. The resulting conjugate had a molar ratio of 3.4 adriamycin molecules to 1 molecule of protein and was obtained in 24% yield from chimeric BR96.

EXAMPLE 23

Conjugate of Maleimidocaproyl Hydrazone of Adriamycin with DTT reduced Human IgG ("Relaxed Human IgG")

Human IgG (obtained from Rockland, Gilbertsville, Pa.) was diluted with 0.0095 M PBS to a protein concentration of 10.98 mg/mL. This solution (350 mL) was heated to 37° C. in a water bath under a nitrogen atmosphere. Dithiothreitol (16.8 mL, 10 mM) in PBS was added and the solution was stirred for 3 hrs at 37° C. The solution was divided equally between two Amicon (Amicon Division of W. R. Grace and Co., Beverly, Mass. 01915) Model 8400 Stirred Ultrafiltration Cells, each fitted with an Amicon YM 30 Ultrafilter membrane (MW cutoff 30,000, 76 mm diam.) and connected via an Amicon Model CDS10 concentration/dialysis selector to an Amicon Model RC800 mini-reservoir. Each reservoir contained 700 mL of 0.0095 M PBS-0.1 M L-histidine. The protein solutions were dialyzed until concentration of free thiol in the filtrate was 41 $\mu$M. The molar ratio of —SH/protein in the retentate was determined to be 8.13.

The retentate was transferred from the cells to a sterile container maintained under a nitrogen atmosphere and a solution of maleimidocaproyl hydrazone of adriamycin (36.7 mL, 5 mg/mL in water) was added with stirring. The conjugate was incubated at 4° C. for 48 hrs after which it was filtered through a 0.22$\mu$ cellulose acetate membrane. A Bio-Rad Econocolumn™ (2.5 cm×50 cm, Bio-Rad Laboratories, Richmond, Calif. 94804) was packed with a slurry of 100 g of BioBeads™ SM-2 (Bio-Rad Laboratories, Richmond, Calif. 94804) in 0.00095 M-0.1 M L-histidine buffer. The beads had been prepared by washing in methanol, followed by water and then several volumes of buffer. The filtered conjugate was percolated through this column at 2 mL/min. After chromatography the conjugate was filtered through a 0.22$\mu$ cellulose acetate membrane and frozen in liquid nitrogen and stored at −80° C. The conjugate obtained had an average molar ratio of 7–45 molecules of adriamycin per molecule of protein and was obtained in 99% yield from human IgG.

EXAMPLE 24

Conjugate of Relaxed BR64 with Maleimidocaproyl Hydrazone of Adriamycin

A solution of BR64 (435 mL; 11.31 mg/mL, 7.07×10$^{-5}$ M) was treated with DTT (947 mg) and heated at 42°–43° C. with gentle stirring for 2 hrs. The solution was cooled in ice, transferred into 2 dialysis tubes and each tube was dialyzed 5 times against PBS (14 L per dialysis) for 8 hrs at 4° C. The contents of the tubes were combined (400 mL) and the protein and —SH content determined (10.54 mg/mL, 6.58×10$^{-5}$ M; 5.14×10$^{-4}$ M, respectively). The molar ratio of —SH to protein was 7.8.

A solution of maleimidocaproyl hydrazone of adriamycin in DMF (5 mg/mL, 32.6 mL) was added to the antibody solution with gentle stirring and then incubated at 4° C. for 24 hrs. The solution was filtered through a 0.22$\mu$ cellulose acetate filter and then transferred to two dialysis tubes and dialyzed as described above. After dialysis, the contents of the tubes were combined, filtered and shaken with Bio-Beads™ SM-2 (Bio-Rad Laboratories, Richmond, Calif. 94804) for 24 hrs at 4° C. The beads were filtered off using a cellulose acetate filter to yield the conjugate solution. The concentration of protein and adriamycin were determined (8.66 mg/mL, 5.42×10$^{-5}$ M; 168 $\mu$g/mL, 2.89×10$^{-4}$ M, respectively). The protein yield is 97%. The molar ratio of adriamycin to protein is 5.33; and, unconjugated adriamycin is 0.5%.

EXAMPLE 25

General Procedure for Conjugating the Maleimidocaproylhydrazone of Adriamycin to a Relaxed Antibody 1. A solution (300 mL) of antibody (3 g, 10 mg/mL) in PBS buffer is continuously blanketed with nitrogen, immersed in a 37° C. water bath and stirred gently with a magnetic stirrer. The solution is treated with 7 molar equivalents of DTT for 3 hrs. The —SH group molar ratio ("MR") to protein is determined initially and hourly and, for a maximally conjugate product, should remain constant at about 14.

2. The solution is transferred as quickly as possible to an Amicon diafiltration cell (Amicon, Division of W. R. Grace & Co., Beverly, Mass. 01915) (note 1) maintained at about 4° C. to about 7° C. The system is pressurized with argon or nitrogen and diafiltration is started using PBS buffer containing 0.1 M histidine which had been precooled to about 4° C. to about 7° C.). The initial temperature of the effluent, immediately after starting the diafiltration, is 16–18° C. and drops to 8°–9° C. within about 90 minutes. The effluent is monitored for a MR of —SH to protein and, when this value is <1, the diafiltration is complete (note 2).

3. The solution is transferred back to a round bottom flask equipped with a magnetic stirrer and kept in ice. The solution continuously is blanketed by nitrogen. The volume of the solution is noted. Aliquots of 0.1 mL are taken out and diluted with PBS buffer to 1.0 mL to determine the amount of protein in mg/mL (and also the molar equivalent of protein and the molarity of the —SH groups (and hence the MR of the —SH to protein). A solution of maleimidocaproylhydrazone of adriamycin in distilled water (5 mg/mL, 6.3×10$^{-3}$ M) is prepared (note 3, 4). The amount (in mL) of this solution needed for conjugation is determined by the formula:

$$\frac{(\text{molarity of -}SH) \times (\text{volume of protein solution}) \times 1.05}{6.3 \times 10^{-3}}$$

(note 5) and this amount is added slowly to the protein solution which is stirred gently. The solution is kept a 4° C. for 30 min.

4. A column of Bio-Beads™ SM-2, mesh 20–50 (Bio-Rad Laboratories, Richmond, Calif. 94804) is prepared (note 6) at 4° C. The red protein solution is filtered through a 0.22μ cellulose acetate filter, then passed through the column at a rate of 2.5 mL/min and the red effluent collected. Finally PBS-0.1 M histidine buffer is poured on top of the column and the effluent collected until it is colorless. The volume of the collected red solution is noted. An aliquot of 0.1 mL is diluted to 1 mL with PBS buffer and the amount of protein and adriamycin is measured. The amount of conjugated adriamycin is determined by absorbance at 495 nm ($\epsilon$=8030 cm$^{-1}$M$^{-1}$) and expressed in micromoles and micrograms per mL. The amount of protein, expressed in mg per mL and micromoles, is determined as above by reading the absorbance at 280 nm with a correction for the absorbance of adriamycin at the same wavelength according to the general formula $$\text{Antibody (mg/mL)} = \frac{A_{280} - (0.724 \times A_{495})}{1.4}$$

where A is the observed absorbance at the noted wavelength. The MR of adriamycin to protein then is calculated.

5. An aliquot of 5 mL of conjugate is passed over an Econo-Pac™ 10 SM-2 column (a prepacked Bio-Beads™ SM-2 column (Bio-Rad Laboratories, Richmond, Calif. 94804), volume 10 mL, that has been washed and equilibrated with PBS-0.1 M histidine buffer) in the manner described above. The amount of protein and conjugated adriamycin is determined and the MR determined. This value should be the same as that of the bulk of the solution (note 7).

6. The conjugate is frozen in liquid nitrogen and stored at –80° C. Aliquots can be taken for determining cytotoxicity, binding and presence of free adriamycin (note 8).

1. On a scale of 3 g/300 mL, two Amicon cells of 350 mL each are used, dividing the solution into two portions of 150 mL per cell.

2. On the reaction scale provided, the diafiltration usually takes 2–4 hrs. The duration will depend on factors such as the age of the membrane, rate of stirring of solution and pressure in cell.

3. The hydrazone is not very soluble in PBS and a precipitate is formed in a short while.

4. Brief applications of a sonicator will facilitate dissolution in distilled water. The resulting solution is stable.

5. This amount provides for a 5% excess of the hydrazone. The process described generally takes about 15–20 minutes.

6. The Bio-Beads™ are prepared for chromatography by swelling them in methanol for at least one hr., preferably overnight, washing them with distilled water and finally equilibrating them with PBS-0.1 M histidine buffer. For 3 g of protein 100 g of beads are used to form a column of 2.5 cm×30 cm.

7. Because of the inherent error of the spectroscopic methods used, a variation of 1 MR unit is accepted to be a satisfactory result. Generally, however, the MR varies less than 0.5 MR units.

8. The values of free adriamycin in the conjugate are generally much less than 1%.

EXAMPLE 26

Conjugate of Relaxed Chimeric BR96 with Maleimidocaproyl Hydrazone of Adriamycin Chimeric BR96, prepared in the manner previously described, was diluted with 0.0095 M PBS to a protein concentration of 10.49 mg/mL. This solution (500 mL) was heated to 37° C., under a nitrogen atmosphere, in a water bath. Dithiothreitol (26.2 mL, 10 mM) in PBS was added and the solution was stirred for 3 hrs at 37° C. The solution was divided equally between two Amicon Model 8400 stirred ultrafiltration cells each fitted with a YM 30 ultrafilter (MW cutoff 30,000, 76 mm diam.) and connected via a Model CDS10 concentration/dialysis selector to a Model RC800 mini-reservoir (Amicon, Division of W. R. Grace and Co., Beverly Mass. 01915-9843). Each reservoir contained 800 mL of 0.0095 M PBS-0.1 M L-histidine. The protein solutions were dialyzed until the concentration of free thiol in the filtrate was 63 μM. The molar ratio of —SH/protein in the retentate was determined to be 8.16. The retentate was transferred from the cells to a sterile container under nitrogen and a solution of maleimidocaproyl hydrazone of adriamycin (42.6 mL, 5 mg/mL in water) was added with stirring. The conjugate was incubated at 4° C. for 48 hrs after which it was filtered through a 0.22μ cellulose acetate membrane. A 2.5 cm×50 cm Bio-Rad Econocolumn was packed with a slurry of 100 g of BioBeads™ SM-2 (Bio-Rad Laboratories, Richmond Calif. 94804) in 0.0095 M–0.1 M L-histidine buffer. The beads had been prepared by washing in methanol, followed by water then several volumes of buffer. The filtered conjugate was percolated through this column at 2 mL/min. After chromatography the conjugate was filtered through a 0.22μ cellulose acetate membrane, frozen in liquid nitrogen and stored at –80° C. The conjugate obtained had a molar ratio of 6.77 Adriamycin to protein and was obtained in 95% yield from chimeric BR96.

EXAMPLE 27

Conjugate of Relaxed Murine Antibody L6 with Maleimidocaproyl

Hydrazone of Adriamycin

Murine antibody L6, prepared as defined earlier, was diluted with 0.0095 M PBS to a protein concentration of 11.87 mg/mL. This solution (350 mL) was heated to 37° C., under a nitrogen atmosphere, in a water bath. Dithiothreitol (18.2 mL, 10 mM) in PBS was added and the solution was stirred for 3 hrs at 37° C. The solution was divided equally between two Amicon Model 8400 stirred ultrafiltration cells each fitted with a YM 30 ultrafilter (MW cutoff 30,000, 76 mm diam.) and connected via a Model CDS10 concentration/dialysis selector to a Model RC800 mini-reservoir (Amicon, Division of W. R. Grace and Co., Beverly Mass. 01915-9843). Each reservoir contained 800 mL of 0.0095 M PBS–0.1 M L-histidine. The protein solutions were dialyzed until concentration of free thiol in the filtrate was 14 μM. The molar ratio of —SH/protein in the retentate was determined to be 9.8. The retentate was transferred from the cells to a sterile container under nitrogen and a solution of maleimidocaproyl hydrazone of adriamycin (40.4 mL, 5 mg/mL in water) was added with stirring. The conjugate was incubated at 4° C. for 48 hrs after which it was filtered through a 0.22μ cellulose acetate membrane. A 2.5 cm×50 cm Bio-Rad Econocolumn was packed with a slurry of 100 g of BioBeads™ SM-2 (Bio-Rad Laboratories, Richmond, Calif. 94804) in 0.00095 M–0.1 M L-histidine buffer. The beads had been prepared by washing in methanol, followed by water then several volumes of buffer. The filtered conjugate was percolated through this column at 2 mL/min. After chromatography the conjugate was filtered through a 0.22μ cellulose acetate membrane, frozen in liquid nitrogen and stored at –80° C. The conjugate obtained had a molar ratio of 7.39 Adriamycin to protein and was obtained in 100% yield from murine L6.

Biological Activity

Representative conjugates of the present invention were tested in both in vitro and in vivo systems to determine biological activity. In these tests, the potency of conjugates of cytotoxic drugs was determined by measuring the cytotoxicity of the conjugates against cells of human cancer origin. The following describes representative tests used and the results obtained. Throughout the data presented, the conjugates are referred to using the form ligand-drug-molar ratio of ligand to drug. Thus, for example, "BR64-ADM-5.33", refers to a conjugate between antibody BR64 and adriamycin and the mole ratio of drug to antibody is 5.33. One skilled in the art will recognize that any tumor line expressing the desired antigen could be used in substitution of the specific tumor lines used in the following analyses.

TEST I

In vitro Activity of BR64-Adriamycin Conjugates

The immunoconjugates of Examples 18 and 19 were tested in vitro against a human lung carcinoma line, L2987 [obtained from I. Hellström. Bristol-Myers Squibb Seattle; See also I. Hellström, et al., Cancer Research 50: 2183 (1990)], which expresses the antigens recognized by monoclonal antibodies BR64, L6 and BR96. Monolayer cultures of L2987 cells were harvested using trypsin-EDTA (GIBCO, Grand Island, N.Y.), and the cells counted and resuspended to $1 \times 10^5$/mL in RPMI-1640 containing 10% heat inactivated fetal calf serum ("RPMI-10% FCS"). Cells (0.1 mL/well) were added to each well of 96-well flat bottom microtiter plates and incubated overnight at 37° C. in a humidified atmosphere of 5% $CO_2$. Media was removed from the plates and serial dilutions of adriamycin or the antibody conjugates of adriamycin were added to the wells. All dilutions were performed in quadruplicate. Following a 2 hr drug or conjugate exposure, the plates were centrifuged (100× g, 5 min), the drug or conjugate removed, and the plates washed three times with RPMI-10%FCS. The cells were cultured in RPMI-10% FCS for an additional 48 hours. At this time the cells were pulsed for 2 hour with 1.0 $\mu$Ci/well of $^3$H-thymidine (New England Nuclear, Boston, Mass.). The plates were harvested and the counts per minute ("CPM") determined. Inhibition of proliferation was determined by comparing the mean CPM for treated samples with that of the untreated controls. The data presented in FIG. 51 demonstrates the cytotoxicity against L2987 lung cells of binding immunoconjugate (MR of adriamycin to BR64 equal to 7.18, designated "BR64-THADMHZN-7.18") compared to a non-binding immunoconjugate of SN7 and adriamycin (MR of adriamycin to SN7 equal to 4, designated "SN7-THADMHZN-4"). The BR64 conjugates prepared by the method described in Example 18 are active and demonstrate antigen-specific cytotoxicity in this in vitro screen.

TEST II

In Vivo Activity of Br64-Adriamycin Conjugates

The immunoconjugates of Examples 18 and 19 were evaluated in vivo for antigen-specific antitumor activity. Congenitally athymic female mice of BALB/c background (BALB/c nu/nu; Harlan Spraque-Dawley, Indianapolis, Ind.) were used in these studies. Mice were housed in Thoren caging units on sterile bedding with controlled temperature and humidity. Animals received sterile food and water ad libitum. The L2987 human lung tumor line, described above, was used in these studies. This line has been shown to maintain expression of the BR64, BR96 and L6 antigens following repeated passage in vivo. The tumor lines were maintained by serial passage in athymic mice as described previously (P. A. Trail, et al., in vivo 3: 319–24 (1989)). Tumors were measured, using calipers, in 2 perpendicular directions at weekly or biweekly intervals.

Tumor volume was calculated according to the equation:

$$V(\text{mm}^3) = \frac{(L \times W^2)}{2}$$

in which
V=volume (mm$^3$)
L=measurement of longest axis (mm)
W=measurement (mm) of axis perpendiculars to L.

Data are presented as the median tumor size for treated and control groups. Each treatment or control group contained 8–10 animals. Therapy was initiated when tumors had reached a medium size of 50–100 mm$^3$. Therapy was administered by the ip or iv route on various schedule as denoted. Adriamycin was diluted in normal saline and native antibody and adriamycin conjugates were diluted in phosphate buffered saline ("PBS") for administration. All dosages were administered on a weight basis (mg/kg) and were calculated for each animal. In these studies the antitumor activity of binding BR64 immunoconjugates was compared to that of optimized dosages of adriamycin, mixtures of native BR64 and adriamycin, and non-binding conjugates. Unconjugated adriamycin was administered according to the route, dosage, and schedule demonstrated to be optimal for the L2987 human xenograft model. The unconjugated adriamycin, therefore, was administered at a dose of 8 mg/kg by the iv route every fourth day for a total of 3 injections (denoted "8 mg/kg, q4dx3, iv"). The binding (BR64) and non-binding (SN7) immunoconjugates were administered at several doses by the ip route every fourth day for a total of 3 injections (denoted "q4dx3, ip"). As shown in FIG. 52 significant antitumor activity was observed following the administration of tolerated doses (10 and 15 mg/kg/injection) of the BR64-adriamycin conjugate. The antitumor activity observed following therapy with the BR64 conjugate was significantly better than that observed for therapy with optimized adriamycin and matching doses of a non-binding (SN7) conjugate.

In this experiment, complete tumor regressions were observed in 66% of the animals following treatment with 15 mg/kg/injection of the BR64 conjugate and 50% complete tumor regressions were observed following treatment with 10 mg/kg/injection of the BR64 conjugate. Partial or complete regressions of established L2987 tumors have not been observed following therapy with optimized adriamycin, mixtures of native BR64 and adriamycin, or equivalent doses of non-binding conjugates.

To demonstrate that the observed activity required the covalent coupling of the antibody to adriamycin, several control experiments using mixtures of native BR64 and adriamycin were performed. Representative data for several types of combined therapy are shown in FIGS. 5a–c. The antitumor activity observed for various modes of combined therapy with Mab and adriamycin was not significantly different from that observed for therapy with optimized adriamycin alone. Taken together these data indicate that the covalent coupling of BR64 to adriamycin is required to observe the antitumor activity described in FIG. 21.

TEST III

In Vivo Activity of Bombesin Conjugates

The conjugate of Example 21 was evaluated in vivo for antitumor activity. BALB/c athymic nude mice were implanted with H345 human small cell lung carcinoma tumor pieces (obtained from Dr. D. Chen, University of Colorado Medical School, CO), subcutaneously, using trocars. Tumors were allowed to grow to 50–100 mm³ before initiation of treatment. Mice were treated i.v. on 23, 26, 28, and 30 days post-implant with adriamycin alone (1.6 mg/kg), or the conjugates bombesin-adrimycin ("BN-ADM (TH)", in an amount equivalent to 1.6 mg/kg adriamycin) or P77-adriamycin conjugate ("P77-ADM(TH)", in an amount equivalent to 1.6 mg/kg of adriamycin). P77 is a 12 amino acid peptide with an internal cysteine residue (sequence= KKLTCVQTRLKI) that does not bind to H345 cells and was conjugated to the maleimidocaproylhydrazone of adriamycin according to the procedure outlined in Example 21. Thus, the conjugate represents a non-binding conjugate with respect to H345 cells. Tumors were measured with calipers and tumor volume was calculated using formula:

$$V(\text{mm}^3) = \frac{(L \times W^2)}{2}$$

in which V, L, and W are as defined in Test II.

The median tumor volumes were determined and the observed results are shown in FIG. 54.

TEST IV

In Vitro Cytotoxicity Data for Relaxed ChiBR96 Antibody Conjugates

Immunoconjugates of adriamycin an ChiBR96 antibody are prepared using the general method for preparing relaxed antibodies as described in Example 25. The conjugates were tested, using the protocol below, for in vitro cytotoxicity and their cytotoxicity was compared to that of free adriamycin, and SPDP-thiolated immunoconjugates prepared by the method described in Example 18. The results of these tests are provided in FIG. 55.

Monolayer cultures of L2987 human lung cells were maintained in RPMI-1640 media containing 10% heat inactivated fetal calf serum (RPMI-10%FCS). The cells were harvested using trypsin-EDTA (GIBCO, Grand Island, N.Y.), and the cells counted and resuspended to 1×10⁵/ml in RPMI-10%FCS. Cells (0.1 ml/well) were added to each well of 96 well microtiter plates and incubated overnight at 37° C. in a humidified atmosphere of 5% $CO_2$. Media was removed from the plates and serial dilutions of adriamycin or antibody/ADM conjugates added to the wells. All dilutions were performed in quadruplicate. Following a 2 hr drug or conjugate exposure, the plates were centrifuged (200× g, 5 min), the drug or conjugate removed, and the plates washed 3× with RPMI-10%FCS. The cells were cultured in RPMI-10%FCS for an additional 48 hr. At this time the cells were pulsed for 2 hr with 1.0 μCi/well of ³H-thymidine (New England Nuclear, Boston, Mass.). The plates were harvested and the counts per minute ("CPM") were determined. Inhibition of proliferation was determined by comparing the mean CPM for treated samples with that of the untreated control. $IC_{50}$ values are reported as μM of equivalent adriamycin.

TEST V

In Vivo Antitumor Activity of BR64 and Murine L6 Conjugates

The in vivo antitumor activity of immunoconjugates of adriamycin and relaxed BR64 or relaxed L6 was evaluated. The observed data are provided in FIG. 56.

Congenitally athymic female mice of BALB/c background (BALB/c nu/nu; Harlan Sprague-Dawley, Indianapolis, Ind.) were used. Mice were housed in Thoren caging units on sterile bedding with controlled temperature and humidity. Animals received sterile food and water ad libitum.

The L2987 human tumor line was established as tumor xenograft models in athymic mice. The tumor line was maintained by serial passage in vivo. Tumors were measured in 2 perpendicular directions at weekly or biweekly intervals using calipers. Tumor volume was calculated according to the equation:

$$V(\text{mm}^3) = \frac{L \times W^2}{2}$$

in which:

V=volume (mm³)

L=measurement of longest axis (mm)

W=measurement of axis perpendicular to L

In general, there were 8–10 mice per control or treatment group. Data are presented as median tumor size for control or treated groups. Antitumor activity is expressed in terms of gross log cell kill ("LCK") where:

$$LCK = \frac{T - C}{3.3 \times TVDT}$$

T-C is defined as the median time (days) for treated tumors to reach target size minus the median time for control tumors to reach target size and TVDT is the time (days) for control tumors to double in volume (250–500 mm³). Partial tumor regression ("PR") refers to a decrease in tumor volume to ≦50% of the initial tumor volume; complete tumor regression ("CR") refers to a tumor which for a period of time is not palpable; and cure is defined as an established tumor which is not palpable for a period of time ≧10 TVDTs.

For animals bearing the L2987 human lung tumor, therapy was typically initiated when the median tumor size was 75 mm³ (12–14 days after tumor implant). The average TVDT was 4.8–0.9 days and antitumor activity was assessed at a tumor size of 500 mm³. In several experiments (described below in Test VI) therapy was initiated when L2987 tumors were 225 mm³ in size.

Materials under investigation were administered by the ip or iv route. Adriamycin was diluted in normal saline; antibody and antibody/adriamycin conjugates were diluted in phosphate buffered saline. Compounds were administered on a mg/kg basis calculated for each animal, and doses are presented as mg/kg of equivalent adriamycin/injection. Immunoconjugates were administered on a q4dx3 schedule. The maximum tolerated dose ("MTD") for a treatment regimen is defined as the highest dose on a given schedule which resulted in ≦20% lethality.

In the data shown in FIG. 56, injection of optimized doses of adriamycin produced antitumor activity equivalent to 1.1 LCK and tumor regressions were not observed. The BR64-ADM conjugate produced antitumor activity equivalent to >10 LCK at all doses tested and 89%, 78%, and 100% cures were observed at doses of 5 mg/kg, 8 mg/kg, and 10 mg/kg of BR64-ADM, respectively. At doses of 8 mg/kg or 10 mg/kg the L6-ADM conjugate produced antitumor activity (1.8 and 3.5 LCK, respectively) which was significantly better than that of optimized adriamycin but less than that of equivalent doses of internalizing BR64-ADM conjugates.

Thus, the data show that the antitumor activity of binding non-internalizing L6-ADM conjugates is superior to that of unconjugated adriamycin. Treatment with L6-adriamycin conjugate results in lower antitumor activity than is observed with matching doses of the internalizing BR64-adriamycin conjugate.

TEST VI

In Vivo Antitumor Activity of ChiBR96-ADM Conjugates

The antitumor activity of ChiBR96-ADM conjugates was evaluated against established human lung ("L2987"), breast ("MCF7", obtainable from the ATCC under the accession number ATCC HTB 22; see also I. Hellström, et al., *Cancer Research* 50: 2183 (1990)), and colon ("RCA" from M. Brattain, Baylor University; See also I. Hellström, et al., *Cancer Research* 50: 2183 (1990)) tumors.

Animals were maintained and tumor xenograft models were established for the MCF7 and RCA and the L2987 human tumor lines as described for the L2987 in Test V. Materials were administered as described in Test V.

For animals bearing the L2987 human lung tumor, therapy typically was initiated when the median tumor size was 75 mm$^3$ (12–14 days after tumor implant). The average TVDT was 3.8±0.9 days and antitumor activity was assessed at a tumor size of 500 mm$^3$. In several experiments therapy was initiated with L2987 tumors were 225 mm$^3$ in size.

The MCF7 tumor is an estrogen-dependent human breast tumor line. Athymic mice were implanted with 0.65 mg (65 day release rate) estradiol pellets (Innovative Research of America, Toledo, Ohio) on the day of tumor implant. Therapy was initiated when the median tumor size was 100 mm$^3$ (typically 13 days after tumor implant). The MCF7 tumor had an average TVDT of 6.4±2.0 days and antitumor activity was assessed at 500 mm$^3$.

For animals bearing the RCA colon tumor, therapy was initiated 15 days after tumor implant when the median tumor size was 75 mm$^3$. The average TVDT for RCA tumor xenografts was 9.5±1.5 days and antitumor activity was assessed at 400 mm$^3$. Data for the antitumor activity of optimized adriamycin in the L2987, MCF7, and RCA xenograft models is summarized in the following Tables and referenced Figures.

The antitumor activity of the ChiBR96-ADM conjugates was compared to that of optimized adriamycin and equivalent doses of non-binding (IgG) immunoconjugates. In each model, complete tumor regressions and/or cures of established tumors were observed following the administration of tolerated doses of ChiBR96-ADM conjugate.

Representative data demonstrating the antigen-specific antitumor activity of ChiBR96-ADM conjugates is presented in FIGS. 57 and 58. As shown in FIG. 57, the ip administration of ChiBR96-ADM conjugate (MR=4.19) at a dose of 10 mg/kg equivalent of adriamycin produced antitumor activity equivalent to >10 LCK. At this dose of ChiBR96-ADM conjugate, 78% of the mice were cured of the tumor and an additional 11% of mice demonstrated a complete tumor regression. The administration of 5 mg/kg of the ChiBR96-ADM conjugate also produced antitumor activity equivalent to >10 LCK with 88% tumor cures and 12% complete tumor regressions. The antitumor activity observed following administration of ChiBR96-ADM conjugates (>10 LCK) was substantially better than that observed for optimized adriamycin (1.0 LCK). The CHiBR96-ADM conjugate was also more potent than optimized adriamycin; that is; the antitumor activity of the ChiBR96-ADM conjugate tested at a dose of 5 mg/kg equivalent adriamycin was superior to that of adriamycin tested at a dose of 8 mg/kg. The non-binding human IgG conjugate (MR=7.16) was not active against L2987 xenografts when tested at a dose of 10 mg/kg equivalent of adriamycin indicating that the superior activity of the ChiBR96-ADM conjugate was due to antigen specific binding of the immunoconjugate to L2987 tumor cells.

Similar data are presented in FIG. 58. As shown, the ChiBR96-ADM conjugate (MR=5.8) tested at a dose equivalent of 10 mg/kg adriamycin resulted in antitumor activity equivalent to >10 LCK. At this dose, 90% tumor cures and 10% complete tumor regressions were observed. The administration of 5 mg/kg of the ChiBR96-ADM conjugate resulted in 4.8 LCK with 10% cures, 50% complete and 10% partial tumor regressions. The antitumor activity of the ChiBR96-ADM conjugate greatly exceeded that of optimized adriamycin (1.6 LCK) and, as described above, the ChiBR96-ADM conjugate was more potent than unconjugated adriamycin. The non-binding IgG-ADM conjugate (MR=7.16) was not active at a dose of 10 mg/kg.

The antitumor activity of various preparation of ChiBR96-ADM conjugated prepared by the "relaxed" antibody technique and evaluated against established L2987 lung tumor xenografts is presented in Table 15.

TABLE 15

Antitumor Activity of ChiBR96-ADM Conjugates Against Established L2987 Human Lung Tumor Xenografts*

| Conjugate | Dose (mg/kg) | | Route | LCK | % Tumor Regressions | | Cure | No. of Mice |
|---|---|---|---|---|---|---|---|---|
| | ADM | Antibody | | | PR | CR | | |
| ChiBR96-ADM-6.85 | 15 | 615 | ip | >10 | 10 | 0 | 80 | 10 |
| | 10 | 410 | ip | >10 | 0 | 0 | 89 | 9 |
| | 8 | 320 | iv | >10 | 0 | 0 | 100 | 9 |
| | 5 | 205 | iv | >10 | 0 | 22 | 78 | 9 |
| ChiBR96-ADM-4.19 | 15 | 980 | ip | >10 | 0 | 11 | 89 | 9 |
| | 10 | 654 | ip | >10 | 11 | 11 | 66 | 9 |
| | 5 | 327 | iv | >10 | 0 | 11 | 89 | 9 |
| | 2.5 | 164 | iv | >10 | 0 | 22 | 78 | 9 |
| ChiBR96-ADM-6.85 | 10 | 410 | ip | >10 | 11 | 11 | 78 | 9 |
| | 8 | 328 | iv | >10 | 0 | 0 | 100 | 9 |

TABLE 15-continued

Antitumor Activity of ChiBR96-ADM Conjugates Against Established L2987 Human Lung Tumor Xenografts*

|  | Dose (mg/kg) |  |  |  | % Tumor Regressions |  |  |  |
|---|---|---|---|---|---|---|---|---|
| Conjugate | ADM | Antibody | Route | LCK | PR | CR | Cure | No. of Mice |
|  | 5 | 205 | iv | >10 | 0 | 11 | 89 | 9 |
| ChiBR96-ADM-4.19 | 10 | 654 | ip | >10 | 0 | 0 | 100 | 9 |
|  | 5 | 327 | ip | >10 | 0 | 0 | 100 | 9 |
| ChiBR96-ADM-4.19 | 10 | 654 | ip | >8 | 0 | 22 | 78 | 9 |
|  | 5 | 327 | ip | >8 | 0 | 11 | 89 | 9 |
| ChiBR96-ADM-5.80 | 10 | 500 | ip | >10 | 0 | 10 | 90 | 10 |
|  | 5 | 250 | ip | >4.8 | 10 | 50 | 10 | 10 |
| ChiBR96-ADM-6.82 | 5 | 204 | iv | >10 | 22 | 22 | 55 | 9 |
|  | 2 | 82 | iv | 3.5 | 44 | 33 | 0 | 9 |
|  | 1 | 41 | iv | 2.0 | 0 | 22 | 0 | 9 |
| ChiBR96-ADM-6.82 | 10 | 400 | ip | >5.3 | 11 | 11 | 56 | 9 |
|  | 5 | 200 | ip | 4.8 | 30 | 10 | 40 | 10 |
|  | 2.5 | 100 | ip | 2.9 | 30 | 0 | 30 | 10 |
|  | 1.25 | 50 | ip | 1.1 | 11 | 0 | 11 | 9 |
|  | 0.62 | 25 | ip | 0 | 0 | 0 | 0 | 9 |
|  | 5 | 200 | iv | >5.3 | 10 | 20 | 70 | 10 |
|  | 2.5 | 100 | iv | 2.9 | 22 | 33 | 0 | 9 |
|  | 1.25 | 50 | iv | 1.5 | 11 | 11 | 0 | 9 |
|  | 0.62 | 25 | iv | 0.6 | 0 | 0 | 0 | 9 |
| Adriamycin | 8 | — | iv | 1–1.8 | 3.6 | 0 | 0 | 55 |

*All treatment administered on a q4d × 3 schedule

As shown, the antitumor activity of ChiBR96-ADM conjugates is superior to that of optimized adriamycin and the ChiBR96-ADM conjugates are 6–8 fold more potent than unconjugated adriamycin.

The antitumor activity of ChiBR96-ADM conjugates was also evaluated against large (225 mm$^3$) established L2987 tumors (FIG. 59). The administration of the ChiBR96-ADM conjugate (MR=6.85) at a dose of 10 mg/kg equivalent adriamycin resulted in antitumor activity equivalent to <10 LCK and 70% cures and 30% partial tumor regressions were observed.

The antitumor activity of unconjugated ChiBR96 antibody was evaluated using established (50–100 mm$^3$) L2987 human lung tumor xenografts. As shown in Table 10, ChiBR96 antibody administered at doses of 100, 200 or 400 mg/kg was not active against established L2987 tumors. The antitumor activity of mixtures of ChiBR96 and adriamycin was not different from that of adriamycin administered alone. Therefore, the antitumor activity of the CHiBR96-ADM conjugates reflects the efficiency of the conjugate itself rather than a synergistic antitumor effect of antibody and adriamycin.

TABLE 16

Antitumor Activity of Adriamycin, ChiBR96, and Mixtures of ChiBR96 and Adriamycin Against Established L2987 Human Lung Tumor Xenografts

|  | Dose (mg/kg)$^a$ | | Log Cell Kill | % Tumor Regressions | | | No. of Mice |
|---|---|---|---|---|---|---|---|
| Treatment | ADM | ChiBR96 | | PR | CR | Cure | |
| Adriamycin | 8 | — | 1.5 | 0 | 0 | 0 | 9 |
| ChiBR96 | — | 400 | 0 | 0 | 0 | 0 | 8 |
|  | — | 200 | 0 | 0 | 0 | 0 | 8 |
|  | — | 100 | 0 | 0 | 0 | 0 | 8 |

TABLE 16-continued

Antitumor Activity of Adriamycin, ChiBR96, and Mixtures of ChiBR96 and Adriamycin Against Established L2987 Human Lung Tumor Xenografts

|  | Dose (mg/kg)$^a$ | | Log Cell Kill | % Tumor Regressions | | | No. of Mice |
|---|---|---|---|---|---|---|---|
| Treatment | ADM | ChiBR96 | | PR | CR | Cure | |
| Adriamycin + | 8 | 400 | 1.8 | 11 | 0 | 0 | 9 |
| ChiBR96 | 8 | 200 | 1.6 | 0 | 0 | 0 | 9 |
|  | 8 | 100 | 1.9 | 0 | 0 | 0 | 8 |

$^a$Treatment administered iv on a q4d × 3 schedule

In summary ChiBR96-ADM conjugates demonstrated antigen-specific antitumor activity when evaluated against established L2987 human lung tumors. The antitumor activity of ChiBR96-ADM conjugates was superior to that of optimized adriamycin, mixtures of ChiBR96 and adriamycin, and equivalent doses of non-binding conjugates. The ChiBR96-ADM conjugates were approximately 6 fold more potent than unconjugated adriamycin. Cures or complete regressions of established tumors were observed in 50% of animals treated with doses of ≥2.5 mg/kg of ChiBR96-ADM conjugate.

As shown in FIG. 60, ChiBR96-ADM conjugates (MR=7.88) demonstrated antigen-specific antitumor activity against established (745–125 mm$^3$) MCF7 tumors. The activity of ChiBR96-ADM conjugate administered at a dose of 5 mg/kg by either the ip or iv route (4.2 LCK) was superior to that of optimized adriamycin (1.4 LCK) or equivalent doses of non-binding IgG conjugate (1.2 LCK). The antitumor activity of ChiBR96-ADM and non-binding IgG-ADM conjugates is summarized in Table 17. The MTD of CHiBR96-ADM conjugates like that of free adriamycin is lower in the MCF7 model due to the estradiol supplementation required for tumor growth.

TABLE 17

Summary of Antitumor Activity of ChiBR96-ADM Thioether Conjugates Evaluated Against Established MCF7 Human Breast Tumor Xenografts

| Conjugate | Dose (mg/kg)[a] | | Route | Log Cell Kill | % Tumor Regressions | | | No. of Mice |
|---|---|---|---|---|---|---|---|---|
| | ADM | ChiBR96 | | | PR | CR | Cures | |
| ChiBR96- | 10 | 350 | ip | —[b] | — | — | — | 10 |
| ADM-7.88 | 5 | 175 | ip | 4.2 | 30 | 0 | 0 | 10 |
| | 5 | 175 | iv | 4.2 | 50 | 10 | 0 | 10 |
| IgG-ADM-7.16 | 5 | 225 | ip | 1.1 | 0 | 0 | 0 | 10 |
| | 2.5 | 112 | ip | 0.6 | 0 | 0 | 0 | 10 |
| Adriamycin | 2.5 | 112 | iv | 0.8 | 0 | 0 | 0 | 10 |
| | 6 | 0 | iv | 1.4 | 0 | 0 | 0 | 10 |

[a]All therapy administered q4d × 3
[b]40% lethality occurred at this dose of immunoconjugate The antigen-specific antitumor activity and dose response of ChiBR96-ADM conjugates was also evaluated in the RCA human colon carcinoma model. RCA tumors are less senstive to unconjugated adriamycin than are L2987 and MCF7 tumors. In addition, as described previously, RCA tumors have a longer tumor volume doubling time than L2987 or MCF7 tumors, are more poorly vascularized, and the localization of radiolabelled BR64 antibody is lower in RCA tumors than in L2987 tumors. As shown in FIG. 61, the antitumor activity of the ChiBR96-ADM conjugate (MR=7.88) administered at a dose of 10 mg/kg was superior to that of adriamycin and an equivalent dose of non-binding IgG conjugates (MR=7.16). As shown in Table 18, the ChiBR96-ADM conjugate tested at a dose of 10 mg/kg produced antitumor activity equivalent to >3 LCK. At this dose of ChiBR96-ADM conjugate, 89% cures and 11% partial tumor regressions occurred. In this experiment, unconjugated adriamycin showed antitumor activity, equivalent to 0.4 LCK. Thus, in this experiment, the BR96-ADM conjugate produced 89% cures of established tumors whereas unconjugated adriamycin was inactive.

TABLE 18

Summary of Antitumor Activity of ChiBR96-ADM Thioether Conjugates Evaluated Against Established RCA Human Colon Tumor Xenografts

| Conjugate | Dose (mg/kg)[a] | | Route | Log Cell Kill | % Tumor Regressions | | | No. of Mice |
|---|---|---|---|---|---|---|---|---|
| | ADM | ChiBR96 | | | PR | CR | Cures | |
| ChiBR96- | 10 | 350 | ip | >3 | 11 | 0 | 89 | 9 |
| ADM-7.88 | 5 | 175 | ip | 0.6 | 11 | 22 | 11 | 9 |
| | 2.5 | 85 | ip | 0.2 | 0 | 0 | 0 | 9 |
| | 2.5 | 85 | iv | 0.6 | 11 | 0 | 0 | 9 |
| IgG-ADM-7.16 | 10 | 405 | ip | 0 | 0 | 0 | 0 | 9 |
| Adriamycin | 8 | 0 | iv | 0.4 | 0 | 0 | 0 | 9 |

[a]All therapy administered q4d × 3

In summary, the ChiBR96-ADM conjugate demonstrated antigen-specific antitumor activity in the RCA human colon tumor model. Cures and complete regressions of established RCA tumors were observed following the administration of ChiBR96-ADM conjugate at doses of 5–10 mg/kg.

The invention has been described with reference to specific examples, materials and data. As one skilled in the art will appreciate, alternate means for using or preparing the various aspects of the invention may be available. Such alternate means are to be construed as included within the intent and spirit of the present invention as defined by the following claims.

What is claimed is:

1. An immunoconjugate comprising a molecule containing the antigen-binding region of the BR96 monoclonal antibody (ATCC Accession No. 10036) joined to a therapeutic agent.

2. The immunoconjugate of claim 1, wherein the molecule comprises BR96 monoclonal antibody (ATCC Accession No. 10036) or antigen binding fragments thereof.

3. The immunoconjugate of claim 2, wherein the fragments are selected from the group consisting of Fv, F(ab') and F(ab')$_2$ fragments.

4. The immunoconjugate of claim 1, wherein the molecule comprises chimeric human/murine BR96 antibody (ATCC Accession No. 100460) or antigen binding fragments thereof.

5. The immunoconjugate of claim 4, wherein the fragments are selected from the group consisting of Fv, F(ab)' and F(ab')$_2$ fragments.

6. A method for selectively killing tumor cells expressing the antigen that immunospecifically binds to BR96 monoclonal antibody (ATCC Accession No. 10036) comprising reacting the immunoconjugate of claim 1 with said tumor cells.

7. A bispecific antibody with a binding specificity for two different antigens, one of the antigens being that with which the monoclonal antibody of claim 1 binds.

8. The bispecific antibody of claim 7, wherein one of the antigens comprises a variant of Le$^y$ determinant which includes an epitopic site containing fucose $\alpha$1-3.

9. The immunoconjugate of claim 1, wherein the therapeutic agent is an anti-tumor drug, a cytotoxin, a radioactive agent, a second antibody or an enzyme.

10. The immunoconjugate of claim 9, wherein the cytotoxin is a ribosome binding toxin.

11. The immunoconjugate of claim 10, wherein the ribosome binding toxin is ricin A.

12. The immunoconjugate of claim 9, wherein the cytotoxin is an exotoxin.

13. The immunoconjugate of claim 12, wherein the exotoxin is Pseudomonas exotoxin A.

14. The immunoconjugate of claim 12 or 13, wherein the exotoxin is truncated to remove the cell-binding domain.

15. The immunoconjugate of claim 14, wherein the amino terminus of the exotoxin has been modified to include a lysine amino acid residue.

16. A method for treating a subject suffering from a malignant disease characterized by cells having the BR96 antigen on the cell surface which comprises administering to the subject an effective amount of an immunoconjugate of claim 1 such that the immunoconjugate binds the BR96 antigen and kills said cells thereby treating the subject.

17. A pharmaceutical composition useful in killing human cells expressing the BR96 antigen on the cell surface comprising a pharmaceutically effective amount of the immunoconjugate of claim 1, and a pharmaceutically acceptable carrier.

18. An immunoconjugate of claim 1 which is a single-chain immunoconjugate.

19. The single chain immunoconjugate of claim 18, wherein the therapeutic agent is an exotoxin.

20. The single chain immunoconjugate of claim 19, wherein the exotoxin is Pseudomonas exotoxin A.

21. The single chain immunoconjugate of claim 19 or 20, wherein the exotoxin has been modified to remove the cell-binding domain.

22. An immunoconjugate comprising the BR96 monoclonal antibody (ATCC Accession No. 10036) or antigen binding fragments thereof joined to Pseudomonas exotoxin A.

23. An immunoconjugate comprising chimeric human/murine BR96 antibody (ATCC Accession No. 100460) joined to Pseudomonas exotoxin A.

24. An immunoconjugate comprising a Fab' fragment of chimeric human/murine BR96 antibody (ATCC Accession No. 100460) joined to Pseudomonas exotoxin A.

25. An immunoconjugate comprising a F(ab)$_2$ fragment of chimeric human/murine BR96 antibody (ATCC Accession No. 100460) joined to Pseudomonas exotoxin A.

26. A recombinant single-chain immunotoxin molecule comprising a cloned heavy chain Fv portion of the BR96 monoclonal antibody (ATCC Accession No. 10036) and a cloned light chain Fv portion of the BR96 monoclonal antibody joined to a cytotoxic agent.

27. The immunotoxin molecule of claim 26, wherein the cytotoxic agent is an exotoxin.

28. The immunotoxin molecule of claim 27, wherein the exotoxin is Pseudomonas exotoxin A.

29. The immunotoxin molecule of claim 27 or 28, wherein the exotoxin has been modified to remove the cell-binding domain.

30. A method for using the immunotoxin molecule of claim 26, to selectively kill tumor cells expressing the antigen that specifically binds to BR96 monoclonal antibody (ATCC Accession No. 10036) comprising contacting said tumor cells with an effective amount of the immunotoxin molecule effective to kill said tumor cells.

31. A method for selectively killing tumor cells expressing the antigen that specifically binds to BR96 monoclonal antibody (ATCC Accession No. 10036) comprising contacting said tumor cells with an amount of the immunotoxin molecule of claim 26 for a time sufficient to kill said cells.

32. A single-chain immunoconjugate comprising a Fv fragment of BR96 antibody (ATCC Accession No. 10036) joined to Pseudomonas exotoxin A.

33. A single-chain immunoconjugate comprising a Fv fragment of chimeric human/murine BR96 antibody (ATCC Accession No. 100460) joined to Pseudomonas exotoxin A.

34. A method for imaging carcinoma characterized by cells having the BR96 antigen on the cell surface comprising administering to a patient intravenously the BR96 monoclonal antibody (ATCC Accession No. 10036) in an amount effective for detection of the carcinoma, allowing the antibody to bind to carcinoma cells and to localize to the site of carcinoma cells and detecting said antibody bound to the carcinoma cells.

35. The method of claim 34, wherein said antibody is labeled so as to directly or indirectly produce a detectable signal with a label selected from the group consisting of a radiolabel, an enzyme, a chromophore, and a fluorescer.

* * * * *